US008580488B2

(12) United States Patent (10) Patent No.: US 8,580,488 B2
Chen et al. (45) Date of Patent: Nov. 12, 2013

(54) CELL CULTURE MODEL FOR ACQUIRED CHEMORESISTANCE OF CHRONIC MYELOGENOUS LEUKEMIA AND RELATED METHODS FOR IDENTIFYING AGENTS TO OVERCOME RESISTANCE

(75) Inventors: WenYong Chen, Temple City, CA (US); Ravi Bhatia, Duarte, CA (US); Leila Su, Diamond Bar, CA (US); Yate-Ching Yuan, Arcadia, CA (US)

(73) Assignee: City of Hope, Duarte, CA (US)

( * ) Notice: Subject to any disclaimer, the term of this patent is extended or adjusted under 35 U.S.C. 154(b) by 431 days.

(21) Appl. No.: 12/901,139

(22) Filed: Oct. 8, 2010

(65) Prior Publication Data

US 2011/0092695 A1 Apr. 21, 2011

Related U.S. Application Data

(63) Continuation-in-part of application No. 12/026,554, filed on Feb. 5, 2008.

(60) Provisional application No. 60/888,307, filed on Feb. 5, 2007.

(51) Int. Cl.
*C12Q 3/00* (2006.01)
*C12N 5/0787* (2010.01)
*C12N 5/09* (2010.01)

(52) U.S. Cl.
USPC .................. 435/3; 435/325; 702/19; 702/27; 703/11

(58) Field of Classification Search
None
See application file for complete search history.

(56) References Cited

FOREIGN PATENT DOCUMENTS

| WO | WO 2006/006171 | A2 | 1/2006 |
|---|---|---|---|
| WO | WO 2006/081329 | A2 | 8/2006 |
| WO | WO2008029096 | * | 3/2008 |

OTHER PUBLICATIONS

Wang et al (Oncogene, 2012, pp. 1-10).*
Mai (Journal of Medicinal chemistry, 2005, vol. 48, pp. 7789-7795).*
Scappini et al (Cancer, 2004, vol. 100, pp. 1459-1471).*
Talhout et al, JACS, 2003, vol. 125, pp. 10570-10579.*
Abdelmohsen, K., et al., "Phosphorylation of HuR by Chk2 Regulates SIRT1 Expression," Mol Cell. 25(4): 543-557 (2007).
Ahmed, S., et al., "Disease Associated Mutations in the p150$^{Glued}$ Subunit Destabilize the CAP-gly Domain," Biochem. 49:5083-5085 (2010).
Anand, S., et al., "Aurora-A Amplification Overrides the Mitotic Spindle Assembly Checkpoint, Inducing Resistance to Taxol," Cancer Cell 3:51-62 (2003).
Andrews, P. D., "Aurora Kinases: Shining Lights on the Therapeutic Horizon?," Oncogene 24:5005-5015 (2005).
Avalos, J. L., et al., "Structure of a Sir2 Enzyme Bound to an Acetylated p53 Peptide," Mol. Cell 10:523-535 (2002).
Avalos, J. L., et al., "Mechanism of Sirtuin Inhibition by Nicotinamide: Altering the NAD$^+$ Cosubstrate Specificity of a Sir2 Enzyme," Mol Cell 17:855-868 (2005).
Azam, M., et al., "Mechanisms of Autoinhibition and STI-571/Imatinib Resistance Revealed by Mutagenesis of BCR-ABL," Cell 112:831-843 (2003).
Balaban, R. S., et al., "Mitochondria, Oxidants, and Aging," Cell 120:483-495 (2005).
Baselga, J., et al., "Phase I Safety, Pharmacokinetic, and Pharmacodynamic Trial of ZD1839, a Selective Oral Epidermal Growth Factor Receptor Tyrosine Kinase Inhibitor, in Patients with Five Selected Solid Tumor Types," J Clin Oncol 20:4292-4302 (2002).
Baselga, J., "Targeting Tyrosine Kinases in Cancer: The Second Wave," Science 312:1175-1178 (2006).
Bassan, R., et al., "Adult Acute Lymphoblastic Leukaemia," Crit Rev Oncol Hematol 50:223-261 (2004).
Baur, J. A., et al., "Resveratrol Improves Health and Survival of Mice on a High-Calorie Diet," Nature 444:337-342 (2006).
Bedalov, A., et al., "Identification of a Small Molecule Inhibitor of Sir2p," Proc Natl Acad Sci 98:15113-15118 (2001).
Bennardo, N., et al., "Alternative-NHEJ Is a Mechanistically Distinct Pathway of Mammalian Chromosome Break Repair," PLoS Genet. 4(6):e1000110.
Berrigan, D., et al., "Adult Onset Calorie Restriction and Fasting Delay Spontaneous Tumorigenesis in p53-Deficient Mice," Carcinogenesis 23(5): 817-822 (2002).
Bhatia, R., et al., "Persistence of Malignant Hematopoietic Progenitors in Chronic Myelogenous Leukemia Patients in Complete Cytogenetic Remission Following Imatinib Mesylate Treatment," Blood 101:4701-4707 (2003).
Bi, S., et al., "p53 in Chronic Myeloid Leukemia Cell Lines," Leukemia 6:839-842 (1992).
Bitterman, K. J., et al., "Inhibition of Silencing and Accelerated Aging by Nicotinamide, a Putative Negative Regulator of Yeast Sir2 and Human SIRT1," J Biol Chem 277:45099-45107 (2002).
Blume-Jensen, P., et al., "Oncogenic Kinase Signalling," Nature 411:355-365 (2001).
Boily, G., et al., "SirT1-Null Mice Develop Tumors at Normal Rates but are Poorly Protected by Resveratrol," Oncogene 28:2882-2893 (2009).
Boily, G., et al., "SirT1 Regulates Energy Metabolism and Response to Caloric Restriction in Mice," PLoS One 3(3):e1759 (2008).
Bordone, L., et al., "Sirt1 Regulates Insulin Secretion by Repressing UCP2 in Pancreatic β Cells," PLoS Biology 4:210-220 (2006).
Borra, M. T., et al., "Mechanisms of Human SIRT1 Activation by Resveratrol," J. Biol Chem. 280(17):17187-17195 (2005).

(Continued)

*Primary Examiner* — Karen Canella
(74) *Attorney, Agent, or Firm* — Perkins Coie LLP; Lauren Sliger

(57) ABSTRACT

A method of generating a chronic myelogenic leukemia (CML) acquired chemoresistant culture model is provided. Such a method may comprise providing a naïve blast crisis CML cell line; administering/contacting the cell line with a mutation-inducing dose of imatinib; maintaining a culture of the treated cell line for a period of time until the treated cell line relapses and repopulates the culture; and determining the repopulated cell culture is a CML acquired chemoresistant cell line by detecting a BCR-ABL mutation, wherein the acquired chemoresistance is achieved by a BCR-ABL mutation.

6 Claims, 58 Drawing Sheets

(56) References Cited

OTHER PUBLICATIONS

Bradbury, C.A., et al., "Histone Deacetylases in Acute Myeloid Leukaemia Show a Distinctive Pattern of Expression that Changes Selectively in Response to Deacetylase Inhibitors," Leukemia 19:1751-1759 (2005).
Bradeen, H. A., et al., "Comparison of Imatinib Mesylate, Dasatinib (BMS-354825), and Nilotinib (AMN107) in an N-Ethyl-N-Nitrosourea (ENU)-Based Mutagenesis Screen: High Efficacy of Drug Combinations," Blood 108:2332-2338 (2006).
Branford, S., et al., "High Frequency of Point Mutations Clustered Within the Adenosine Triphosphate-Binding Region of BCR/ABL in Patients with Chronic Myeloid Leukemia or Ph-Positive Acute Lymphoblastic Leukemia Who Develop Imatinib (STI571) Resistance," Blood 99:3472-3475 (2002).
Brunet, A., et al., "Stress-Dependent Regulation of FOXO Transcription Factors by the SIRT1 Deacetylase," Science 303:2011-2015 (2004).
Burchert, A., et al., "Compensatory PI3-Kinase/Akt/mTor Activation Regulates Imatinib Resistance Development," Leukemia 19:1774-1782 (2005).
Burgess, M. R., et al., "Comparative Analysis of Two Clinically Active BCR-ABL Kinase Inhibitors Reveals the Role of Conformation-Specific Binding in Resistance," Proc. Natl. Acad. Sci. 102(9):3395-3400 (2005).
Burkhart-Schultz, K. J., et al., "Spectrum of Somatic Mutation at the Hypoxanthine Phosphoribosyltransferase (hprt) Gene of Healthy People," Carcinogenesis 17(9):1871-1883 (1996).
Canitrot, Y., et al., "Mutator Phenotype of BCR-ABL Transfected Ba/F3 Cell Lines and Its Association with Enhanced Expression of DNA Polymerase β," Oncogene 18:2676-2680 (1999).
Carter, M. G., et al., "Mice Deficient in the Candidate Tumor Supresor Gene Hic1 Exhibit Developmental Defects of Structures Affected in the Miller-Dieker Syndrome," Hum Mol Genet 9:413-419 (2000).
Carter, T. A., et al., "Inhibition of Drug-Resistant Mutants of ABL, KIT, and EGF Receptor Kinases," Proc Natl Acad Sci USA 102(31):11011-11016 (2005).
Chen, P.M., et al., "Insulin Receptors on Leukemia and Lymphoma Cells," Blood 62(2):251-255 (1983).
Chen, W. Y., et al., "Epigenetic and Genetic Loss of Hic1 Function Accentuates the Role of p53 in Tumorigenesis," Cancer Cell 6:387-398 (2004).
Chen, W. Y., et al., "Heterozygous Disruption of Hic1 Predisposes Mice to a Gender-Dependent Spectrum of Malignant Tumors," Nat Genet 33:197-202 (2003).
Chen, W. Y., et al., "Inactivation of Tumor Suppressor Genes," Cell Cycle 4:10-12 (2005).
Chen, W. Y., et al., "Tumor Suppressor HIC1 Directly Regulates SIRT1 to Modulate p53-Dependent DNA-Damage Responses," Cell 123:437-448 (2005).
Cheng, H.L., et al., "Developmental Defects and p53 Hyperacetylation in Sir2 Homolog (SIRT1)-Deficient Mice," Proc Natl Acad Sci 100:10794-10799 (2003).
Chu, F., et al., "Control of Multidrug Resistance Gene MDR1 and Cancer Resistance to Chemotherapy by the Longevity Gene SIRT1," Cancer Res 65(22):10183-10187 (2005).
Cohen, H. Y., et al., "Calorie Restriction Promotes Mammalian Cell Survival by Inducing the SIRT1 Deacetylase," Science 305:390-392 (2004).
Cohen, M. H., et al., "United States Food and Drug Administration Drug Approval Summary: Gefitinib (ZD1839; Iressa) Tablets," Clin Cancer Res 10:1212-1218 (2004).
Cohen, H. Y., et al., "Acetylation of the C Terminus of Ku70 by CBP and PCAF Controls Bax-Mediated Apoptosis," Mol Cell 13:627-638 (2004).
Cragg, M. S., et al., "Gefitinib-Induced Killing of NSCLC Cell Lines Expressing Mutant EGFR Requires BIM and Can Be Enhanced by BH3 Mimetics," PLoS Med 4:1681-1690 (2007).
Crane, R., et al., "Requirements for the Destruction of Human Aurora-A," J Cell Sci 117:5975-5983 (2004).
Czechowska, A., et al., "Imatinib (STI571) Induces DNA Damage in BCR/ABL-Expressing Leukemic Cells But Not in Normal Lymphocytes," Chem Biol Interact 152:139-150 (2005).
Daitoku, H., et al., "Silent Information Regulator 2 Potentiates Foxo 1-Mediated Transcription Through its Deacetylase Activity," Proc Natl Acad Sci USA 101(27):10042-10047 (2004).
De Ruijter, A. J. M., et al., "Histone Deacetylases (HDACs): Characterization of the Classical HDAC Family," Biochem J 370:737-749 (2003).
Deininger, M. W. N., et al., "Specific Targeted Therapy of Chronic Myelogenous Leukemia with Imatinib," Pharmacol Rev 55(3):401-423 (2003).
Deininger, M. W. N., et al., "The Tyrosine Kinase Inhibitor CGP57148B Selectively Inhibits the Growth of BCR-ABL-Positive Cells," Blood 90(9):3691-3698 (1997).
Dinkelmann, M., et al., "Multiple Functions of MRN in End-Joining Pathways During Isotype Class Switching," Nat Struct Mol Biol 16(8):808-813 (2009).
Engelman, J. A., et al., "Allelic Dilution Obscures Detection of a Biologically Significant Resistance Mutation in EGFR-Amplified Lung Cancer," J Clin Invest 116(10):2695-2706 (2006).
Engelman, J. A., et al., "MET Amplification Leads to Gefitinib Resistance in Lung Cancer by Activating ERBB3 Signaling," Science 316:1039-1043 (2007).
Finnin, M. S., et al., "Structure of the Histone Deacetylase SIRT2," Nat Struct Biol 8(7):621-325 (2001).
Firestein, R., et al., "The SIRT1 Deacetylase Suppresses Intestinal Tumorigenesis and Colon Cancer Growth," PLoS One 3(4):e2020 (2008).
Ford, J., et al., "Cancer-Specific Functions of SIRT1 Enable Human Epithelial Cancer Cell Growth and Survival," Cancer Res 65(22):10457-10463 (2005).
Ford, J., et al., "JNK2-Dependent Regulation of SIRT1 Protein Stability," Cell Cycle 7(19):3091-3097 (2008).
Frommer, M., et al., "A Genomic Sequencing Protocol That Yields a Positive Display of 5-Methylcytosine Residues in Individual DNA Strands," Proc. Nati. Acad. Sci. USA 89:1827-1831 (1992).
Frye, R. A., "Characterization of Five Human cDNAs with Homology to the Yeast SIR2 Gene: Sir2-like Proteins (Sirtuins) Metabolize NAD and May Have Protein ADP-Ribosyltransferase Activity," Biochem Biophys Res Commun 260:273-279 (1999).
Frye, R. A., "Phylogenetic Classification of Prokaryotic and Eukaryotic Sir2-Like Proteins," Biochem Biophys Res Commun 273:793-798 (2000).
Gambacorti-Passerini, C. B., et al., "Molecular Mechanisms of Resistance to Imatinib in Philadelphia-Chromosome-Positive Leukaemias," Lancet Oncol 4:75-85 (2003).
Gaymes, T. J., et al., "Myeloid Leukemias Have Increased Activity of the Nonhomologous End-Joining Pathway and Concomitant DNA Misrepair that Is Dependent on the Ku70/86 Heterodimer," Cancer Res 62:2791-2797 (2002).
Giles, F. J., et al., "MK-0457, a Novel Kinase Inhibitor, is Active in Patients with Chronic Myeloid Leukemia or Acute Lymphocytic leukemia with the T315I BCR-ABL Mutation," Blood 109:500-502 (2007).
Gorre, M. E., et al., "Clinical Resistance to STI-571 Cancer Therapy Caused by BCR-ABL Gene Mutation or Amplification," Science 293:876-880 (2001).
Grozinger, C. M., et al., "Identification of a Class of Small Molecule Inhibitors of the Sirtuin Family of NAD-Dependent Deacetylases by Phenotypic Screening," J Biol Chem 276(42):38837-38843 (2001).
Guarente, L., "Sir2 Links Chromatin Silencing, Metabolism, and Aging," Genes Devel 14:1021-1026 (2000).
Guerardel, C., et al., "Identification in the Human Candidate Tumor Suppressor Gene HIC-1 of a New Major Alternative TATA-Less Promoter Positively Regulated by p53," J Biol Chem 276(5):3078-3089 (2001).
Haber, D.A., et al., "Molecular Targeted Therapy of Lung Cancer: EGFR Mutations and Response to EGFR Inhibitors," Cold Spring Harb Symp Quant Biol 70:419-426 (2005).
Harrington, E. A., et al., "VX-680, A Potent and Selective Small-Molecule Inhibitor of the Aurora Kinases, Suppresses Tumor Growth In Vivo," Nat. Med. 10:262-267 (2004).

(56) References Cited

OTHER PUBLICATIONS

Harvey, M., et al., "Spontaneous and Carcinogen-Induced Tumorigenesis in p53-Deficient Mice," Nat. Genet. 5:225-229 (1993).
Heltweg, B., et al., "Antitumor Activity of a Small-Molecule Inhibitor of Human Silent Information Regulator 2 Enzymes," Cancer Res 66(8):4368-77 (2006).
Hennighausen, L., et al., "Interpretation of Cytokine Signaling Through the Transcription Factors STAT5A and STAT5B," Genes Dev 22:711-721 (2008).
Herman, J. G., et al., "Methylation-Specific PCR: A Novel PCR Assay for Methylation Status of CpG Islands," Proc. Natl. Acad. Sci. USA 93:9821-9826 (1996).
Hirao, M., et al., "Identification of Selective Inhibitors of $NAD^+$-Dependent Deacetylases Using Phenotypic Screens in Yeast," J Biol Chem 278(52):52773-52782 (2003).
Hoelbl, A., et al., "Clarifying the Role of Stat5 in Lymphoid Development and Abelsoninduced Transformation," Blood 107(12):4898-4906 (2006).
Holtz, M. S., et al., "Imatinib Mesylate (STI571) Inhibits Growth of Primitive Malignant Progenitors in Chronic Myelogenous Leukemia Through Reversal of Abnormally Increased Proliferation," Blood 99:3792-3800 (2002).
Howitz, K. T., et al., "Small Molecule Activators of Sirtuins Extend *Saccharomyces cerevisiae* Lifespan," Nature 425:191-196(2003).
Hu, Y., et al., "Targeting Multiple Kinase Pathways in Leukemic Progenitors and Stem Cells is Essential for Improved Treatment of $Ph^+$ Leukemia in Mice," Proc Nat Acad Sci 103(45):16870-16875 (2006).
Huffman, D. M., et al., "SIRT1 is Significantly Elevated in Mouse and Human Prostate Cancer," Cancer Res 67(14):6612-6618 (2007).
Huntly, B. J. P., et al., "Double Jeopardy from a Single Translocation: Deletions of the Derivative Chromosome 9 in Chronic Myeloid Leukemia," Blood 102:1160-1168 (2003).
Ilaria, R. L., et al., "P210 and $P190^{BCR/ABL}$ Induce the Tyrosine Phosphorylation and DNA Binding Activity of Multiple Specific STAT Family Members," J Biol Chem 271(49):31704-31710 (1996).
Imai, S., et al., "Transcriptional Silencing and Longevity Protein Sir2 Is an NAD-Dependent Histone Deacetylase," Nature 403:795-800 (2000).
Inukai, M., et al., "Presence of Epidermal Growth Factor Receptor Gene T790M Mutation as a Minor Clone in Non-Small Cell Lung Cancer," Cancer Res 66(16):7854-7858 (2006).
Issa, J.P. J., et al., "HIC1 Hypermethylation Is a Late Event in Hematopoietic Neoplasms," Cancer Res 57:1678-1681 (1997).
Jamieson, C. H.M., et al., "Granulocyte—Macrophage Progenitors as Candidate Leukemic Stem Cells in Blast-Crisis CML," New Eng J Med 351:657-667 (2004).
Jang, K. Y., et al., "SIRT1 Expression is Associated with Poor Prognosis of Diffuse Large B-Cell Lymphoma," Am. J. Surg. Pathol. 32:1523-1531 (2008).
Jang, K. Y., et al., "Expression and Prognostic Significance of SIRT1 in Ovarian Epithelial Tumours," Pathology 41(4):366-371 (2009).
Jiang, X., et al., "Instability of BCR-ABL Gene in Primary and Cultured Chronic Myeloid Leukemia Stem Cells," J Natl Cancer Inst 99:680-93 (2007).
Jin, L., et al., "Crystal Structures of Human SIRT3 Displaying Substrate-Induced Conformational Changes," J Biol Chem 284(36):24394-24405 (2009).
Jones, P. A., et al., "The Fundamental Role of Epigenetic Events in Cancer," Nat Rev Genet 3:415-428 (2002).
Jordan, C. T., et al., "Cancer Stem Cells," N Eng J Med 355(12):1253-1261 (2006).
Jung-Hynes, B., et al., "Role of Sirtuin Histone Deacetylase SIRT1 in Prostate Cancer: A Target for Prostate Cancer Management Via Its Inhibition?" J Biol Chem 284(6):3823-3832 (2009).
Kabra, N., et al., "SIRT1 Is an Inhibitor of Proliferation and Tumor Formation in Colon Cancer," J Biol Chem 284(27):18210-18217 (2009).

Kaeberlein, M., et al., "The SIR 2/3/4 Complex and SIR2 Alone Promote Longevity in *Saccharomyces cerevisiae* by Two Different Mechanisms," Genes Devel 13:2570-2580 (1999).
Kaeberlein, M., et al., "Substrate-specific Activation of Sirtuins by Resveratrol," J Biol Chem 280(17):17038-17045 (2005).
Kantarjian, H., et al., "Nilotinib in Imatinib-Resistant CML and Philadelphia Chromosome-Positive ALL," N Engl J Med 354:2542-2551 (2006).
Karpinets, T.V., et al., "Bacterial Stationary-State Mutagenesis and Mammalian Tumorigenesis as Stress-Induced Cellular Adaptations and the Role of Epigenetics," Current Genomics 7:481-496 (2006).
Kawano, T., et al., "Depsipeptide Enhances Imatinib Mesylate-Induced Apoptosis of BCR-ABL-Positive Cells and Ectopic Expression of Cyclin D1, c-MYC or Active MEK Abrogates This Effect," AntiCancer Res 24:2705-2712 (2004).
Keen, N., et al., "Aurora-Kinase Inhibitors as Anticancer Agents," Nat Rev Cancer 4:927-936 (2004).
Kelly, D. P., et al., "Transcriptional Regulatory Circuits Controlling Mitochondrial Biogenesis and Function," Genes Devel 18:357-368 (2004).
Khanna, K. K., et al., "DNA Double-Strand Breaks: Signaling, Repair and the Cancer Connection," Nat Genet 27:247-254 (2001).
Kharbanda, S., et al., "Functional Interaction Between DNA-PK and c-Abl in Response to DNA Damage," Nature 386:732-735 (1997).
Kiel, M. J., et al., "SLAM Family Receptors Distinguish Hematopoietic Stem and Progenitor Cells and Reveal Endothelial Niches for Stem Cells," Cell 121:1109-1121 (2005).
Klejman, A., et al., "Phosphatidylinositol-3 Kinase Inhibitors Enhance the Anti-Leukemia Effect of STI571," Oncogene 21:5868-5876 (2002).
Kobayashi, S., et al., "EGFR Mutation and Resistance of Non-Small-Cell Lung Cancer to Gefitinib," N Engl J Med 352:786-792 (2005).
Kojima, K., et al., "A Role for SIRT1 in Cell Growth and Chemoresistance in Prostate Cancer PC3 and DU145 Cells," Biochem. Biophys. Res. Commun. 373:423-428 (2008).
Koptyra, M., et al., "BCR/ABL Kinase Induces Self-Mutagenesis Via Reactive Oxygen Species to Encode Imatinib Resistance," Blood 108:319-327 (2006).
Kosaka, T., et al., "Analysis of Epidermal Growth Factor Receptor Gene Mutation in Patients with Non-Small Cell Lung Cancer and Acquired Resistance to Gefitinib," Clin Cancer Res 12(19):5764-5769 (2006).
Kowolik, C. M., et al., "HIV Vector Production Mediated by Rev Protein Transduction," Mol Ther 8(2):324-331 (2003).
Kubonishi, I., et al., "Establishment of a Ph1 Chromosome-Positive Cell Line from Chronic Myelogenous Leukemia in Blast Crisis," Int J Cell Cloning 1:105-117 (1983).
Kuzmichev, A., et al., "Composition and Histone Substrates of Polycomb Repressive Group Complexes Change During Cellular Differentiation," Proc Natl Acad Sci USA 102(6):1859-1864 (2005).
Kwak, E. L., et al., "Irreversible Inhibitors of the EGF Receptor May Circumvent Acquired Resistance to Gefitinib," Proc Natl Acad Sci USA 102(21):7665-7670 (2005).
Ladbury, J. E., et al., "Adding Calorimetric Data to Decision Making in Lead Discovery: A Hot Tip," Nat. Rev. Drug Discov. 9:23-27 (2010).
Lagouge, M., et al., "Resveratrol Improves Mitochondrial Function and Protects Against Metabolic Disease by Activating SIRT1 and PGC-1α," Cell 127:1109-1122 (2006).
Lain, S., et al., "Discovery, In Vivo Activity, and Mechanism of Action of a Small-Molecule p53 Activator," Cancer Cell 13(5-2):454-463 (2008).
Lamb, J., et al., "The Connectivity Map: Using Gene-Expression Signatures to Connect Small Molecules, Genes, and Disease," Science 313:1929-1935 (2006).
La Rosee, P., et al., "Activity of the BCR-ABL Kinase Inhibitor PD180970 Against Clinically Relevant BCR-ABL Isoforms That Cause Resistance to Imatinib Mesylate (Gleevec, STI571)," Cancer Res 62:7149-7153 (2002).
La Rosee, P., et al., "In Vitro Efficacy of Combined Treatment Depends on the Underlying Mechanism of Resistance in Imatinib-Resistant BCR-ABL-Positive Cell Lines," Blood 103:208-215 (2004).

(56) References Cited

OTHER PUBLICATIONS

Landry, J., et al., "The Silencing Protein SIR2 and Its Homologs are NAD-Dependent Protein Deacetylases," Proc Natl Acad Sci USA 97:5807-5811 (2000).
Le Coutre, P., et al., "In Vivo Eradication of Human BCR/ABL-Positive Leukemia Cells with an ABL Kinase Inhibitor," J Natl Cancer Inst 91:163-168 (1999).
Li, H., et al., "Finite Reservoir Replica Exchange to Enhance Cononical Sampling in Rugged Energy Surfaces," J. Chem. Phys. 125:144902-1—144902-5 (2006).
Li, H., et al., "Simulated Scaling Method for Localized Enhanced Sampling and Simultaneous "Alchemical" Free Energy Simulation: A General Method for Moleculars Mechanical, Quantum Mechanical, and Quantum Mechanical/Molecular Mechanical Simulations," J Chem Phys 126:024106-1-024106-12 (2007).
Li, M. J., et al., "Inhibition of HIV-1 Infection by Lentiviral Vectors Expressing Pol III-Promoted Anti-HIV RNAs," Mol Ther 8(2):196-206 (2003).
Li, M.J., et al., "Specific Killing of Ph+ Chronic Myeloid Leukemia Cells by a Lentiviral Vector-Delivered Anti-BCR/ABL Small Hairpin RNA," Oligonucleotides 13:401-409 (2003).
Li, Y., et al., "SirT1 Inhibition Reduces IGF-I/IRS-2/Ras/ERK1/2 Signaling and Protects Neurons," Cell Metab 8(1):38-48 (2008).
Lin, S. J., et al., "Requirement of NAD and SIR2 for Life-Span Extensión by Calorie Restriction in *Saccharomyces cerevisiae*," Science 289:2126-2128 (2000).
Littlepage, L. E., et al., "Identification of a New APC/C Recognition Domain, the A Box, Which is Required for the CDH1-Dependent Destruction of the Kinase Aurora-A During Mitotic Exit," Genes Devel 16:2274-2285 (2002).
Littlepage, L. E., et al., "Identification of Phosphorylated Residues That Affect the Activity of the Mitotic Kinase Aurora-A," Proc Natl Acad Sci USA 99:15440-15445 (2002).
Loots, G. G., et al., "rVISTA 2.0: Evolutionary Analysis of Transcription Factor Binding Sites," Nucleic Acids Res 32:W217-W221 (2004).
Lucas, C. M., et al., "Chronic Myeloid Leukemia Patients with the e13a2 BCR-ABL Fusion Transcript have Inferior Responses to Imatinib Compared to Patients with the e14a2 Transcript," Haematologica 94(10):1362-1367 (2009).
Luo, J., et al., "Negative Control of p53 by Sir2α Promotes Cell Survival Under Stress," Cell 107:137-148 (2001).
Ly, C., et al., "BCR-ABL Kinase Modulates the Translation Regulators Ribosomal Protein S6 and 4E-BP1 in Chronic Myelogenous Leukemia Cells Via the Mammalian Target of Rapamycin," Cancer Res 63:5716-5722 (2003).
Lynch, T. J., et al., "Activating Mutations in the Epidermal Growth Factor Receptor Underlying Responsiveness of Non-Small-Cell Lung Cancer to Gefitinib," N Engl J Med 350:2129-2139 (2004).
Maguer-Satta, V., et al., "BCR-ABL Accelerates C2-Ceramide-Induced Apoptosis," Oncogene 16:237-248 (1998).
Mahon, F. X., et al., "Selection and Characterization of BCR-ABL Positive Cell Lines with Differential Sensitivity to the Tyrosine Kinase Inhibitor STI571: Diverse Mechanisms of Resistance," Blood 96:1070-1079 (2000).
Mai, A., et al., "Design, Synthesis, and Biological Evaluation of Sirtinol Analogues as Class III Histone/Protein Deacetylase (Sirtuin) Inhibitors," J Med Chem 48:7789-7795 (2005).
Marumoto, T., et al., "Aurora-A—A Guardian of Poles," Nat Rev Cancer 5:42-50 (2005).
McWhirter, J. R., et al., "A Coiled-Coil Oligomerization Domain of BCR Is Essential for the Transforming Function of BCR-ABL Oncoproteins," Mol Cell Biol 13(12):7587-7595 (1993).
Michan, S., et al., "Sirtuins in Mammals: Insights into Their Biological Function," Biochem J. 404(1):1-13 (2007).
Michor, F., et al., "Dynamics of Chronic Myeloid Leukaemia," Nature 435:1267-1270 (2005).
Melo, J. V., et al., "Chronic Myeloid Leukaemia as a Model of Disease Evolution in Human Cancer," Nat. Rev. Cancer 7:441-453 (2007).

Min, J., et al., "Crystal Structure of a SIR2 Homolog—NAD Complex," Cell 105:269-279 (2001).
Mossessova, E., et al., "Ulp1-SUMO Crystal Structure and Genetic Analysis Reveal Conserved Interactions and a Regulatory Element Essential for Cell Growth in Yeast," Mol Cell 5:865-876 (2000).
Motta, M. C., et al., "Mammalian SIRT-1 Represses Forkhead Transcription Factors," Cell 116:551-563 (2004).
Moynihan, K. A., et al., "Increased Dosage of Mammalian Sir2 in Pancreatic β Cells Enhances Glucose-Stimulated Insulin Secretion in Mice," Cell Metab 2:105-117 (2005).
Napper, A. D., et al., "Discovery of Indoles as Potent and Selective Inhibitors of the Deacetylase SIRT1," J Med Chem 48:8045-8054 (2005).
Narala, S. R., et al., "SIRT1 Acts as a Nutrient-sensitive Growth Suppressor and Its Loss Is Associated with Increased AMPK and Telomerase Activity," Mol Biol Cell 19:1210-1219 (2008).
Narayan, G., et al., "Frequent Promoter Methylation of CDHI, DAPK, RARB, and HICI Genes in Carcinoma of Cerviz Uteri: Its Relationship to Clinical Outcome," Mol Cancer 2:24 (2003).
Neering, S. J., et al., "Leukemia Stem Cells in a Genetically Defined Murine Model of Blast-Crisis CML," Blood 110:2578-2585 (2007).
Nemoto, S., et al., "Nutrient Availibility Regulates SIRT1 Through a Forkhead-Dependent Pathway," Science 306:2105-2108 (2004).
Neubauer, A., et al., "Genetic Alterations in the p53 Gene in the Blast Crisis of Chronic Myelogeneous Leukemia: Analysis by Polymerase Chain Reaction Based Techniques," Leukemia 7(4):593-600 (1993).
North, B. J., et al., "Sirtuins: Sir2-Related NAD-Dependent Protein Deacetylases," Genome Biol 5:224 (2004).
Nosho, K., et al., "SIRT1 Histone Deacetylase Expression is Associated with Microsatellite Instability and CpG Island Methylator Phenotype in Colorectal Cancer," Modern Pathology 22:922-932 (2009).
Nowell, P. C., "A Minute Chromosome in Human Chronic Granulocytic Leukemia," Science 132:1497 (1960).
Nowicki, M. O., et al., "BCR/ABL Oncogenic Kinase Promotes Unfaithful Repair of the Reactive Oxygen Species-Dependent DNA Double-Strand Breaks," Blood 104:3746-3753 (2004).
O'Hare, T., et al., "Toward a Cure for Chronic Myeloid Leukemia," Clin Cancer Res 14(24):7971-7974 (2008).
Oberdoerffer, P., et al., "DNA Damage-Induced Alterations in Chromatin Contribute to Genomic Integrity and Age-Related Changes in Gene Expression," Cell 135(5):907-918 (2008).
Ogino, A., et al., "Emergence of Epidermal Growth Factor Receptor T790M Mutation During Chronic Exposure to Gefitinib in a Non-Small Cell Lung Cancer Cell Line," Cancer Res 67(16):7807-7814(2007).
Osterholm, A. M., et al., "Classification of Mutations at the Human HPRT-Locus in T-Lymphocytes of Bus Maintenance Workers by Multiplex-PCR and Reverse Transcriptase-PCR Analysis," Carcinogenesis 16(8):1909-1912 (1995).
Ota, H., et al., "Sirt1 inhibitor, Sirtinol, Induces Senescence-Like Growth Arrest with Attenuated Ras—MAPK Signaling in Human Cancer Cells," Oncogene 25:176-185 (2006).
Pacholec, M., et al., "SRT1720, SRT2183, SRT1460, and Resveratrol Are Not Direct Activators of SIRT1," J Biol Chem 285(11):8340-8351 (2010).
Paez, J. G., et al., "EGFR Mutations in Lung Cancer: Correlation with Clinical Response to Gefitinib Therapy," Science 304:1497-1500 (2004).
Pan, J., et al., "An Aurora Kinase Is Essential for Flagellar Disassembly in *Chlamydomonas*," Devel Cell 6:445-451 (2004).
Pao, W., et al., "Acquired Resistance of Lung Adenocarcinomas to Gefitinib or Erlotinib Is Associated with a Second Mutation in the EGFR Kinase Domain," PLoS Med 2:225-235 (2005).
Pao, W., et al., "EGF Receptor Gene Mutations are Common in Lung Cancers from "Never Smokers" and are Associated with Sensitivity of Tumors to Gefitinib and Erlotinib," Proc Natl Acad Sci USA 101:13306-13311 (2004).
Pear, W. S., et al., "Efficient and Rapid Induction of a Chronic Myelogenous Leukemia-Like Myeloproliferative Disease in Mice Receiving P210 BCR/ABL-Transduced Bone Marrow," Blood 92(10):3780-3792 (1998).

(56) References Cited

OTHER PUBLICATIONS

Peng, B., et al., "Clinical Pharmacokinetics of Imatinib," Clin Pharmacokinet 44:879-894 (2005).
Podlutsky, A., et al., "Spectrum of Point Mutations in the Coding Region of the Hypoxanthine-Guanine Phosphoribosyltransferase (hprt) Gene in Human T-Lymphocytes In Vivo," Carcinogenesis 19(4):557-566 (1998).
Posakony, J., et al., "Inhibitors of Sir2: Evaluation of Splitomicin Analogues," J Med Chem 47:2635-2644 (2004).
Ramaraj, P., et al., "Effect of Mutational Inactivation of Tyrosine Kinase Activity on BCR/ABL-Induced Abnormalities in Cell Growth and Adhesion in Human Hematopoietic Progenitors," Cancer Res 64:5322-5331 (2004).
Rapozzi, V., et al., "Efficient Silencing of BCR/ABL Oncogene by Single- and Double-Stranded siRNAs Targeted Against b2a2 Transcripts," Biochem 43:16134-16141 (2004).
Rass, E., et al., "Role of Mre11 in Chromosomal Nonhomologous End Joining in Mammalian Cells," Nat. Struct. Mol. Biol. 16(8):819-824 (2009).
Rathi, A., et al., "Aberrant Methylation of the HIC1 Promoter Is a Frequent Event in Specific Pediatric Neoplasms," Clin Cancer Res 9:3674-3678 (2003).
Ray, A., et al., "Identification of BCR-ABL Point Mutations Conferring Resistance to the ABL Kinase Inhibitor AMN107 (Nilotinib) by a Random Mutagenesis Study," Blood 109:5011-5015 (2007).
Reynolds, A., et al., "Rational siRNA Design for RNA Interference," Nat Biotechnol 22(3):326-330 (2004).
Ricci, C., et al., "Mutation in the ATP-binding Pocket of the ABL Kinase Domain in an STI571-Resistant BCR/ABL-Positive Cell Line," Cancer Res 62:5995-5998 (2002).
Roche-Lestienne, C., et al., "Several Types of Mutations of the ABL Gene can be Found in Chronic Myeloid Leukemia Patients Resistant to STI571, and They can Pre-Exist to the Onset of Treatment," Blood 100:1014-1018 (2002).
Rodgers, J. T., et al., "Nutrient Control of Glucose Homeostasis Through a Complex of PGC-1α and SIRT1," Nature 434:113-118 (2005).
Rosenberg, S. M., "Evolving Responsively: Adaptive Mutation," Nat. Rev. Genetics 2:504-515 (2001).
Rosenhahn, J., et al., "Cytogenetic Characterisation and Proteomic Profiling of the Imatinib-Resistant Cell Line KCL22-R," Int J Oncol 31:121-128 (2007).
Rowley, J. D., "Chromosomal Patterns in Myelocytic Leukemia," N Eng J Med 289(4):220-221 (1973).
Santini, V., et al., "Changes in DNA Methylation in Neoplasia: Pathophysiology and Therapeutic Implications," Ann Intern Med 134:573-586 (2001).
Sattler, M., et al., "The BCR/ABL Tyrosine Kinase Induces Production of Reactive Oxygen Species in Hematopoietic Cells," J Biol Chem 275(32):24273-24278 (2000).
Saunders, L.R., et al., "Sirtuins: Critical Regulators at the Crossroads Between Cancer and Aging," Oncogene 26:5489-5504 (2007).
Sauve, A. A., et al., "Chemical Activation of Sir2-Dependent Silencing by Relief of Nicotinamide Inhibition," Mol Cell 17:595-601 (2005).
Schindler, T., et al., "Structural Mechanism for STI-571 Inhibition of Abelson Tyrosine Kinase," Science 289:1938-1942 (2000).
Schuetz, A., et al., "Structural Basis of Inhibition of the Human NAD+-Dependent Deacetylase SIRT5 by Suramin," Structure 15:377-389 (2007).
Shafman, T., et al., "Interaction Between ATM Protein and c-Abl in Response to DNA Damage," Nature 387:520-523 (1997).
Shah, N. P., et al., "Mechanisms of Resistance of STI571 in Philadelphia Chromosome-Associated Leukemias," Oncogene 22:7389-7395 (2003).
Shah, N. P., et al., "Multiple BCR-ABL Kinase Domain Mutations confer Polyclonal Resistance to the Tyrosine Kinase Inhibitor Imatinib (STI571) in Chronic Phase and Blast Crisis Chronic Myeloid Leukemia," Cancer Cell 2:117-125 (2002).

Shah, N. P., et al., "Overriding Imatinib Resistance With a Novel ABL Kinase Inhibitor," Science 305:399-401 (2004).
Shi, J., et al., "Detection of Ultrarare Somatic Mutation in the Human TP53 Gene by Bidirectional Pyrophosphorolysis-Activated Polymerization Allele-Specific Amplification," Hum. Mutat. 28(2):131-136 (2007).
Skorski, T., et al., "Phosphatidylinositol-3 Kinase Activity Is Regulated by BCR/ABL and Is Required for the Growth of Philadelphia Chromosome-Positive Cells," Blood 86:726-736 (1995).
Slupianek, A., et al., "BCR/ABL Modifies the Kinetics and Fidelity of DNA Double-Strand Breaks Repair in Hematopoietic Cells," DNA Repair 5:243-250 (2006).
Smith, K. M., et al., "Autoinhibition of BCR-ABL Through Its SH3 Domain," Mol Cell 12:27-37 (2003).
Solomon, J. M., et al., "Inhibition of SIRT1 Catalytic Activity Increases p53 Acetylation but Does Not Alter Cell Survival following DNA Damage," Mol Cell Biol 26(1):28-38 (2006).
Soverini, S., et al., "Contribution of ABL Kinase Domain Mutations to Imatinib Resistance in Different Subsets of Philadelphia-Positive Patients: By the GIMEMA Working Party on Chronic Myeloid Leukemia," Clin Cancer Res 12(24):7374-7379 (2006).
Stamos, J., et al., "Structure of the Epidermal Growth Factor Receptor Kinase Domain Alone and in Complex with a 4-Anilinoquinazoline Inhibitor," J Biol Chem 277(48):46265-46272 (2002).
Sun, S., et al., "Solid-State and Solution NMR Studies of the CAP-Gly Domain of Mammalian Dynactin and Its Interaction with Microtubules," J Am Chem Soc 131:10113-10126 (2009).
Szabo, P. E., et al., "The Chicken β-Globin Insulator Element Conveys Chromatin Boundary Activity But Not Imprinting At the Mouse Igf2/H19 Domain," Development 129:897-904 (2002).
Talpaz, M., et al., "Dasatinib in Imatinib-Resistant Philadelphia Chromosome-Positive Leukemias," N Engl J Med 354(24):2531-2541 (2006).
Tang, S. H. E., et al., "A Cre/IoxP-Deleter Transgenic Line in Mouse Strain 129S1/SvlmJ," Genesis 32:199-202 (2002).
Tanner, K. G., et al., "Silent Information Regulator 2 Family of NAD-Dependent Histone/Protein Deacetylases Generates a Unique Product, 1-0-Acetyl-ADP-Ribose," Proc Natl Acad Sci USA 97(26):14178-14182 (2000).
Tanny, J. C., et al., "Coupling of Histone Deacetylation to NAD Breakdown by the Yeast Silencing Protein Sir2: Evidence for Acetyl Transfer from Substrate to an NAD Breakdown Product," Proc Natl Acad Sci USA 98(2):415-420 (2001).
Tipping, A. J., et al., "Comparative Gene Expression Profile of Chronic Myeloid Leukemia Cells Innately Resistant to Imatinib Mesylate," Exp. Hematol. 31:1073-1080 (20030.
Tissenbaum, H. A., et al., "Increased Dosage of a SIR-2 Gene Extends Lifespan in *Caenorhabditis elegans*," Nature 410:227-230 (2001).
Van Der Horst, A., et al., "FOXO4 Is Acetylated Upon Peroxide Stress and Deacetylated by the Longevity Protein hSir2$^{SIRT1}$," J Biol Chem 279(28):28873-28879 (2004).
Van Etten, R.A., "Abberant Cytokine Signaling in Leukemia," Oncogene 26:6738-6749 (2007).
Vaziri, H., et al., "hSIR2$^{SIRT1}$ Functions as an NAD-Dependent p53 Deacetylase," Cell 107:149-159 (2001).
Venkatachalam, S., et al., "Retention of Wild-Type p53 in Tumors from p53 Heterozygous Mice: Reduction of p53 Dosage can Promote Cancer Formation," EMBO J 17(16): 4657-4667 (1998).
Ventura, A., et al., "Cre-Iox-Regulated Conditional RNA Interference from Transgenes," Proc Natl Acad Sci USA 101(28):10380-10385 (2004).
Von Bubnoff, N., et al., "A Cell-Based Screen for Resistance of BCR-ABL-Positive Leukemia Identifies the Mutation Pattern for PD166326, an Alternative ABL Kinase Inhibitor," Blood 105:1652-1659 (2005).
Von Bubnoff, N., et al., "BCR-ABL Resistance Screening Predicts a Limited Spectrum of Point Mutations to be Associated with Clinical Resistance to the ABL Kinase Inhibitor Nilotinib (AMN107)," Blood 108:1328-1333 (2006).

(56) References Cited

OTHER PUBLICATIONS

Von Bubnoff, N., et al., "Resistance of Philadelphia-Chromosome Positive Leukemia Towards the Kinase Inhibitor Imatinib (STI571, Glivec): a Targeted Oncoprotein Strikes Back," Leukemia 17:829-838 (2003).
Wales, M. M., et al., "p53 Activates Expression of HIC-1, a New Candidate Tumour Suppressor Gene on 17p13.3," Nat Med 1(6):570-577 (1995).
Wang, R.H., et al., "Impaired DNA Damage Response, Genome Instability, and Tumorigenesis in SIRT1 Mutant Mice," Cancer Cell 14(4):312-323 (2008).
Wang, C., et al., "Interactions Between E2F1 and SirT1 Regulate Apoptotic Response to DNA Damage," Nat Cell Biol 8(9):1025-1031 (2006).
Weinstock, D. M., et al., "Assaying Double-Strand Break Repair Pathway Choice in Mammalian Cells Using a Targeted Endonuclease or the RAG Recombinase," Methods in Enzymology 409:524-540 (2006).
Weisberg, E., et al., Characterization of AMN107, a Selective Inhibitor of Native and Mutant BCR-ABL Cancer Cell 7:129-141 (2005).
Wertheim, J. A., et al., "BCR-ABL-Induced Adhesion Defects are Tyrosine Kinase-Independent," Blood 99:4122-4130 (2002).
Westerheide, S. D., et al., "Stress-Inducible Regulation of Heat Shock Factor 1 by the Deacetylase SIRT1," Science 323:1063-1066 (2009).
Willis, S. G., et al., "High-Sensitivity Detection of BCR-ABL Kinase Domain Mutations in Imatinib-Naive Patients: Correlation with Clonal Cytogenetic Evolution but Not Response to Therapy," Blood 106:2128-2137 (2005).
Wolff, N. C., et al., "Establishment of a Murine Model for Therapy-Treated Chronic Myelogenous Leukemia Using the Tyrosine Kinase Inhibitor STI571," Blood 98:2808-2816 (2001).
Woo, R. A., et al., "Activated Oncogenes Promote and Cooperate with Chromosomal Instability for Neoplastic Transformation," Genes Devel 18:1317-1330 (2004).
Wood, J. G., et al., "Sirtuin Activators Mimic Caloric Restriction and Delay Ageing in Metazoans," Nature 430:686-689 (2004).
Xiao, H., et al., "Acidic pH Induces Topoisomerase II-Mediated DNA Damage," Proc Natl Acad Sci USA 100(9):5205-5210 (2003).
Xie, A., et al., "Role of Mammalian MRE11 in Classical and Alternative Nonhomologous End Joining," Nat Struct Mol Biol 16(8):814-818 (2009).
Ye, D., et al., "STAT5 Signaling is Required for the Efficient Induction and Maintenance of CML in Mice," Blood 107:4917-4925 (2006).
Yu, C., et al., "Histone Deacetylase Inhibitors Promote STI571-Mediated Apoptosis in STI571-Sensitive and -Resistant BCR/ABL+ Human Myeloid Leukemia Cells," Cancer Res 63:2118-2126 (2003).
Yuan, H., et al., "BCR-ABL Gene Expression is Required for Its Mutations in a Novel KCL-22 Cell Culture Model for Acquired Resistance of Chronic Myelogenous Leukemia," J Biol Chem 285(7):5085-5096 (2010).
Yuan, Z., et al., "SIRT1 Regulates the Function of the Nijmegen Breakage Syndrome Protein," Mol Cell 27:149-162 (2007).
Zhang, B., et al., "Effective Targeting of Quiescent Chronic Myelogenous Leukemia Stem Cells by Histone Deacetylase Inhibitors in Combination with Imatinib Mesylate," Cancer Cell 17:427-442 (2010).
Zhao, X., et al., "Retention of Wild-Type p53 in Tumors from p53 Heterozygous Mice: Reduction of p53 Dosage can Promote Cancer Formation," Nat Struct Biol 9(2):117-120 (2002).
Zhao, K., et al., "Structure and Autoregulation of the Yeast Hst2 Homolog of Sir2," Nat Struct Biol 10(10):864-871 (2003).
Zhelev, Z., et al., "Suppression of BCR-ABL Synthesis by siRNAs or Tyrosine Kinase Activity by Glivec Alters Different Oncogenes, Apoptotic/Antiapoptotic Genes and Cell Proliferation Factors (Microarray Study)," FEBS Letters 570:195-204 (2004).
Beger, H. G., et al., "Treatment of Pancreatic Cancer: Challenge of the Facts," World J. Surg. 27:1075-1084 (2003).
Chabner, B. A., et al., "Chemotherapy and the War on Cancer," Nat. Rev. Cancer 5:65-72 (2005).
Leaf, C., "Why We're Losing the War on Cancer—And How to Win It," Fortune 149(6):1-29 (2004).
Martinelli, G., et al., "Dual Tyrosine Kinase Inhibitors in Chronic Myeloid Leukemia," Leukemia 19:1872-1879 (2005).
O'Hare, T., et al., "Targeted CML Therapy: Controlling Drug Resistance, Seeking Cure," Curr. Opin. Genet. Devel. 16:92-99 (2006).
Rich, J. N., et al., "Development of Novel Targeted Therapies in the Treatment of Malignant Glioma," Nat. Rev. Drug Disc. 3:430-446 (2004).
Xiong, W.N., et al., "Synthesis of Novel Analogues of Marine Indole Alkaloids: Mono(Indolyl)-4-Trifluoromethlypyridines and Bis(Indolyl)-4-Trifluoromethylpyridines as Potential Anticancer Agents," Bioorg. Med. Chem. 9:1773-1780 (2001).

\* cited by examiner

Figure 9
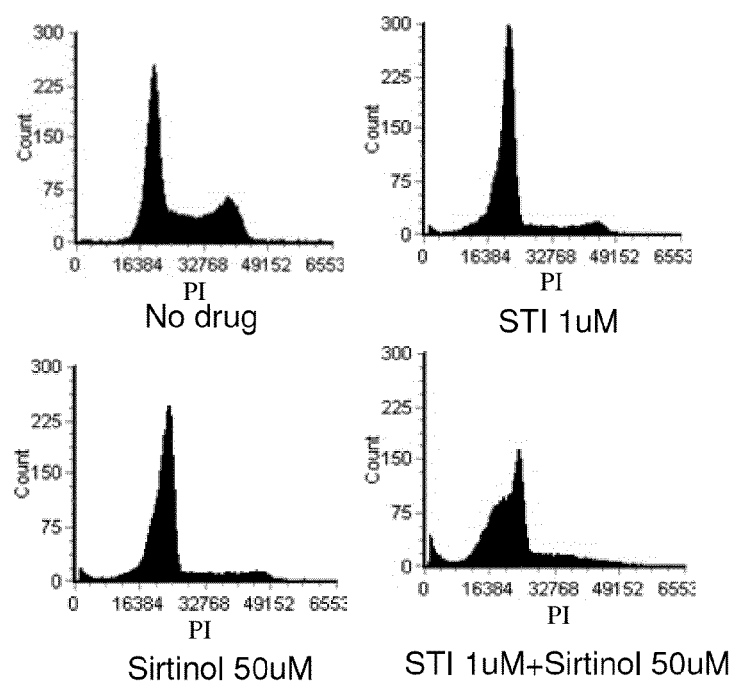
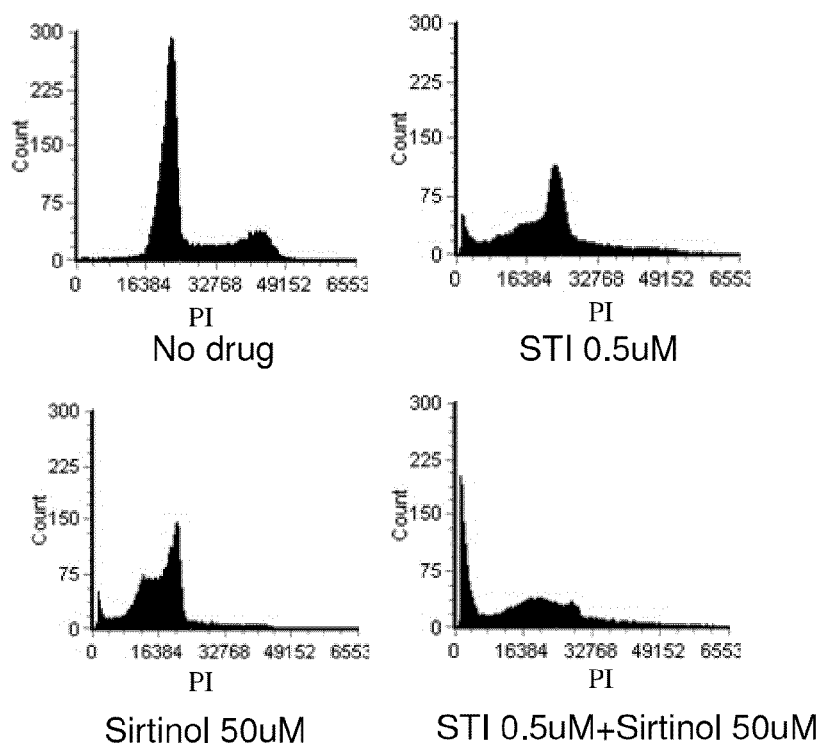

Figure 12
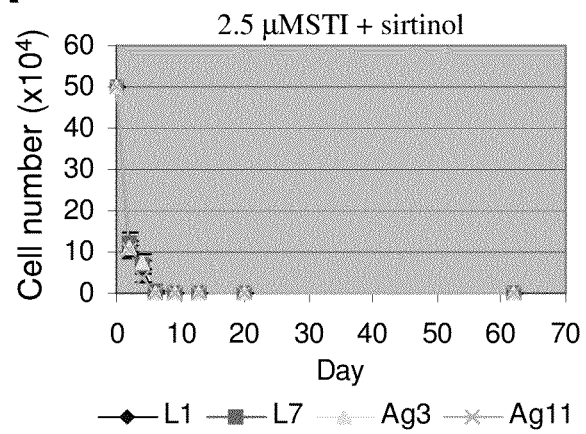
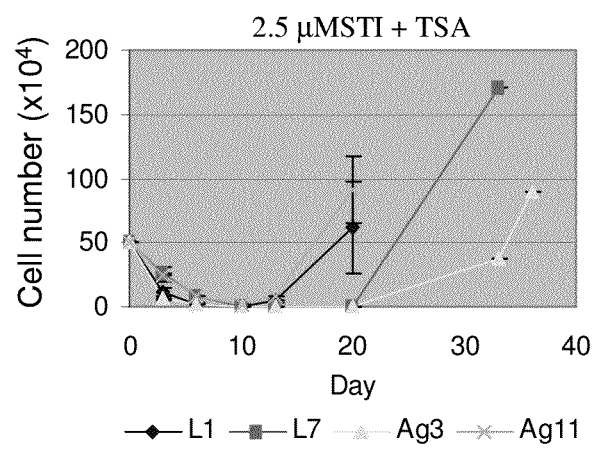
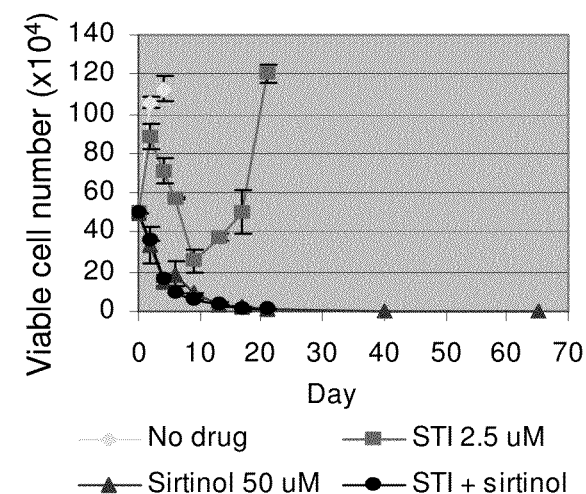

Figure 14
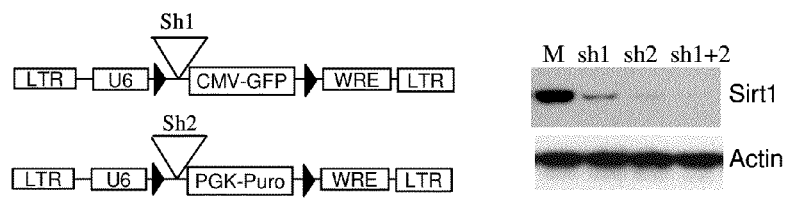
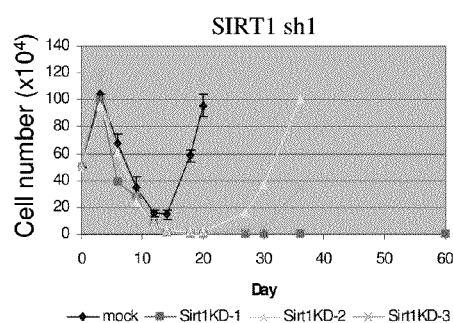
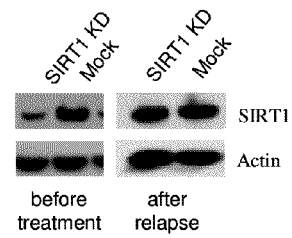
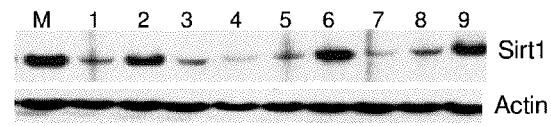
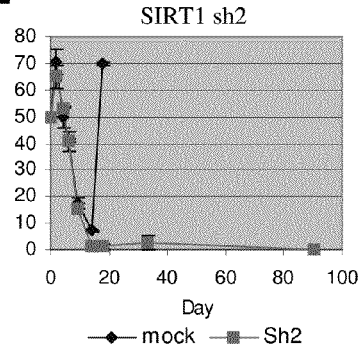
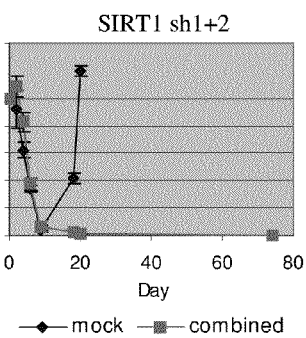

Figure 16
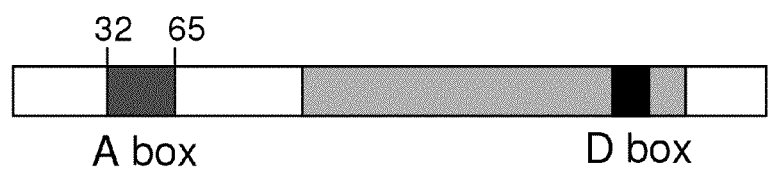
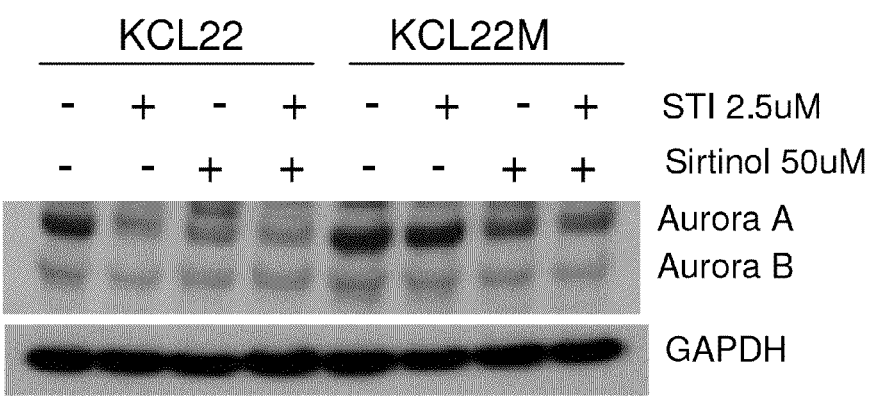

Figure 18

CATTCAACGGTGGCCGACGGGCTCATCACCACGCTCCATTATCCAGCCCCAAAGCGCAACAAGCC
C
                                 PcDNA →
ACTGTCTATGGTGTGTCCCCCAACTACGACAAGTGGGAGATGGAACGCACGGACATCACCATGAA
GCACAAGCTGGGCGGGGGCCAGTACGGGGAGGTGTACGAGGGCGTGTGGAAGAAATACAGCCT
GACGGTGGCCGTGAAGACCTTGAAGGT/<intron>/AGGAGGACACCATGGAGGTGGAAGAGTTCTTG
AAAGAAGCTGCAGTCATGAAAGAGATCAAACACCCTAACCTGGTGCAGCTCCTTGGTGAGTAAGCCC
GGGGCTCTGAAGAGAGGGTCTCGCGCCGCACCCCCAGGGTGACACAGGCGCTGGGGAAGACGCA
CGGGCGGCTCACTGCACAAAACCTCGTTGGAATATTTGTGCTCTGCCGACGTTCAGCCGCGGGTAA
AATGAGGCCTGTATGGGATGGGTGTGTGCGTGTGTGCACATATGCACATGTATGTATGAGAGGGAG
AATGTGATTATTTTAAGTGGATACCTAAAAGCAGTCAAATGCAAATCTGAAATTAGTTTCTGAAACTTG
GGCATTTTCCAGAGTTTTCTCACTGAAGTGATTCTGTAAGTAGACACATAACCATCAGACCTAACCAT
TCAGGGGTAAACTGACGGTGGTGAAGGTCATTTGAGGTGGGGCCAGGTCTGCGTCTGAATTCTGTG
GCAGCCTCTCCCTGCGTAAATTCAAGTTCACTGGCTTGAGAAGAAGAAAAGAGCCTGGCCATGTCCC
TCCCACACGAGCACAGTCTCAGGATGCAGGTGCTTGGGACCATGTTGGAAGTTGGGCCCAGGACTG
AGGA*GCAGAGTCAGAATCCTTCAG*AAGGCTTTTTCTTTAGACAGTTGTTTGTTCAGTTGG
   PgDNA GAGCG*GAGCCACGTGTTGAAGTCCT*CGTTGTCTTGTTGGCAGGGGTCTGCACCCGGGAGCCCCCG
      PgDNA
TTCTATATCATCACTGAGTTCATGACCTACGGGAACCTCCTGGACTACCTGAGGGAGTGCAACCGG
CAGGAGGTGAACGCCGTGGTGCTGCTGTACATGGCCACTCAGATCTCGTCAGCCATGGAGTACCTG
GAGAAGAAAAACTTCATCCACAGGTAGGGGCCTGGCCAGGCAGCCTGCGCCATGGAGTCACAG GGCGTGGA*GCCGGGCAGCCTTTTACAAA*AAGCCCC/<intron>/TCTTAGAGATCTTGCTGCCCGAAAC
TGCCT
   PgDNA
GGTAGGGGAGAACCACTTGGTGAAGGTAGCTGATTTTGGCCTGAGCAGGTTGATGACAGGGGACAC
CTACACAGCCCATGCTGGAGCCAAGTTCCCCATCAAATGGACTGCACCCGAGAGCCTGGCCTA
                                    PcDNA

CAACAAGTTCTCCATCAAGTCCGACGTCTGGGGTAAGGGCTGCTGCTGCACTGAAGTGGTCCTT

Figure 19

GCAGCAGGTACAGAGGCCCTGAGGCCTTTTATTGTGTCTTTTTGCTTGAGCGAGTA
ACTTAGAGCACACGTAGAGAAAGACAGCAGAAGTGATCTTCTAAACACTCTGTCCT
GTGTGGAGAGCTCCTTATGTGAGATTTTGCTGTGTAGTGAATTAAGGCTCAGCCAA
ACTGGCTCACGTGAGCTCTTTGAGCTT<u>GCCTGTCTCTGTGGGCTGAAG</u>GCTGTTC
CCTGTTTCCTTCAGCTCTACGTCTCCTCCGAGAGCCGCTTCAACACCCTGGCCGA
GTTGGTTCATCATCATTCAACGGTGGCCGACGGGCTCATCACCACGCTCCATTAT
CCAGCCCCAAAGCGCAACAAGCCCACTGTCTATGGTGTGTCCCCCAACTACGAC
AAGTGGGAGATGGAACGCACGGACATCACCATGAAGCACAAGCTGGGCGGGGG
CCAGTACGGGGAGGTGTACGAGGGCGTGTGGAAGAAATACAGCCTGACGGTGG
CCGTGAAGACCTTGAAGGTAGGCTGGGACTGCCGGGGGTGCCCAGGGTACGTG
GGG<u>CAAGGCGTCTGCTGGCATTA</u>GGCGATGCATCTGCCTGGAAGTCTACCTCCTG
CCTGCTGTCCGAGGGCTTCATTGGCGCCACGGAATTGACTTTTCCGTCTTATATCA
TTCCTGTGTCTTTGTAGGAGTGGAATCATTCTCATAGTCCGAGTGTGTTTCCACATA
TGGTGAGAGCTGACAAGCATGGAGGGGTTTTGGTGTAAAAAGATTAGTCATTTGGA
GAGGTTTTCTCATTTTATGGCAAGGTTCTTTTAAAGCCGTGGATTTCCATG

Forward: 5'-GCCTGTCTCTGTGGGCTGAAG-3'
Reverse: 5'-TAATGCCAGCAGACGCCTTG-3'

Figure 20

```
TCTTGCTGCGCCTCCGCCTCCTCCTCTGCTCCGCCACCGGCTTCCTCCTCCTGAGCAGTCAGCCCG
CGCGCCGGCCGGCTCCGTTATGGCGACCCGCAGCCCTGGCGTCGTGATTAGTGATGATGAACCAG
GTTATGACCTTGATTTATTTTGCATACCTAATCATTATGCTGAGGATTTGGAAAGGGTGTTTATTCCTC
ATGGACTAATTATGGACAGGACTGAACGTCTTGCTCGAGATGTGATGAAGGAGATGGGAGGCCATC
ACATTGTAGCCCTCTGTGTGCTCAAGGGGGGCTATAAATTCTTTGCTGACCTGCTGGATTACATCAAA
GCACTGAATAGAAATAGTGATAGATCCATTCCTATGACTGTAGATTTTATCAGACTGAAGAGCTATTG
TAATGACCAGTCAACAGGGGACATAAAAGTAATTGGTGGAGATGATCTCTCAACTTTAACTGGAAAGA
ATGTCTTGATTGTGGAAGATATAATTGACACTGGCAAAACAATGCAGACTTTGCTTTCCTTGGTCAGG
CAGTATAATCCAAAGATGGTCAAGGTCGCAAGCTTGCTGGTGAAAAGGACCCCACGAAGTGTTGGAT
ATAAGCCAGACTTTGTTGGATTTGAAATTCCAGACAAGTTTGTTGTAGGATATGCCCTTGACTATAAT
GAATACTTCAGGGATTTGAATCATGTTTGTGTCATTAGTGAAACTGGAAAAGCAAAATACAAAGCCTA
AGATGAGAGTTCAAGTTGAGTTTGGAAACATCTGGAGTCCTATTGACATCGCCAGTAAAATTATCAAT
GTTCTAGTTCTGTGGCCATCTGCTTAGTAGAGCTTTTTGCATGTATCTTCTAAGAATTTTATCTGTTTT
GTACTTTAGAAATGTCAGTTGCTGCATTCCTAAACTGTTTATTTGCACTATGAGCCTATAGACTATCAG
TTCCCTTTGGGCGGATTGTTGTTTAACTTGTAAATGAAAAAATTCTCTTAAACCACAGCACTATTGAGT
GAAACATTGAACTCATATCTGTAAGAAATAAAGAGAAGATATATTAGTTTTTTAATTGGTATTTTAATTT
TTATATATGCAGGAAAGAATAGAAGTGATTGAATATTGTTAATTATACCACCGTGTGTTAGAAAAGTAA
GAAGCAGTCAATTTTCACATCAAAGACAGCATCTAAGAAGTTTTGTTCTGTCCTGGAATTATTTTAGTA
GTGTTTCAGTAATGTTGACTGTATTTTCCAACTTGTTCAAATTATTACCAGTGAATCTTTGTCAGCAGT
TCCCTTTTAAATGCAAATCAATAAATTCCCAAAAATTT
```

Figure 36
a
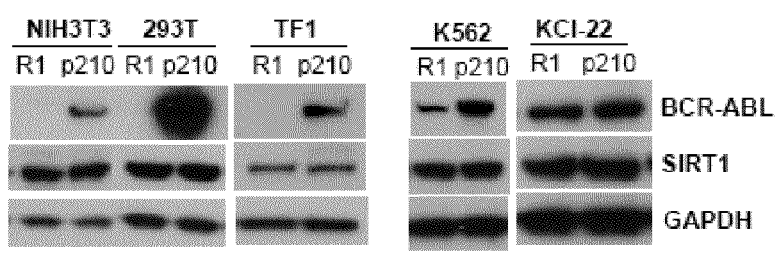
b
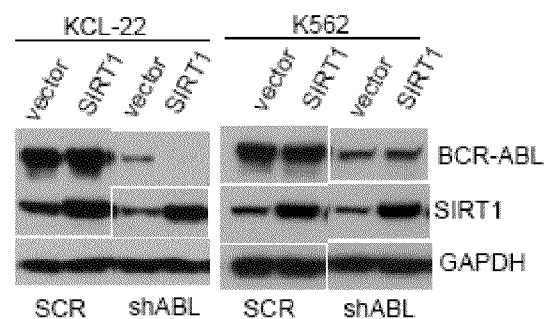
c
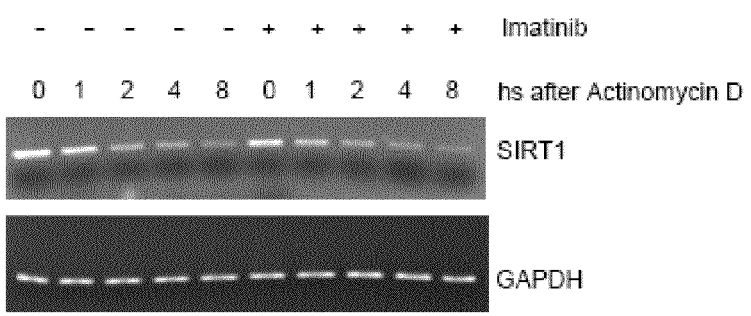

Figure 38
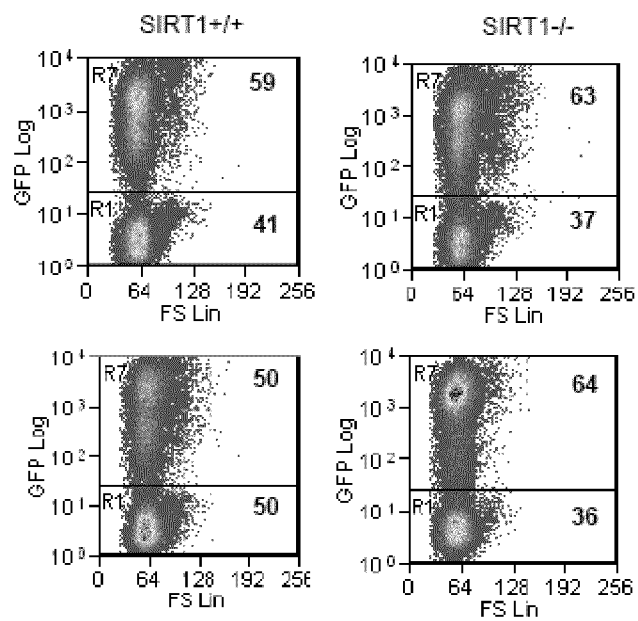
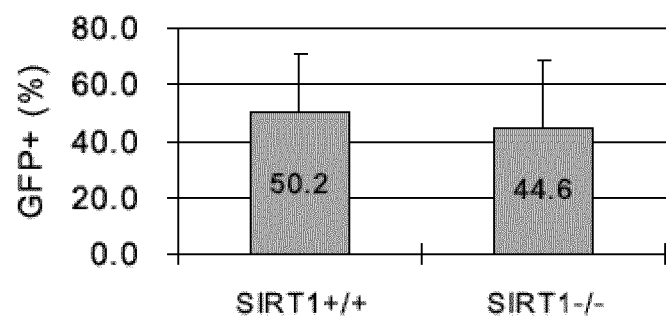

Figure 41
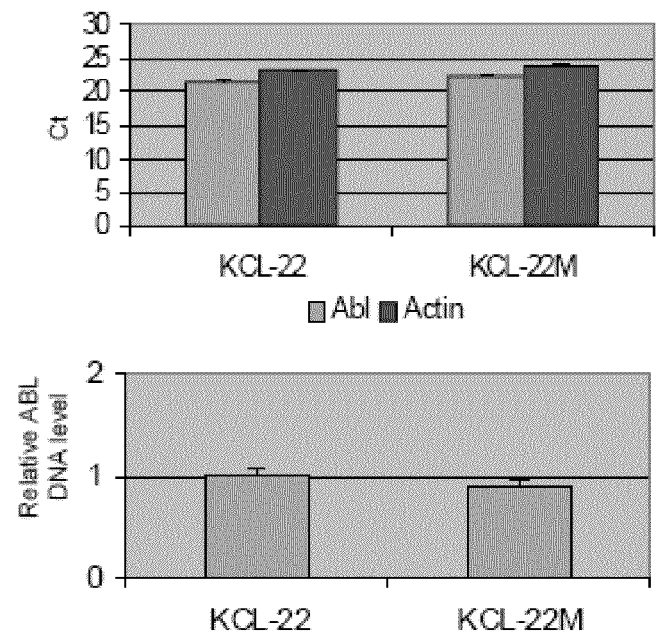
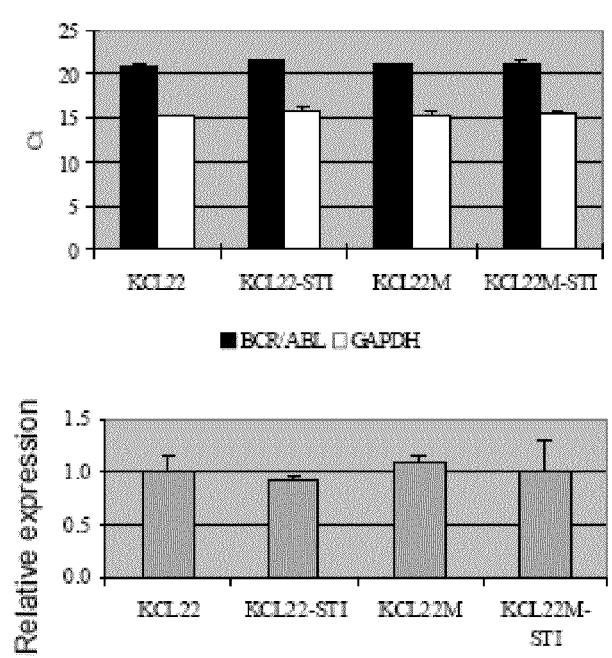

Figure 43
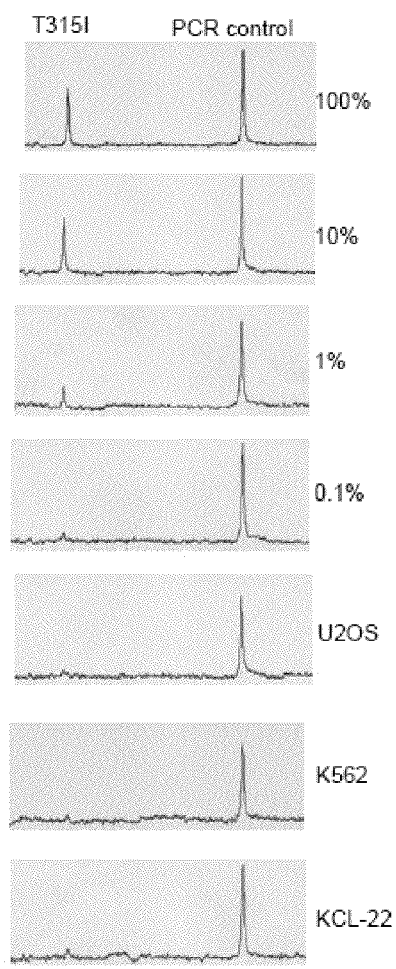
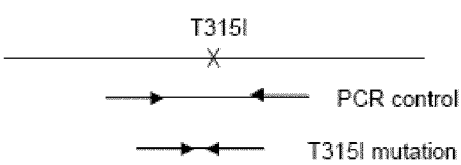
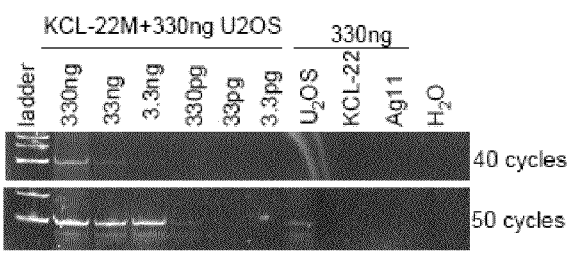

Figure 44
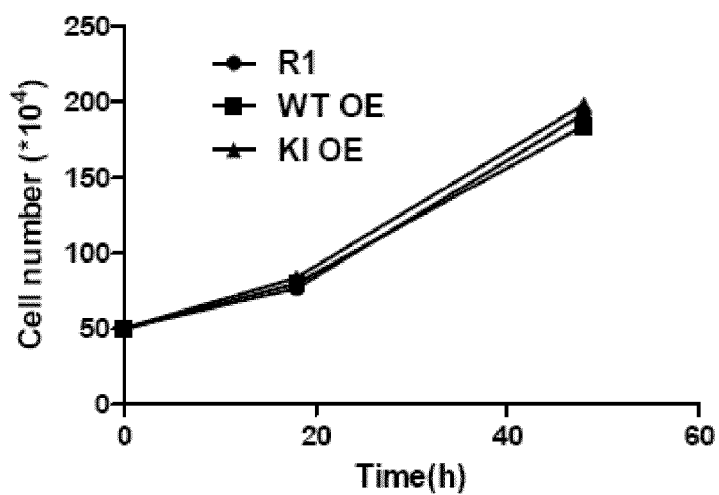
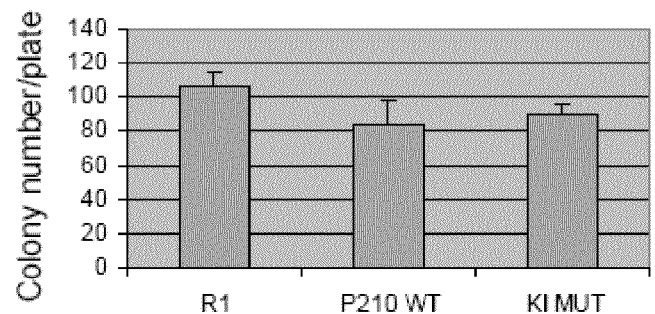

Figure 47
A
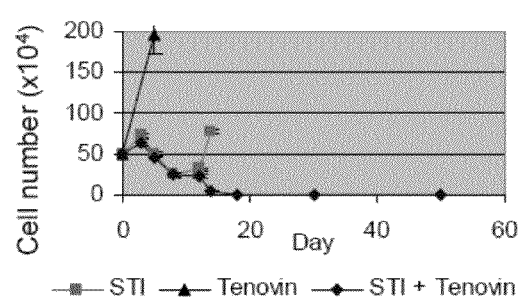
B
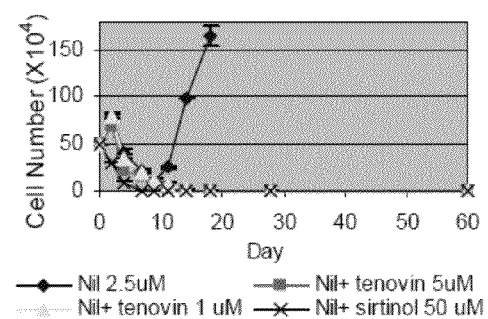
C
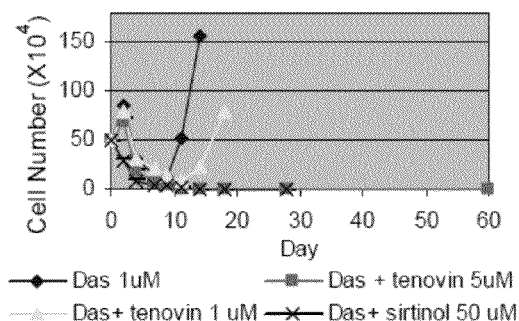
D
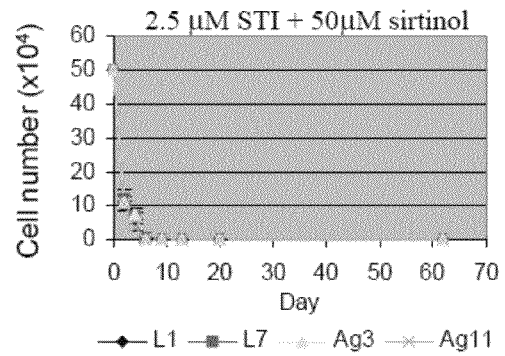

Figure 50
A
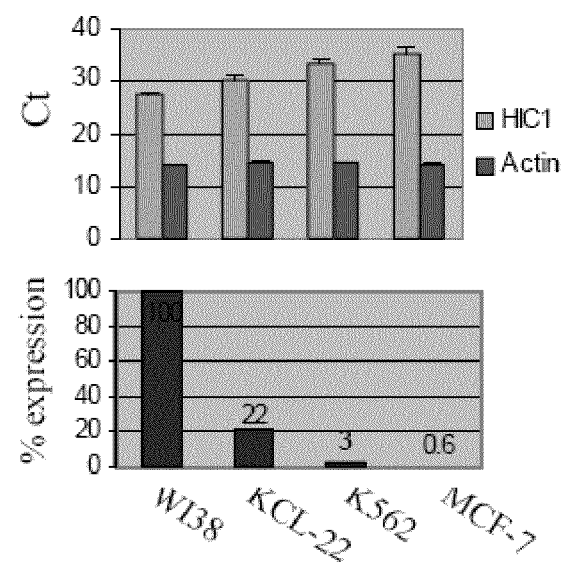
B
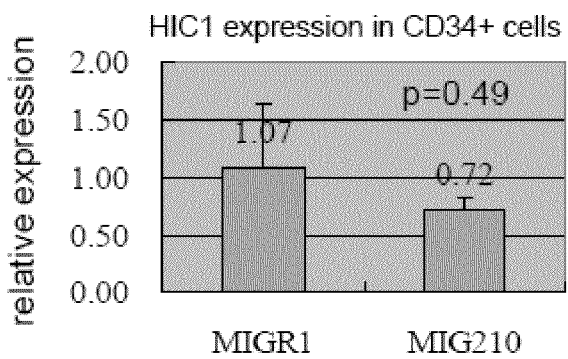

Figure 51

```
mutUTF :: TF85 in the alignment
                 ************************************************************
hg19_xenoRefGen  CATCTCTGACCTCTCAGCATACTAACAATAATATTGATCACATAGCATTTCTTGTAGTTC
hg19_refGene_NM  CATCTCTGACCTCTCAGCATACTAACAATAATATTGATCACAT▮▮▮▮▮▮▮▮▮▮GTTC  2760
                 ******************************************      **** *****
                                                           STAT5A   -2235
hg19_xenoRefGen  ATAAACTTCACGTGTCAATAATATACTATAAATATAAATGAATTAATGAACAACAGGATG
hg19_refGene_NM  ATAAACTTCACGTGTCAATAATATACTATAAATATAAATGAATTAATGAACAACAGGATG  2820
                 ************************************************************ hg19_xenoRefGen  CTCATAAGCTTACAGACATCTTTTTCTCAAAAAAGCTGGGAATTTTGTTTCTGTTTTATT
hg19_refGene_NM  CTCATAAGCTTACAGACATCTTTTTCTCAAAAAAGCTGGGAATTTTGTTTCTGTTTTATT  2880
                 ************************************************************ hg19_xenoRefGen  GGGATACTGACTCTCAACATTTCATATATTGCATTCCACCAACGTAGCTGAGAGTCAATT
hg19_refGene_NM  GGGATACTGACTCTCAACATTTCATATATTGCATTCCACCAACGTAGCTGAGAGTCAATT  2940
                 ************************************************************ hg19_xenoRefGen  TATGAAATATTTTGTAGTGTAAGACAGAAAGTGGGGAGGACCAAGTATGTCAACCACTAG
hg19_refGene_NM  TATGAAATATTTTGTAGTGTAAGACAGAAAGTGGGGAGGACCAAGTATGTCAACCACTAG  3000
                 ************************************************************ hg19_xenoRefGen  GAGTGTGGTGCCTAGTCAGGAATTGGGAGGAGTGTAGCAAGAAAGGAAGGACAACAGGAT
hg19_refGene_NM  GAGTGTGGTGCCTAGTCAGGAATTGGGAGGAGTGTAGCAAGAAAGGAAGGACAACAGGAT  3060
                 ************************************************************ hg19_xenoRefGen  TTGGTCATTGATTGGTCAGATGGATTTCAGAGGGATTGGTATGAAGGAACGCTTCAAAGA
hg19_refGene_NM  TTGGTCATTGATTGGTCAGATGGATTTCAGAGGGATTGGTATGAAGGAACGCTTCAAAGA  3120
                 ************************************************************ hg19_xenoRefGen  TTTTTTTTTTAATTTAAGTTCCAGGATACAGGTGCAGAATGTGTAGGTTTGTTACATACT
hg19_refGene_NM  TTTTTTTTTTAATTT▮▮▮▮▮▮▮▮▮▮▮▮▮▮GTGCAGAATGTGTAGGTTTGTTACATACT  3180
                 ***************                ******************************
                                STAT5B   -1838
hg19_xenoRefGen  TATAGGTGAGCCATGGTGGTTTGCTGCACCAATCAACCCCTCATCTAGGTTTTATTTATA
hg19_refGene_NM  TATAGGTGAGCCATGGTGGTTTGCTGCACCAATCAACCCCTCATCTAGGTTTTATTTATA  3240
                 ************************************************************
```

CELL CULTURE MODEL FOR ACQUIRED CHEMORESISTANCE OF CHRONIC MYELOGENOUS LEUKEMIA AND RELATED METHODS FOR IDENTIFYING AGENTS TO OVERCOME RESISTANCE

PRIORITY CLAIM

This application is a continuation-in-part application of U.S. patent application Ser. No. 12/026,554, filed Feb. 5, 2008, which claims the benefit of U.S. Provisional Patent Application Ser. No. 60/888,307, filed Feb. 5, 2007, both of which are incorporated herein by reference in their entirety.

GOVERNMENT INTEREST

The present invention was supported by the Department of Defense (Grant No. W81XWH-06-1-0268). The government may have certain rights in the present invention.

BACKGROUND

Epigenetic disruptions of gene expression such as by DNA methylation and histone modifications are profoundly involved in tumorigenesis. For leukemia, the gene hypermethylated in cancer 1("HIC1") is unique because hypermethylation of the gene's promoter region occurs progressively towards the late phases of hematologic malignancies. HIC1 encodes a DNA-binding, zinc finger transcriptional factor that is essential for mammalian development. The HIC1 gene is inactivated but not mutated in certain human cancers such as chronic myelogeneous leukemia (CML) and relapsed acute lymphocytic leukemias following chemotherapy. Using mouse genetics, the importance of HIC1 in of tumorigenesis has recently been demonstrated. Germline disruption of one copy of HIC1 predisposes mice to a late on-set and gender-dependent spectrum of malignant tumors wherein promoter hypermethylation of the wild type HIC1 allele is associated with loss of function of this gene. It is also known that HIC1 plays a synergistic role with p53 in suppressing the development of age-dependent cancers. Germline disruption of one copy each of HIC1 and p53 on opposite (trans) chromosomes or same (cis) chromosomes in mice results in altered tumor spectrum, earlier appearance and increased prevalence and aggressiveness of osteosarcomas. Indeed, a low frequency of blast crisis megakaryocytic leukemia is found in cis HIC1 and p53 double heterozygous mice. See FIG. 1.

A key mechanism by which HIC1 suppresses tumorigenesis is through its regulation of the stress and DNA damage responsive gene, SIRT. SIRT1 is a mammalian orthologue of yeast silent information regulator 2(Sir2) that is required for yeast lifespan extension upon calorie restriction (Lin et al., 2000). An extra copy of Sir2 extends life span in yeast, fly and worm. SIRT1 is a class III histone deacetylase whose enzymatic activity is dependent on cofactor NAD. SIRT1 is insensitive to histone deacetylase inhibitor trichostatin A (TSA) which inhibits class I and II deacetylases. SIRT1 is involved in regulation of a variety of cellular functions including survival, glucose homeostasis and fat metabolism through deacetylating histones and non-histone proteins (Saunders & Verdin 2007). SIRT1 levels increase in response to metabolic stresses such as calorie restriction and nutrient starvation (Cohen et al. 2004; Nemoto et al. 2004). The mammalian SIRT1 promotes cell survival under oxidative stress, genotoxic stress and DNA damage through multiple substrates including p53(Luo et al. 2001; Vaziri et al. 2001), Ku70 (Cohen et al. 2004) and FOXO proteins. For example, SIRT1 promotes cell survival using p53 via a pathway that includes deacetylation of p53 and attenuation of its ability to activate downstream targets to control apoptosis. HIC1 forms a complex with SIRT1 protein. This HIC1/SIRT1 protein complex directly binds to the SIRT1 promoter in vivo to repress SIRT1 gene transcription. Loss of HIC1 expression by promoter hypermethylation upregulates SIRT1 in cancer cells, attenuates p53 activity by deacetylation and allows cells to bypass apoptosis and survive stress and DNA damage. Inhibition of SIRT1 function in cells without HIC1 abolishes the resistance to apoptosis.

Chronic myelogenous leukemia (CML) is a fatal hematopoietic disorder resulting from malignant transformation of bone marrow progenitor cells. The disease progresses from chronic phase, to accelerated phase, to terminal blast crisis phase. CML is characterized by a reciprocal translocation of chromosome 9 and 22 that creates an oncogenic fusion gene, BCR-ABL. This gene produces a protein with deregulated BCR-ABL tyrosine kinase activity. Imatinib mesylate (also known as imatinib, Gleevac or STI-571) is a potent ABL tyrosine kinase inhibitor. In most chronic phase patients, treatment with imatinib results in complete cytogenic responses (CCR) or remission and infrequent relapse. However, in most blast crisis patients, there is a poor response to imatinib treatment and a high frequency of relapse in those patients having an initial response. The molecular mechanisms of the resistance to imatinib may consist of both BCR-ABL dependent and independent pathways. BCR-ABL dependent pathways are characterized by genetic alterations of the BCR-ABL gene.

The clinical resistance to imatinib treatment is mediated primarily by genetic mutations of the BCR-ABL kinase domain, and to a lesser extent, by amplification of the BCR-ABL gene. In relapsed CML patients, more than 15 BCR-ABL mutations have been identified. These mutations confer various degrees of resistance to imatinib. Mechanisms for formation of BCR-ABL mutations in CML are not clear. The vast majority of BCR-ABL mutations are detected in relapsed patients, but pre-existing mutations including a T315I mutation are also found in patients before imatinib treatment (Gorre et al., 2001; Shah et al., 2002). The T315I mutation has been identified thus far as being frequent and the most resistant mutation. Located in the center of the imatinib binding site is $Thr^{315}$ and the T315I mutation blocks the drug from binding to the ABL kinase. In addition, imatinib suppresses proliferation of human CML leukemic progenifor cells, but cannot eliminate them in vivo. Thus, most subjects in CCR or remission continue to harbor residual leukemia cells (Bhatia et al. 2003). Similarly, imatinib treatment results in remission of CML in mouse models of the disease, but fails to eliminate leukemic stem cells (Hu et al. 2006; Neering et al. 2007). Because of this, in vitro studies of the process by which BCR-ABL is mutated in CML cells is difficult because, unlike what occurs in vivo, nearly all CML cell lines derived from blast crisis CML are sensitive to 1 µM STI-571 treatment. (Deininger et al. 1997). Nilotinib (AMN107) is a recently developed BCR-ABL inhibitor having greater potency. It inhibits most of the known mutants with the exception of the T315I mutation. Similarly, the potent dual SRC-ABL kinase inhibitor dasatinib (BMS-354825) inhibits 14 of 15 BCR-ABL mutants but not T315I. However, in vivo, CML patients with a T315I mutation do not respond to either nilotinib or dasatinib. Without further effective treatment, these blast crisis patients are terminal. Accordingly, a method of treating these relapsed patients or preventing formation of this resistant mutation is highly desired.

Several resistant CML cell lines have been developed by gradually exposing cells to increasing concentrations of STI-571(Mahon et al., 2000). However, these resistant cell lines all have BCR-ABL gene amplification but lack mutations. This is opposite to the results seen in patients. Today, most in vitro mutation studies are carried out using murine cell lines such as Ba/F3 cells, a murine pro-B cell line transfected with genetically engineered BCR-ABL mutations. (La Rosee et al. 2002; Shah et al., 2004; von Bubnoff et al., 2006; von Bubnoff et al., 2005; Weisberg et al., 2005). Although these cell lines are important for addressing mutant kinase activity, they do not reflect in vivo mechanisms of BCR-ABL mutagenesis, and thereby cannot be used to address mechanisms of BCR-ABL mutagenesis in natural cellular and molecular contexts of CML, and cannot be applied to development of strategies for preventing such mutations. The use of these cells also excludes the possibility of studying other genetic and epigenetic alterations accompanying the BCR-ABL mutagenesis process in mutant CML cells. Thus, a CML cell line having one or more BCR-ABL mutations is also highly desired because it is useful as a model system for CML disease. Use of such cell lines will facilitate further study of the mechanism of disease development and progression and assist in the further identification of therapeutic treatments for this disease.

SUMMARY

A method for making a model of acquired resistance in human cancers which simulates a patient's chemoresistance response is provided. Such a method allows for the study of mechanisms involved in the development of acquired resistance such as through induction of genetic mutations of oncogenic tyrosine kinases as well as through alteration of DNA damage response pathways. Cell line models are also provided. Use of these model systems allow for the screening, identification, testing and discovery of therapeutic compounds useful for treating cancer and especially cancer relapse from chemoresistant cell growth.

A novel CML resistance model using naïve blast crisis CML cells is also provided. Using this model, key features of clinical resistance such as rapid growth of cancer cells after direct exposure of the cancer cells to therapeutically effective concentrations of chemotherapeutic compounds can be replicated. Cancer cells which survive chemotherapeutic treatment (also referred to herein as "relapse" growth) exhibit genetic mutations at the BCR-ABL locus. This model will serve as a useful system for designing, testing, screening and identifying new therapeutic strategies for treating chemoresistant cancer. The methods provided herein are also useful for developing cell culture models of acquired resistance in solid tumors such as non-small cell lung carcinomas. Overactive SIRT1 pathway is a mechanism by which acquired resistance develops in, but not limited to, hematologic malignancies. The present invention provides treatment and diagnostic modalities based upon this discovery.

In one embodiment, a method of generating a chronic myelogenic leukemia (CML) acquired chemoresistant culture model is provided. Such a method comprises providing a naïve blast crisis CML cell line, contacting the cell line with a mutation-inducing dose of imatinib, maintaining a culture of the treated cell line for a period of time until the treated cell line relapses and repopulates the culture, and determining the repopulated cell culture is a CML acquired chemoresistant cell line by detecting a BCR-ABL mutation on the native BCR-ABL locus, wherein the acquired chemoresistance is achieved by the mutation.

In some embodiments, the naïve blast crisis CML cell line is a KCL-22 cell line. In another embodiment, the mutation-inducing dose is (a) about 2.5 µM or higher, (b) between about 2.5 µM and about 10 µM or (c) selected from: about 2.5 µM, about 5 µM and about 10 µM. In another embodiment, the BCR-ABL mutation is a BCR-ABL kinase domain mutation. In one aspect, the BCR-ABL kinase domain mutation is a T315I BCR-ABL mutation.

In another embodiment, a SIRT1 inhibitor compound for preventing chemoresistance or treating CML and a method for developing such a SIRT1 inhibitor for treating cancer is provided. Such a method may comprise generating a pharmacophore model of SIRT1 inhibitors for a SIRT1 substrate binding pocket, identifying one or more SIRT1 inhibitor test compounds based on the pharmacophore model, administering the one or more SIRT1 inhibitor test compounds to a CML acquired resistant culture model, determining an effective test dosage for the one or more SIRT1 inhibitor test compounds that blocks CML cell relapse, comparing the effective test dosage to an effective dosage of a known inhibitor, such as sirtinol, and selecting one or more of the SIRT1 inhibitor test compounds as a SIRT1 inhibitor lead compound when the effective test dosage is lower than the effective known inhibitor dosage. In some embodiments, the CML acquired resistant culture model is a culture model produced by the presently described methods.

Another embodiment is the generation of a pharmacophore model for discovering any compound or combination of compounds useful for treating or preventing chemoresistance and/or cancer. The pharmacophore model may comprise one or more of the steps of initiating mutation, identifying the mutation, identifying the cells that have undergone cellular repair, and testing survival of the mutant cells. The mutation or mutations may be from a variety of cancer-related genes. There may be other components that also have effect on blocking cancer relapse from drug treatment that can be added to the model. Candidate therapeutically effective drugs may then be tested against the pharmacophore model for efficacy alone or in comparison to a known cancer treatment standard. Preferably, the cancer is CML and the treatment standard is sirtinol.

SIRT1 inhibitor lead compounds may be optimized. In some aspects, optimizing the one or more lead compounds is accomplished by using the one or more lead compound to improve the pharmacophore model. In other aspects, optimizing the one or more lead compounds is accomplished by isothermal titration calorimetry (ITC). In some embodiments, the method further comprises determining the efficacy of the one or more lead compounds and/or determining the cytotoxicity of the one or more lead compounds.

In another embodiment, a method for inhibiting or delaying tumor growth in a cancer patient is provided. The cancer may be any cancer, including, but not limited to, leukemia. In some embodiments, the cancer is chronic myelogenous leukemia (CML). Such a method may comprise administering an effective amount of a SIRT1 inhibitor to the cancer patient. In some embodiments, the SIRT1 inhibitor is one or a combination of sirtinol, a sirtinol analogue, splitomicin, a splitomicin analogue, napthol, a napthol derivative, an indole, an indole derivative, siRNA, shRNA and antisense RNA. In other embodiments, the SIRT1 inhibitor is a lead compound produced by the methods described herein.

In other embodiments, the method may further comprise administering an effective dose of a tyrosine kinase inhibitor in combination with the SIRT1 inhibitor. In some aspects, the tyrosine kinase inhibitor is one or a combination of imatinib, gefitinib, nilotinib, dasatinib, and VX-680. In other aspects, the tyrosine kinase inhibitor may be any other suitable substance that inhibits tyrosine kinase activity.

In yet other embodiments, methods of treating or preventing BCR-ABL drug resistance in chronic myelogenous leukemia comprise administering a therapeutically effective amount of one or more SIRT1 modulators to the cells or subject in need thereof. Thus, in one aspect, the invention provides a method of inhibiting growth of a tumor cell. If the tumor cell is a leukemia cell, it may be chronic myelogenous leukemia, acute myelogenous leukemia, chronic lymphocytic leukemia, acute lymphocytic leukemia, or hairy cell leukemia. In another aspect, the invention provides a method of inhibiting relapse growth of cancer cells or preventing chemoresistance. This method comprises use of a modulator of SIRT1 such as a SIRT1 inhibitor. A modulator includes inhibitors of SIRT1 protein, inhibitors of the SIRT1 gene (transcription or translation inhibition, or both). A SIRT1 inhibitor may be a napthol compound (for example, sirtinol or splitomicin), an indole, siRNA, a derivative of a SIRT1 inhibitor, an analogue of a SIRT1 inhibitor or any combination thereof. Chemoresistance, such as BCR-ABL drug resistance, may be caused by administration of a cancer treating drug such as STI-571(imatinib), nilotinib, dasatinib, or another cancer treating drug. Alternatively, drug resistance may be caused by another drug or compound administered to the patient, environmental factors, or may be a naturally occurring resistance. The drug resistance may be the result of a genetic mutation such as the T315I mutation of the BCR-ABL gene. The SIRT1 inhibitor may also treat or prevent insulin and transferrin-induced resistance.

BRIEF DESCRIPTION OF THE DRAWINGS

In FIG. 1(A), the triangle is germline deletion of HIC1, the asterisk is HIC1 promoter hypermethylation, and the rectangle represents somatic HIC1 deletion. FIG. 1(B) shows how HIC1 inactivation is mediated by promoter hypermethylation in trans HIC1+/−p53+/− mice, but genetic deletion in cis mice. Interstitial chromosomal deletion between 20 and 66 cM occurs after loss of wild type p53 in trans tumors, but the entire chromosome harboring wild type p53 and HIC1 is deleted in cis tumors. The diamond and triangle are germline deletion of p53 and HIC1, respectively; the asterisk is HIC1 promoter hypermethylation, and the rectangle is somatic p53 deletion.

FIG. 2(A) shows mouse SIRT1 protein level in MEF nuclear extract from HIC1, LSH or INK4a locus knockout. The numbers underneath Western blots are relative SIRT1 levels normalized to lamins. FIG. 2(B) shows SIRT1 RNA levels in HIC1 knockout MEF by Northern blot. 18S RNA was used as a loading control. The numbers underneath the SIRT1 blot are relative SIRT1 levels normalized to 18S RNA. FIG. 2(C) shows overexpression of HIC1, but not lacZ or mutant HIC1, repressed nuclear SIRT1 in breast cancer MCF-7 cells. FIG. 2(D) shows luciferase reporter assay of SIRT1 promoter. A DNA fragment covering the entire SIRT1 promoter CpG island (from −1231 to +900) was isolated to drive luciferase expression in a pGL2 vector. The luciferase activity was assayed in COS-7 cells with expression of the constructs and infection with recombinant adenoviral vectors as shown. FIG. 2(E) shows ChIP assay with HIC1 and SIRT1 on the SIRT1 promoter using HIC1-expressing W138 cells. Two HIC1 binding sites (−1116 and −1039 in the same orientation), as indicated by wide arrows, are located 5' to the promoter CpG island, and the other two (+575 and +660) in the opposite orientation to one another are located inside intron 1 towards the 3' end of the island. ChIP was performed with HIC1 polyclonal antibody or SIRT1 monoclonal antibody, and both 5' and 3' binding regions were examined by multiplex PCR with GAPDH as an internal non-binding control. CTL (R), normal rabbit IgG control; CTL (M), normal mouse IgG control. The triangles indicate increasing amount of HIC1 or SIRT1 antibodies. FIG. 2(F) shows ChIP upon ChIP assay for 5' HIC1 binding sites on SIRT1 promoter. Sonicated W138 cell chromatin was first immunoprecipitated with rabbit HIC1 antibody and the eluted product was re-immunoprecipitated with mouse SIRT1 antibody (HIC1, SIRT1). For control, normal rabbit IgG was used for the first round of immunoprecipitation and normal mouse IgG for the second (CTL(R,M)). ChIP upon ChIP was also performed with a reverse order of immunoprecipitation, namely SIRT1 ChIP, first, followed by HIC1 ChIP (SIRT1, HIC1); or control mouse IgG followed by rabbit IgG (CTL (M,R)). PCR amplification of 5' HIC1 binding sites was carried out as in panel E. (Chen, et al 20005, Cell 123, 437-448.).

FIG. 9 shows cell cycle change upon sirtinol and STI-571 treatment. KCL-22(A) and K-562(B) cells were treated with conditions as indicated for two days and cells were labeled with propidium iodide (PI) for cell cycle analysis.

FIG. 12 shows effects of deacetylase inhibitors on clonal CML cells and BCR-ABL positive ALL cells. (A, B) One half million each of clonal KCL-22 CML cells were treated with 2.5 µM imatinib plus 50 µM sirtinol (A) or 1 µM TSA (B). (C) SD-1 ALL cells were treated with 2.5 µM imatinib, 50 µM sirtinol or combination. Cells relapsed on imatinib treatment alone without detectable BCR-ABL mutations.

FIG. 14 shows SIRT1 is essential for CML acquired resistance. (A) Structures of SIRT1 shRNA lentiviral vectors and effects of SIRT1 knockdown in KCL-22 cells. The first shRNA (Sh1) was cloned into the pSicoR CMV-GFP vector and the second (Sh2) was cloned into the pSicoR PGK-puro vector. Scrambled shRNA was packaged in both vectors for mock controls. (B) SIRT1 Sh1 knockdown or mock knockdown KCL-22 cells were enriched by FACS, and one half million cells each were treated with 5 µM STI-571 in triplicate. All triplicate samples of mock knockdown relapsed at the same time and were plotted as a single curve with error bars shown. The triplicate SIRT1 knockdown samples were plotted individually as they either did not relapse (sample 1) or delayed the relapse (sample 2 and 3). (C) Western blot analysis of SIRT1 expression in SIRT1 knockdown cells before and after relapse on STI-571 treatment. (D) SIRT1 expression in clones of SIRT1 knockdown KCL-22 cells with Sh1 vector. The FACS-enriched cells were cloned by limiting dilution and single cell seeding was confirmed by microscope. M, mock knockdown. (E) Effects of SIRT1 knockdown with the second shRNA (Sh2) cloned in pSicoR PGK-pure. The transduced cells were selected with puromycin for one week before analysis. The protein knockdown was shown in (A). (F) Effects of SIRT1 knockdown by Sh1 and Sh2. The protein knockdown was shown in (A).

FIG. 16 illustrates expression of Aurora kinases in KCL-22 and KCL-22M cells. FIG. 16(A) shows structure of Aurora A kinase. Destruction box (D box, in black) and A box (dark grey) are required for degradation of Aurora A during cell cycle. The kinase domain is in light grey. FIG. 16(B) shows expression of Aurora A and B in KCL-22 and KCL-22M cells following two days of drug treatment.

FIG. 18 shows the BCR-ABL kinase domain sequence (SEQ ID NO:26). The primers for sequencing cDNA (PcDNA) are underlined. (The first three primers underlined in the figure correspond to SEQ ID NOS: 1, 3, and 4, respectively.) The primers for sequencing genomic templates (PgDNA) are underlined and in italic text. The 579-bp kinase domain is located between the two PcDNA primers. Mutation sites are indicated in large font. Accession information: >gi|71648777|gb|DQ145721.1| Homo sapiens v-abl Abelson murine leukemia viral oncogene homolog 1(ABL1) gene, complete cds.

FIG. 19 shows additional primers for BCR-ABL kinase domain sequencing: Two primers for sequencing genomic templates for E255 and Y253 mutations are located at introns and are indicated in underlined text. Additional primers for BCR-ABL kinase domain sequencing: >gi|71648777|gb|DQ145721.1|. The bolded sequence is Exon 5. The top sequence is SEQ ID NO: 27. The Forward primer is SEQ ID NO:6 and the Reverse primer is SEQ ID NO:7.

FIG. 20 shows the HPRT sequence (SEQ ID NO:28). Sequence corresponding to sequencing primers is underlined. Start and stop codons are in bold text. Accession information: >gi|4504482|ref|NM_000194.1| Homo sapiens hypoxanthine phosphoribosyltransferase 1(Lesch-Nyhan syndrome) (HPRT1), mRNA.

FIG. 36 illustrates SIRT1 expression in cell lines after BCR-ABL transduction. (A) Cells were transduced with BCR-ABL vector MIG210(p210) or empty vector MIG R1(R1) for 7 days, and harvested for protein analysis. (B) Expression of exogenously introduced SIRT1 was not affected by BCR-ABL knockdown. KCL-22 and K562 cells were stably transduced with empty or SIRT1 expressing vector, followed by mock (SCR) or BCR-ABL knockdown (shABL). (C) Analysis of SIRT1 mRNA stability. Twelve hours after imatinib treatment, actinomycin D was added and cells were harvested at times indicated following actinomycin D addition. RNA was analyzed by RT-PCR.

FIG. 38 illustrates measurement of transduction and engraftment efficiency. (A) Similar transduction and engraftment efficiency was observed for SIRT1$^{+/+}$ and SIRT1$^{-/-}$ bone marrow cells transduced by the MIG R1 vector. (B) Peripheral blood mononuclear cells were analyzed for GFP expression.

FIG. 41 illustrates real-time PCR analysis of ABL DNA content and BCR-ABL RNA level. (A), ABL DNA content in KCL-22M cells was the same as in KCL-22 cells. (B), BCR-ABL RNA level in KCL-22M cells with or without imatinib (STI) treatment was the same as in KCL-22 cells.

FIG. 43 shows detection of T315I mutation by ASO-PCR and Bi-PAP assays (A) ASO-PCR assay. RNA from KCL-22M cells was serially diluted with RNA from a human osteosarcoma cell line U2OS. ASO-PCR was able to detect at least 1% mutant allele among the wild type allele. No T315I mutation was found in KCL-22 or K562 cells. A pair of outer primers was included in each PCR reaction to amplify a longer fragment of templates as PCR amplification control. (B) Bi-PAP assay. Various amounts of genomic DNA of KCL-22M cells were mixed with 330 ng of U20S genomic DNA, and Bi-PAP was able to detect 1% T315I mutant allele DNA. No T315I mutation in KCL-22 and clone Ag11 was found with this level of sensitivity.

FIG. 44 shows a comparison of cell growth between BCR-ABL over-expressing cells. Growth curves (A) and Soft agar plating efficiency (B) of R1, Wt and KI mutant BCR-ABL over-expressing cells.

FIG. 47 shows that pharmacological inhibition of SIRT1 blocks acquisition of BCR-ABL mutations and relapse of CML cells on tyrosine kinase inhibitors. (A) KCL-22 cells were treated with 1 µM tenovin-6 and 2.5 µM imatinib alone or in combination. (B) KCL-22 cell relapsed on 2.5 µM Nilotinib (Nil) with T315I mutation, but combination with tenovin-6 or sirtinol blocked relapse. (C) KCL-22 cell relapsed on 1 µM Dasatinib (Das) with T315I mutation. Combination with sirtinol or 5 µM tenovin-6 blocked relapse, and combination with 1 µM tenovin-6 delayed the relapse. (D) Relapse of clonal KCL-22 cells (L1, L7, Ag3 and Ag11) on STI plus TSA treatment.

FIG. 50 illustrates HIC1 expression in CML cells. (A) Analysis of HIC1 expression in cell lines by qRT-PCR. Ct of HIC1 or control actin for PCR amplification was first determined (top) and relative abundance of HIC1 level was calculated with WI-38 cells as positive control (100% expression) and MCF-7 as silencing control (bottom). (B) Analysis of HIC1 expression in human $CD34_+$ cells transduced with MIGR1 or MIG210 by qRT-PCR.

FIG. 51 shows STAT5 binding sites on SIRT1 promoter between −1484 and −2852 bp. Putative STAT5 binding sites were identified by rVista program. Relative positions for STAT5 and other known transcriptional factor binding sites are shown at the bottom panel. hg19_xenoRefGen is SEQ ID NO:44 and hg19_refGene_NM is SEQ ID NO:45.

DETAILED DESCRIPTION

Figure 1:
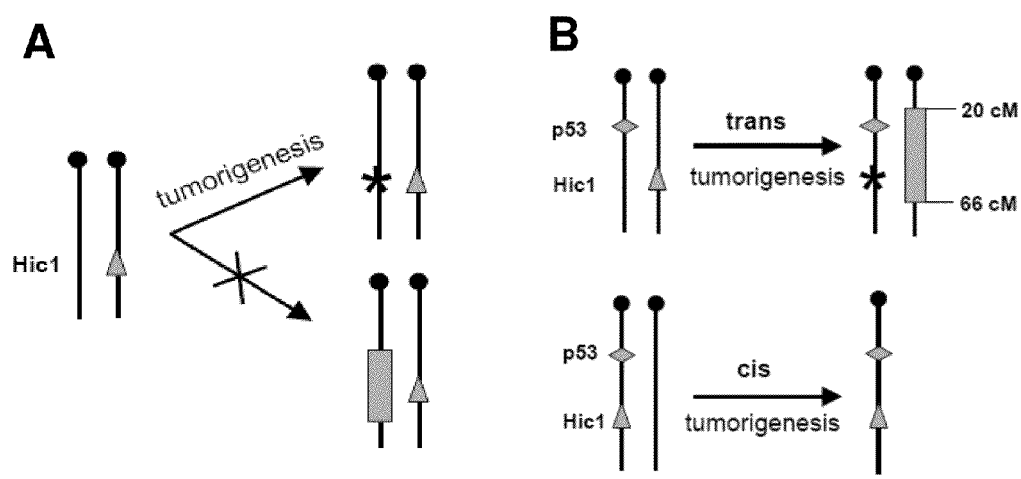
FIG. 1 illustrates roles of HIC1 in tumor suppression. In tumors from HIC1$^{+/-}$ mice, HIC1 inactivation is mediated by promoter hypermethylation but not genetic deletion.

A cell culture model for chronic myelogenous leukemia (CML) acquired chemoresistance and related methods are provided herein. Compounds for treating CML and methods for the discovery of those compounds are also provided. The following definitions are to assist with review of the present disclosure and are meant to encompass any equivalents.

"Agonist" refers to a ligand that interacts with or binds to its receptor to up-regulate, accelerate, or activate the activity of a compound, receptor, gene, or protein.

"Antagonist" refers to a ligand that interacts with or binds to its receptor to downregulate, suppress, or inhibit the activity of a compound, receptor, gene, or protein.

"Antisense molecule" refers to a nucleic acid molecule that hybridizes to all or a portion of a target gene or all or a portion of an mRNA encoded by a target gene. Hybridization of an antisense molecule to a target gene or a portion thereof may inhibit expression of the target gene by inhibiting transcription of the gene sequence, while hybridization of an antisense molecule to a transcript encoded by a target gene may inhibit expression of the target gene by inhibiting translation of the transcript into a polypeptide sequence.

"Cell culture" refers to a cell strain or a cell line.

"Chemotherapeutic agent" refers to any chemical compound or treatment method that induces cell damage, results in cell death, or both. Specific chemotherapeutic agents include but are not limited to kinase inhibitors such as tyrosine kinase inhibitors (TKI), which include, imatinib, gefitinib, erlotinib, lapatinib, CI-1033, PKI-166, GW-2016, as well as others that will be known to one of ordinary skill in the art. Other chemotherapeutic agents include imatiactinomycin-D, adriamycin, androgens, asparagine, azathioprine, BCG, bleomycin, camptothecin, cisplatin, epirubicin, etoposide, gemcitabine, hydroxyurea, interferon alpha, interferon beta, interferon gamma, mitomycin C, paclitaxel, thioguanine, 5-fluorouracil, 6-mercaptopurine, or other drugs. In addition, "chemotherapeutic agent" may refer to radiation and waves, such as electroemissions, gamma radiation, microwaves, UV-irradiation, or X-rays. Other chemotherapeutic agents may include natural or synthetic antibodies, tyrosine kinase inhibitors, enzymatic inhibitors, growth factor inhibitors, metastases-inhibiting compounds, or oncogenic protein inhibitors, such as compounds that inhibit RAS, protein kinase, or DNA topoisomerase.

"SIRT1 inhibitor" refers to one or more compound that inhibits SIRT1 activity. Such inhibition includes direct as well as indirect inhibition of SIRT1 activity. Exemplary SIRT1 inhibitors include, but are not limited to, one or more agent or compound which results in inhibition of SIRT1 function, inhibition of expression of SIRT1 protein, inhibition of transcription or translation of the SIRT1 gene, or both. For example, a SIRT1 inhibitor includes sirtinol as well as its derivatives and other small molecule compounds able to reduce or inhibit SIRT1 activity. SIrt1 inhibitors include sirtinol, a sirtinol analogue or derivative, splitomicin, a splitomicin analogue, napthol, a napthol derivative, an indole, an indole derivative, siRNA, shRNA, antisense RNA, or any combination thereof.

"Duration" refers to the amount of time a desired gene is expressed, and may be measured, for example, in months, weeks, days, hours, minutes and/or seconds.

"Inhibit" with regards to an activity means to suppress the activity, either by decreasing the level or rate of the activity, blocking or preventing the activity entirely, or preventing an increase in the activity under conditions in which the activity would normally be increased.

"In combination with" refers to two or more substances being administered simultaneously or in series close enough in time to bring about a therapeutically effective result.

"Leukemic disorder" refers to a cancerous disorder of blood forming tissues (e.g., spleen, bone marrow, lymphatics, liver) characterized by excessive leukocyte production. The term encompasses myeloid leukemias such as, for example, acute myeloid leukemia (AML), chronic myeloid leukemia (CML), and various subtypes thereof, and lymphocytic leukemias such as, for example, acute lymphocytic leukemia (ALL), chronic lymphocytic leukemia (CLL), hairy cell leukemia (HCL), and various subtypes thereof.

"Pharmaceutically acceptable carrier" refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or some combination thereof. Each component of the carrier must be "pharmaceutically acceptable" in that it must be compatible with the other ingredients of the formulation. It also must be suitable for contact with any tissue, organ, or portion of the body that it may encounter, meaning that it must not carry a risk of toxicity, irritation, allergic response, immunogenicity, or any other complication that excessively outweighs its therapeutic benefits.

"Polynucleotide" refers to any polyribonucleotide, polydeoxyribonucleotide, or hybrid polyribo-polydeoxyribonucleotide, including naturally occurring polynucleotides, synthetic polynucleotides, or any chemically, enzymatically, or metabolically modified forms of naturally occurring polynucleotides. The term encompasses both single- and double-stranded molecules, including DNA-DNA, DNA-RNA, or RNA-RNA duplexes, as well as molecules that are a mixture of single- and double-stranded regions. "Polynucleotide" also refers to triple-stranded molecules comprising DNA, RNA, or both DNA and RNA. Polynucleotides may contain any of the standard pyrimidine or purine bases (i.e., adenine, guanine, cytosine, thymine, uracil), as well as any modified or uncommon bases such as tritylated bases or inosine. In addition, the backbone of a polynucleotide may be modified for stability or for other reasons. "Polynucleotides" also refers to relatively short polynucleotides, often referred to as oligonucleotides, and to peptide nucleic acids (PNAs) formed by conjugating bases to a peptide backbone.

"Prodrug" as used herein refers to a derivative of a pharmaceutically or therapeutically active drug that is transformed into the active drug by an enzymatic or chemical process. Prodrugs may be developed to alter the metabolic stability or transport characteristics of a drug, to mask side effects or toxicity of a drug, or to improve or alter other characteristics of the drug. See, for example, Notari, R. E. 1985. Theory and practice of prodrug kinetics. Methods Enzymol 112:309-323; Bodor, N. 1981. Novel approaches in prodrug design. Drugs of the Future 6:165-182; Bundgaard, H. 1985, "Design of prodrugs: bioreversible derivatives for various functional groups and chemical entities," Chap. 1 in Design of Prodrugs, H. Bundgaard, Ed., Elsevier, N.Y., 1985.

"RNA interference" (RNAi) refers to a post-transcriptional gene silencing (PGSR) process whereby one or more exogenous small interfering RNA (siRNA) molecules are used to silence expression of a target gene.

"siRNAs" (short interfering RNAs) are double-stranded RNA molecules, generally around 15-30 nucleotides in length, that are complementary to the sequence of the mRNA molecule transcribed from a target gene. Following introduction into a cell, the siRNA molecule associates with one or more cellular proteins to form a siRNA/protein complex (RISC), which then binds to the mRNA transcript of the target gene. RISC binding results in degradation of the mRNA molecule, thereby preventing translation.

"shRNAs" (small hairpin RNAs) are short "hairpin-turned" RNA sequences that may be used to inhibit or suppress gene expression.

"Subject" refers to any animal, including a human, having a cell that may be treated by the methods or products discovered or tested by the methods of this disclosure.

"Route of administration" may refer to any administration pathway known in the art, including but not limited to aerosol, enteral, nasal, ophthalmic, oral, parenteral, rectal, transdermal (e.g., topical cream or ointment, patch), or vaginal. "Transdermal" administration may be accomplished using a topical cream or ointment or by means of a transdermal patch. "Parenteral" refers to a route of administration that is generally associated with injection, including infraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal.

"Therapeutically effective amount," "therapeutically effective concentration" or "therapeutically effective dose" is an amount of a compound that produces a desired therapeutic effect in a subject, such as preventing or treating a target condition, alleviating symptoms associated with the condition, or producing a desired physiological effect. A population of cells may be contacted with a therapeutically effective amount of a compound to study its effect in vitro or to produce a desired therapeutic effect ex vivo or in vitro. The precise therapeutically effective amount is an amount of the composition that will yield the most effective results in terms of efficacy of treatment in a given subject. This amount will vary depending upon a variety of factors, including but not limited to the characteristics of the therapeutic compound (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a therapeutically effective amount through routine experimentation, namely by monitoring a subject's response to administration of a compound and adjusting the dosage accordingly. For additional guidance, see Remington: The Science and Practice of Pharmacy $21^{st}$ Edition, Univ. of Sciences in Philadelphia (USIP), Lippincott Williams & Wilkins, Philadelphia, Pa., 2005.

"Treating" or "treatment" of a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

According to embodiments of the disclosure and as discussed in detail in Example 1 below, a cell culture model for chronic myelogenous leukemia (CML) acquired chemoresistance and related methods for generating such a model is provided. In some embodiments, the cell culture model is generated by utilizing a naïve blast crisis CML cell line treated with a cytotoxic agent and allowed to relapse and acquire BCR-ABL mutations. In some embodiments, the naïve blast crisis CML cell line is a KCL-22 cell line.

Blast crisis CML cell line KCL-22 is insensitive to treatment with 1 µM imatinib (Deininger et al. 1997). Treating KCL-22 cells with mutation-inducing doses of imatinib, induced apoptosis of the KCL-22 cells, however, relapse occurred within two weeks of the development of T315I BCR-ABL mutation.

A "mutation-inducing dose," "mutation-inducing concentration" or "mutation-inducing amount" is an amount of a compound that, when exposed to a cell, stimulates a nucleic acid mutation in the cell. In some embodiments, a mutation-inducing dose is about 2.5 µM, about 5 µM, about 10 µM, about 2.5 µM or higher, or between about 2.5 µM and about 10 µM. In some embodiments, a mutation-inducing dose is a concentration that may have a therapeutic effect when administered to a subject.

Following the initial apoptosis upon STI-571 treatment with dosages that are equivalent or nearly equivalent to therapeutically effective doses found in human plasma, the KCL-22 cells developed the T315I mutation of the BCR-ABL kinase domain at high frequency in two weeks. However, when small molecule inhibitors of SIRT1 were used in combination with STI-571, the BCR-ABL mutation was prevented and CML cells were eliminated without relapse. These results demonstrate T315I mutation can be rapidly induced by Imatinib treatment but is preventable.

Therefore, the culture system developed provides, among other things, an in vitro system to study mechanisms of BCR-ABL mutagenesis in the natural molecular and cellular contexts of CML. The methods and system provided herein can be used to develop strategies to treat and prevent formation of such a mutation. The discovery that SIRT1 inhibitors can block T315I mutation and completely eliminate CML cells when administered with imatinib also provides a novel treatment modality for CML patients. In addition, the T315I mutant cells generated from this system also provide invaluable tools for studying mechanisms of resistance after mutation and strategies to eradicate these highly resistant cells.

In contrast to previous cell line models that are involved with gene amplification, altered BCR-ABL expression, and/or additional chromosomal rearrangements (Mahon et al. 2000; Rosenhahn et al. 2007; Tipping et al. 2003), genetic mutations of BCR-ABL primarily account for resistance in the model. Development of BCR-ABL mutations in this model is highly reproducible and occurs in 2 weeks with a single dose of imatinib treatment. T315I mutation has been shown in CML cell line KBM5 after several months of treatment with gradually increasing concentrations of imatinib (Ricci et al. 2002), but the mutation induction time in KCL-22 cells is much shorter. Although a relatively short period of time (3-6 weeks) is also reported for developing BCR-ABL mutations in primary CML cells cultured in vitro (Koptyra et al. 2006; Jiang et al. 2007), the model described herein is simpler and more advantageous, because, for example, it utilizes a commercially available cell line and routine culture conditions. Therefore, this model is valuable for studying mechanisms of acquired resistance and developing strategies to prevent relapse.

Finding that BCR-ABL mutations are dependent on BCR-ABL gene expression is in line with the previous finding that BCR-ABL can promote self-mutagenesis (Koptyra et al. 2006), which indicates that genome instability caused by BCR-ABL transformation is perhaps the driving force for its mutations. Consistent with this notion, we observe that clonal cells can derive mutations without pre-existing mutations from the original patient and that these clonal cells can develop distinct BCR-ABL mutations as well as resistance without mutations. Development of resistant BCR-ABL mutations may resemble adaptive mutations promoting survival and growth in bacteria under stressful conditions, which involves multiple DNA repair pathways (Rosenberg 2001; Karpinets et al. 2006). BCR-ABL transformation alters regulation of multiple DNA repair pathways causing genome instability (Melo & Barnes 2007). It would be interesting to determine how altered DNA repair may influence mutations with this model in the future.

Although BCR-ABL cDNA has been widely used to study its mutagenesis, comparison between the mutagenesis potential of randomly integrated BCR-ABL cDNA versus the native BCR-ABL locus has not been shown before. Based on the studies discussed above, the BCR-ABL translocation locus itself may play a role in promoting mutations, as mutagenesis on the locus is far more efficient than on randomly integrated BCR-ABL cDNA in the same cells. This locus-dependent influence is validated by showing that HPRT mutation rate is relatively constant although the BCR-ABL mutation rate is more dynamic. Further, distinct clonal mutations resulted from the cell cloning process, which affects the mutagenesis process. This indicates that there is a dynamic process for BCR-ABL mutagenesis on its native locus. Such BCR-ABL mutations may be influenced by the epigenome structure of the translocation locus, and the environmental change or cloning process can result in subtle alteration of the local epigenome producing altered mutation hot spots.

The specific inhibition of BCR-ABL kinase activity in KCL-22 cells is a complex process. Cellular phosphorylation in KCL-22 cells is not affected by overexpression of K1176R kinase-inactive BCR-ABL or by efficient delivery of BCR-ABL antibody. Mutation phenotype in mutant BCR-ABL-overexpressing cells does not change with 2.5 µM imatinib treatment, but mutant BCR-ABL blocks mutations at 5 µM imatinib. The precise mechanism for this difference is not yet clear. Because cells harboring mature tetramer BCR-ABL protein (Smith et al. 2003; McWhirter et al. 1993) wholly from mutant monomers may not be able to grow in culture, most cells for analysis should carry hybrid BCR-ABL protein with wild type and mutant monomers. The e13a2 BCR-ABL, expressed in KCL-22 cells, is known to have high tyrosine kinase activity (Lucas et al. 2009). The hybrid BCR-ABL may retain normal phosphorylation ability on most substrates but may affect certain substrates regulating BCR-ABL mutations, and its effect would not be shown unless strong selection is applied. Alternatively, the mutant BCR-ABL may affect mutations independent of its kinase activity. K1176R BCR-ABL retains certain functions, such as the intact cellular localization and adhesion regulation (Wertheim et al. 2002), and may continue recruiting proteins necessary for mutagenesis but in a less efficient way.

Although ROS production was previously found to promote BCR-ABL mutations (Koptyra et al. 2006), inhibition of ROS by high concentrations of anti-oxidants was unable to prevent BCR-ABL mutations and relapse as discussed above. However, these two studies use quite different cell culture systems. KCL-22 cells have a basal level of ROS, compared with high levels of ROS in blast crisis CML cells previously studied, although low levels of ROS are also noticed in a subpopulation of CML cells (Koptyra et al. 2006). In addition, primary CML cell culture uses growth factor-supplemented medium (Koptyra et al. 2006; Jiang et al. 2007), whereas KCL-22 cells are growth factor-independent. Given that ABL kinase domain mutations can be detected even in normal human progenitor cells cultured in the growth factor medium (Jiang et al. 2007), growth factor culture may affect ROS production and mutations.

Figure 2:
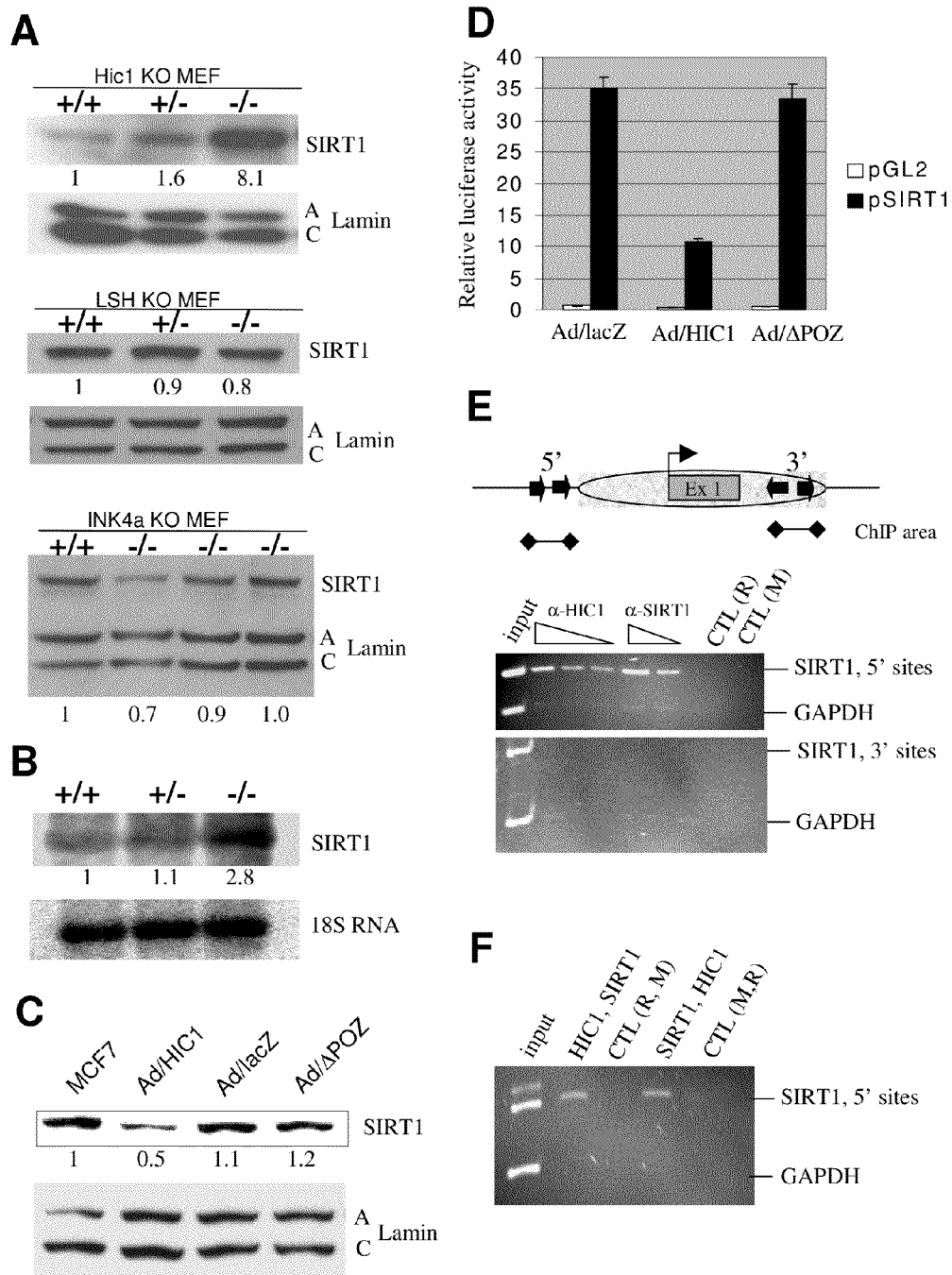
FIG. 2 shows how HIC1 directly regulates SIRT1 transcription.

According to some embodiments the present disclosure also includes novel mechanisms for acquired resistance through active induction of genetic mutations of oncogenic tyrosine kinases in human cancer. As discussed above, HIC1 suppresses tumorigenesis is through regulation of stress and DNA damage responsive gene, SIRT. SIRT1 is a key gene for controlling active induction of genetic mutations on tyrosine kinases through altering DNA damage pathways. HIC1 directly regulates SIRT1 transcription as shown in FIG. 2. Inhibitors of SIRT1 will inhibit acquired resistance through prevention of genetic mutations, and thus are especially useful in the clinical setting where a combination of cancer therapeutics is applicable or utilized. The present disclosure, however, is not limited to CML. Rather, as is understood by a person of ordinary skill in the art, the mechanisms of acquired resistance and functions of SIRT1 and its inhibitors described herein can also be applied to treatment of acquired resistance in other cancers. In addition, the mechanisms of acquired resistance and functions of other genes and their inhibitors can be applied to the treatment of acquired resistance in cancer.

Clonal cells derived from parental KCL-22 cells also predominantly develop resistance to imatinib by BCR-ABL mutations including the T315I, E255K and Y253H mutations. The mutations exhibited by the clonal cells encompass the most frequently observed mutations in CML patients (Shah et al. 2002; Soverini et al. 2006). Furthermore, the rapid relapse is similar to that seen in blast crisis patients. The ability to form BCR-ABL mutations in clonal cells indicates that pre-existing rare mutant cells from the original patient are not required for development of resistance. The BCR-ABL mutation frequency varies among clones while HP RT (hypoxanthine phosphoribosyl transferase) mutation frequency remains relatively constant. Unlike the broad mutation spectrum of HPRT observed in parental or clonal cells, BCR-ABL mutations may be limited to one mutation in a parental cell or a clone. Additionally, while the spontaneous mutation frequency of HPRT remains relatively constant throughout cell passages, frequency of BCR-ABL mutation declines in later passages. See, for example, FIG. 20. The data provided herein indicate that BCR-ABL mutations upon imatinib treatment are not always derived from random DNA replication error during clonal expansion or cell propagation, but are actively induced by imatinib treatment. The disclosure includes a novel model system for testing and identifying therapeutic modalities and compounds for treating CML. The disclosure includes systems, methods and cell lines based on the discovery that the targeting of a tyrosine kinase (as an anti-cancer treatment) may in itself be mutagenic and thereby induce DNA mutations thereby directly or indirectly contributing to clinical acquired chemoresistance.

Figure 34:
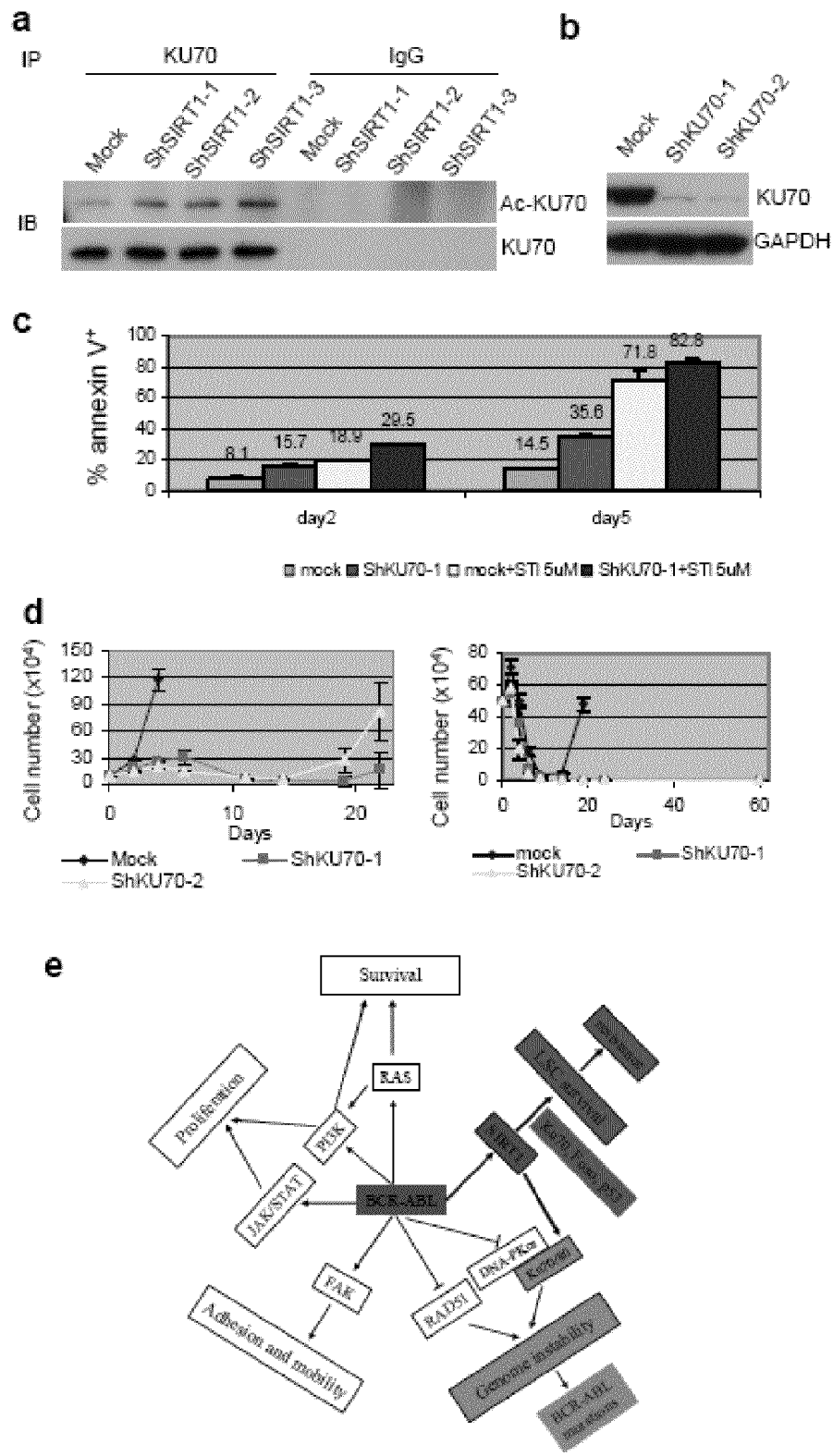
FIG. 34 illustrates that Ku70 is an important downstream target of SIRT1 for CML acquired resistance. (A) Acetylation of endogenous Ku70 after SIRT1 knockdown in KCL-22 cells. (B) Knockdown of Ku70 by two sets of shRNA vectors in KCL-22 cells 4 days after lentiviral transduction. (C) Three days after scrambled shRNA (mock) or shKu70 transduction, 2.5 µM imatinib was added for another 2 or 5 days, and apoptosis was analyzed. Two sets of shRNAs showed similar results and data from one set was shown. (D) Left, Ku70 knockdown significantly suppressed cell growth, but cells re-grew eventually. Right, Ku70 knockdown blocked KCL-22 cell relapse on 5 µM imatinib. Imatinib was applied three days after shRNA transduction. (E) Model for CML chemoresistance. In addition to classic survival and proliferation pathways (unshaded), BCR-ABL activates SIRT1 pathways (shaded) that enhance leukemic stem/progenitor cell (LSC) survival and promote genome instability and mutations for acquired resistance.

SIRT1 activation is essential for efficient BCR-ABL oncogenic transformation and development of a CML-like myeloproliferative disorder. Further, SIRT1 activation by BCR-ABL is more selective to hematopoietic stem/progenitor cells, which produce massive expansion of granulocyte-macrophage lineage, and SIRT1 knockout inhibits such biased differentiation and myeloproliferative disorder. This is consistent with the role of BCR-ABL in promoting proliferation of myeloid progenitor cells (Jamieson et al. 2004). Although activated by BCR-ABL, inhibition of SIRT1 overcomes CML cell resistance to imatinib and has a synergistic effect with BCR-ABL inhibition to induce apoptosis, indicating that SIRT1-regulated pathways including Ku70 may confer a survival advantage for CML progenitor cells in addition to those classic survival pathways (FIG. 34E). SIRT1 is also an important intermediate factor for BCR-ABL functions in CML to deacetylate and activate Ku70, thereby promoting CML genome instability through increasing infidelity DNA repair (FIG. 34E). It was also found that high levels SIRT1 promote de novo genetic mutations in prostate cancer cells upon DNA damage. Because SIRT1 is overexpressed in a variety of cancers, SIRT1 likely plays an important role in tumorigenesis to promote cancer genome instability. This in turn facilitates cancer cells to rapidly evolve and develop mutations for acquired resistance.

The studies described herein improve the understanding of SIRT1 and its roles in tumorigenesis. Further, the studies provide a strong rationale for developing inhibitors of SIRT1 activity or expression to overcome CML resistance to BCR-ABL inhibitors. Although the current application is directed to developing cancer treatments directed to SIRT1 inhibitors, other cancer treatments may be developed as well. SIRT1 activation is a novel mechanism for CML stem/progenitor cell proliferation and survival and to promote cancer genome instability resulting mutations for acquired resistance. Accordingly, SIRT1 targeting is a valuable cancer treatment pathway.

The novel tissue culture method provided herein closely simulates in vivo CML relapse on imatinib treatment using KCL-22 cells. By direct exposure of cells to Imatinib with concentrations pertinent to those in patient plasma, the T315I mutation of BCR-ABL can be induced rapidly with high frequency. The resultant T315I mutant cells differ from parental KCL-22 cells in size, morphology and cell cycle, and they are highly resistant to various treatments. *Streptococcus Faecalis*(SF) medium or supplying insulin in serum medium will also provide CML cells resistance to Imatinib treatment. Finally, the combination of Imatinib with SIRT1 inhibitors will prevent CML relapse and abolish growth-factor-induced resistance. Thus, the methods outlined herein provide a platform for studying strategies for preventing formation of drug resistance and screening for small molecule inhibitors for blocking CML relapse.

The present discoveries may be used for methods for treating or preventing cancer cell growth, treating or preventing resistance of a cancer cell to chemotherapy, or treating or preventing the relapse growth of one or more cancer cell. Using the culture model described above, key features of clinical resistance such as rapid relapse through BCR-ABL mutations after imatinib treatment can be replicated. This model may serve as a system for designing, testing, screening and identifying new therapeutic strategies for treating CML. For example, the resistance model can be used to screen modulators of enzymatic activity or small molecule inhibitors such as those which inhibit SIRT1, chemotherapeutics, compounds, or anti-cancer modalities having therapeutic efficacy or those able to inhibit BCR-ABL mutation based resistance. The resistance model may also be used for further studies of resistance mechanisms, which will allow for the design of new therapeutic strategies, such as use of small molecule inhibitors to prevent the induction of those mutations that accompany a cancer drug treatment.

According to one embodiment, a method for screening for a candidate SIRT1 inhibitor for reducing chemoresistance or relapse in a cancer cell culture can be broadly applied and has the following steps. First, a base level of chemoresistance or relapse is established in a cancer cell culture, such as a cancer cell line, after administration of one or more chemotherapeutic agents by treating the cancer cell culture with the chemotherapeutic agent under conditions which induce chemoresistance or relapse in the cell culture. Then, the candidate SIRT1 inhibitor is administered to previously untreated cells of the cell culture before, during, and/or after administering the one or more chemotherapeutic agents. Finally, the level of chemoresistant or relapsed cells after treatment with the candidate SIRT1 inhibitor and the chemotherapeutic drug is measured. A reduction or absence of chemoresistant or relapsed cells as compared to base level of chemoresistance or relapse established at the outset of the model indicates that the compound is a SIRT1 inhibitor.

According to another embodiment, a SIRT1 inhibitor compound for preventing chemoresistance or treating CML and a method for developing such a SIRT1 inhibitor for treating cancer is provided. In some embodiments, such a method may include the following steps. First, a pharmacophore model of SIRT1 inhibitors of a SIRT1 substrate binding pocket is generated. Then, one or more SIRT1 inhibitor test compounds are identified. Next, the one or more SIRT1 inhibitor test compounds are administered to a CML acquired resistant culture model, such as the model described herein. Next, an effective test dosage for the one or more SIRT1 inhibitor test compounds that block CML cell relapse is determined and compared to an effective sirtinol dosage. An effective sirtinol dosage is an amount of sirtinol that, is able to prevent, in whole or in part, chemoresistance related to BCR-ABL mutation, relapse after treatment with a tyrosine kinase inhibitor, or elicits another desirable effect in a CML cell, including, but not limited to inhibition of cell growth or induce cell death. Finally, one or more of the SIRT1 inhibitor test compounds is selected as a SIRT1 inhibitor lead compound when the effective test dosage is lower than the effective sirtinol dosage.

As described below, a computational (pharmacophore) model of SIRT1 inhibitors for blocking substrate binding is provided. In one embodiment, 3D pharmacophore search from NCI chemical library of 250,253 compounds was performed, followed by two rounds of the cell-based screening. As described below, a group of one or more lead compounds that inhibited CML acquired resistance at 1-5 µM and blocked SIRT1 deacetylase activity was identified. According to one embodiment, the one or more lead compounds are water soluble and have better inhibitory effect than other known SIRT1 inhibitors. In some embodiments, the lead compounds have two distinct SIRT1 binding moieties: one to block substrate binding and the other to block NAD binding. A computational docking study confirmed that these compounds can be docked into both substrate and NAD binding pockets. Blocking both substrate binding and NAD binding pocket individually has synergistic effect on SIRT1 inhibition. In one embodiment, a nitrogen-bond linker structure was identified that enhances specific hydrophilic interaction between the lead compounds and SIRT1 and also increases the water solubility of the lead compounds.

The cancer or cancer cell is usually a hematologic disorder or a solid tumor. Commonly, the hematologic disorder is chronic myelogenous leukemia (CML). An exemplary cancer cell associated with a solid tumor is non-small cell lung carcinoma (NSCLC). A therapeutically effective amount of a SIRT1 modulator or a combination of multiple SIRT1 modulators is administered to a subject in need thereof. Frequently, a therapeutically effective amount of a modulator such as a SIRT1 inhibitor is administered. A SIRT1 inhibitor includes one or more inhibitors of sirtuins (class III histone/protein deacetylases), such as sirtinol or its analogue, which is administered in combination with the chemotherapeutic agent. Generally, the SIRT1 modulator is administered at or about the same time as the chemotherapeutic agent, but can also, if desired, be administered prior to or subsequent to the administration of the chemotherapeutic agent. The SIRT1 modulator may either be an agonist or antagonist of SIRT1 and may be any molecule, compound or agent that acts to modulate SIRT1. Such modulators include, but are not limited to, derivatives, analogues, small molecules, decoy molecules, drugs or prodrugs, polynucleotides, particularly antisense molecules and RNA interference using siRNA, shRNA, polypeptides, antibodies, including chimeric antibodies, or any other substance that acts on SIRT1 in an intended manner. If the SIRT1 modulator is a SIRT1 antagonist, acting to inhibit SIRT1, the inhibitor is preferably a napthol compound (for example, sirtinol or splitomicin), EX-527, an indole or its derivative, siRNA, shRNA, or any combination thereof.

Drug resistance or cancer cell relapse may be caused by administration of a chemotherapeutic agent such as imatinib, gefitinib, nilotinib, dasatinib, or another cancer-treating drug. Imatinib is a tyrosine kinase inhibitor. It interferes with BCR-ABL protein function. Gefinitib inhibits EGFR kinase. BCR-ABL drug resistance may be caused by administration of a chemotherapeutic agent such as imatinib, nilotinib, dasatinib, VX-680(a dual Aurora kinase and BCR-ABL inhibitor) or another cancer-treating drug. Alternatively, resistance may be caused by another drug or compound administered to the patient, environmental factors, or may be a naturally occurring resistance. Relapse in chronic myeloid leukemia patients treated with imatinib, such as STI-571, is an example of one form of clinical chemoresistance associated with a point mutation or amplification of the BCR-ABL gene. Thus, the SIRT1 modulator may also be administered in conjunction with a tyrosine kinase inhibitor.

Both the SIRT1 modulator and the chemotherapeutic agent are to be applied in therapeutically effective amounts and for any duration necessary to treat the cancer or prevent relapse of the cancer. A clinician can gauge the dosages for each required by the subject using known methods of optimizing drug performance and delivery by taking into account clinical data regarding tolerances, age, gender, severity of the disease, health of the subject, and the like. Preferably, the SIRT1 modulator is an inhibitor that is administered to the subject in a pharmaceutically acceptable carrier. The route of administration may be any route effective to carry the therapeutic SIRT1 modulator to the cancer cells in the subject, including any of the routes discussed above. In addition, the SIRT1 modulator may also be used treat or prevent insulin and transferrin-induced resistance as well as EGFR (epidermal growth factor receptor) associated resistance.

A method of preventing chemoresistance in CML cells comprising administering a therapeutic drug or combination of therapeutic drugs that prevent formation of a T315I mutation and other BCR-ABL mutations is also provided. These BCR-ABL mutations in cancer cells, particularly, CML cells are responsible for anti-apoptotic activity and, as such, prevent the cancerous cells from responding to traditional chemotherapy, radiotherapy, or other cytotoxic agents. Preferably, the therapeutic drug is comprises a SIRT1 antagonist, such as sirtinol, a sirtinol analogue, splitomicin, an indole, siRNA, shRNA, Aurora kinase inhibitor, or any combination thereof.

Another embodiment improves the efficacy of a cytotoxic agent directed to CML cells, in a subject, by administering to the subject at least one cytotoxic agent directed to CML cells, and administering to the subject a SIRT1 inhibitor in a therapeutically effective amount, so that the SIRT1 inhibitor enhances the efficacy of the cytotoxic agent relative to the effect of the cytotoxic agent in the absence of the SIRT1 inhibitor. The cytotoxic agent may be a BCR-ABL inhibitor, such as STI-571, imatinib, nilotinib, or dasatinib, or any combination thereof and the SIRT1 inhibitor is siRNA, a napthol compound, sirtinol, splitomicin, an indole, or any combination thereof. This method also treats or prevents insulin and transferrin-induced resistance. The methods of the present disclosure may be performed on any animal with cancer or CML, but are preferably for humans.

Having described the invention with reference to the embodiments and illustrative examples, those in the art may appreciate modifications to the invention as described and illustrated that do not depart from the spirit and scope of the invention as disclosed in the specification. The Examples are set forth to aid in understanding the invention but are not intended to, and should not be construed to limit its scope in any way. The examples do not include detailed descriptions of conventional methods. Such methods are well known to those of ordinary skill in the art and are described in numerous publications. Further, all references cited above and in the examples below are hereby incorporated by reference in their entirety, as if fully set forth herein.

EXAMPLE 1

An In Vitro Model of CML Chemoresistance

Materials and Methods

Cell lines and culture and drugs. CML cell lines KCL-22 and K562 were purchased from German Collection of Cell Cultures, Braunschweig, Germany, and grown in RPMI 1640 medium with 10% fetal bovine serum (Hyclone). STI-571 was provided by Novartis, Basel, Switzerland. 6-thioguanine (6-TG) was purchased from Sigma and 2.5 µg/ml final concentration was used for selection. Sirtinol, splitomicin, nicotinamide, trichostatin A 5-aza-2-deoxycytidine and HAT were also purchased from Sigma. For serum-free culture, basic supplements (ITS I-1884), EGF and HDL were purchased from Sigma and insulin from Roche.

Resistance assay. $5 \times 10^5$ KCL-22 or K562 cells in 1 ml medium per well in 24-well plates, and treated with various combinations of drugs. Cells were maintained in these cultures without changing medium. Aliquots of cells at specified time points were removed and cell numbers were counted on a hematocytometer. Cell viability was assessed by trypan blue exclusion whenever necessary. Typically, after three to five weeks in culture when their medium volume significantly decreased, fresh drug-free medium was supplied to the cells.

Isolation of nucleic acids. Total RNA and DNA are isolated using standard protocols. For sequencing the EGFR kinase domain, the EGFR kinase domain is amplified by RT-PCR of total RNA or by PCR of genomic DNA with a high fidelity DNA polymerase (Strategene) using primers previously described (Pao et al., 2004). PCR products are cloned into the pCR2.1 vector using TOPO TA Cloning kit (Invitrogen). At least ten clones for each treatment are sequenced. For mutant-enriched PCR sequencing of T790M mutation, the EGFR exon 20 is amplified using primers described (Inukai et al., 2006). After digestion of the first round PCR product with BstUI (NEB), the second round nested PCR is performed and the PCR products are sequenced directly.

Soft agar colony formation assay. A standard two-layer soft agar culture was performed with a bottom layer of 0.7% agarose and top layer of 0.35% agarose. Five hundred cells per well in 6-well plates were seeded with warm top agar and were incubated for three weeks. Plates were then stained with 0.005% Crystal Violet for 1 hour, and colonies were scored with aid of microscope. For resistance assay in soft agar, one million cells were added per well and imatinib (STI-571) or 6-TG added to both top and bottom agar to their final concentrations. To clone or recover soft agar colonies for further analysis, individual colonies were plucked and expanded in liquid culture.

Cell cycle, cell proliferation and apoptosis analysis. Cell cycle was analyzed by fixing cells with 70% ethanol at −20° C. overnight. After washing, cells were resuspended in phosphate-buffered saline containing 1 mg/ml RNase A, incubated for 30 min at 37° C., and then stained with propidine iodine (50 µg/ml) for 30 min at room temperature before flow cytometry analysis. Cell proliferation was analyzed using a XTT Cell Proliferation kit (Roche Applied Science), and apoptosis was analyzed with annexin V kit (BD Pharmingen) as per the manufacturer's instruction.

Spectral Kayotyping and Fluorescent in Situ Hybridization (FISH) Analysis. For spectral karyotyping analysis, 10 mitotic cells of each sample were analyzed, 5 by GTG-band analysis and 5 by 24-color karyotyping. Triple-color FISH was performed with LSI ABL1/AASS (9q34.1)/BCR (22q11.2) probes (Vysis, Inc.) (Huntly et al. 2003), and 200 cells of each sample were evaluated. These assays were done by City of Hope Cytogenetics Core Laboratory.

Sequencing ABL kinase domain and HPRT (hypoxanthine phosphoribosyl transferase). The ABL kinase domain (ABL-k) was amplified by RT-PCR of total RNA or by PCR of genomic DNA with a high fidelity DNA polymerase (Strategene) using the primers for the 579 bp kinase domain using cDNA templates shown below as previously described (Gorre et al., 2001).

```
ABL-k Forward primer:
5' GCGCAACAAGCCCACTGTCTATGG 3'   (SEQ ID NO: 1)

ABL-k Reverse primer:
5' GCCAGGCTCTCGGGTGCAGTCC 3'     (SEQ ID NO: 2)
```

To confirm mutations, the ABL kinase domain was also amplified by PCR using genomic DNA as templates with the intron primers below which span ABL exon 6 for T315I mutation (T315I), and intron primers below, which span ABL exon 5 for E255K and Y253H mutations (E255K/Y253H).

```
T315I Forward primer A:
5'-GCAGAGTCAGAATCCTTCAG-3'     (SEQ ID NO: 3)

T315I Forward primer B:
5'-GAGCCACGTGTTGAAGTCCT-3'     (SEQ ID NO: 4)

T315I Reverse primer:
5'-TTTGTAAAAGGCTGCCCGGC-3'     (SEQ ID NO: 5)

E255K/Y253H Forward:
5'-GCCTGTCTCTGTGGGCTGAAG-3'    (SEQ ID NO: 6)

E255K/Y253H Reverse:
5'-TAATGCCAGCAGACGCCTTG-3'     (SEQ ID NO: 7)
```

PCR products were cloned into the pCR2.1 vector using TOPO TA Cloning kit (Invitrogen). At least ten clones for each treatment were sequenced by Sequencing Facility of Beckman Research Institute. For analysis of genomic DNA mutations PCR products were directly sequenced without subcloning. For HPRT sequencing, the codon sequence was amplified by RT-PCR using primers previously described (Osterholm et al. 1995). PCR products were purified with a PCR product clean-up kit (Qiagen) and sequenced directly. Reverse transcription-PCR for sequencing BCR-ABL oligomerization and Src homology 3/2(SH3/2) domains was also performed. For sequencing the BCR-ABL SH3/2 domain, primers described previously (Ray et al. 2007) were used. For the oligomerization domain, the following primers (BCR-ABL-oligo) were used.

```
BCR-ABL-oligo Forward:
5'-GAGTGGGCGGGCATTGTTC-3'      (SEQ ID NO: 8)

BCR-ABL-oligo Reverse:
5'-GGGACTTTTTGCGCTCCATCT-3'    (SEQ ID NO: 9)
```

For sequencing HP RT, the codon sequence was amplified by reverse transcription-PCR using the primers below:

```
HPRT Forward:
5'-ACCGGCTTCCTCCTCCTGAG-3'     (SEQ ID NO: 10)
```

```
Forward (1a):
5'-GGACGGACCAGCAGGACA-3'       (SEQ ID NO: 14)

Reverse (Exon 2):
5'-GCGCTGGTTGTTGAGCTG-3        (SEQ ID NO: 15)
```

-continued
```
HPRT Reverse:
5'-GATAATTTTACTGGCGATGT-3'     (SEQ ID NO: 11)
```

Other Primers. Primers described above and elsewhere in the specification are as follows:
Nested RT-PCR from BCR-ABL junction:

```
Forward:
5'GAAGCTTCTCCCTGACATCCGT       (SEQ ID NO: 12)
```

Additional primers for BCR-ABL kinase domain sequencing:

```
Forward primers:
GCCTGTCTCTGTGGGCTGAAG          (SEQ ID NO: 6)

Reverse primer:
CAAGGCGTCTGCTGGCATTA           (SEQ ID NO: 13)
```

Cell cloning by limiting dilution. Cells were counted and diluted to 5 cells per ml, and seeded onto 96-well plate with 100 μl (or 0.5 cell) per well. Individual cell seeding was then confirmed by microscopy, and single cell clones were grown and expanded for further analysis.

Immunoprecipitation. BCR-ABL expression and phosphorylation were directly analyzed by Western blot using anti-c-ABL monoclonal antibody (BD Pharmingen, 554148) and anti phospho-tyrosine antibody (Upstate Biotechnology, Inc., 05-321). To validate BCR-ABL phosphorylation, BCR-ABL from 500 μg of total cell lysate of KCL-22 cells was isolated with 2 μg of anti-c-ABL and 100 μl of 50% slurry of protein A-agarose beads (Upstate Biotechnology, Inc.). Alternatively, protein G-agarose beads or a mixture or protein A and G-agarose beads may be used for isolating BCR-ABL.

Western blot. For protein analysis by Western blot, the following antibodies are used: rabbit monoclonal anti-SIRT1 (1:5000, Epitomics), and anti-GAPDH (1:5000, Trevigen). Apoptosis analysis was performed using a TMR-red In situ Cell Death Detection Kit (Roche) as per manufacturer's protocol. Normal human lung lysate are purchased from ProSci.

Analysis of Reactive Oxygen Species (ROS) and DNA Damage. ROS was analyzed using redox-sensitive fluorochrome 2'.7'-dichlorofluorescein diacetate (Sigma) as described previously (Koptyra et al. 2006). When coupled with the apoptosis analysis, cells were labeled with annexin V first and then 2'.7'-dichlorofluorescein diacetate. An H2AX phosphorylation assay kit (Millipore, 17-344) was used to analyze DNA damage by flow cytometry as per the manufacturer's suggestions.

Gene expression analysis. Total cellular RNA with Trizol (Invitrogen) using a standard protocol. First strand DNA was synthesized and HIC1 expression by quantitative real-time RT-PCR using a kit with SYBR Green label (Invitrogen) as per the manufacture's instruction on a BioRad machine OPTICON. The following are the HIC1 primers (spanning introns), 5'-GGACGGACCAGCAGGACA-3'(exon 1a) and 5'-GCGCTGGTTGTTGAGCTG-3' (Exon 2). [>ref|NT_010718.15|Hs17_10875:1561637-1565694 *Homo sapiens* chromosome 17 genomic contig, reference assembly]

SIRT1 expression was analyzed by Western blot using 1:5000 diluted rabbit monoclonal SIRT1 antibody (Epitomics). Controls used were GAPDH or actin as loading controls with rabbit anti-GAPDH (Trevigen) or anti-actin (Sigma) at 1:5000 dilution. GAPDH [>ref|NT_009759.15|Hs12_9916:6497433-6502281 *Homo sapiens* chromosome 12 genomic contig, reference assembly] primers used are as follows:

```
Forward:
5'-GGAAGGTGAAGGTCGGAGTC-3'     (SEQ ID NO: 16)

Reverse:
5'-TTCCCGTTCTCAGCCTTGAC-3'.    (SEQ ID NO: 17)
```

Production of lentiviral vectors. For production of lentiviral vectors, four million 293T cells are co-transfected with 15 μg of the vector, 15 μg of gag-pol, 5 μg of VSV-G, and 5 μg of Rev plasmids by the method of calcium phosphate co-precipitation (Kowolik, C. M., P. Yam, Y. Yu, and J. K. Yee. 2003. HIV vector production mediated by Rev protein transduction. *Mol Ther* 8:324-331). The supernatant is collected at 24 hours and 36 hours after transfection. The supernatants are pooled and passed through a 0.45 um filter, concentrated by ultracentrifugation. To determine vector titer, $1 \times 10^5$ 293T cells are seeded in a six-well plate in the presence of 4 mg/ml polybrene, and cells are transduced for 5 hours and analyzed by FACS for GFP expression within 24 hours.

shRNA Lentiviral Vectors and Gene Knockdown. Oligonucleotides for ABL shRNA (GTTGGTTCATCATCAT-TCA) (SEQ ID NO:29) were synthesized and cloned into the pSicoR vector (Ventura et al. 2004) that contains a selection cassette for puromysin by a standard protocol. A scrambled shRNA was subcloned into the vector as a mock control The VSV-G (G-protein of vesicular stomatitis virus) pseudotyped lentiviral vectors were produced using a four-plasmid transfection system as described previously (Kowolik et al. 2003). High titer lentiviral stocks, typically 1 to $3 \times 10^7$ infectious units/ml, were used for the studies with multiplicity of infection (MOI) around 5. For SIRT1 knockdown in transformed CD34$_+$ cells, SIRT1 shRNA sequences were cloned into the HIV7-SF-RFP lentiviral vector. MIG210 or MIGR1(GFP)

and shRNA (RFP) double transduced cells were sorted by flow cytometry for CD34+GFP+RFP+ for in vitro apoptosis and proliferation study described above. For BCR-ABL knockdown, one millions cells were infected overnight with recombinant lentivirus by multiplicity of infection of 3 each in the presence of 8 µg/ml Polybrene. Under this condition, the transduction rate in these cells was typically about 99%.

DNA damage assay. The assay was performed as described (Xiao et al., 2003). KCL-22 cells were pre-selected for four days in HAT medium to remove pre-existing HPRT mutations. The efficiency of HAT selection was confirmed by plating these cells on soft agar with 2.5 µg/ml 6-thioguanine, which produced zero colony. HAT-selected cells were then treated with 0.5 µM CPT for 1 hour and used for soft agar clonogenic assay with 6-thioguanine. The rest of HAT-selected cells were cultured in medium without selection. Soft agar colonies were scored after three weeks as described (Yuan et al., 2008).

BCR-ABL overexpression analysis. Amphotropic retroviral vectors for wild type p210 BCR-ABL, K1176R p210 mutant and the empty vector MIG R1 were produced using Phoenix-Ampho packaging cells (ATCC) and the transduction was carried out as previously described (Ramaraj et al., 2004; Pear et al., 1998). Briefly, KCL-22 cells were transduced with the aforementioned vectors at a multiplicity of infection of around 6. Cells were spin-infected by centrifugation at 1000×g for 90 min and then returned to the incubator and cultured overnight. After removing viruses, cells were expanded in culture for 5 days, and green fluorescent protein (GFP)-expressing cells were isolated by fluorescent-activated cell sorting (FACS). For second round transduction, FACS-enriched cells were re-infected with the above vectors using the same conditions. Genomic DNA sequencing analysis of imatinib-resistant soft agar colonies was performed using the intron primers for the T315I mutation on the endogenous BCR-ABL locus and exon primers for 579-bp transduced BCR-ABL cDNA as described above. To increase PCR efficiency on the transduced BCR-ABL cDNA, another reverse primer (5'-TAGTCCAGGAGGTTCCCGTAG) (SEQ ID NO:21) was used to pair with the same exon forward primer used for 579-bp cDNA, which produced a 321-bp PCR product.

Real-time PCR for gene amplification and expression analysis. Quantitative real-time PCR was performed with SuperScript III platinum two-step qRT-PCR kit with SYBR Green (Invitrogen) as per the manufacturer's instruction on the BioRad machine OPTICON. For BCR-ABL RNA analysis, we extracted total cellular RNA with Trizol (Invitrogen) using a standard protocol. The primer pairs for ABL genomic DNA analysis were 5'-GCCTGTCTCTGTGGGCTGAAG-3' (SEQ ID NO:6) and 5'-CAAGGCGTCTGCTGGCATTA-3' (SEQ ID NO:13); primers for BCR-ABL RNA analysis were 5'-CGTGCAGAGTGGAGGGAGAAC-3' (SEQ ID NO:30) and 5'-GCATCTGACTTTGAGCCTCAGG-3' (SEQ ID NO:31). PCR cycling conditions were: 94° C. 5 min followed by 94° C. 30s, 60° C. 30s, 55° C. 30s for 40 cycles.

Fluorescent allele-specific oligonucleotide-polymerase chain reaction (ASO-PCR) assay. A fluorescent ASO-PCR was carried out as previously described, with modifications. Purified T315I-positive RNA from T315I BCR-ABL cells was diluted with T315I-negative RNA to 1:10, 1:100 and 1:1000, and all RNAs were reverse transcribed using random hexamers and SuperScript III kit (Invitrogen). PCR was carried out with 1 µl of RT reaction each with optimal conditions of 45 cycles and 60° C. annealing temperature. The primers for ASO-PCR are as follows: forward outer primer 5'-CGTGAAGACCTTGAAGGAGGACACCATG-3' (SEQ ID NO:32), reverse outer primer 5'-FAM-TTCTCCAGGTACTCCATGGCTGACGAGA-3' (SEQ ID NO:33), reverse T315I mutation primer 5'-FAM-TCCAGGAGGTTCCCGTAGGTCATGAACTAAA-3' (SEQ ID NO:34), forward primer 5'-CCCGGGAGCCCCCGTTCTATATCATAAC-3' (SEQ ID NO:35). PCR products were diluted and run on ABI 3100 Genetic Analyzer (Applied BioSystems). Care was taken to avoid contamination by performing PCR reactions in a separate room from that for nucleic acid extraction and PCR product electrophoresis, and personal return to PCR reaction room in the same day is prohibited after he handles nuclei acid extraction and electrophoresis.

Bidirectional Pyrophosphorolysis-Activated Polymerization Allele-Specific Amplification (Bi-PAP). Bi-PAP assay was performed as previously described[2] with the primer pairs (T3151-F*: 5'-GGAGCCCCCGTTCTATATCATCAddT-3'; SEQ ID NO:36) and T3151-R*: 5'-AGGTTCCCGTAGGTCATGAACTCAddA-3'; SEQ ID NO:37) and PAPase (all purchased from BioVision USA). The PCR cycling conditions were: 1 cycle of 95° C. 60 s, 60° C. 30 s, 62° C. 30 s, 68° C. 45 s and 72° C. 45 s followed by 40 or 50 cycles of 95° C. 30 s, 60° C. 30 s, 62° C. 30 s, 68° C. 40 s and 72° C. 5 min. Similar to ASO-PCR, Bi-PAP reactions were performed in a separate room from that for nucleic acid extraction and PCR product analysis.

Treatment of KCL-22 Cells with 2.5 uM STI-571 or Higher Leads to Relapse and Formation of KCL-22M Cells Having a T315I Mutation.

In contrast to the in vivo resistance observed in blast crisis CML patients treated with STI-571, CML cell lines derived from blast crisis patients are sensitive to STI-571 treatment. STI-571 at 1 µM selectively kills CML cells in BCR-ABL dependent manner with the exception of KCL-22 cells, whereas 10 µM STI-571 can result in non-specific cell killing. In chronic phase CML patients, STI-571 is given at 400 mg/day that produces the average peak plasma concentration at 4.4 µM and trough concentration at 2.0 µM. For blast crisis patients, STI-571 dosage is increased to 600 mg/day. Therefore, effects of imatinib concentrations at 1, 2.5, 5 and 10 µM were examined on the survival of KCL-22 cells during prolonged culture.

$5 \times 10^5$ KCL-22 or K562 cells were seeded in 1 ml medium per well in 24-well plates, and treated with various combinations of drugs. Cells were maintained in these cultures without changing medium. Aliquots of cells were taken out at specified time points and cell numbers counted using a hematocytometer. Cell viability was accessed by trypan blue exclusion where necessary. Typically, after three to five weeks in culture when medium volume significantly decreased, fresh drug-free medium was supplied to the cells to restore the wells to the original volume for prolonged culture.

Figure 3:
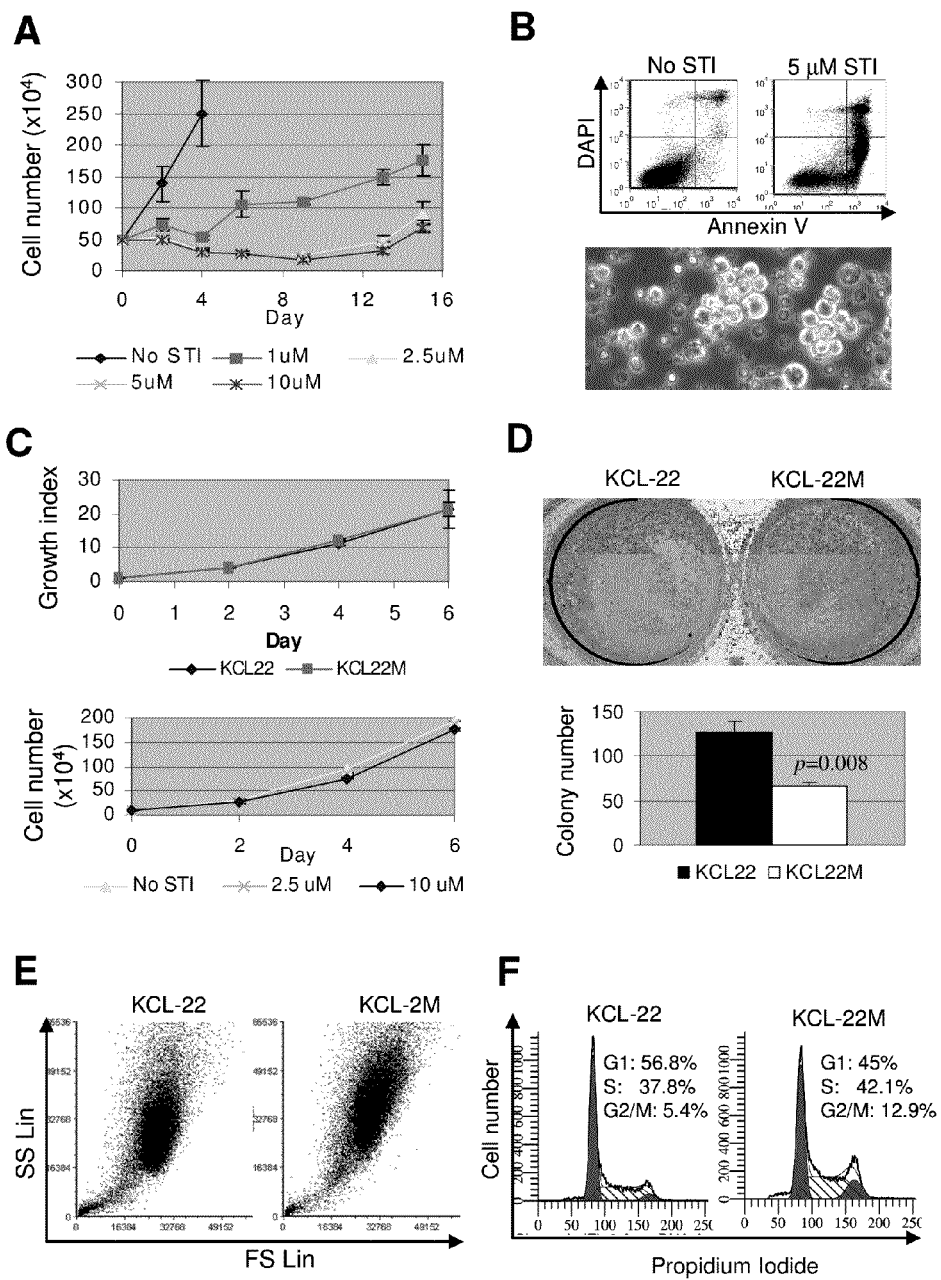
FIG. 3 shows a model of CML acquired resistance. (A) KCL-22 cells treated with 1, 2.5, 5, and 10 μM imatinib (STI), then survival cells were counted at days after treatment, as indicated. Relapse on 2.5 μM and higher concentrations of imatinib two weeks post treatment. (B) Top: apoptosis of KCL-22 cells after treatment with imatinib was analyzed by annexin V staining. Bottom: formation of clusters of resistant cells (light) among scattered dead cells (dark). (C) Top: growth curves for resistant cells (KCL-22M) and KCL-22 cells analyzed by XTT. Growth indexes were relative XTT readings normalized to the initial XTT readings at day 0. Bottom: comparison of growth of KCL-22M cells in the absence and presence of imatinib. (D) Soft agar colony formation of KCL-22 and KCL-22M cells. (E) Comparison of cell size and complexity of KCL-22 and KCL-22M cells. KCL-22M cells exhibited increase at both forward scatter (FS) and side scatter (SC) parameters. (F) Comparison of cell cycle of KCL-22 and KCL-22M cells with propidium iodide (PI) staining.

It was found that KCL-22 cells were insensitive to 1 µM STI-571 treatment as they continued to grow but at a lower rate than in the absence of the drug. STI-571 at 2.5 µM and above effectively suppressed cell growth and induced partial cell death over time (FIG. 3A). Small clusters of cells formed after about 10 days in treatment groups with 2.5 µM and above of STI-571 and these cells appeared visibly larger with frequent bizarre shapes (FIG. 3B). After two weeks they repopulated the culture, indicating the relapse on the drug treatment. These emerging cells, named KCL-22M, grew equally well as KCL-22 cells, and no longer responded to presence of imatinib in the medium (FIG. 3C). They formed fewer and smaller soft agar colonies (FIG. 3D). The abnormal size and shape of KCL-22M cells were confirmed by flow cytometric analysis, showing increase on both forward scatter (for size) and side scatter (for complexity) (FIG. 3E). KCL- 22M cells also exhibited different cell cycle status from KCL-22 cells by increasing S/G2 population (FIG. 3F).

Figure 21:
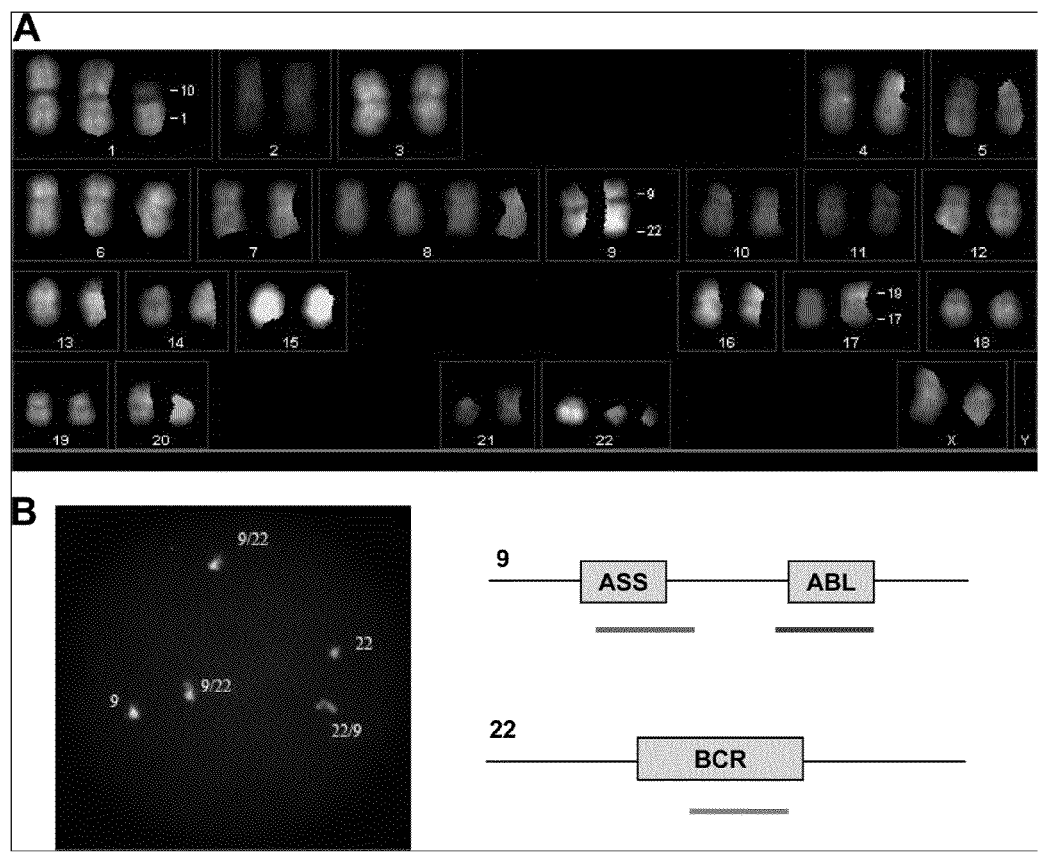
FIG. 21 illustrates cytogenetic characteristics of KCL-22M cells. (A) Karyogram of 24-color spectral karyotyping. The composite karyotype is 51,X,del(X) (p11.2p22.3), +der (1;10)(q10;p10), +6, +8, +8,t(9;22) (q34.1;q11.2),der(17;19) (q10;q1), +19,i(21)(q10), +der(22),(9;22). (B) Representative three-color FISH of BCR-ABL (left). Two Philadelphia chromosomes (9/22) were present in all cells. The code for FISH probes. ASS, argininosuccinate synthetase gene is shown on the right.

Molecular characterization of KCL-22M cells was also performed. The KCL-22 cells were resistant to imatinib treatment. By spectral karyotyping and FISH analyses, it was found that KCL-22M cells maintained the same cytogenetic profile as KCL-22 cells, i.e., 51,X,del(X)(p11.2p22.3), +der(1;10)(q10;p10), +6,+8,+8,t(9;22) (q34.1;q11.2), der(17;19)(q10;q10),+19,i(21)(q10), +der(22)t(9;22), and carried two Philadelphia chromosomes in all cells examined (FIG. 21). This cytogenetic data was in line with previously reported karyotype for KCL-22 cells (Kubonishi et al., 1983; Rosenhahn, et al. 2007). In contrast to another KCL-22 cell-derived imatinib-resistant cell line (KCL-22R) that had additional translocations (Rosenhahn, et al. 2007), no novel chromosomal rearrangements were shown in KCL-22M cells. Using real time PCR, the ABL DNA content and BCR-ABL RNA level in KCL-22M cells remained the same as in KCL-22 cells (FIG. 41).

Figure 4:
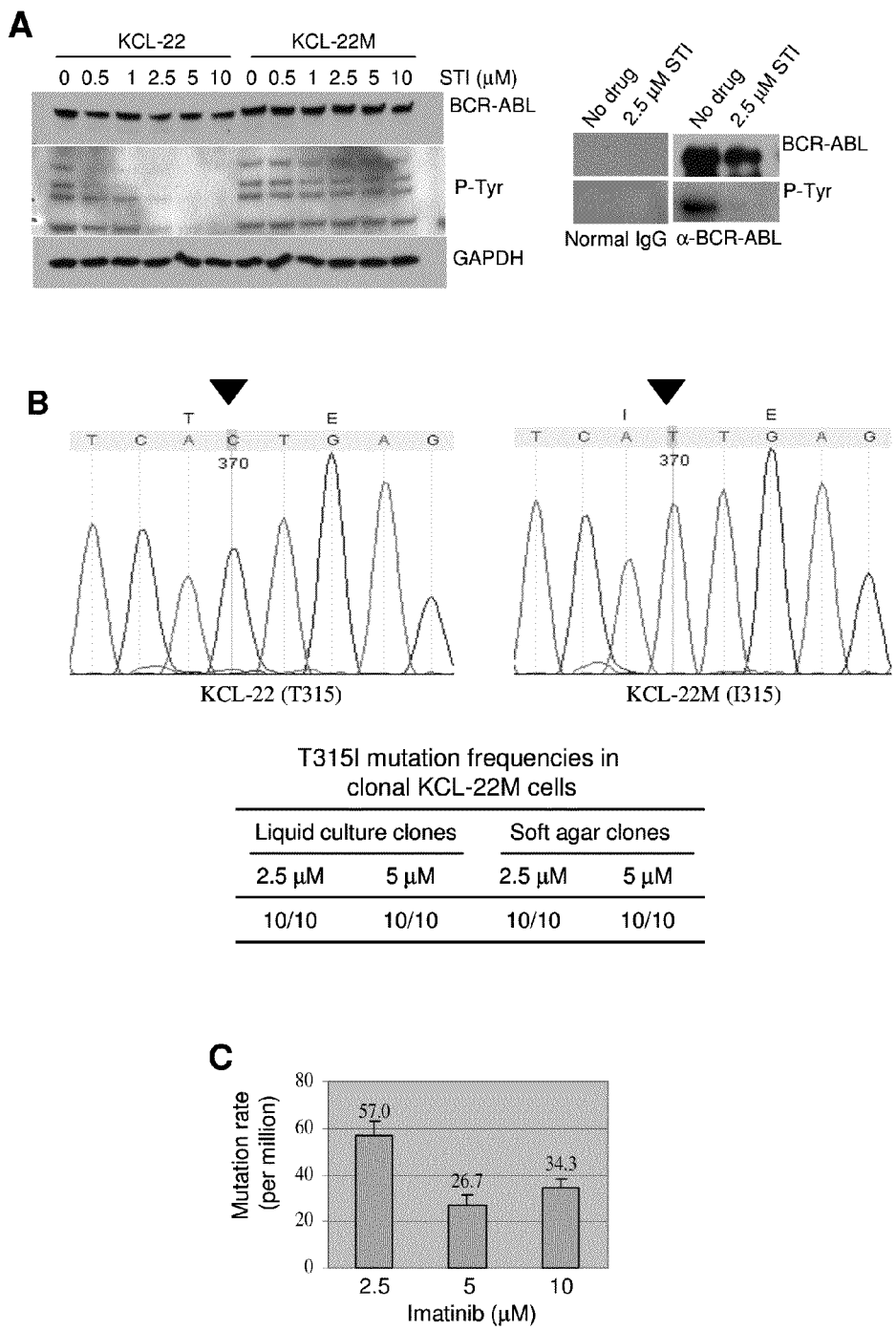
FIG. 4 shows the molecular characterization of a CML resistance model. (A) Left: Western blot analysis of BCR-ABL expression and phosphorylation in KCL-22 and KCL-22M cells with and without imatinib treatment. The top band (arrow) detected by the tyrosine phosphorylation antibody corresponds to the position of BCR-ABL. Right: immunoprecipitation of BCR-ABL in KCL-22 cells followed by Western analysis for expression and phosphorylation. (B) Left: sequencing analysis of BCR-ABL kinase domain with cDNA or genomic DNA from KCL-22 and KCL-22M cells. The point mutation of C to T (arrow heads) resulting in a T315I amino acid change. Right: sequencing of BCR-ABL kinase domain mutations in clonal cells. The table shows T315 mutation frequencies in clonal KCL-22M cells. (C) Is a bar graph illustrating the mutation frequencies of KCL-22 cells. One million KCL-22 cells were seeded on soft agar with the indicated concentrations of imatinib, and resistant colonies were scored after 3 weeks. Mutation rates with 5 μM and 10 μM imatinib were significantly lower than with 2.5 μM imatinib. p=0.003(5 μM); p=0.008(10 μM).

Imatinib effectively inhibited tyrosine phosphorylation by direct Western blot analysis of total cell lysate or immunoprecipitation of BCR-ABL protein (FIG. 4A). Tyrosine phosphorylation was not altered by imatinib treatment in KCL-22M cells (FIG. 4A). Since genetic mutations are predominant mechanisms for in vivo resistance of STI-571, it was examined whether mutations occurred in the KCL-22M cells. Both cDNA and genomic DNA were sequenced for BCR-ABL kinase domain using the strategies described by Gorre et al (2001). See, for example, FIGS. 18-19. In the 579-bp cDNA region of BCR-ABL kinase domain covering the ATP-binding pocket and activation loop, a single mutation (C to T nucleotide change that resulted in amino acid T315I mutation at ABL) was found in KCL-22M but not parental KCL-22 cells (FIG. 4B). This is the same mutation as identified in patients. The mutant clones represented 40% for 2.5 µM STI-571 or 30% for 5 µM STI-571 treatment in all clones sequenced respectively. Given that KCL-22 cells have a normal copy of ABL gene, which is also be amplified during RT-PCR, half of clones are expected to be wild type. Therefore, the results show that at least 60 to 80% of KCL-22M clones may carry T315I mutation. Sequencing of genomic DNA further confirmed such a mutation. To search for mutations on other BCR-ABL domains important for its kinase activity, oligomerization and SH3/2 domains were sequenced (Zhao et al., 2002; Smith et al., 2003), but no additional mutations were identified. Even when the SH3/2 sequencing fragment was extended through most of the 579-bp kinase domain, only the T315I mutation was found. Because the T315I mutation is one of the most powerful mutations generated upon relapse in response to STI-571 treatment, this model encompasses the BCR-ABL mutagenesis observed in clinical relapse.

Figure 42:
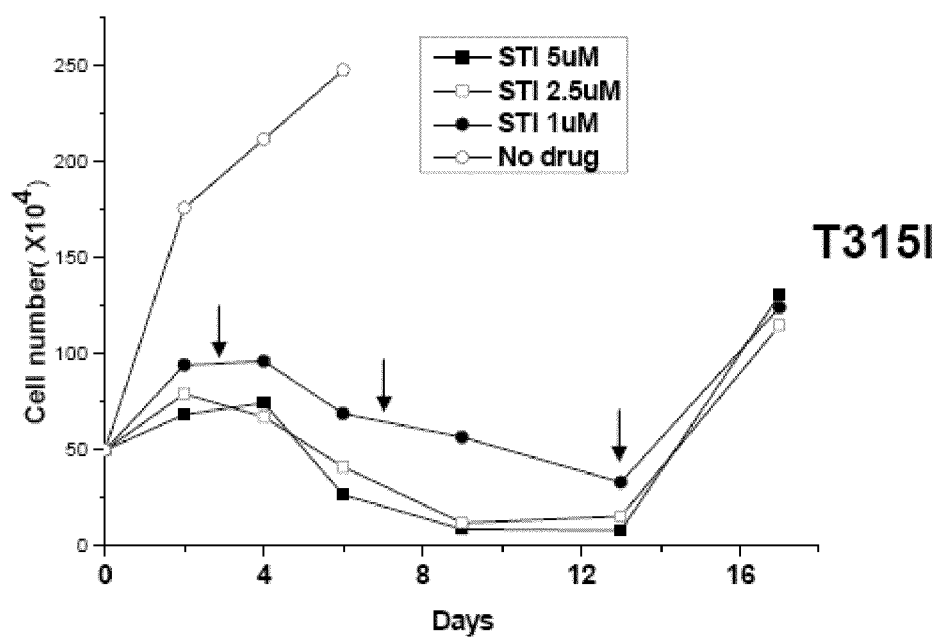
FIG. 42 illustrates a relapse time course of KCL-22 cells on repeated imatinib treatment. Following initial imatinib treatment, fresh imatinib was added at day 3, 7 and 11(indicated by arrows) by replacing the top half culture medium with the fresh medium. KCL-22 cells relapsed in similar time courses as in the treatment with a single dose of imatinib and developed T315I mutation as well.

To determine whether the KCL-22M cells were a mixture of T315I mutants and non-mutants, a limiting dilution was performed to obtain individual mutant cells from KCL-22M relapsed on 2.5 and 5 µM imatinib, respectively. Ten clones for each BCR-ABL mutation were sequenced using genomic templates. It was found that 20 clones carried the T315I mutation (FIG. 4B). Clonal resistant cells were separately derived by plating KCL-22 cells on soft agar with 2.5 or 5 µM imatinib and cell colonies were grown. After three weeks, resistance cell colonies were randomly picked and expanded for DNA sequence analysis. Twenty clones (10 from each concentration of imatinib) carried the T315I mutation (FIG. 4B). KCL-22 cells at various passages relapsed on imatinib and all recurrent cells had the T315I mutation. KCL-22 cells were also found to relapse in similar time courses with repeated doses as with a single dose (FIG. 42). These results indicate that KCL-22 cells develop acquired resistance predominantly through the T315I BCR-ABL mutation.

T315I mutation rate. The T315I mutation rate was measured by plating KCL-22 cells on soft agar with imatinib. A standard two-layer soft agar culture was performed with bottom layer of 0.7% agarose and top layer of 0.35% agarose. One million cells per well in 6-well plates on warm top agar with imatinib in both top and bottom agar layers to their final concentrations were incubated for three weeks. Plates were then stained with 0.005% Crystal Violet for 1 hour, and colonies were scored with aid of microscope. The mutation rate with 5 and 10 µM imatinib was around $3\times10^{-5}$, and $5.7\times10^{-5}$ with 2.5 µM imatinib (FIG. 4C). The mutation rate in liquid culture was also measured by serial two-fold dilutions of KCL-22 cells followed by treatment with 5 µM imatinib. The lowest number of cells that consistently relapsed on imatinib was determined. The medium T315I mutation rate was about $1/12,500$ or $8\times10^{-5}$. This is in general agreement with the rate observed in soft agar analysis given that the plating efficiency for KCL-22 cells in soft agar was about 25%. These results indicate that imatinib treatment of KCL-22 cells results in acquired resistance through rare T315I mutation. This model encompasses a key BCR-ABL mutagenesis process that occurs in clinical relapse. This is the first CML resistance model through BCR-ABL mutations that can be rapidly reproduced within two weeks after exposing cells to in vivo effective concentrations of imatinib.

Figure 22:
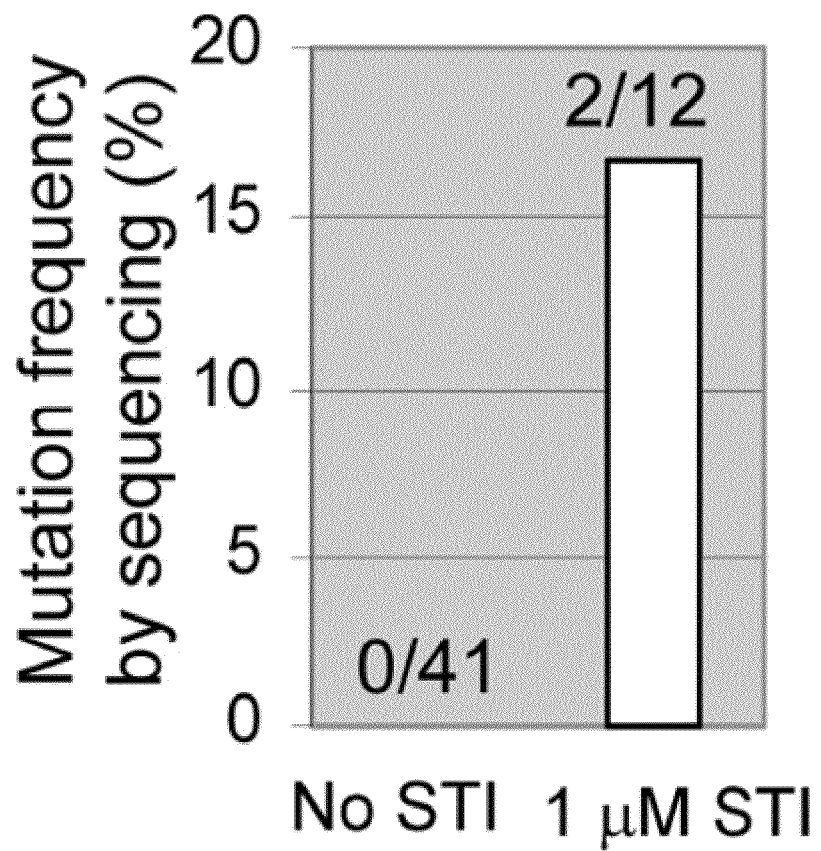
FIG. 22 is a bar graph illustrating mutation detection by conventional DNA sequencing. KCL-22 cells cultured without or with 1 μM imatinib for 2 weeks were analyzed. Forty one bacterial clones for untreated cells and 12 for treated cells were sequenced. Mutations were found in only two clones in the latter.

To determine whether there is a pre-existing T315I mutation in KCL-22, two sensitive methods were used to detect T315I mutations in cDNA (by allele-specific oligonucleotide-PCR) or genomic DNA (by bidirectional pyrophosphorolysis activated polymerization allele-specific amplification) from untreated KCL-22 cells: (1) a modified fluorescent allele-specific oligonucleotide-PCR assay (Willis et al., 2005) and (2) a bidirectional pyrophosphorolysis-activated polymerization allele-specific amplification assay (Shi et al., 2007). Both methods reliably detected at least 1% mutant allele, but no T315I mutation was found in KCL-22 cells (FIG. 43). The sensitivity of these methods could not be further increased without sacrificing specificity, and therefore such methods should not be used to completely rule out the existence of rare mutant cells in KCL-22 cells. However, after continuous culture of KCL-22 cells in a refractory dose of imatinib (1 µM) for 2 weeks, T315I mutation became readily detectable by conventional DNA sequencing (FIG. 22). Because T315I is the most resistant mutation for BCR-ABL inhibitors (Weisberg et al., 2005; von Bubnoff et al., 2006; Shah et al., 2004), this model encompasses one key BCR-ABL mutagenesis process in clinical relapse. However, directly exposing cells to mutation-inducing concentrations of imatinib did not work for CML cell lines K562 and KU812 that underwent rapid apoptosis as previously reported (Deininger et al., 1997). This is likely because the cells underwent apoptosis before BCR-ABL mutations could be fully developed. This method may be applied to other CML cell lines. Compared with the standard approach that requires the cells to be exposed to multiple rounds of gradually increasing concentrations of the drug for a period of several months, the culture model described herein offers a unique advantage in that BCR-ABL mutations can be rapidly produced within 2 weeks after a single exposure of cells to concentrations of imatinib that are effective in vivo.

Acquired Resistance of Clonal KCL-22 Cells is Through BCR-ABL Mutations.

In vivo, most BCR-ABL mutations are found in relapsed CML patients although pre-existing T315I mutation is detected in some CML patients before imatinib treatment (Shah et al., 2002; Soverini et al., 2006; Roche-Lestienne et al., 2002). Whether the pre-existing BCR-ABL mutant cells originating in the patient is a requirement for development of resistance was investigated. Individual KCL-22 cell clones were isolated by limiting dilution or soft agar plating without drug treatment. Eleven liquid culture clones (L1-L11) and thirteen soft agar clones (Ag1-Ag13) were expanded for analysis (Table 1, below). Most of the clones failed to relapse, but four relapsed in two weeks with high frequency at different concentrations of imatinib. These were clones L1, L7, Ag3 and Ag11(Table 1 and FIG. 5A). After sequence analysis of relapsed cells, it was determined that clone L1 relapsed on 2.5 and 5 µM with E255K BCR-ABL mutation; clone L7 relapsed on all doses of the drug with Y253H BCR-ABL mutation; clone Ag3 relapsed without BCR-ABL kinase domain mutations on 2.5 and 5 µM imatinib, but with T315I mutation on 10 µM imatinib; clone Ag11 relapsed with T315I mutation on 2.5 µM imatinib which is similar to parental cells (Table 1). In Table 1, no mutations have been detected in clones L1, L7, Ag3 and Ag11 before STI treatment. ND was not done. The asterisk indicates that there was relapse after 50 days and remaining sensitivity to 2.50 STI 571.

Figure 23:
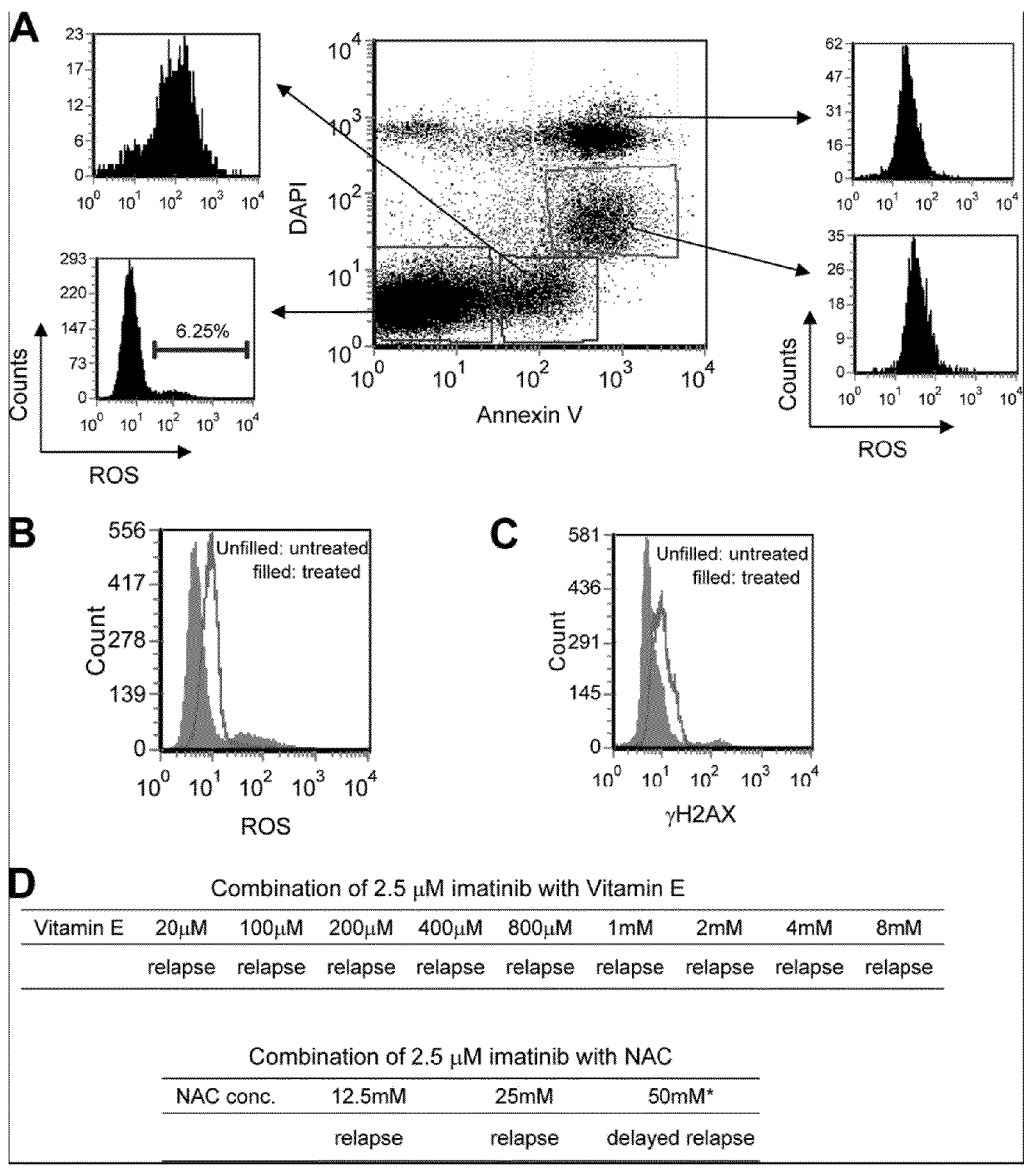
FIG. 23 illustrates ROS and DNA damage in KCL-22 cells upon imatinib treatment. (A) analysis of ROS in different apoptotic fractions of KCL-22 cells treated with 2.5 μM imatinib for 4 days. ROS increased in all apoptotic fractions of the cells with early apoptotic cells (top left square) having the highest level. Nonapoptotic fraction of the cells (bottom left square) had the lowest level of ROS. DAPI, 4',6-diamidino-2-phenylindole. (B) bulk ROS level decreased in nonapoptotic fraction of KCL-22 cells that were treated with 2.5 μMimatinib for 2 days. Similar results were seen for 1 day of drug treatment. (C) bulk γH2AX level decreased in KCL-22 cells treated with 2.5 μM imatinib for 2 days. (D) treatment with anti-oxidants. No effects of NAC or vitamin E were seen to prevent or delay KCL-22 cells from relapse on 2.5 μM imatinib except for 50 mM NAC that itself has significant cytotoxicity.

22 cells while ROS increased in the apoptotic fractions (FIGS. 23A and 23B). Accordingly, the bulk DNA damage analyzed by γH2AX staining decreased in the nonapoptotic fraction of cells (FIG. 23C). In previous experiments, 200 µM of the anti-oxidant vitamin E or N-acetylcysteine is able to reduce ROS and BCR-ABL mutations. However, in the studies described herein, even a 100× higher concentration of NAC (25 mM) or a 40× higher vitamin E (8 mM) failed to prevent imatinib-induced BCR-ABL mutations and relapse (FIG. 23D). These data reveal that BCR-ABL mutations in KCL-22 cells cannot be explained simply due to a change in ROS.

It was then determined whether BCR-ABL gene expression is required for its own mutations. KCL-22 cells express a e13a2 BCR-ABL fusion transcript, and the junction region sequence does not meet optimal shRNA design criteria (Reynolds et al., 2004). As previously reported (Li et al., 2003), shRNA that targets this region produced poor gene knockdown. Therefore a shRNA that targeted the ABL sequence was used (Zhelev et al., 2004) to knock down BCR-ABL. It was found that BCR-ABL knockdown rapidly inhibited proliferation and induced apoptosis of both KCL-22 and KCL-22M cells (FIG. 24A), showing continued dependence of

TABLE 1

Relapse and mutation analysis in clonal cells

| Clone | STI 2.5 uM Relapsed wells/ seeded wells | Mutation | STI 5 uM Relapsed wells/ seeded wells | mutation | STI 10 uM Relapsed wells/ seeded wells | mutation |
|---|---|---|---|---|---|---|
| L1 | 7/8 | E255K | 4/5 | E255K | 0/5 | |
| L2 | 0/6 | | 0/3 | | ND | |
| L3 | 0/6 | | 0/3 | | ND | |
| L4 | 0/6 | | 1/3 | No | ND | |
| L5 | 1/6 | G250E | 0/3 | | ND | |
| L6 | 0/6 | | 0/3 | | ND | |
| L7 | 8/8 | Y253H | 4/5 | Y253H | 4/5 | Y253H |
| L8 | 0/6 | | 0/3 | | ND | |
| L9 | 0/6 | | 0/3 | | ND | |
| L10 | 0/6 | | 0/3 | | ND | |
| L11 | 0/6 | | 0/3 | | ND | |
| Ag1 | 0/6 | | 0/3 | | ND | |
| Ag2 | 1/6* | ND | 0/3 | | ND | |
| Ag3 | 8/8 | No | 2/2 | No | 5/5 | T315I |
| Ag4 | 0/6 | | 0/3 | | ND | |
| Ag5 | 0/6 | | 0/3 | | ND | |
| Ag6 | 0/6 | | 0/3 | | ND | |
| Ag7 | 1/6 | No | 0/3 | | 0/3 | |
| Ag8 | 5/6* | ND | 0/3 | | 0/3 | |
| Ag9 | 1/6 | No | 0/3 | | 0/3 | |
| Ag10 | 0/6 | | 0/3 | | ND | |
| Ag11 | 8/8 | T315I | 2/2 | ND | 5/5 | ND |
| Ag12 | 0/6 | | 0/3 | | ND | |
| Ag13 | 0/6 | | 0/3 | | ND | |

Figure 5:
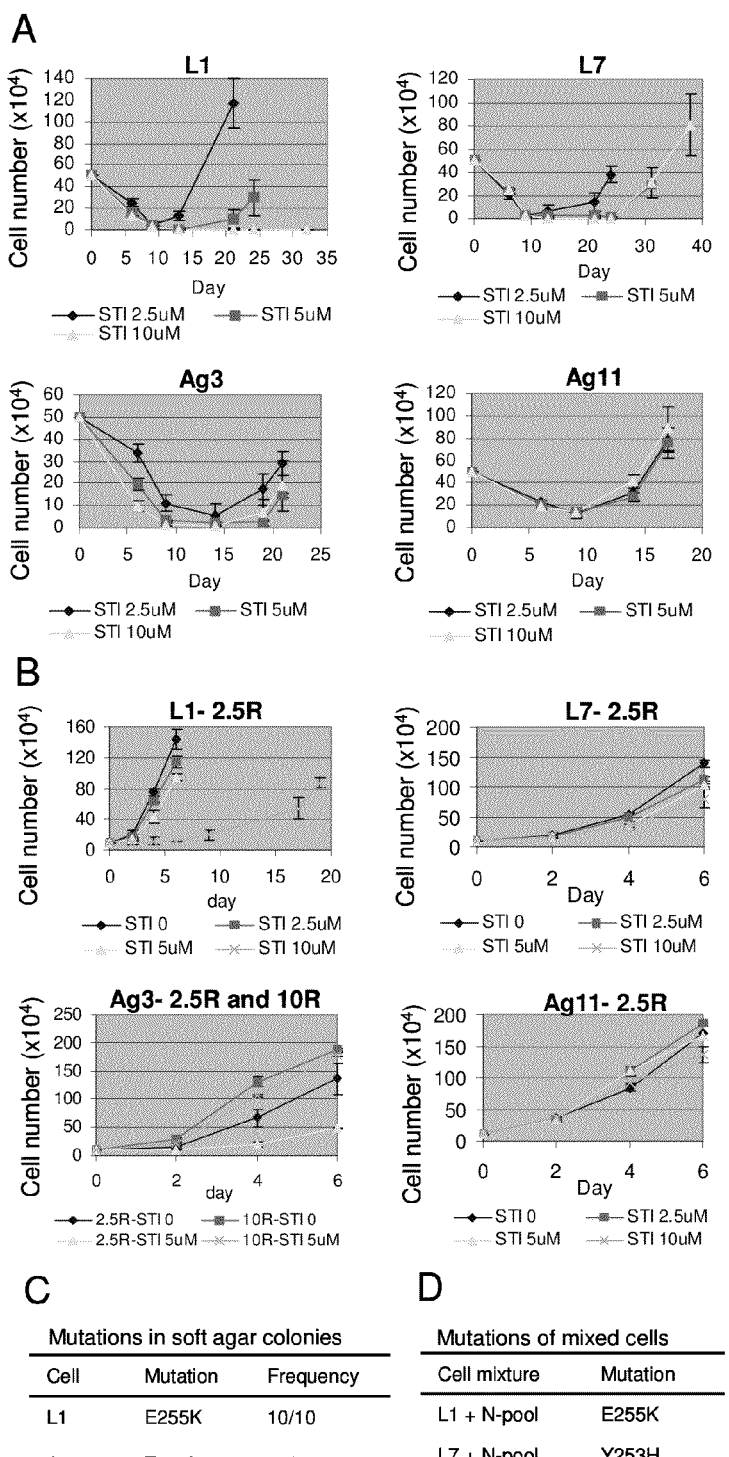
FIG. 5 shows acquired resistance of clonal CML cells on imatinib treatment. (A) Time course of relapse for four KCL-22 clones as analyzed in FIG. 3A. (B) Resistance of recurrent clonal cells to higher concentrations of imatinib. Recurrent cells derived from 2.5 μM imatinib treatment are labeled as 2.5R and recurrent Ag3 cells derived from 10 μM imatinib labeled as Ag3-10R. The different levels of resistance of L1-2.5R (E255K mutation), L7-2.5R (Y253H mutation) and Ag11-2.5R (T315I mutation) to the higher concentrations of imatinib. Growth of Ag3-2.5R (no mutation) was inhibited by 5 µM imatinib, but not for Ag-3-10R (T315I mutation). (C) Cells from clones L1 and Ag11 were plated on soft agar with 2.5 µM imatinib for three weeks and ten colonies each were picked for sequencing analysis of BCR-ABL kinase domain mutations. (D) Mutations from mixed clonal cells. Equal numbers of eight never-relapse clones were mixed to form a non-relapse pool (N-pool). Clone L1, L7 or Ag3 was then mixed 1:1 with N-pool respectively for resistance analysis in liquid culture, and recurrent cells were analyzed for BCR-ABL mutations. Similarly, equal numbers of clones L1, L7, Ag3 and Ag11 were mixed for resistance and mutation analysis.

These mutations conferred resistance of clonal cells to imatinib with T315I having the greatest protective effect against proliferation inhibition by high concentrations of the drug (FIG. 5B). Compared to parental cells, more BCR-ABL mutations emerged from these clones. The ability of these clones to develop resistance through BCR-ABL kinase domain mutations indicates that a pre-existing mutant cell originating from a patient is not required for resistance.

BCR-ABL Mutations are Dependent on BCR-ABL Gene Expression.

The effects of imatinib treatment on ROS and DNA damage was examined in the culture method system described above were examined. Following imatinib treatment, the bulk ROS level was reduced in the nonapoptotic fraction of KCL- BCR-ABL for proliferation and survival of BCR-ABL mutant CML cells. A lower apoptosis rate was observed in KCL-22M cells (FIG. 24A), indicating that cells acquire additional survival advantage during development of resistance. In contrast, a BCR-ABL-negative leukemia cell line HL-60 proliferation was not inhibited nor was apoptosis induced when ABL was knocked down, showing that effects in CML cells are BCR-ABL-specific.

Figure 24:
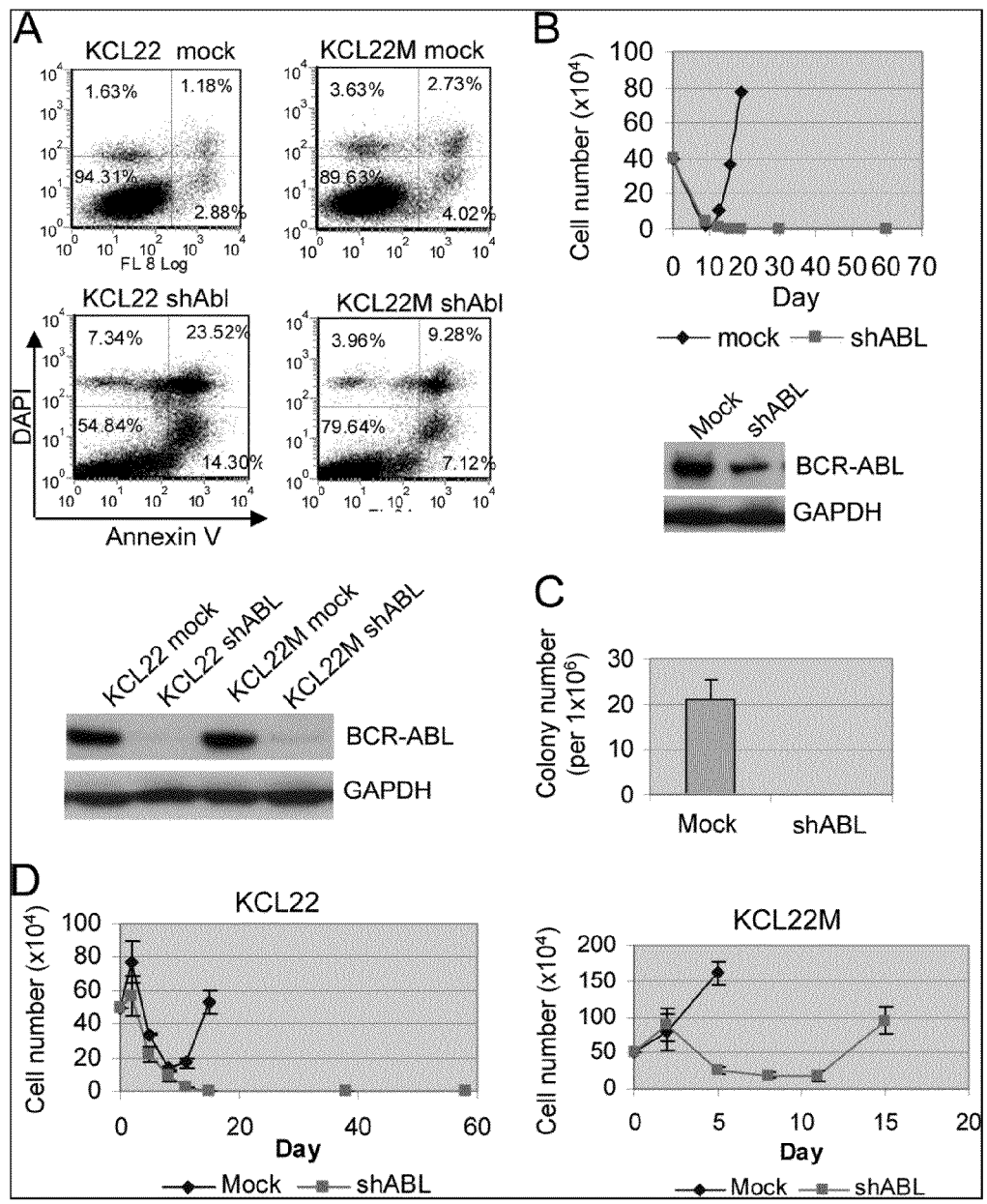
FIG. 24 illustrates the dependency of BCR-ABL mutation induction on BCR-ABL expression. (A) Top: analysis of apoptosis of KCL-22 and KCL-22M cells 6 days after BCR-ABL knockdown. Scrambled shRNA was used for mock knockdown. Fewer apoptotic cells were noticed in KCL-22M. Bottom: BCR-ABL protein levels after knockdown. DAPI, 4',6-diamidino-2-phenylindole; GAPDH, glyceraldehyde-3-phosphate dehydrogenase. (B) Top: effects of BCR-ABL knockdown on acquired resistance on imatinib. After the knockdown, cells regrew, and they were selected for 5 days in puromycin and expanded in drug-free medium. These re-grown BCR-ABL knockdown KCL-22 cells and mock knockdown cells were treated with 5 μM imatinib, and cells were followed as described in FIG. 3. Bottom: BCR-ABL levels in the re-grown knockdown cells. (C) effects of BCR-ABL knockdown on formation of imatinib-resistant colonies on soft agar. The re-grown BCR-ABL knockdown (shABL) or mock knockdown KCL-22 cells were plated on soft agar with 5 μM imatinib. The plating efficiency for mock and ABL knockdown was the same. (D) effects of combining BCR-ABL knockdown with imatinib treatment on acquired resistance. Cells were transduced overnight with lentiviral vectors, and imatinib was added right after the removal of viruses.

Both KCL-22 and KCL-22M cells with BCR-ABL knockdown re-grew after 2 weeks. BCR-ABL expression was partially restored in re-grown knockdown KCL-22 cells but remained at a lower level than in mock knockdown cells (FIG. 24B). When treated with imatinib, re-grown BCR-ABL knockdown KCL-22 cells failed to relapse in liquid culture or form imatinib-resistant colonies on soft agar (FIGS. 24B and 24C). Similarly, BCR-ABL knockdown immediately followed by imatinib treatment also blocked relapse in KCL-22 cells but failed to prevent KCL-22M cells from regrowing (FIG. 24D). Although the shRNA knocks down both ABL and BCR-ABL, loss of the DNA repair protein ABL would have been expected to further increase genetic mutation, which would contradict the above findings. Therefore, these unexpected results show that formation of BCR-ABL mutations is dependent on BCR-ABL gene expression and that combination of BCR-ABL knockdown and imatinib can block acquired resistance of KCL-22 cells on the drug.

Expression of Functional BCR-ABL from Endogenous BCR-ABL Locus for Acquisition of BCR-ABL Mutation.

To determine roles of BCR-ABL kinase activity for its mutation, wild type p210 BCR-ABL cDNA and K1176R p210 BCR-ABL mutant cDNA were overexpressed in KCL-22 cells. The mutant BCR-ABL has an abolished kinase activity (Ramaraj et al., 2004; Wertheim et al., 2002) or controls empty MIG retroviral vectors (Pear et al., 1998). The transduced cells were isolated by FACS for GFP expression. Overexpression of wild type BCR-ABL increased cellular phosphorylation, but overexpression of the mutant BCR-ABL did not reduce cellular phosphorylation (FIG. 25A), indicating that K1176R BCR-ABL is not a dominant negative mutant in these cells. Neither wild type nor mutant BCR-ABL expression changed cell growth or soft agar cloning efficiency (FIG. 44).

Figure 25:
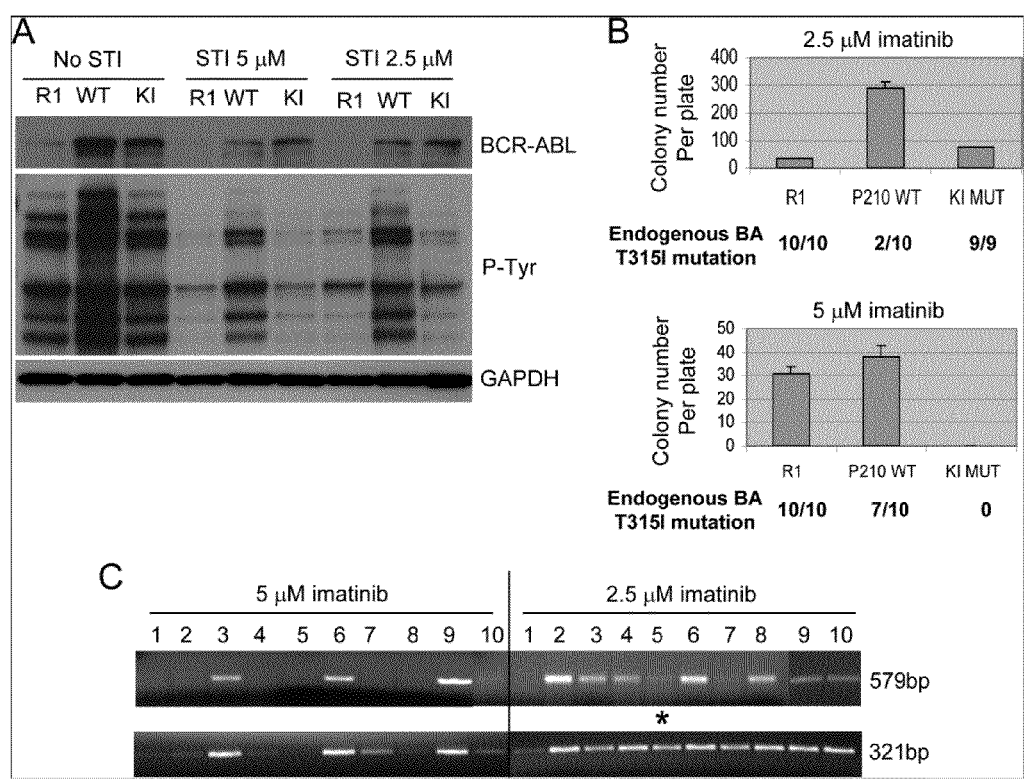
FIG. 25 illustrates the effects of BCR-ABL overexpression on mutations. (A) analysis of BCR-ABL expression and total cellular phosphorylation. KCL-22 cells were transduced with empty vector (R1), wild type p210 BCR-ABL (WT), or kinase-inactive p210 mutant (KI). Lysates were collected without or with 2.5 and 5 μM imatinib treatment. (B) clonogenic assay of BCR-ABL-overexpressing cells for imatinib resistance with 1,000,000 cells plated each well in triplicate. Imatinib-resistant colonies were plucked and expanded for genomic sequencing of the endogenous BCR-ABL (BA) kinase domain. The number of colonies found with T315I mutation over the total number of colonies sequenced is listed below each category of graph bars. (C) analysis of the transduced BCR-ABL cDNA in imatinib-resistant colonies overexpressing wild type BCR-ABL by PCR amplification of 579- and 321-bp fragments of BCR-ABL cDNA from genomic templates using exon primers. Both 579- and 321-bp fragments were sequenced. Only one colony, clone 5 from 2.5 μM imatinib treatment group (marked by an asterisk), had BCR-ABL mutation (T315I). Colonies with T315I mutation of the endogenous BCR-ABL were as follows: clones 1, 2, 4, 5, 7, 8, and 10 from 5 μM imatinib group, and clones 1 and 7 from 2.5 μM imatinib group.

When treated with 2.5 μM imatinib, wild type BCR-ABL-overexpressing cells developed significantly higher numbers of imatinib-resistant colonies than empty vector or mutant BCR-ABL-transduced cells, and the majority of resistant colonies (8 out of 10) from wild type BCR-ABL-overexpressing cells did not harbor the T315I mutation of the endogenous BCR-ABL (FIG. 25B). This indicated that the transduced BCR-ABL cDNA may function as BCR-ABL gene amplification for resistance. In contrast, all resistant colonies in the empty vector or mutant BCR-ABL-transduced cells harbored T315I mutation of the endogenous BCR-ABL (FIG. 25B).

When treated with 5 μM imatinib, resistance provided by wild type BCR-ABL cDNA was largely diminished, and the majority of resistant colonies (7 out of 10) from wild type BCR-ABL-overexpressing cells harbored T315I mutation of the endogenous BCR-ABL (FIG. 25B). Unexpectedly, under these conditions, mutant BCR-ABL completely blocked imatinib-resistant colony formation (FIG. 25B). Similar results were obtained when a second round of transduction was carried out using these vectors on the first round of GFP-enriched cells, aiming to further increase cDNA expression. These results indicate a role of BCR-ABL kinase activity for its mutation when cells are under treatment with a high concentration of imatinib. However, overexpression of mutant BCR-ABL did not enhance reduction of total cellular or a BCR-ABL substrate CRKL protein phosphorylation upon imatinib treatment (FIG. 25A). Therefore, functionally intact BCR-ABL may be important for generating mutations, but kinase activity may not be absolutely required.

BCR-ABL cDNA has been previously expressed in non-CML cells to generate random BCR-ABL mutations (5-7, 10-15) and is presumed to have similar mutagenesis capability. Mutations on the transduced wild type BCR-ABL cDNA were examined in KCL-22 cells. The transduced gene was distinguished from the endogenous BCR-ABL by using exon primers that span multiple introns for genomic DNA PCR and sequencing. All 20 imatinib-resistant clones from 2.5 and 5 μM drug treatment had visible GFP expression, indicating that they all carried functional transduced BCR-ABL cDNA. Clones that did not harbor T315I mutation of the endogenous BCR-ABL tended to have a higher yield of PCR products, revealing a higher copy number of the transduced BCR-ABL in these clones for resistance (FIG. 25C). Only one clone developed a BCR-ABL kinase domain mutation (T315I) on the transduced BCR-ABL among all 20 clones sequenced (FIG. 25C). Therefore, although the transduced BCR-ABL cDNA was capable of mutagenesis in KCL-22 cells, the mutation efficiency was significantly lower than that of the endogenous BCR-ABL (9 of 20 clones, p=0.008). This difference is not a result of experimental artifacts for the following reasons.

First, wild type BCR-ABL cDNA was transduced into KCL-22 cells using retroviral virions and would readily integrate into the genome of replicating KCL-22 cells. Nonintegrated viral DNA would have been lost during the lengthy procedure for expanding transduced cells before and after FACS sorting, colony formation of imatinib-resistant cells on soft agar, followed by expanding clonal cells in liquid culture for assay. The stable integration of the cDNA was also evidenced by nearly homogeneous GFP expression of the expanded clonal cells in liquid culture.

Second, mutations were analyzed within the clonal population of wild type BCR-ABL-transduced cells, and both endogenous and transduced alleles for each clone were analyzed and compared. This is an internally controlled comparison, and therefore mutation efficiency is not affected by external factors such as retroviral transduction efficiency.

Third, although KCL-22 cells have two translocation chromosomes, the lower mutation rate of transduced BCR-ABL cDNA is unlikely a result of lower copy number of the transduced BCR-ABL cDNA. The cDNA copy number may vary from clone to clone, but at least one copy of the cDNA is expected for each of 10 clones (clones 1, 2, 4, 5, 7, 8, and 10 under 5 μM and clones 1, 5, and 7 under 2.5 μM) that did not efficiently amplify the longer cDNA template (579 bp, FIG. 25C), whereas the other 10 clones would have higher copy numbers. However, the single clone that developed BCR-ABL cDNA mutation (clone 5 under 2.5 μM) carried a low copy number of cDNA. Accordingly, increasing cDNA copy number did not increase its mutation frequency. Together, these results show that the native BCR-ABL translocation locus in KCL-22 cells has inherently high mutagenesis potential, and expression of functional BCR-ABL from the locus promotes acquisition of BCR-ABL mutations.

Induction of BCR-ABL Mutations by Imatinib: BCR-ABL Versus HPRT Mutations.

Figure 6:
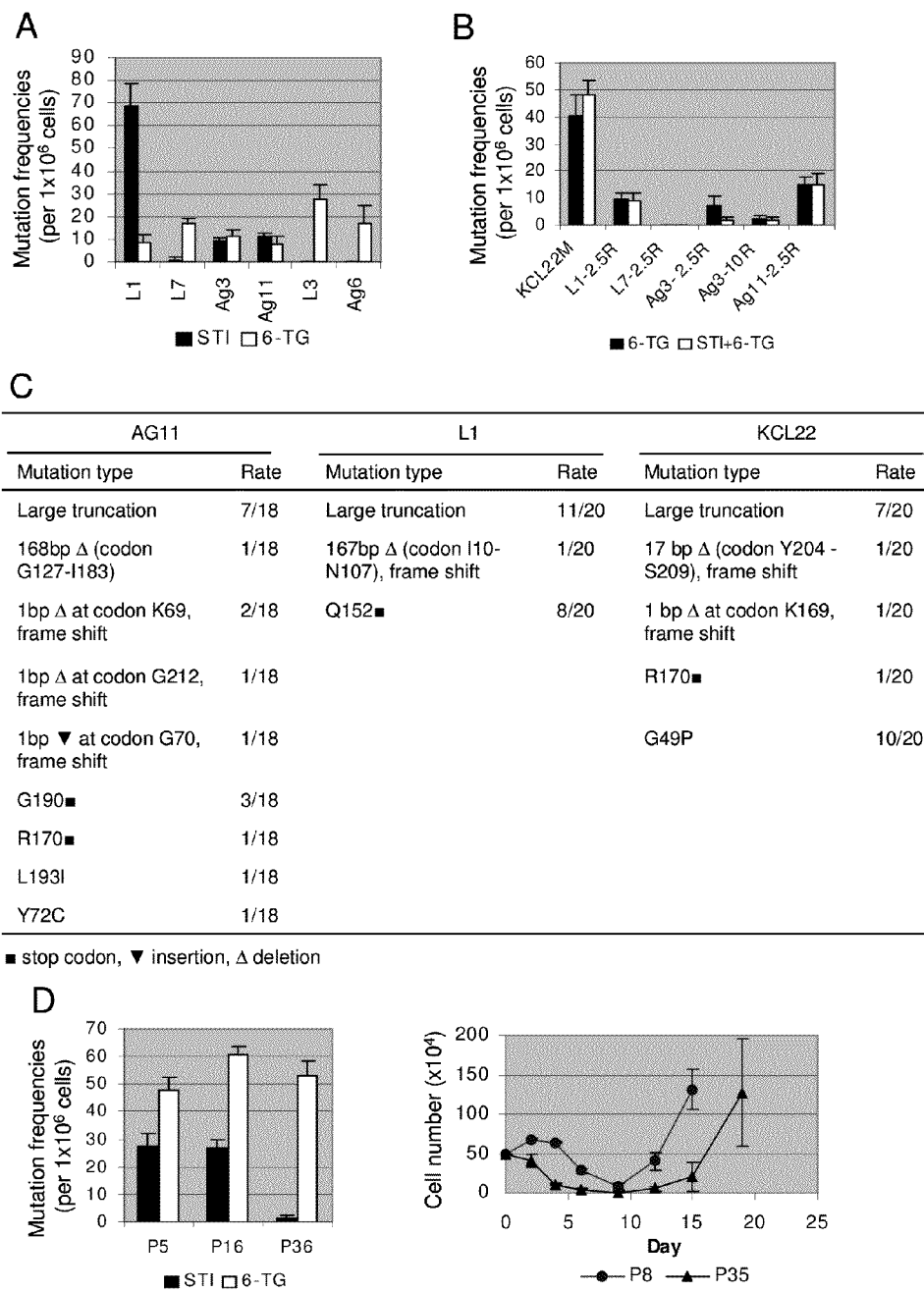
FIG. 6 shows induction of BCR-ABL mutations as compared to spontaneous HPRT (hypoxanthine phosphoribosyl transferase) mutations. (A) Comparison of BCR-ABL and HPRT mutation rates. Clone Ag3 developed imatinib-resistant colonies through non-BCR-ABL mutation mechanisms. (B) Effects of imatinib treatment on HPRT mutation rate. (C) HPRT mutation spectrum in clone Ag 11, L1 and parental KCL-22 cells. (D) Left: BCR-ABL and HPRT mutation rates of KCL-22 cells at passages 5, 16, and 36 measured by soft agar clonogenic assay. Imatinib, 5 µM; 6-TG, 2.5 µg/ml. Right: time courses for relapse of KCL-22 cells on 2.5 µM imatinib at passages 8 and 35.

Because blast crisis CML cells are genetically unstable, overexpression of BCR-ABL alters the fidelity of DNA double-strand break repair (Slupianek et al., 2006) and increases expression and activity of error-prone DNA polymerase which increases DNA replication error (Canitrot et al., 1999). Whether DNA replication error is a cause of rare mutations in clonal or parental cells during clonal expansion and cell propagation was assessed. BCR-ABL mutation rates versus spontaneous mutation rates introduced by DNA replication error were determined. The latter was measured by spontaneous mutations on the HPRT (hypoxanthine phosphoribosyl transferase) gene that resulted in cells resistant to 6-thioguanine (6-TG). As shown in FIG. 6A, BCR-ABL mutation rate was compared side by side with HPRT mutation rate in four relapse-prone clones (L1, L7, Ag3 and Ag11) and two never-relapse clones (L3 and Ag6). HP RT showed relatively constant mutation rate (0.8 to $2.5\times10^{-5}$) among all clones regardless of their ability to relapse, whereas BCR-ABL mutation rate was highly clone-dependent, from none (clone L3 and Ag6) to $7\times10^{-5}$. The stable HPRT mutation rate among clones reflects the nature of random mutations introduced by DNA replication error in these clones during clonal expansion, which appears different from BCR-ABL mutations that are highly clone-dependent.

Treatment of CML cell lines K562 and BV173 with low doses of imatinib for a short time will specifically induce DNA damage in these cells, but has no effect on non-BCR-ABL expressing leukemic or normal cells (Czechowska et al., 2005). Whether imatinib treatment increases HPRT mutation rate through elevating overall DNA damage level was determined. Since naïve CML cells cannot survive the prolonged culture required for a clonogenic assay, recurrent cells derived from parental and clonal cells were used for treatment with 6-TG and 2.5 µM. As shown in FIG. 6B, imatinib treatment did not alter overall DNA damage levels among these cells.

HPRT mutation types in 6-TG resistant cells were also examined. Loss of function for human HPRT has been well characterized with a broad mutation spectrum including large truncation, deletion, insertion and point mutations on codons (Burkhart-Schultz et al., 1996; Podlutsky et al., 1998). From DNA sequencing analysis of 6-TG resistant soft agar colonies derived from clones Ag11, L1 and parental KCL-22 cells, numerous HPRT truncation, deletion, insertion and point mutations were identified in all these colonies (FIG. 6C). This is consistent with previous observations (Burkhart-Schultz et al., 1996; Podlutsky et al., 1998). The broad spectrum of HPRT mutations differs from the single mutations seen for the above-described parental cells and clones indicating the possibility of a different mutagenesis pathway for BCR-ABL on imatinib.

The T315I mutation frequency in parental KCL-22 cells was stable in early passages (p8 and p16) but declined significantly in the late passage (p36) (FIG. 6D). Thus, the relapse of late-passage KCL-22 cells was delayed, although the recurrent cells still harbored T315I mutation. In contrast, HPRT mutation rates remained relatively constant even in the late passages of KCL-22 cells. This indicates that BCR-ABL mutations are actively induced by imatinib treatment.

Development of Different Mutations from Clonal Cells.

The development of different mutations from clonal cells was examined using the model system of the present disclosure. It was verified that the clonal cells did develop different mutations. L1 and Ag11 cells were plated on soft agar with 2.5 µM imatinib and ten imatinib-resistant colonies were isolated after three weeks. All resistant L1 colonies carried the E255K mutation only and all resistant Ag11 colonies carried the T315I mutation only (FIG. 5C), indicating clone-specific mutation patterns exist for resistance.

Whether the parental mutation type (T315I) could be restored in clonal cells when re-supplied with a culture environment with the mixture of clonal cells was determined. Clones L1, L7 or Ag3, respectively, were mixed with an equal number of cells from a pool consisting of eight never-relapse clones (N-pool). Identical mutation phenotypes were maintained for relapsed L1, L7 and Ag3 even after treatment with 2.5 or 5 µM imatinib (FIG. 5D). Whether T315I mutation dominates over other mutations for resistance development was also determined. Equal numbers of cells from clones L1, L7, Ag3 and Ag11 were mixed together and treated with imatinib. In recurrent cells from liquid culture, both E255K and T315I mutations were readily detected (FIG. 5D), which was consistent with the fact that L1 and Ag 11 were fast relapse clones whereas L7 and Ag3 had slower relapse time courses (FIG. 5A), indicating that T315I is not superior to E255K for imatinib resistance. Together, these data indicate a certain plasticity of mutagenesis process in CML cells that may allow induction of different mutations in clonal cells. This plasticity is particularly evident in clone Ag3 which exhibits concentration-dependent induction of T315I mutation at 10 µM imatinib. Mutation phenotypes of some clonal cells are distinguished from that of parental cells and become clone-dependent. Such results evidence that each clone adapts to a stable resistance mechanism.

The limitation of BCR-ABL mutations to certain clonal cells prompted further examination into whether the ability to form BCR-ABL mutations is restricted to a rare subpopulation of cells such as stably formed mutant cells or "premutant" cells that are not yet mutated but destined to form mutations. Cell pool analysis was performed by evenly dividing (by volume) $1\times10^5$ KCL-22 cells (calculated 25 mutants under 5 µM imatinib) into 24 wells, with an average of calculated 1 mutant cell per well, and the cells grew for 10 days in the absence of imatinib. If mutant cells were fully derived from a fixed mutant subpopulation, they would have been randomly seeded into wells according to Poisson distribution. Therefore, at least one mutant or pre-mutant cell would have been expect to be in each of the 15 wells. After 10 days, cells in all wells exhibited similar growth and reached an average of $1.8\times10^6$ cells per well. All cells in each individual well were then analyzed for imatinib-resistant clones by clonogenic assay with 5 µM imatinib. Only 3 of the 15 wells produced resistant colonies (p=0.0008) (Table 2). Even if it was assumed that all mutants or pre-mutants happened to be seeded into these three wells (an unlikely event), enrichment of mutant or pre-mutant cells should have been seen in these three wells. However, an increased mutation frequency was not observed (Table 2).

TABLE 2

Cell pool analysis of BCR-ABL mutant cells with pre-expansion Expected number of wells receiving mutant cells was calculated by assuming stable "pre-existing" mutant cells were randomly distributed according to Poisson distribution.

| | |
|---|---|
| Starting KCL-22 cell number | $1 \times 10^5$ |
| Number of wells that cells were seeded | 24 |
| Calculated mutant cell number/well | 1 |
| Expected number of wells receiving mutant cells (total number of wells) | 15 (24)[a] |
| Average cell number/well after 10-day expansion | $1.8 \times 10^6$ |
| Actual number of resistant colonies under 5 µM imatinib detected for cells from each well (number of wells) | 1 (1) |
| | 2 (1) |
| | 51 (1) |
| | 0 (21) |
| Actual number of wells having mutant cells (total number of wells) | 3 (24)[a] |
| p value for expected versus actual number of wells having mutant cells | 0.0008 |

[a]The assumed mutant frequency under 5 µM imatinib was $2.5 \times 10^{-4}$ as described in the text or 25 cells in $1 \times 10^5$ KCL-22 cells. p value was calculated with two-tailed Fisher exact test.

To validate this finding, another cell pool assay was performed by evenly dividing $1\times10^5$ KCL-22 cells (calculated 48 mutants under 2.5 µM imatinib) into 40 wells in the presence of 2.5 µM imatinib, an average of 1.2 mutant cell per well. Similarly, 20 KCL-22M cells were evenly divided into 20 wells in the presence of 2.5 µM imatinib. By Poisson distribution, 28 wells should have received mutant or pre-mutant cells for KCL-22 plating, and 12 wells should have received cells for KCL-22M plating. However, only one well of KCL-22 cells relapsed and re-grew. In contrast, five wells of KCL-22M cells re-grew (p=0.006) (Table 3). These data indicate that most BCR-ABL mutant cells found in KCL-22 cells upon imatinib treatment are unlikely to have been derived from a fixed mutant or pre-mutant subpopulation, although the presence of a small portion of pre-existing mutant cells can not be completely ruled out. Together with the cell cloning analysis, these results indicate that the emergence of BCR-ABL mutations may be a dynamic process influenced by culture and environmental conditions.

TABLE 3

Cell pool analysis of BCR-ABL mutant cells without pre-expansion Expected number of wells receiving mutant cells was calculated by the same assumption of Table 2. The assumed mutant frequency under 2.5 μm imatinib was $4.8 \times 10^{-4}$ as described in the text or 48 cells in $1 \times 10^5$ KCL-22 cells. The re-growing cell numbers were counted 25 days after seeding of KCL-22 and 22 days for KCL-22M cells.

| | Cell type | |
| --- | --- | --- |
| Starting cell no. | KCL-22 ($1 \times 10^5$) | KCL-22M (20) |
| Number of wells that cells were seeded | 40 | 20 |
| Calculated mutant cell number per well | 1.2 | 1 |
| Expected number of wells receiving mutant cells | 28 | 12 |
| Number of re-growing cells in each well with 2.5 μM imatinib (number of wells) | $1.3 \times 10^6$ (1) 0 (39) | $1 \times 10^4$ (2) $3.2 \times 10^4$ (1) $5 \times 10^4$ (1) $1.2 \times 10^6$ (1) 0 (15) |
| Actual number of wells with mutant cells re-growing (expected number of wells receiving mutant cells) | 1 (28)$^a$ | 5 (12)$^a$ |
| p value for actual/expected number of wells with mutant cells for KCL-22 versus KCL-22 M | 0.006 | |

$^a$p value was two-tailed Fisher exact test.

EXAMPLE 2

SIRT1 as a Primary Factor in Chemoresistance of CML

Materials and Methods

In combination with the materials and methods described in Example 1 above, the following additional materials and methods were used.

Isolation and retroviral transduction of human CD34$^+$ cells. Study of human samples was approved by the Institutional Review Board. CD34$^+$ cells were isolated from frozen bone marrow samples and transduced by retroviral vector MIG210 BCR-ABL or empty vector MIGR1 as previously described (Ramaraj et al., 2004). Cells were harvested 48 hours later and labeled with anti CD34-APC. CD34+ GFP+ cells were collected by flow cytometry. After cells were expanded in culture for seven days, total RNA and protein lysate were prepared using standard protocols.

SIRT1 promoter assay. CML cells were seeded at $4 \times 10^4$/well in 96 well plates and co-transfected with SIRT1 promoter-luciferase reporters (2.8 kb and 90 bp promoter fragments) (Nemoto et al., 2004) and a control plasmid pmaxGFP (Lonza). FeOfection reagent (GENOVIS) was used to transfect 0.18 μg reporter and 0.02 μg pmaxGFP each well per the manufacturer's instruction. Six hours after transfection, cells were treated with imatinib and harvested after another 30 hs. Luciferase activity was measured using Dual-Luciferase Assay System (Promega), and normalized to GFP reading in each lysate.

RNA and protein analyses. RNA was extracted with Trizol (Invitrogen), synthesized the first strand DNA with Super-script III kit (Invitrogen), and analyzed gene expression using SYBR GreenER qPCR SuperMix kit (Invitrogen). For Western blots, rabbit monoclonal anti-human SIRT1(Epitomics), rabbit anti-mouse SIRT1(Upstate Biotech), mouse monoclonal anti-c-ABL (BD Pharmingen), mouse monoclonal anti-Ku70(Neomarker), rabbit polyclonal anti-acetylated p53 (Cell Signaling) and rabbit polyclonal anti-acetylated FOXO1(Santa Cruz Biotech) were used. To analyze Ku70 acetylation, Ku70 was pulled down from total cell lysate with anti-Ku70 and protein A-agarose beads (Upstate Biotech) followed by acetylation detection with rabbit anti-acetyl lysine antibody (Cell Signaling).

Statistical analysis. For animal studies, Kaplan-Meier survival analysis was performed and statistical significance was calculated using log-rank test. For other data analysis, t-test was performed. Two-tailed analysis was used in all cases and P<0.05 is considered statistically significant.

SIRT1 is Essential for CML Chemoresistance.

The effects of SIRT1 stable knockdown on blockage of CML relapse by SIRT1 inhibitors were determined. SIRT1 shRNAs were designed as described previously (Reynolds et al., 2004). The first SIRT1 shRNA, Sh1, was subcloned into a lentiviral vector pSicoR (Ventura et al., 2004) which contains an expression cassette for green fluorescent protein (GFP) (FIG. 14A). A scrambled shRNA was subcloned into the vector as a mock control. The VSV-G (G protein of vesicular stomatitis virus) pseudotyped lentiviral vectors were produced using a four-plasmid transfection system as described (Kowolik et al., 2003). These vectors transduced KCL-22 and K562 cells with high efficiency and significant SIRT1 knockdown was observed in both cell lines (FIG. 14A). Mock or SIRT1 knockdown cells were enriched by fluorescent activated cell sorting (FACS) for GFP expression. No significant growth inhibition by SIRT1 knockdown on CML cells was observed. Treatment with imatinib resulted in relapse of the mock knockdown KCL-22 cells after two weeks. The SIRT1 knockdown showed significantly delayed or abolished relapse with relapse ranging from complete blockage during the two-month culture to delay by 27 days (FIG. 14B). SIRT1 expression in the relapsed SIRT1 knockdown cells was restored to the same level as that in the mock knockdown cells indicating that relapse in the SIRT1 Sh1 knockdown cells is mediated by those cells which contain little SIRT1 knockdown in the original knockdown pool (FIG. 14C).

SIRT1 shRNAs were based on *Homo sapiens* sirtuin type 1(SIRT1) mRNA, complete cds (Accession No. AF083106), and are as follows:

Sh1 Sense:
(SEQ ID NO: 22)
5' TGTTGACCTCCTCATTGTTATTCAAGAGATAACAATGAGGAGGTCAAC

TTTTTT3'

Sh1 Anti sense:
(SEQ ID NO: 23)
5' TCGAGAAAAAAGTTGACCTCCTCATTGTTATCTCTTGAATAACAATGA

GGAGGTCAACA-3'

Sh2 Sense:
(SEQ ID NO: 24)
5' TGTTGGATGATATGACACTGTTCAAGAGACAGTGTCATATCATCCAAC

TTTTTT3'

-continued

Sh2 Anti sense:

(SEQ ID NO: 25)
5'TCGAGAAAAAAGTTGGATGATATGACACTGTCTCTTGAACAGTGTCAT
ATCATCCAACA-3'

The heterogeneity of SIRT1 knockdown in the pooled population was confirmed using limiting dilution to clone individual SIRT1 knockdown and mock knockdown cells. About one-third of SIRT1 knockdown clones did not have significant SIRT1 knockdown (FIG. 14D) while SIRT1 level in mock knockdown clones remained unchanged.

Additional SIRT1 knockdown was also generated using different shRNA targets. Sh2 was cloned into a vector similar to pSicoR CMV-GFP with a PKG-puro expression cassette instead of CMV-GFP cassette (FIG. 14A). This allows for enrichment of transduced cells using puromycin selection. SIRT1 Sh2 exhibited a higher knockdown efficiency than Sh1(FIG. 14A). The mock knockdown KCL-22 cells relapsed after two weeks but SIRT1 Sh2 knockdown completely blocked the relapse for two months (FIG. 14E). Whether the vector sequence affects shRNA function was also assessed. SIRT1 Sh1 was subcloned into pSicoR PGK-puro vector and found to function similarly to Sh1 in pSicoR CMV-GFP vector—only able to delay the relapse. This indicates that it is the level of knockdown but not the type of vector used that affects resistance. SIRT1 knockdown using both Sh1 and Sh2 resulted in a further decreased SIRT1 level (FIG. 14A), completely blocking relapse of KCL-22 cells for two months (FIG. 14F). This indicates that SIRT1 is a gene that regulates CML acquired resistance by promoting BCR-ABL mutagenesis during imatinib treatment.

Figure 52:
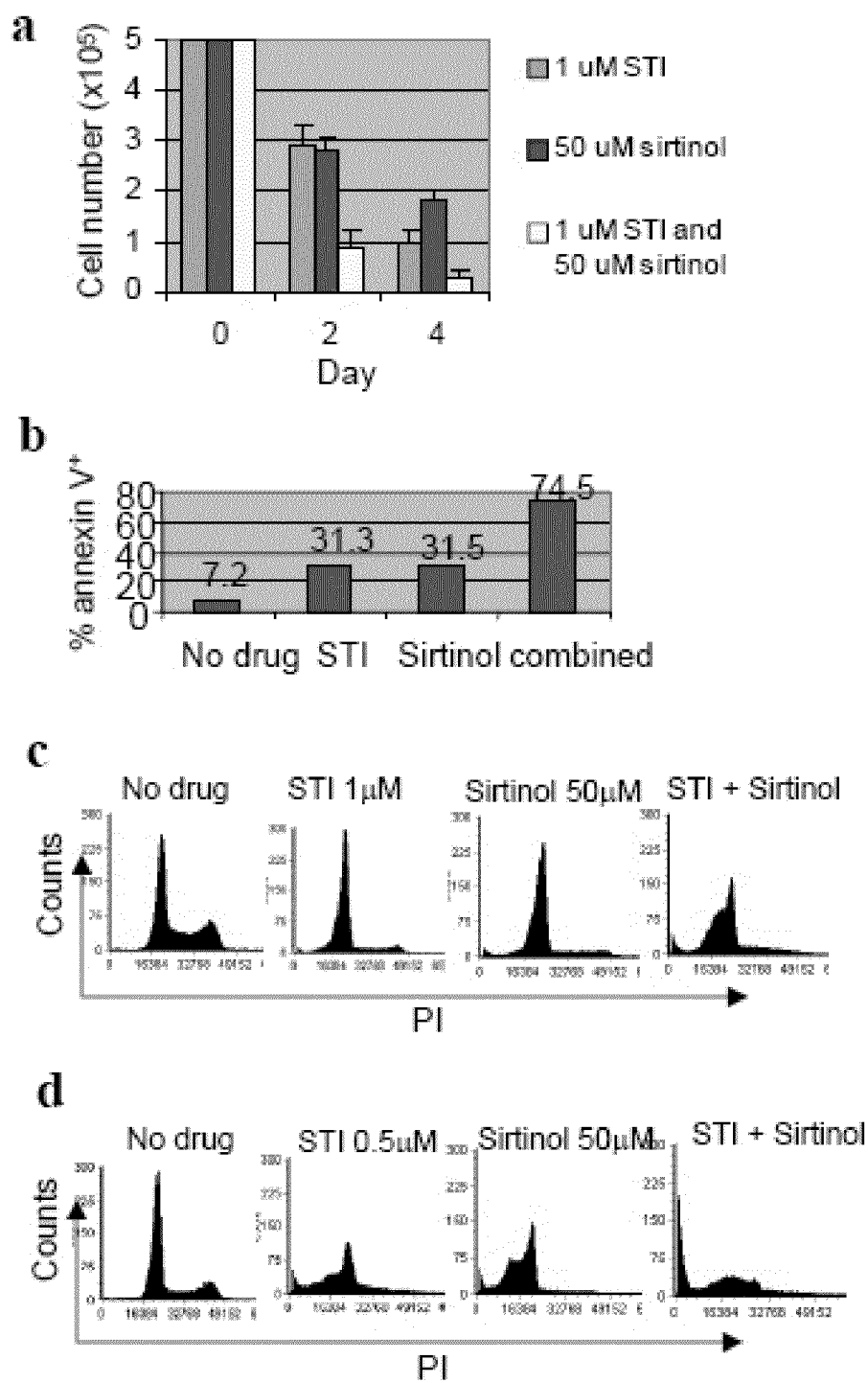
FIG. 52 illustrates the effect of sirtinol treatment on CML cell lines. (A, B) Effect of sirtinol on cell growth and apoptosis of K562 cells. (C, D) Cell cycle analysis. KCL-22(A) and K-562(B) cells were treated with conditions as indicated for two days and cells were labeled with propidium iodine (PI) for cell cycle analysis.

To determine the consequence of SIRT1 activation, KCL-22 and K562 cells were treated with a small molecule inhibitor of SIRT1, sirtinol, with or without imatinib. Sirtinol alone inhibited the growth and induced apoptosis of both cell lines, and the combination of sirtinol with imatinib further enhanced their inhibitory effects and apoptosis induction (FIGS. 8A-B and FIGS. 52A-B). Sirtinol and imatinib both affected cell cycle of CML cells, reducing S/G2/M and increasing sub-G1 population in KCL-22 cells while rapidly increased sub-G1 and apoptotic fraction in K562 cells (FIGS. 52C-D).

Figure 28:
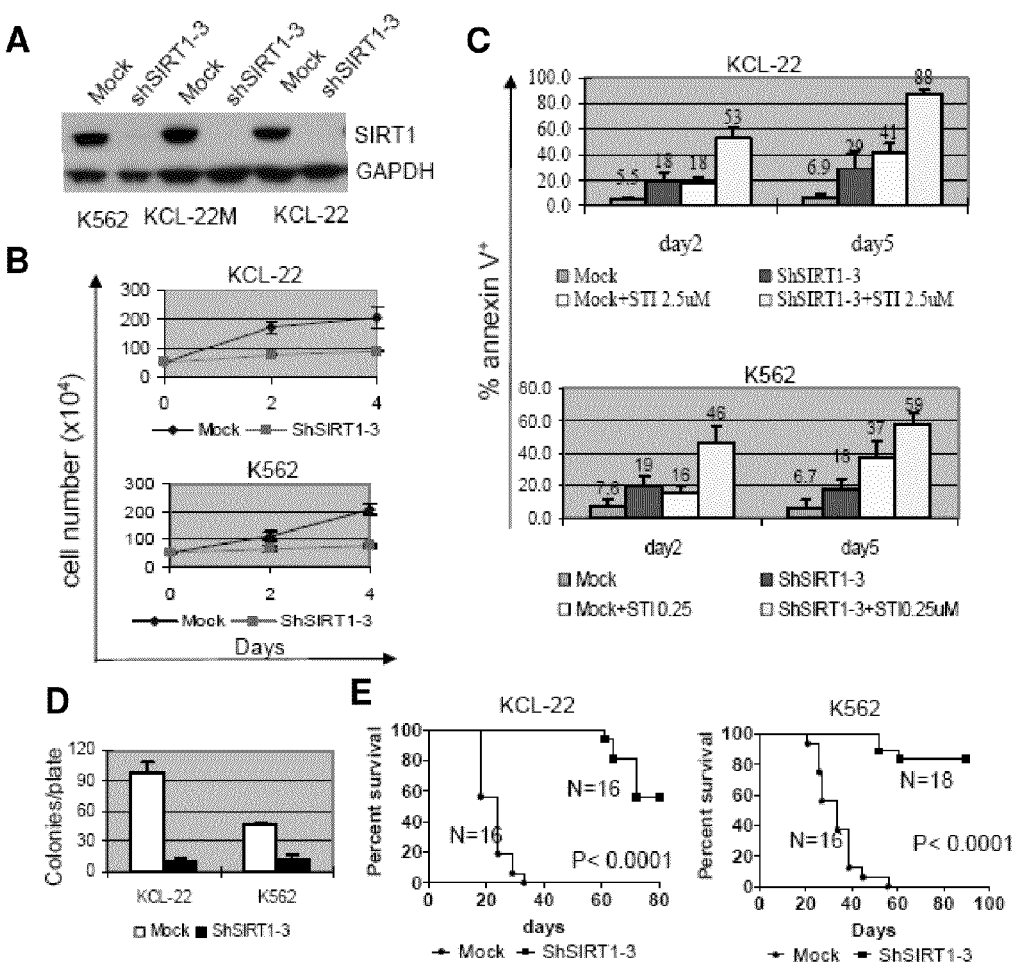
FIG. 28 illustrates that SIRT1 inhibition suppresses growth and induces apoptosis of CML cells. (A) Knockdown of SIRT1 in KCL-22, KCL-22M and K562 cells using lentiviral vectors (shSIRT1-3). (B) Three days after scrambled shRNA (mock) or shSIRT1-3 transduction, $1 \times 10^5$ cells were plated in triplicate in 24-well-plate and viable cells were counted at days indicated. (C) Three days after mock or shSIRT1-3 infection, $5 \times 10^5$ cells were cultured with or without 2.5 µM imatinib (STI) for another 2 or 5 days for apoptosis analysis. The percentage of annexin V+ cells was plotted. Error bars are standard deviations. (D) Soft agar colony formation assay. Three days after mock or shSIRT1-3 transduction, five hundred cells per plate were seeded on standard two-layer soft agar. The numbers of colonies were counted after 21 days with aid of microscope. (E) Survival curves of mice receiving xenografted CML cells. After overnight infection with shRNA vectors, three million cells each were inoculated into NOD-SCID mice.
Figure 33:
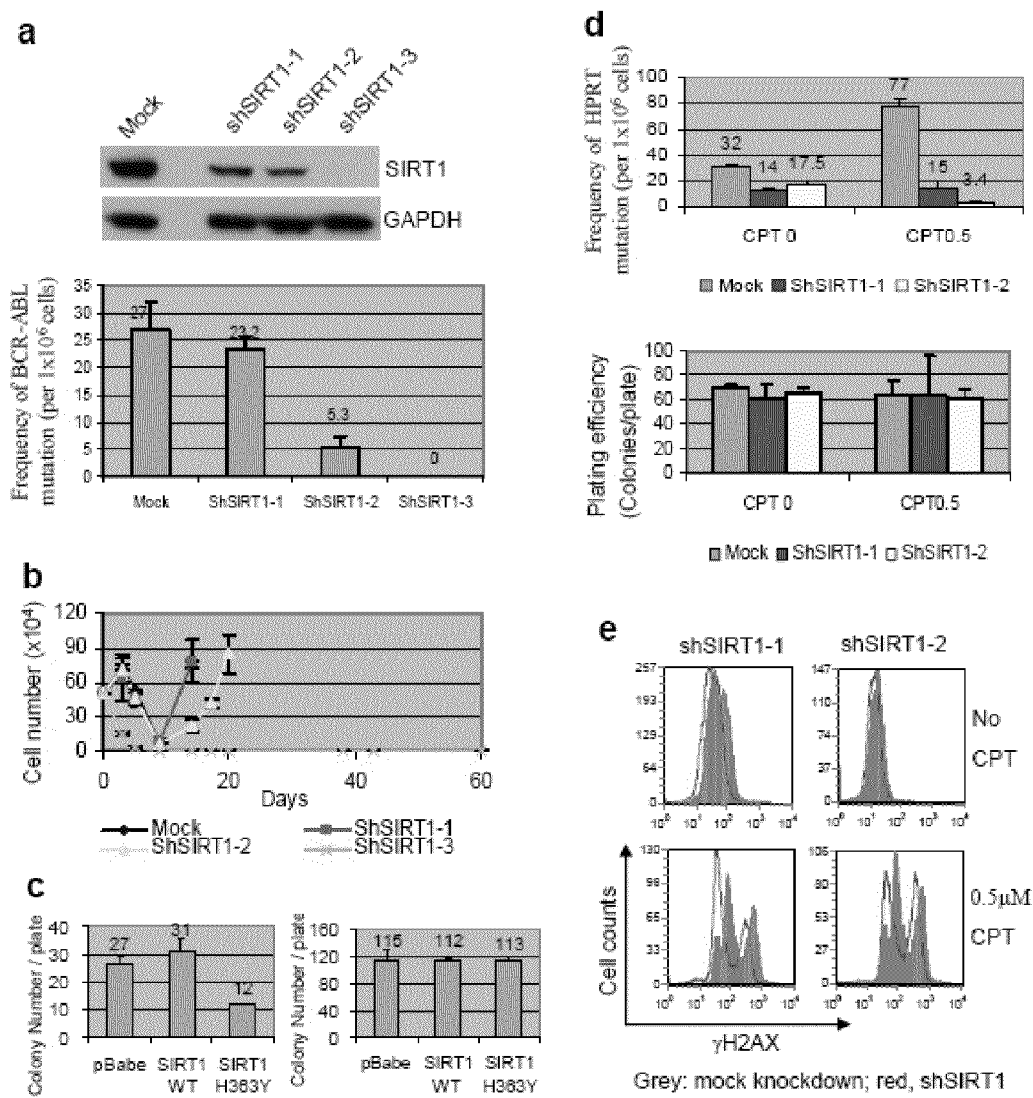
FIG. 33 illustrates that SIRT1 knockdown inhibits BCR-ABL mutations and camptothecin-induced HPRT mutations. (A) Top: SIRT1 protein levels in KCL-22 cells after 3 sets of SIRT1 shRNA knockdown. Scrambled shRNA was used as mock control. Bottom: Three days after shRNA transduction, one million of mock or SIRT1 knockdown KCL-22 cells were seeded in soft agar in triplicate with 5 µM imatinib (STI). At day 21, resistant colonies were scored. (B) Three days after shRNA transduction, one half million of mock or SIRT1 knockdown KCL-22 cells were treated with 5 µM STI in triplicate and viable cell numbers were counted at indicated days. (C) KCL-22 cells were stably transduced with pBabe retroviral vectors expressing wild type or H363Y mutant SIRT1. Left, puromycin-selected transduced cells were analyzed for BCR-ABL mutation frequency on imatinib by clonogenic assay. Right, plating efficiency. (D) Top: de novo HPRT mutation rate occurred spontaneously or after 0.5 µM CPT treatment. Bottom: plating efficiency. (E) Flow cytometry analysis of γH2AX in SIRT1 knockdown cells with or without CPT treatment. Mock knockdown was shown in grey to compare with either shSIRT1-1 or shSIRT1-2 knockdown.
Figure 37:
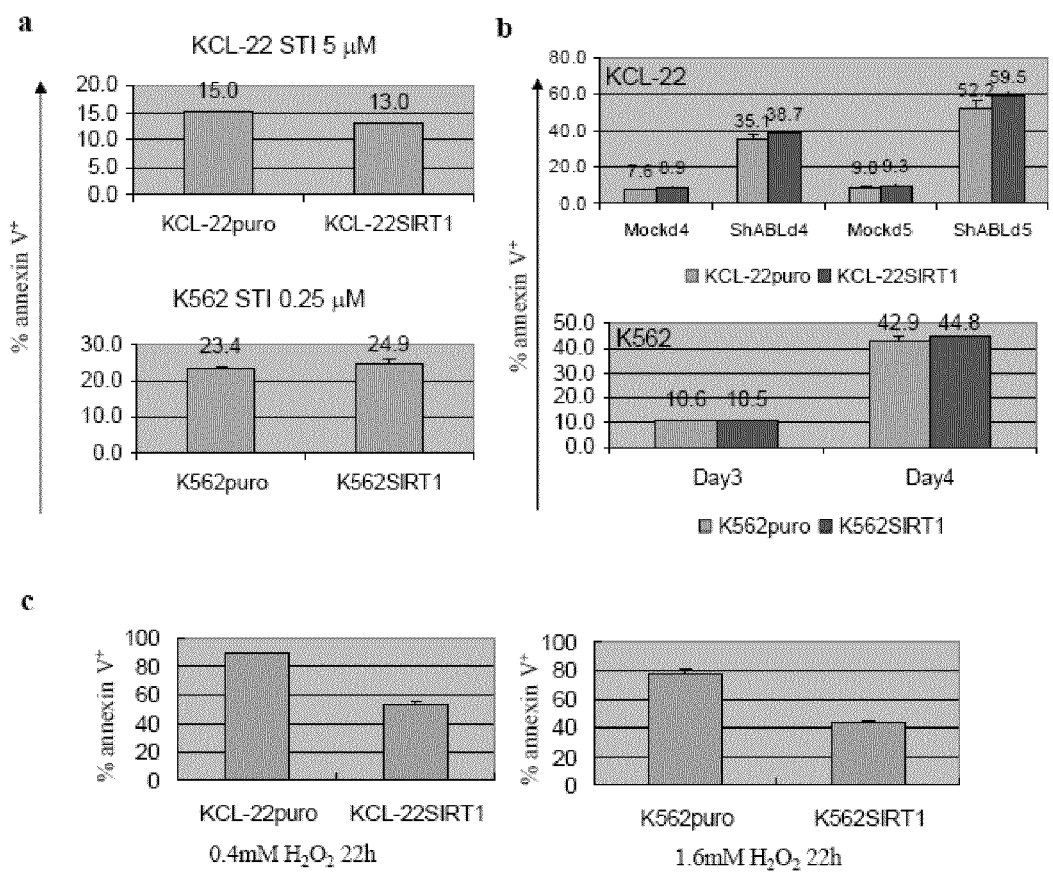
FIG. 37 illustrates that SIRT1 over-expression protects CML cells from oxidative stress but does not rescue apoptosis induced by BCR-ABL inhibition. (A) SIRT1 over-expression and imatinib treatment. KCL-22 and K562 cells were stably transduced with SIRT1(KCL-22SIRT1, K562SIRT1) over-expressing or empty (KCL-22puro, K562puro) retroviral vectors. Transduced cells were then treated with indicated concentrate ions of imatinib (STI) for 48 h. Apoptosis was analyzed by flow cytometry and the percentage of annexin V+ cells was plotted. Levels of SIRT1 over-expression were shown in FIG. 1F. (B) SIRT1 over-expression and BCR-ABL knockdown. BCR-ABL was knocked down by shABL lentiviral vector in control (puro vector) or SIRT1 over-expressing cells, shown in A. Apoptosis was analyzed at day 4 and 5 after shABL transduction. (C) SIRT1 over-expression protected CML cells from oxidative stress. Control or SIRT1 over-expressing CML cells were treated with $H_2O_2$ for 22 h, and analyzed for apoptosis by flow cytometry.

Since the level of SIRT1 knockdown affected the CML resistance, to further determine specific roles of SIRT1 on CML cells, SIRT1 was knocked down using a third and most potent set of lentiviral shRNA (shSIRT1-3) (FIGS. 28A and 33A). It was found that the knockdown suppressed proliferation of KCL-22 and K562 cells (FIG. 28B), and had synergistic effects with imatinib on induction of apoptosis in these cells (FIG. 28C). Further, it was found that overexpression of SIRT1 failed to protect CML cells from apoptosis induced by imatinib or BCR-ABL knockdown (FIGS. 37A and 37B), although SIRT1 overexpression protected CML cells from oxidative stress (FIG. 37C), which is consistent with the fact that BCR-ABL expression activates multiple survival pathways (Melo et al., 2007).

Next, SIRT1 knockdown was found to significantly inhibit soft agar colony formation of CML cells (FIG. 28D). To examine tumor growth in vivo, CML cells were transduced overnight with SIRT1 shRNA and transplanted the cells into non-obese diabetic severe combined immunodeficiency (NOD-SCID) mice. SIRT1 knockdown significantly delayed the tumor growth of xenografted CML cells and prolonged the survival of mice (P<0.0001, FIG. 28E).

Figure 45:
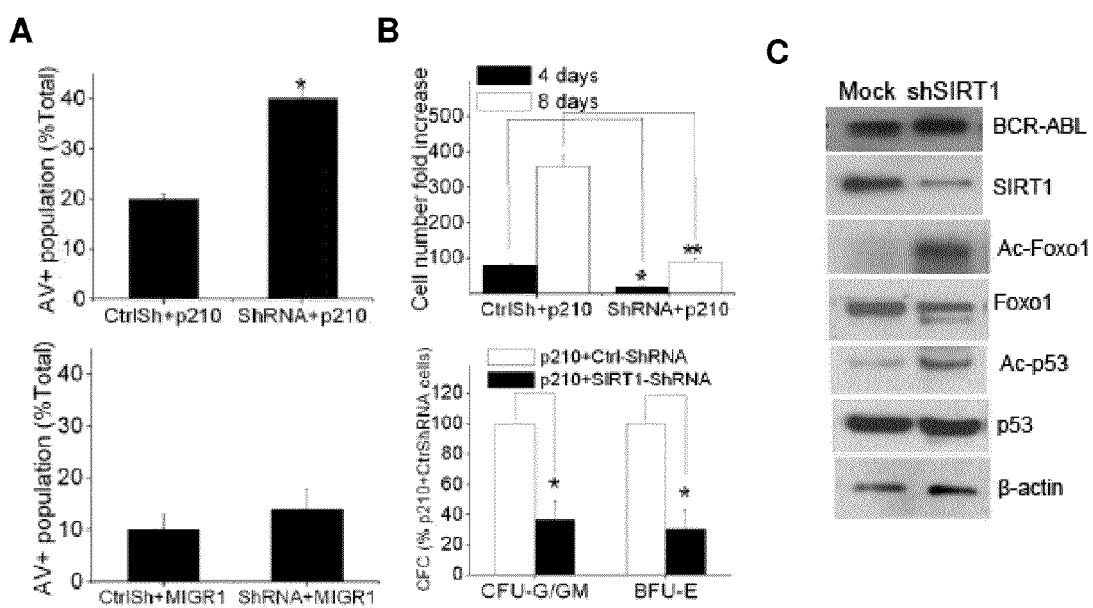
FIG. 45 shows that SIRT1 inhibition suppresses growth and induces apoptosis of CML cells. (A) Apoptosis of MIG210 or MIGR1 transduced normal CD34 + cells with mock (CtrlSh) or SIRT1(shRNA) knockdown. The double transduced CD34+ cells were sorted and then analyzed for annexin V+ cells after 48 hours culture in low concentrations of growth factors similar to those present in long-term BM culture stroma-conditioned medium67. (B) Analysis of total cell numbers (top) and CFC formation (bottom) of MIG210 transduced normal CD34+ cells with mock or SIRT1 knockdown. * indicates p<0.05 and ** indicates p<0.01. (C) Increased acetylation of FOXO1 and p53 upon SIRT1 knockdown in MIG210 transduced normal CD34 + cells.

Further, to determine the effect of SIRT1 inhibition for BCR-ABL transformation in primary CD34+ cells, we co-infected the cells with MIG210 and SIRT1 shRNA. SIRT1 knockdown increased apoptosis of BCR-ABL transduced CD34+ cells but had minimal effect on normal $CD34_+$ cells (FIG. 45A). SIRT1 knockdown suppressed proliferation and colony forming cell (CFC) formation of the transduced CD34+ cells (FIG. 45B). SIRT1 knockdown induced FOXO1 and p53 acetylation in BCR-ABL transduced CD34+ cells (FIG. 45C). Together, these results indicate that SIRT1 knockdown suppresses growth and transformation of human CML cells.

Using lentiviral shRNA to knock down SIRT1, it was found that the ability for KCL-22 cells to form BCR-ABL mutations was dependent on the residual amount of SIRT1 left, and the shSIRT1-3 vector that resulted in the most robust knockdown completely inhibited BCR-ABL mutations (FIG. 33A). Accordingly, the relapse of KCL-22 cells on imatinib was delayed more with better SIRT1 knockdown, with complete block of relapse by shSIRT1-3(FIG. 33B). To determine if SIRT1 deacetylase activity is required for BCR-ABL mutagenesis, wild type or H363Y dominant-negative deacetylase-deficient SIRT1(Vaziri et al., 2001) was overexpressed in KCL-22 cells. Expression of either wild type or H363Y SIRT1 did not affect cell growth or induce apoptosis; however, H363Y SIRT1 expression significantly reduced BCR-ABL mutations (FIG. 33C). Together, these results reveal that high levels of SIRT1 in CML cells promote BCR-ABL mutations for acquired resistance, a process that is dependent on SIRT1 deacetylase function.

Downstream Targets of SIRT1.

The potential downstream targets of SIRT1 that are involved in controlling the CML cell resistance are determined. p53 is a key downstream target of SIRT1 for apoptotic control in solid tumors. However, p53 is mutated in both KCL-22 and K562 cells, indicating that other SIRT1 targets might be involved. Involvement of another SIRT1 target, peroxisome proliferator-activated receptor-gamma coactivator 1 alpha (PGC-1α), for induction of BCR-ABL mutations through regulating reactive oxygen species (ROS) is examined. The ROS production is dramatically increased in blast crisis CML, which results in accumulation of DNA damage product 7,8-dihydro-8-oxo-2'-deoxyguanosine (8-oxoG). Overexpression of BCR-ABL in murine cells induces ROS production, DNA damage and BCR-ABL mutations. However, cellular ABL plays an important role in cellular DNA damage repair and treatment with STI-571 will also inhibit ABL and inactivate cellular DNA repair system. Most of the cellular ROS is produced by electron transport chain of active mitochondrial metabolism. PGC-1α is a master activator for mitochondrial biogenesis and respiration that promotes ROS production. SIRT1 plays a critical role in this regulation by deacetylating PGC-1α and thus activating its function. STI-571 treatment inhibits BCR-ABL function and cell growth but simultaneously reduces ability of cellular DNA damage repair and results in T315I mutation, unless SIRT1 is inactivated by sirtinol or PGC-1α is inactivated.

Ku70 is an important downstream target of SIRT1 for acquired resistance of CML cells. A search for essential SIRT1 pathways involved in regulating both CML cell survival and DNA damage responses was performed. Among known SIRT1 substrates, p53 is mutated in both KCL-22 and K562 cells. Another target, Ku70, is an important downstream effecter for SIRT1-mediated cell survival (Cohen et al., 2004), and is also an important component of error-prone, non-homologous end joining (NHEJ) DNA repair machinery (Khanna et al., 2001). As shown in FIG. 34A, the acetylation levels of endogenous Ku70 in CML cells are increased in proportion to the levels of SIRT1 knockdown. When Ku70 is knocked down (FIG. 34B), the combination of Ku70 shRNA with imatinib resulted in more apoptosis of KCL-22 cells than each individual agent (FIG. 34C). However, the combination of Ku70 knockdown with imatinib did not result in a synergistic induction of apoptosis that was seen with the combination of SIRT1 knockdown and imatinib treatment (FIG. 28C), indicating that Ku70 contributes in part to SIRT1-mediated CML cell survival. Ku70 knockdown completely blocked BCR-ABL mutations and KCL-22 cell relapse on imatinib (FIG. 34D), indicating that Ku70 is an important downstream target of SIRT1 for promoting BCR-ABL mutations and acquired resistance. Therefore, high levels of SIRT1 in cancer cells may activate Ku70 by deacetylation to promote error-prone DNA damage repair, which results in mutations for acquired resistance.

Figure 49:
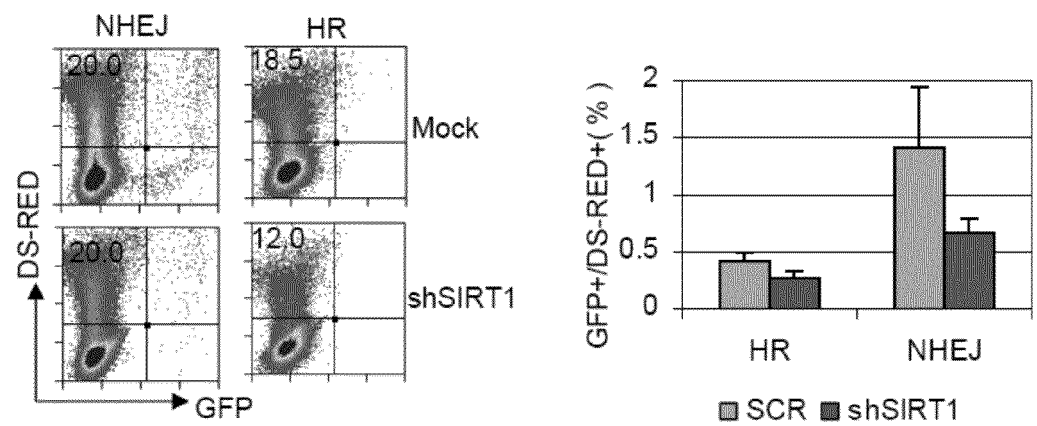
FIG. 49 illustrates the downstream targets of SIRT1 for CML acquired resistance. Flow cytometry analysis of SIRT1 knockdown on HR and NHEJ repair using stably integrated reporter constructs in KCL-22 cells. GFP was produced after proper DNA damage repair. DS-Red was used for transfection control and repair rate was normalized to DS-Red. Cells were analyzed 48 hours after electroporation of I-SceI.

To further determine the role of SIRT1 in DNA damage repair, stable KCL-22 cell clones bearing a NHEJ reporter construct EJ5-GFP were generated. For comparison with homologous recombination (HR) repair, KCL-22 cell clones carrying a HR reporter DR-GFP were also generated. After introducing DNA damage on these reporters using endonuclease I-SceI, it was found that NHEJ was much more efficient than HR for DNA damage repair in KCL-22 cells, and that SIRT1 knockdown suppressed both HR and NHEJ activity with more prominent effect on NHEJ (FIG. 49), consistent with SIRT1 regulation of Ku70 functions as described above.

Figure 56:
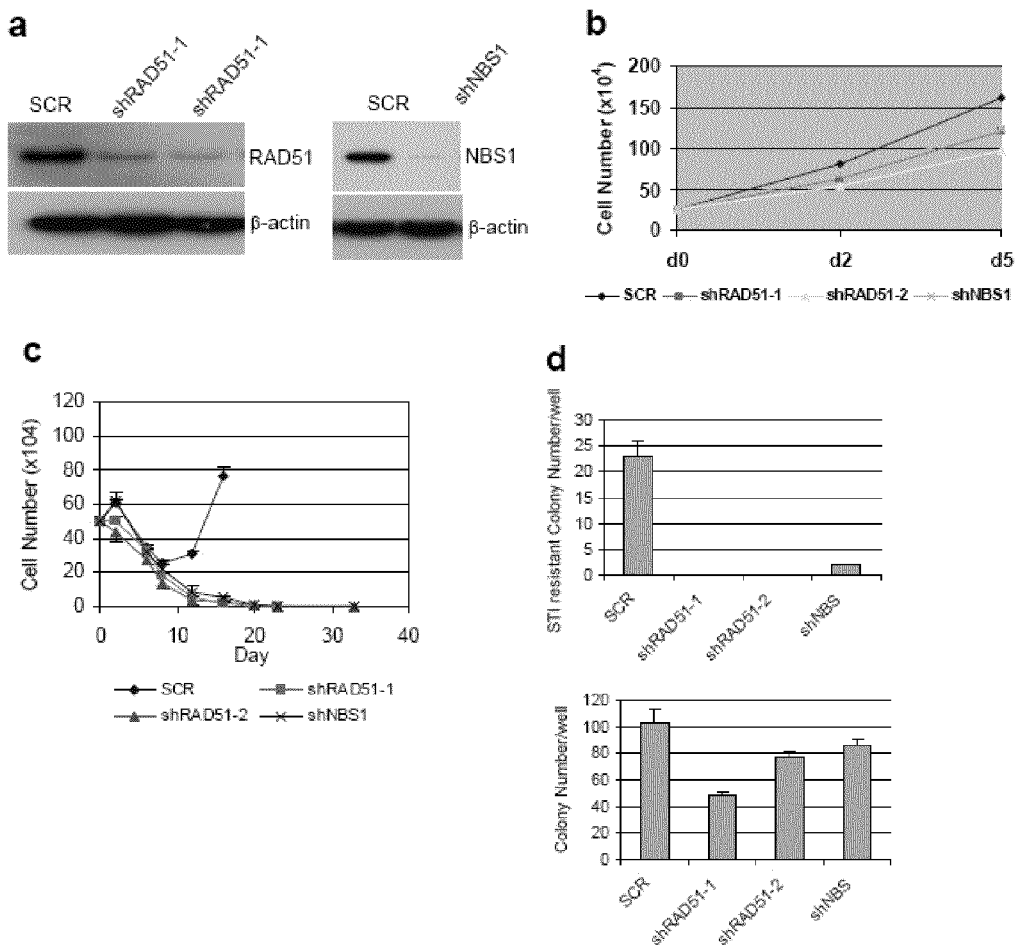
FIG. 56 shows the influence of HR repair factors on BCR-ABL mutations. (A) Levels of RAD51 and NBS1 in stable knockdown KCL-22 cells selected with puromycin. (B) Mild effect of RAD51 and NBS1 knockdown on KCL-22 cell growth. (C, D) RAD51 and NBS1 knockdown blocked relapse (C) and suppressed BCR-ABL mutation rate by soft agar clonogenic assay (D). Top of Panel D, imatinib resistant colony/well. Bottom of panel D, plating efficiency.

In addition to modulating Ku70, SIRT1 deacetylates HR repair factor Nijmegen Breakage Syndrome-1(NBS1; a component of MRN (MRE11-RAD50-NBS1) complex) and regulates recruitment of NBS1 and RAD51 to DNA damage foci for repair. It was found that both NBS1 and RAD51 knockdown also suppressed BCR-ABL mutations and CML cell relapse on imatinib (FIG. 56). This result was surprising because HR repair was not efficient in KCL-22 cells. In addition, BCR-ABL expression also compromises the fidelity of HR repair (Nowicki et al. 2004). Thus, high levels of SIRT1 in CML cells may alter functions of cellular repair machineries, in particular, error-prone DNA damage repair, which promotes mutations for acquired resistance.

Roles of Aurora A for Resistance of T315I Mutant CML.

Aurora kinases are evolutionarily conserved family of serine/threonine kinases, with three homologous genes Aurora A, B, and C in mammals. Aurora A is essential for bipolar spindle assembly during mitosis and Aurora B ensures proper chromosome attachment to the mitotic spindle, while Aurora C is involved in regulation of cilia and flagella. Aurora A is overexpressed in various types of human cancer and its gene amplification overrides the mitotic spindle assembly checkpoint, results in defective spindle formation and multinucleation, and increases cellular resistance to chemotherapeutic agent paclitaxel. Selective inhibitors of Aurora kinases have been developed for treatment of various cancers.

The increase of G2/M cell number, enlarged cell size and bizarre morphology of KCL-22M cells show potential defects in cell mitosis, which will deregulate Aurora kinases in these cells. Using Western blot, it was found that the overall level of Aurora B in KCL-22 and KCL-22M cells are similar, but Aurora A was abnormally stabilized in KCL-22M cells that might account for morphological and cell cycle changes in these cells (FIG. 16). It has been found that the Aurora kinase inhibitor, VX-680, potently inhibits T315I BCR-ABL through a different structural mechanism from STI-571. Three CML patients with T315I mutation responded to VX-680 treatment, indicating that clinical responses of CML patients with T315I can be enhanced with inhibition of Aurora kinases, mutant BCR-ABL, or both. Aurora kinase plays a role in the resistance of T315I mutation in CML cells. VX-680 is a useful approach for eradicating mutant cells. Aurora A is abnormally stabilized in KCL-22M cells that have been treated with STI-571, but is degraded by treatment with SIRT1 inhibitor sirtinol (FIG. 16B). Abnormal stabilization of Aurora A can be caused by mutations of its DNA sequences for destruction boxes A and D (FIG. 16A) due to the pressure imposed by STI-571 treatment. Where inhibition of BCR-ABL alone is insufficient to eradicate T315I BCR-ABL mutant cells, combination treatment with SIRT1 inhibitors along with a dual BCR-ABL and Aurora inhibitor such as VX-680 is useful for eradicating the resistant cells.

Whether stabilization of Aurora A in KCL-22M cells might be due to alterations of its destruction signals is determined. Aurora A is destructed after mitotic exit through ubiquibin ligase, which is regulated by two conserved short amino acid sequences, an N-terminal A box and a C-terminal D box (FIG. 16A), and mutations of these sequences stabilize Aurora A. Besides, phosphorylation of serine S51 in the A box of human Aurora A or S53 in *Xenopus* also inhibits its destruction. There is structural similarity of kinase domains of BCR-ABL and Aurora, and cross reactivity of their inhibitors. These results show that Aurora A is involved in resistance of KCL-22M cells.

The effects of Aurora A knockdown for KCL-22M cells was also determined. Aurora A shRNAs was designed and tested. The knockdown of Aurora A was confirmed by Western blot. Whether this knockdown reduces G2/M cell population and restores normal cell morphology in KCL-22M cells by flow cytometry, and whether it promotes apoptosis or inhibits growth of KCL-22M cells is also assessed.

To determine the role of Aurora A overexpression in CML chemoresistance, Aurora A is expressed with an exogenous promoter in KCL-22 cells to examine whether it accelerated resistance, and in STI-571 sensitive K562 cells to examine whether it helped these cells to develop resistance. Wild type and/or mutant Aurora A is used depending on the sequencing results from the first experiment. Full length cDNA of Aurora A was PCR-amplified and subcloned into an expression cassette with Simian virus 40(SV40) promoter in a lentiviral vector carrying CMV-GFP, which is similar to the vector used for shRNA packaging. When a mutant is needed, site-directed mutagenesis is performed in the subcloned Aurora A vector. Recombinant viruses are then produced and used to infect KCL-22 or K-562 cells, and overexpression of Aurora A is verified by Western blot. Infected cells are isolated by FACS sorting for GFP expression, and if necessary, cloning of individual cells. Resistance in these cells was measured by rate of mutation, time for relapse, and concentrations of STI571 needed to repress cell growth and induce apoptosis.

Knockdown of BCR-ABL has a greater impact on KCL-22 cells than KCL-22M cells, and other gene changes such as Aurora A also have important roles in resistance of KCL-22M cells. Overexpression of Aurora A can render KCL-22 cells more resistant to STI-571 treatment and may develop resistant cells even without genetic mutations, and persistent Aurora A may also render K-562 cells resistant to 1 µM STI-571 treatment. Simultaneous knockdown of BCR-ABL and Aurora A can have a more significant impact than individual knockdown on cell growth and apoptosis of KCL-22M cells. Treatment with VX-680 kills KCL-22M and KCL-22 cells efficiently as it inhibits both Aurora kinases and wild type or T315I BCR-ABL.

SIRT1 is Required for STI-571 Resistance in Mouse Models and in Primary Human CML Cells.

It is examined whether the mechanisms that SIRT1 inhibition enhances CML apoptosis and prevents relapse on STI-571 in vitro applies to in vivo treatment. First, a xenograft model of human CML cells was used in non-obese diabetic severe combined immunodeficient (NOD-SCID) mice and examined whether the combined treatment with sirtinol and STI-571 eliminates KCL-22 cells in recipient mice and prolongs their survival without relapse. Also examined was another CML cell line KU-812 for xenograft study. KU-812 is very sensitive to STI-571 in vitro, but in vivo one third of mice with KU-812 xenograft relapse on STI-571 treatment after 48 to 60 days. It is determined whether the combination of STI-571 and sirtinol blocks this relapse. Second, murine bone marrow retroviral transduction and transplantation model was used to define specific roles of SIRT1 in vivo for BCR-ABL transformation and STI-571 resistance with SIRT1 knockout mice. Many hallmarks of human CML are faithfully reproduced in BALB/c mouse models employing retroviral transduction of bone marrow cells with P210 BCR-ABL followed by transplantation to syngeneic recipients. Mice develop CML-like myeloproliferative disease characterized by massive extramedullary hematopoiesis in spleen, liver and bone marrow with striking peripheral blood granulocytosis, and die within 3-4 weeks after transplantation. Treatment with STI-571 prolongs survival in 80% of mice, while the rest exhibit primary resistance and no mice can be cured by the treatment. It is examined whether homozygous SIRT1 knockout inhibits development of myeloproliferative disease in this model or significantly enhances the effects of STI-571 treatment to inhibit resistance and even cure the disease, and whether combination of sirtinol and STI-571 will significantly improve treatment of the disease generated with wild type mouse bone marrow. In vitro colony-forming-unit (CFU) assay is used to determine whether combination of sirtinol with STI-571 will suppress blast-forming unit-erythroid (BFU-E) and CFU-granulocyte-monocyte (CFU-GM) colonies from late phase CML patients more efficiently than STI-571 itself.

Since no animal studies have been conducted with sirtinol before, the pharmacokinetics of the compound was first determined. Female NOD-SCID mice 6 to 8 weeks of age were given a single dose of sirtinol intraperitoneally (i.p.) and at seven time points, namely 0.5, 1, 2, 4, 6, 8, and 24 hours, mice are sacrificed and blood, bone marrow and liver are collected for HPLC-MS analysis.

Figure 17:
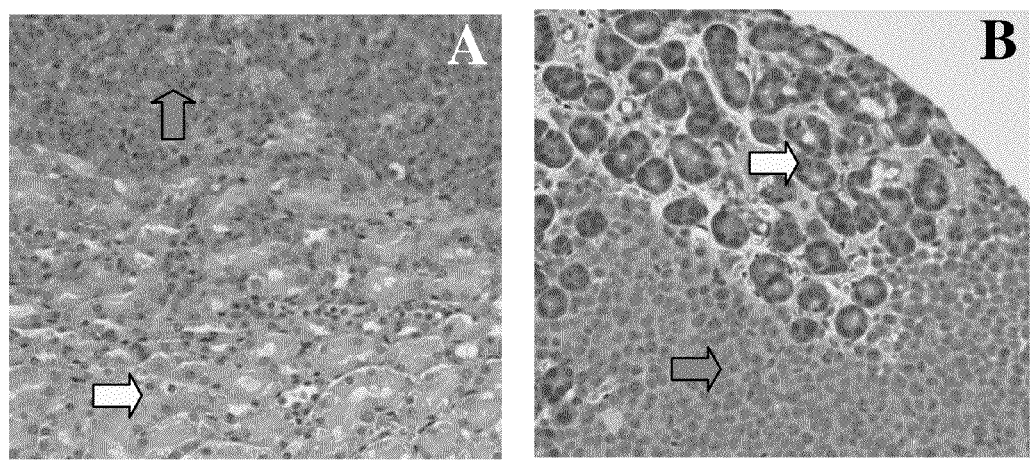
FIG. 17 shows a xenograft of human KCL-22 CML cells in NOD-SCID mice. The KCL-22 leukemia cells (shaded arrows) infiltrate kidney (FIG. 17A) and pancreas (FIG. 17B). Normal surrounding tissues are indicated by clear arrows for kidney (FIG. 17A) and pancreatic acini (FIG. 17B).

Second, the effects of the combination of sirtinol and STI-571 for treatment of xenografted CML cells were determined. Induction of tumors by KCL-22 cells in NOD-SCID mice was tested. Mice were irradiated with 270 Rads, and 4 to 6 hours later, transplanted with 3 million cells in phosphate-buffered saline each through tail vein. Of 12 recipients, one died within one week likely due to infection and the other 11 recipients developed tumors between 3 to 5 weeks. Most of mice exhibited visible tumors on neck, eye, and abdomen. Necropsy and histopathological examination revealed that these solid tumors were derived from lymph nodes throughout the body, with the highest frequency in axillary, pancreatic and renal nodes, and tumors frequently infiltrated kidney, eye and muscle (FIG. 17). A significant number of human cells were not detected in peripheral blood by flow cytometric analysis of CD45+ cells in all 11 mice before they were sacrificed for tumor burden. Microscopically visible tumors were not found in the spleen, liver and lung.

To facilitate non-invasive assessment of in vivo anti-tumor activity of drugs, KCL-22 cells stably expressing firefly luciferase were generated. Cells were examined for their responses for STI-571 and sirtinol treatment to ensure that luciferase expression does not alter effects of drugs. Luciferase-expressing KCL-22 cells are transplanted into NOD-SCID mice. Mice with established tumors (by luciferase imaging) are divided into 4 groups with 5 mice each: group 1, vehicle control; group 2, oral administration of STI-571 twice daily with a morning dose of 50 mg/kg and an evening dose of 100 mg/kg; group 3, single i.p. injection of sirtinol with a dose producing stable plasma concentration of at least 50 µM; group 4, combination of STI-571 and sirtinol. Mice were imaged 5 to 7 days after treatment, and total body bioluminescence was collected to quantify the changes of tumor progression and regression.

Resistance in Acute Lymphocytic Leukemia.

The ability of sirtinol and imatinib to block resistance related to BCR-ABL mutations and non-mutants was determined in acute lymphocytic leukemia (ALL) cells. In humans, adult BCR-ABL bearing (ALL) is highly chemoresistant and treatments are rarely successful, resulting in a poor survival rate ranging from <10% to 20% (Bassan et al., 2004). Similar to KCL-22 cells, the ALL cell line, SD1 is resistant to STI-571 treatment (Deininger et al., 1997). Here, it was observed that prolonged treatment of SD1 cells with STI-571 induced partial cell death, with cells relapsing after ten days without BCR-ABL mutations (FIG. 12C). SIRT1 inhibitor sirtinol alone or in combination with STI-571 could eliminated these cells during prolonged cell culture (FIG. 12C) indicating again, that SIRT1 controls key molecular pathways for chemoresistance of BCR-ABL positive leukemia. Suppression of SIRT1 along with BCR-ABL is an effective therapeutic approach.

EXAMPLE 3

SIRT1 Knockout Model

Materials and Methods

In combination with the materials and methods described in Examples 1 and 2 above, the following additional materials and methods were used.

Animal studies. The use of animals was approved by the Institutional Animal Care and Use Committee. For CML tumor xenograft assay, three million virally transduced cells were inoculated subcutaneously into the right flank of NOD-SCID mice conditioned by 270 Rad irradiation. Tumor length (L), height (H) and width (W) were measured weekly with a caliper. Tumor volume is estimated from the formula, $V=\pi$ (L×H×W/6). Mice were euthanized when the tumor volume reached 1000 mm$^3$. For bone marrow transduction/transplantation studies, SIRT1$^{+/-}$ mice were backcrossed to BALB/c background for eight generations. Retroviral transduction of bone marrow cells and transplantation were performed as described previously (Pear et al., 1998). PE-labeled lineage (Gr-1, Mac-1, B220, Ter119 and CD3e) antibodies (BD Pharmingen), and APC-labeled CD150 antibody (Biolegend) were used for cell analysis or sorting.

For the in vivo drug treatment study, imatinib was prepared freshly in pure $H_2O$ and tenovin-6 was prepared in 20% cyclodextrin (w/v) (Sigma, #C0926) and 10% DMSO (v/v) as described (Lain et al. 2008), and both were filtered sterile. At day 10 post transplantation, drugs were administrated continuously for 10 days. Imatinib was administered by oral gavage with 75 mg/kg in the morning and 125 mg/kg in the afternoon. Tenovin-6 was given by intraperitoneal injection at 50 mg/kg in the morning. Vehicle control animals were treated with solution containing 20% cyclodextrin and 10% DMSO.

SIRT1 Knockout Inhibits Development of a CML-Like Disease in a Mouse Model.

Figure 53:
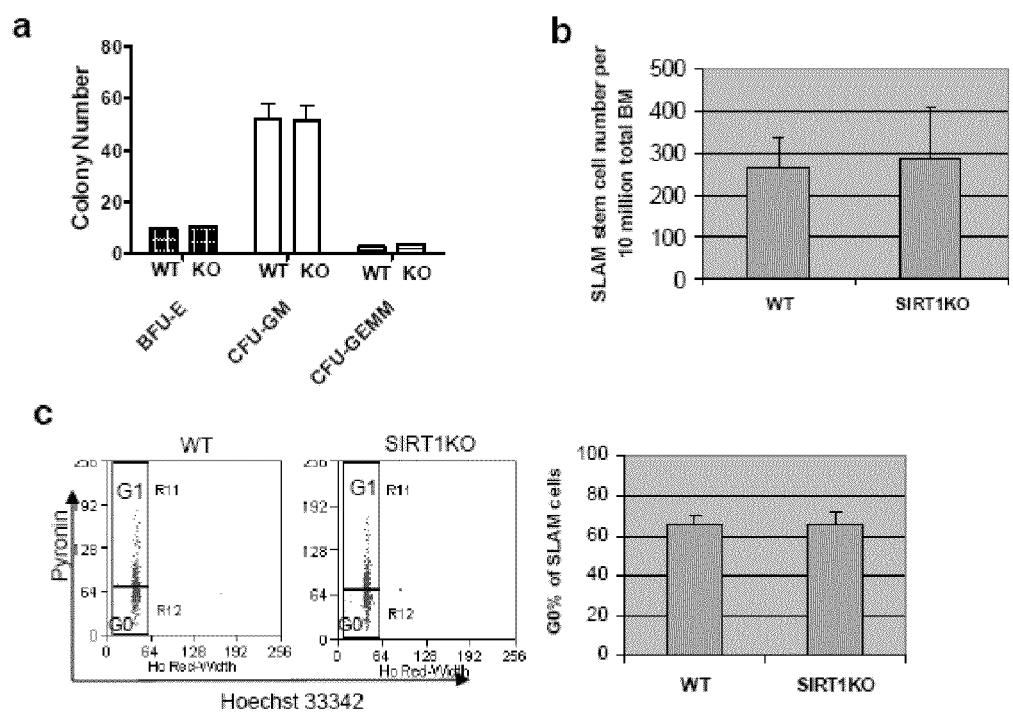
FIG. 53 illustrates the effects of SIRT1 knockout on functions of mouse hematopoietic progenitor cells, transduction and engraftment efficiency. (A) Colony formation assay. Bone marrow cells from three-month old wild type (WT) and SIRT1 knockout (KO) mice were plated with methylcellulose medium and colonies were scored after two weeks. (B, C) Analysis of hematopoietic stem cell frequency and cell cycle. Hematopoietic stem cells were identified by SLAM markers using Lin-CD150+CD41-CD48—combination in BABL/c strain. (B). Hematopoietic stem cells were further analyzed for cell cycle status using Hoechst 33342 and pyronin Y staining (C). n=3 each genotype

To further understand roles of SIRT1 in CML, the impact of SIRT1 knockout on CML disease development in a mouse bone marrow transduction/transplantation model (Pear et al., 1998) was examined. Many hallmarks of human CML are reproduced in this model and recipient mice develop a CML-like myeloproliferative disease and die within 2-4 weeks after transplantation. Since the efficiency for generating the CML-like disease in this model is about 100% in BABL/c strain, SIRT1 knockout mice (Cheng et al., 2003) were backcrossed to the BALB/c strain for at least eight generations. A portion of SIRT1$^{-/-}$ mice survived through adulthood with relatively normal development, although smaller body stature and closed eye lids were noticed in some mice as previously described (Cheng et al., 2003). Consistent with a previous report (Narala et al., 2008), no significant difference in blood lineage differentiation and hematopoietic stem cell frequency were found in SIRT1$^{-/-}$ mice compared to wild type littermates (FIGS. 53A-C).

Figure 29:
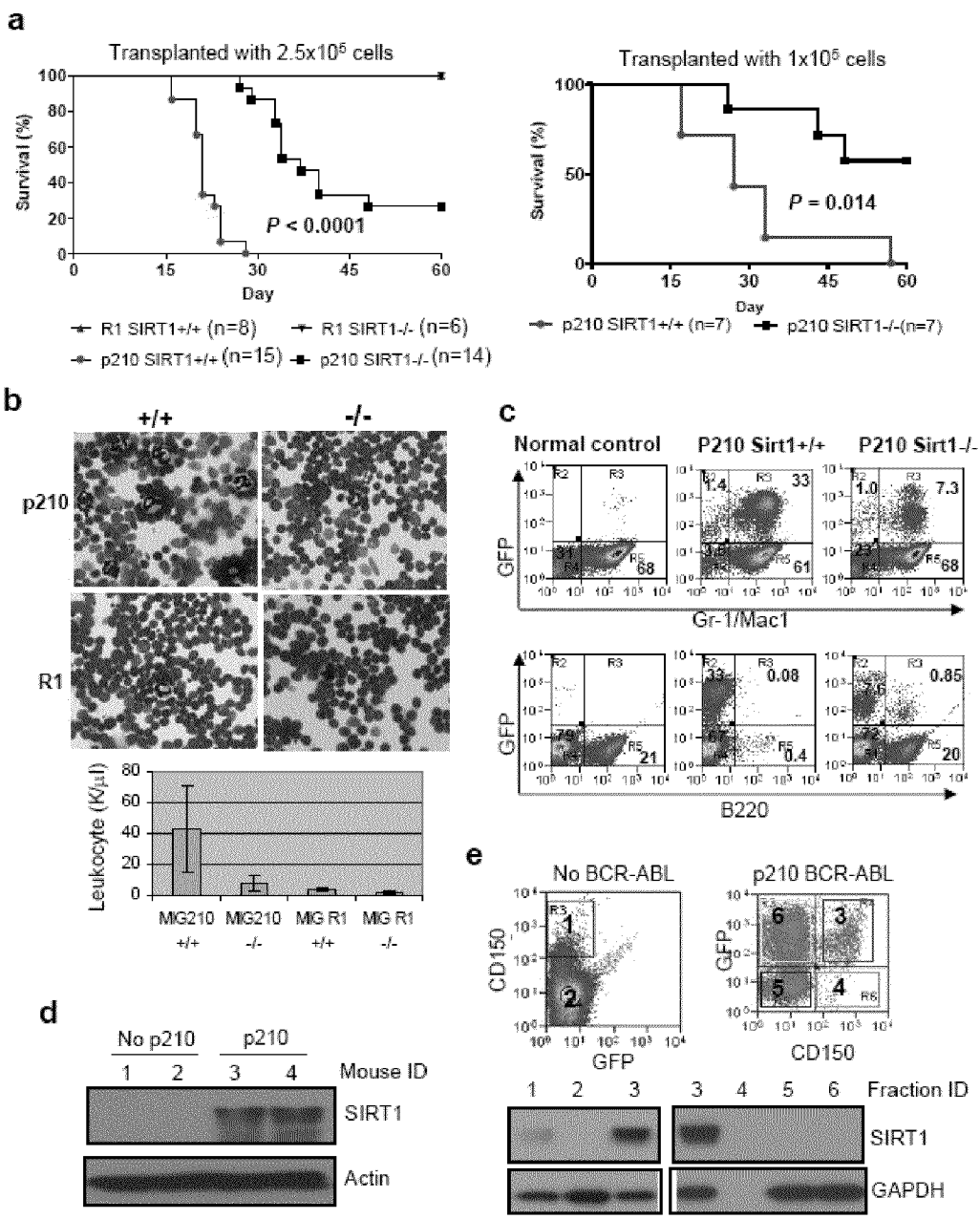
FIG. 29 illustrates that SIRT1 knockout inhibits development of CML-disease in a mouse bone marrow transduction/transplantation model. (A) Survival curves for mice receiving $2.5 \times 10^5$ (left) and $1 \times 10^5$ (right) cells transduced by BCR-ABL MIG210 vector (p210) or empty vector (R1). (B) Blood smears (top) and total leukocyte counts (bottom) for mice receiving $2.5 \times 10^5$ transduced cells at 18 days after transplantation. (C) Bone marrow cell lineage analysis in normal BALB/c (control) and mice receiving MIG210 transformed SIRT1$^{+/+}$ or SIRT1$_{-/-}$ cells. (D) SIRT1 protein expression in total bone marrow mononuclear cells from normal BALB/c and mice receiving MIG210 transformed SIRT1$^{+/+}$ cells, two mice each group. (E) Bone marrow from normal BALB/c and mice receiving MIG210 transformed SIRT1$^{+/+}$ cells were sorted for GFP and CD150 expression (Top). Bold numbers indicated the sorted fractions that were used for analysis of SIRT1 protein expression (Bottom). GFP$^+$CD150$^+$ (fraction 3) cells were loaded with fractions 1 and 2 from BALB/c mice for comparison.

Bone marrow cells from 3-month old SIRT1$^{-/-}$ and SIRT1$^{+/+}$ mice were transduced with BCR-ABL (MIG210) or control vector (MIG R1), both bearing green fluorescent protein as a marker, and transplanted $2.5 \times 10^5$ or $1 \times 10^5$ transduced cells into lethally irradiated BALB/c recipients (FIG. 29A). It was found that the transduction and engraftment efficiency for both wild type and knockout cells were similar (FIG. 38), and mice receiving $2.5 \times 10^5$ BCR-ABL transformed SIRT1$^{+/+}$ bone marrow cells developed the CML-like disease within three to four weeks with signature characteristics of the disease: markedly elevated white blood cell (WBC) counts predominated by granulocytes, splenomegaly, and multiple organ involvement (FIGS. 29A-B) (Pear et al., 1998). Mice receiving BCR-ABL transformed SIRT1$^{-/-}$ cells showed significantly delayed disease development with markedly lower peripheral blood WBC counts (P<0.0001) (FIG. 29B). In contrast to mice receiving transformed SIRT1$^{-/-}$ cells (10% B220$^+$GFP$^+$ in all GFP$^+$ population), bone marrow exhibited dramatic expansion of the Gr-1/Mac-1 lineage in mice receiving transformed SIRT1$^{+/+}$ cells, and occurred at the expense of B220 lineage differentiation (0.24% B220$^+$GFP$^+$ in all GFP$^+$ population) (FIG. 29C). As a consequence, mice receiving transformed SIRT1$^{-/-}$ cells survived much longer than mice receiving transformed SIRT1$^{+/+}$ cells (P<0.0001) (FIG. 29A). No significant difference was observed with empty vector transformation (FIGS. 29A and 29B).

Figure 26:
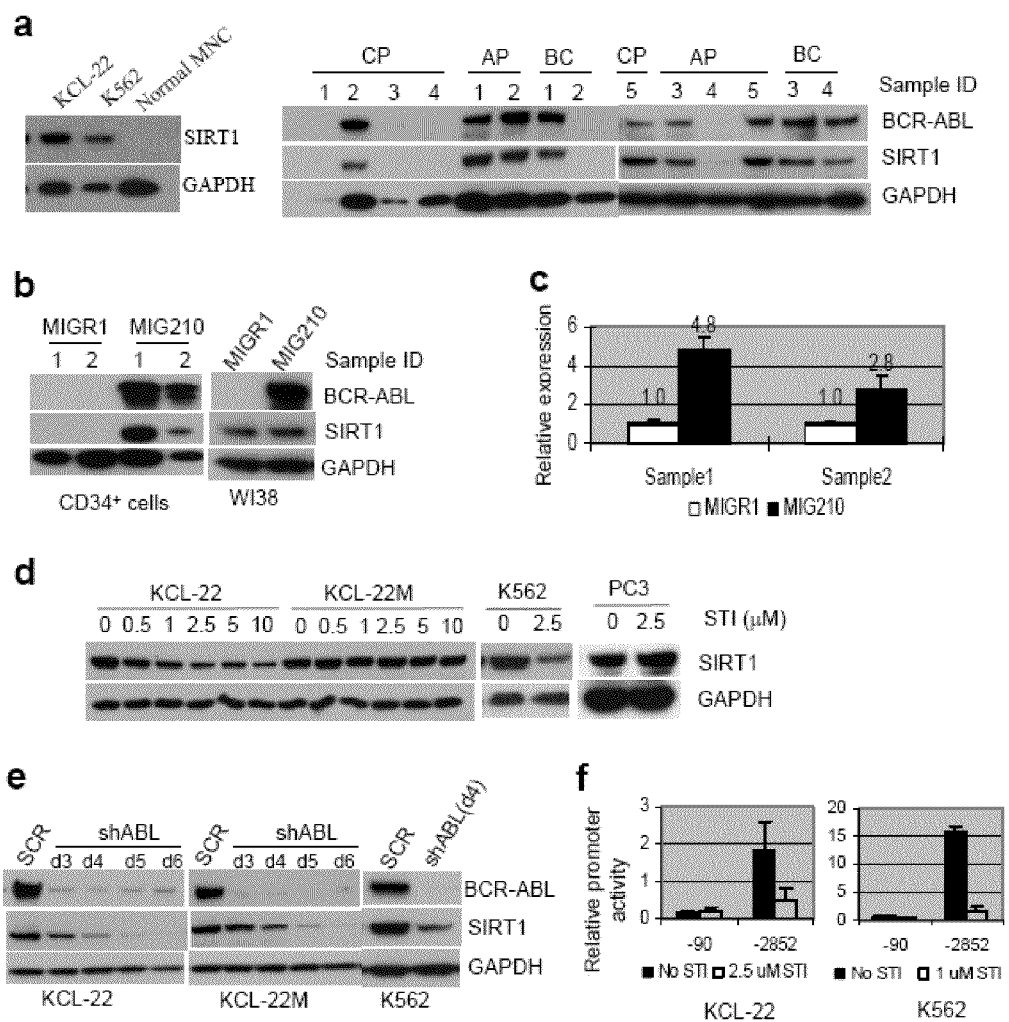
FIG. 26 shows that BCR-ABL expression activates SIRT1 in human hematopoietic progenitor cells (A) SIRT1 protein levels in CML cell lines (left), and primary CD34+CML cells (right). CP, chronic phase; AP, accelerated phase; BC, blast crisis CML. PBL, peripheral blood mononuclear cells. SIRT1 protein (B) and RNA (C) levels increased after BCR-ABL transduction (MIG210) in normal CD34+ cells from two independent healthy donors, but not in W138 cells. Empty vector MIGR1 was used as a control. RNA was analyzed by reverse transcription followed by real-time PCR. (D) SIRT1 protein levels decreased upon imatinib (STI) treatment for 48 hours in KCL-22 and K562 cells, but not in KCL-22M cells or prostate cancer PC3 cells. (E) BCR-ABL knockdown by shABL lentiviral vector reduced SIRT1 expression 3 to 6 days after initial transduction. SCR, scrambled shRNA. (F) BCR-ABL activated SIRT1 promoter. Luciferase reporter constructs of SIRT1 promoter (2852 and 90 bp fragments respectively) were transfected into CML cells and treated with imatinib for 30 hours. Relative promoter activity was calculated by normalizing luciferase activity to the GFP level from a transfection control plasmid.
Figure 46:
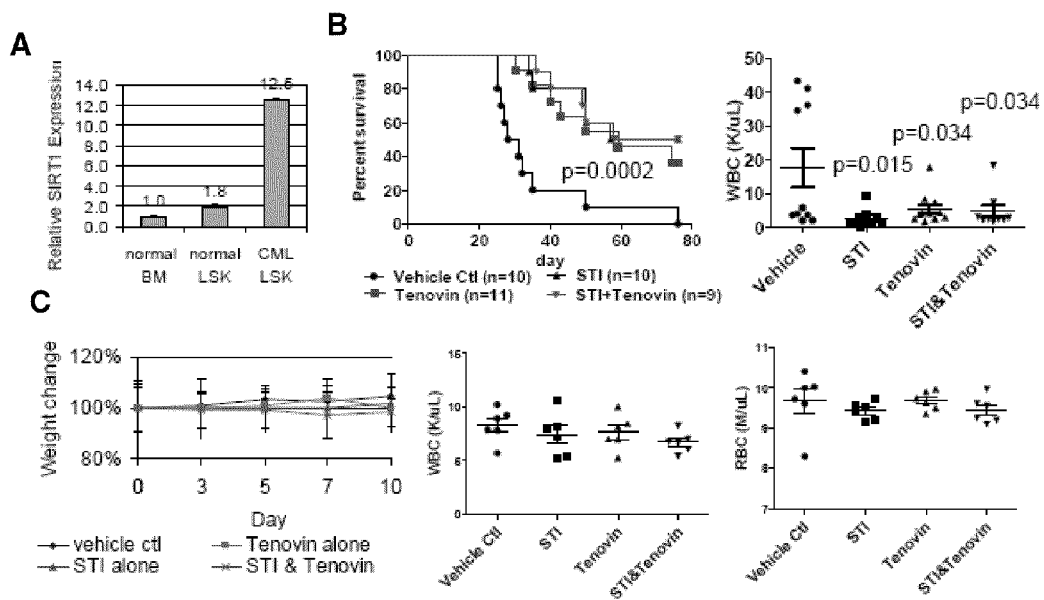
FIG. 46 shows that SIRT1 knockout or inhibition suppresses development of CML-like disease in the mouse bone marrow transduction/transplantation model. (A) SIRT1 mRNA levels in normal BALB/c bone marrow and LSK cells as compared to LSK cells purified from CML mice. (B) Survival curves (left) for CML mice with drug treatment. Ten days after receiving 1×10$^5$ bone marrow cells transduced by MIG210, mice were treated by vehicle, imatinib (200 mg/kg/day), tenovin-6(50 mg/kg/day), or combination for 10 days. Total blood leukocyte counts (right) were analyzed at day 20 after transplantation. (C) Physiological indexes of normal BALB/c mice after the same 10 day treatment with vehicle, imatinib, tenovin-6 or combination. Body weight was monitored during drug treatment, and total leukocyte and erythrocyte counts were analyzed at day 16.

It was found that SIRT1 expression was dramatically upregulated in bone marrow cells from mice receiving BCR-ABL transformed SIRT1$^{+/+}$ cells (FIG. 29D). To determine cell populations with SIRT1 expression change, bone marrow cells were sorted for expression of hematopoietic stem/progenitor cell marker CD150(Kiel et al., 2005) and green fluorescent protein (GFP) marker from the retroviral vector for transformation. It was found that SIRT1 activation occurred specifically in GFP$^+$CD150$^+$ transformed progenitor cells, but not in GFP$^+$CD150$^-$ cells or non-transformed cells (FIG. 29E), similar to that seen for human CD34$^+$ progenitor cells (FIGS. 26B and 26C). To further validate this finding, CML progenitor cells were sorted using classic Lin-Sca1$_+$cKit$^+$ (LSK) markers, and found that SIRT1 RNA was significantly elevated in CML progenitor cells (FIG. 46A).

Figure 54:
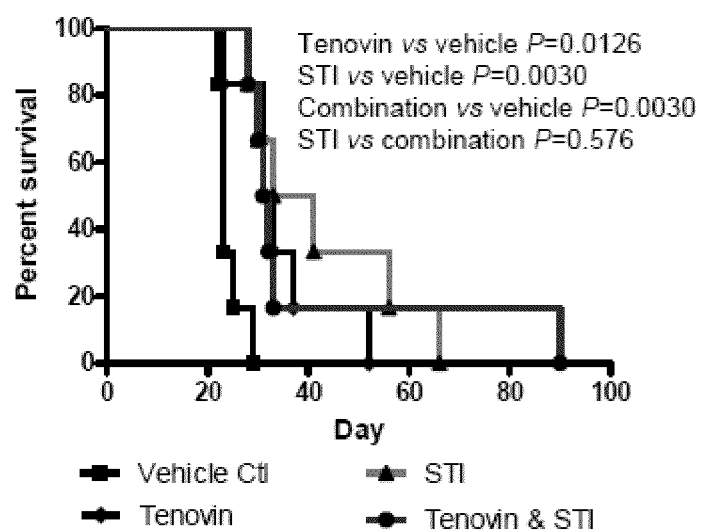
FIG. 54 illustrates the effects of tenovin-6 treatment on CML mice. The experiment was performed as described in FIG. 46B, with the exception that the transduced donor cells were $2.5 \times 10^5$ for each mouse. N=6 for each group.
Figure 55:
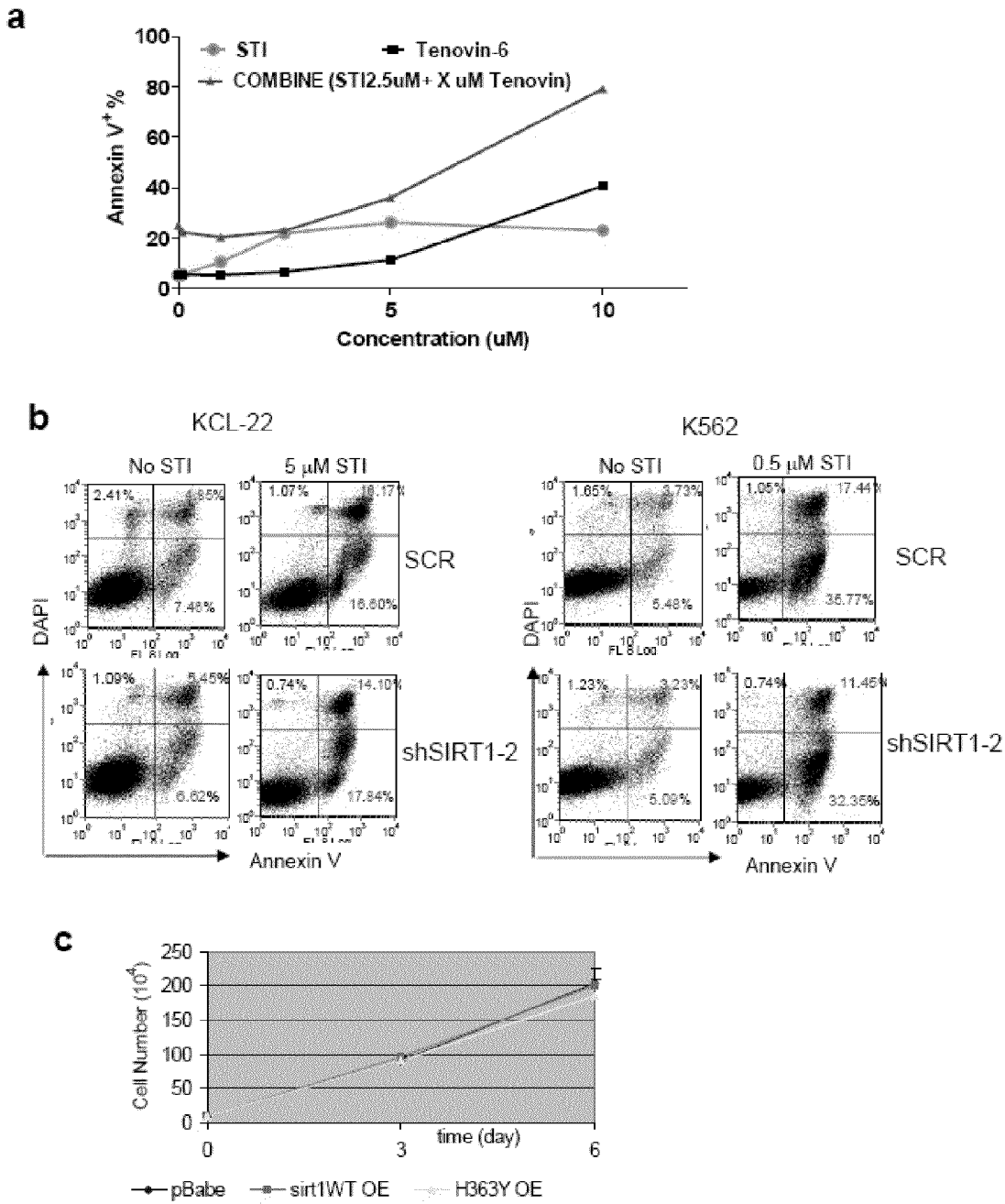
FIG. 55 shows that moderate inhibition of SIRT1 did not induce significant apoptosis. (A) Apoptosis induction in KCL-22 cells by tenovin-6, imatinib and combination. Apoptosis was analyzed after 72 h treatment with various concentrations of individual drugs as indicated. For combination treatment, 2.5 µM imatinib was combined with various concentrations of tenovin-6. Annexin V+ cells were analyzed by flow cytometry. (B) No significant effect of apoptosis induction in KCL-22 and K562 cells by shSIRT1-2 that resulted in moderately SIRT1 knockdown. (C) Over-expression of wild type of H363Y mutant SIRT1 did not affect KCL22 cell growth.

Next, it was determined whether treatment of CML mice with a SIRT1 inhibitor would deter the disease. Due to the solubility, an effective concentration of sirtinol was not obtainable in vivo. Therefore, a more potent and water soluble inhibitor tenovin-6 that inhibits SIRT1 and SIRT2 was tested. Treatment with tenovin-6 at 5 µM and higher concentrations sensitized CML cells to imatinib-induced apoptosis (FIG. 55A). It was found that tenovin-6, administrated at 50 mg/kg/day, significantly extended CML mouse survival (FIG. 46B). No noticeable toxicity was detected with tenovin-6 alone or in combination with imatinib (FIG. 46C). Some mice with the combination treatment were the longest survivors (FIG. 54). These results show that SIRT1 activation is required for efficient BCR-ABL transformation of hematopoietic stem/progenitor cells and CML disease development.

EXAMPLE 4

SIRT1 Promotes Genetic Instability and Oncogenic Evolution in Cancer

Materials and Methods

In combination with the materials and methods described in Examples 1, 2 and 3 above, the following additional materials and methods were used.

Cell lines and culture. H3255 cell line is obtained from National Cancer Institute and H1650 cell line from American Type Culture Collection (ATCC). Gefitinib is obtained from AstraZeneca or purchased from Euroasia Pharmaceuticals, and sirtinol is purchased from Sigma. For resistance assay, $2.5 \times 10^5$ H3255 or H1650 cells are seeded per well in 6-well plates overnight, and treat with drugs in 3 ml culture medium each. Cells are maintained in culture without medium changes. Relative cell numbers are analyzed over time in triplicate wells. Cells are fixed with 4% formaldehyde, stained with 0.1% crystal violet and quantified by using Odyssey Infrared Imaging System (LI-COR Biosciences). When relapse occurs, emerging cells reach confluence rapidly and are expanded into larger culture dishes. If the H3255 cells are unable to survive the applied dosage of gefitinib, then a lower therapeutic dose is used such as 0.4 µM, or the lowest therapeutically effective dose.

Using the above procedures, resistance models may be reproduced for H1650 cells. In addition, a faster relapse for H3255 cells with T790M mutation may be obtained (e.g. in two weeks). Inhibition of SIRT1 by sirtinol or by shRNA may have a synergistic or additive effect with gefitinib for inducing apoptosis and suppressing growth. The relapse normally obtained through mutation or non-mutation mechanisms will be blocked or delayed.

The resistance models may be also reproduced for other cancer cell lines, such as for example, another NSCLC cell line PC-9 that also relapses on gefitinib treatment.

DNA damage induction by camptothecin and de novo mutation analysis. Cells were pre-selected for four days in HAT medium to remove pre-existing HPRT mutations. The efficiency of HAT selection was confirmed by plating these cells on soft agar with 2.5 µg/ml 6-thioguanine, which produced zero colony. HAT-selected cells were then treated with 0.5 µM CPT for 1 hour, and then cultured for 10 days before used for soft agar clonogenic assay with 6-thioguanine selection. The rest of HAT-selected cells were cultured in medium without selection. The change of γH2AX was analyzed with γH2AX Assay Kit (Upstate Biotech).

DNA damage repair assay. Five million KCL-22 cells were transfected with 15 µg linearized repair reporter construct DR-GFP or EJ5-GFP by electroporation, and cells were selected for puromycin resistance. Individual clones were plucked from soft agar and expanded to screen for clones carrying an intact copy of the reporter constructs by Southern blotting as described previously (Bennardo et al. 2008; Weinstock et al.2006). Clonal KCL-22 cells with an intact copy of reporters were transduced by shSIRT1, shRAD51 or shNBS1 for 24 h followed by electroporation with 50 µg I-SceI encoding plasmid plus 10 µg Ds-Red. After another 48 h culture, the cells were analyzed by flow cytometry for GFP and Ds-Red expression to determine the repair efficiency. $GFP_+$ cells were the successfully repaired cells, and repair rate was normalized to Ds-Red transfection efficiency.

DNA methylation analysis. Bisulfite genomic DNA sequencing was performed as previously described (Frommer et al., 1992; Herman et al., 1996). Briefly, 1 µg of genomic DNA is treated with sodium bisulfite for 16 hours, and the DNA is then recovered using Wizard DNA clean-up system (Promega). PCR products are cloned into pCR2.1 vector with TOPO TA cloning kit (InVitrogen). At least ten clones each were sequenced for DNA methylation analysis. For quantitative HIC1 promoter methylation analysis, the MassArray DNA methylation analysis system (Sequenom) was used as per the manufacturer's protocol at City of Hope Functional Genomic Core. The methylation for individual or aggregate CpG sites was analyzed with EpiTyper software v1.0(Sequenom).

ChIP assay. This assay was performed as described previously$_{69}$. We used STAT5A or 5B antibody (Cell Signaling) for immunoprecipitation and used anti-Flag antibody (Santa Cruz) as a control. The following primers were used for ChIP PCR analysis: for STAT5A binding site, 5'-gcatctctgacctct-cagca-3' (sense) (SEQ ID NO: 38) and 5'-cagaaacaaaattc-ccagcttt-3'(antisense) (SEQ ID NO: 39); for STAT5B binding site, 5'-gggattggtatgaaggaacg-3' (SEQ ID NO: 40) and 5'-agc-gaaactccgtctcaaaa-3' (antisense) (SEQ ID NO: 41); for GAPDH, 5'-tctggggactaggggaagga-3' (sense) (SEQ ID NO: 42) and 5'-ccgcaaggagagctcaaggt-3' (antisense) (SEQ ID NO: 43).

SIRT1 mRNA stability. KCL-22 cells were seeded at $5×10^6$/ml in 12-well plate with 2.5 µM imatinib or DMSO as mock control. Twelve hours later, actinomycin D (2 µg/ml) was added and at 0, 1, 2, 4 and 8 hours after actinomycin treatment, total RNA was extracted. First strand cDNA was reverse transcribed from 1.0 µg of total RNA using Superscript III kit (Invitrogen). One microliter of the first strand cDNA synthesis reaction mixture was used for PCR amplification in a total volume of 50 µl. GAPDH was amplified with 25 cycles and SIRT1 was amplified with 30 cycles. The primer sequences used were:

```
SIRT1 Forward:
5'-TGGCTCTATGAAACTGTTCTTGGT-3'   (SEQ ID NO: 18)

SIRT1 Reverse:
5'-CAGCATCTTGCCTGA-TTTGTAA-3'    (SEQ ID NO: 19)

GAPDH Forward:
5'-GGAAGGTGAAGGT-CGGAGTC-3'      (SEQ ID NO: 20)

GAPDH Reverse:
5'-TTCCCGTTCTCAGCCTTGAC-3'       (SEQ ID NO: 17)
```

SIRT1 Promotes De Novo Genetic Mutations of Cancer Cells Upon DNA Damage.

Figure 15:
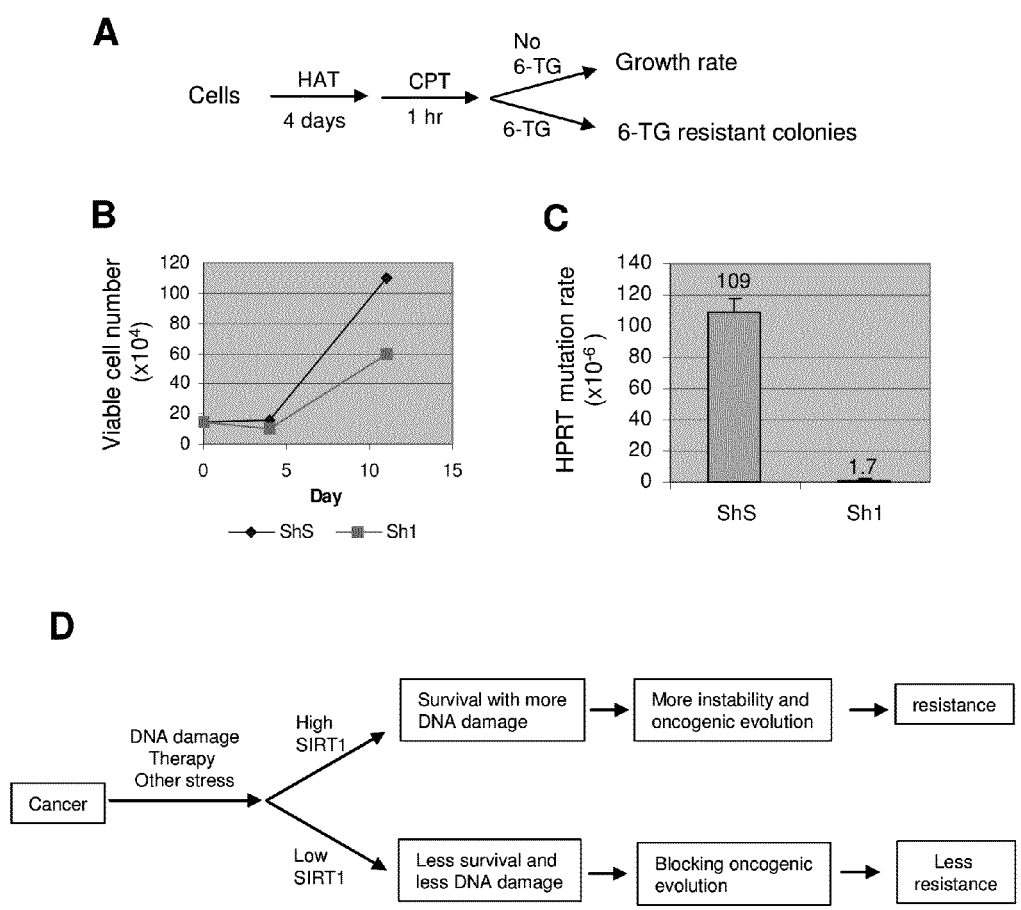
FIG. 15 shows effects of SIRT1 on DNA damage-induced mutations. (A) Schematic of de novo HPRT mutation assay. (B) Survival and proliferation of HAT-selected and CPT treated cells. KCL-22 cells with SIRT1 Sh1 knockdown had half the survival/proliferation rate of mock knockdown cells. (C) HPRT mutation rate of HAT-selected and CPT treated cells. The effectiveness of HAT pre-selection was confirmed by plating one million HAT-selected cells on soft agar with 6-TG and produced no colony. One million HAT-selected and CPT treated cells each from SIRT1 or mock knockdown were analyzed for 6-TG resistance. (D) Model of roles of SIRT1 in cancer chemoresistance. High expression levels of SIRT1 promote cancer cells survival under conditions of DNA damage agents, chemotherapy, and other stress, whereas accumulating DNA damages, promoting genetic instability and evolution of ontogenesis such as resistant mutations, to survive and resist treatments. Inhibition of SIRT1 blocks such process and prevents acquired resistance.

The role of SIRT1 in regulating de novo DNA damage in CML cells was investigated. SIRT1 and mock knockdown KCL-22 cells were treated with hypoxanthine aminopterin thymidine (HAT) to remove preexisting HPRT mutation, followed by treatment with camptothecin (CPT) to induce DNA damage. Cells were then analyzed for survival/proliferation and HPRT mutations. SIRT1 Sh1 knockdown cells exhibited two fold less survival over time than mock cells (FIG. 15B). HPRT mutation rate in SIRT1 knockdown cells was decreased by 64 fold (FIG. 15C). Similar results were obtained by both SIRT1 Sh1 and SIRT1 Sh2 knockdown (FIG. 33D).

Figure 48:
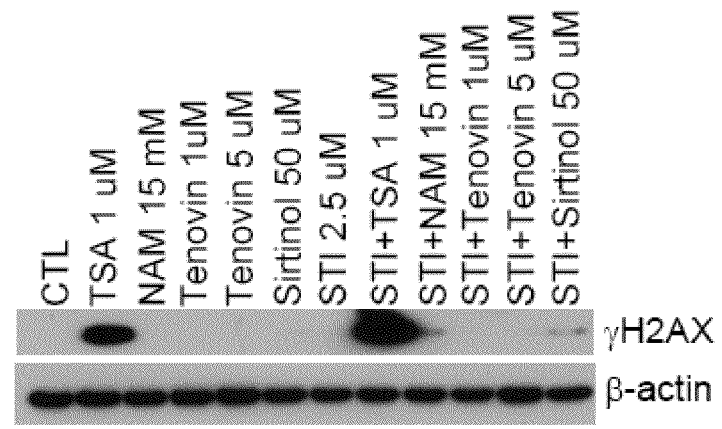
FIG. 48 is an analysis of γH2AX response in KCL-22 cells at 24 h after various drug treatments.

Additionally, SIRT1 knockdown reduced spontaneous HPRT mutations when these cells were maintained for one month in culture (FIG. 33D). Furthermore, SIRT1 knockdown robustly suppressed CPT-induced de novo HPRT mutations in prostate cancer cells (FIG. 39), indicating that SIRT1-mediated mutagenesis is independent of cancer cell types. These results indicate that SIRT1 is a key protein promoting genetic instability and the evolution of oncogenes to resist and survive drug therapy and overcome DNA damage (FIG. 15D). These findings are surprising given that SIRT1 is shown to promote DNA damage repair (Oberdoerffer et al., 2008; Wang et al., 2008). It was also found that SIRT1 knockdown inhibited DNA damage responses by reduction of γH2AX staining (FIG. 33E). SIRT1 inhibitors did not increase γH2AX expression in CML cells in the presence or absence of imatinib, in contrast to HDAC inhibitor trichostatin A (TSA) that elicited robust γH2AX induction (FIG. 48). These results indicate that although a high level of SIRT1 may enhance DNA damage responses in cancer cells, it can also increase de novo genetic mutations. Such paradoxical functions of SIRT1 may be a result of altered DNA damage repair mechanisms in cancer as further described below.

SIRT1 is Activated by BCR-ABL Transformation in Human Hematopoietic Stem/Progenitor Cells.

Figure 35:
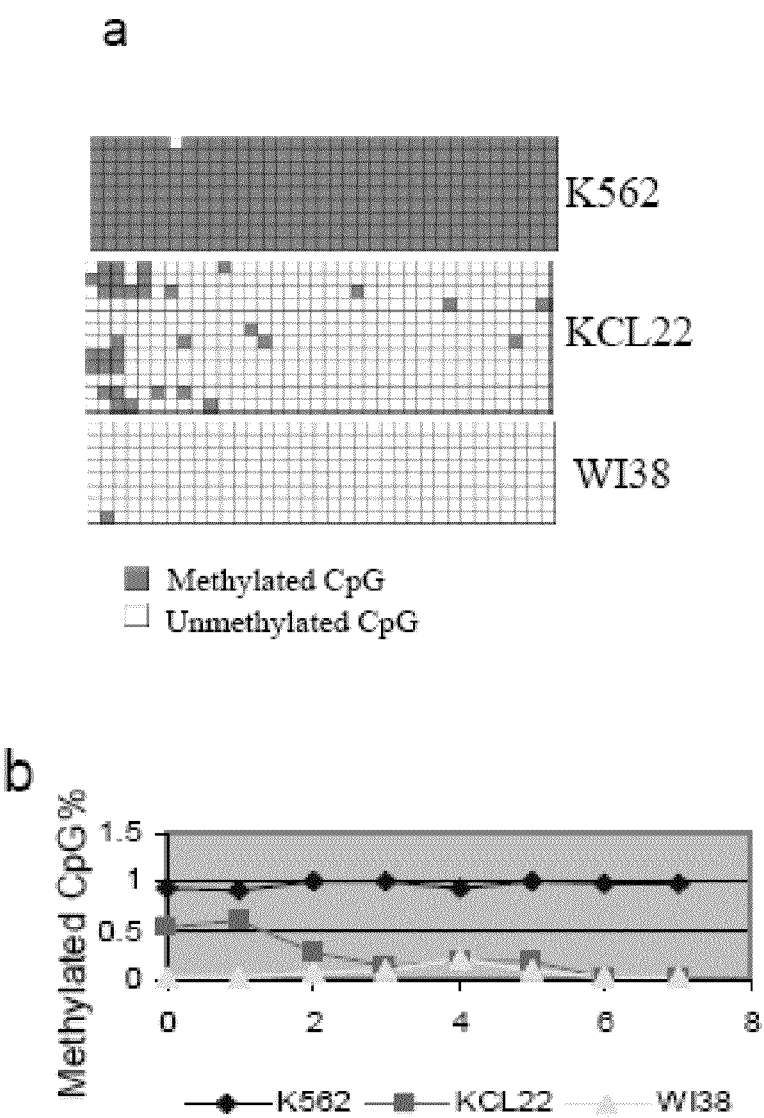
FIG. 35 illustrates epigenetic inactivation of HIC1 in CML cells. HIC11a promoter methylation analyzed by bisulfite sequencing (A) and quantitative MassArray analysis (B).

Promoter hypermethylation of HIC1 increases progressively towards late phases of CML (Issa et al., 1997). We initially hypothesized that upregulated SIRT1 upon HIC1 gene silencing may be important for CML chemoresistance. Indeed, we found that SIRT1 expression levels increased in blast crisis CML cell lines KCL-22 and K562(FIG. 26A), correlated with HIC1 promoter hypermethylation and silencing in these cells (FIG. 35 and FIG. 50). To examine SIRT1 expression in primary human CML, we isolated $CD34^+$CML progenitor cells. It was found that SIRT1 protein levels were tightly correlated with BCR-ABL expression levels from chronic to blast crisis phase patients (FIG. 26A). Noticeably, more advanced-phase samples showed high BCR-ABL levels along with high SIRT1 expression. This finding prompted the determination of the source of the change in SIRT1 expression during BCR-ABL transformation. Normal $CD34^+$ cells were isolated from healthy donors, and transduced with BCR-ABL retroviral vector MIG210(Pear et al., 1998). SIRT1 protein was hardly detectable in normal $CD34^+$ cells by Western blot, but was dramatically upregulated by BCR-ABL transduction (FIG. 26B). SIRT1 RNA level was also significantly upregulated by BCR-ABL (FIG. 26C). BCR-ABL transduction did not increase SIRT1 expression in normal human fibroblasts W138 cells (FIG. 26B), mouse fibroblast NIH3T3 cells, human renal cancer cell line 293, and myeloid leukemia cell TF1, nor did it further increase SIRT1 levels in blast crisis CML cells (FIG. 36A). Accordingly, BCR-ABL transduction selectively activates SIRT1 expression in normal human hematopoietic progenitor cells.

To further examine regulation of SIRT1 expression in CML, KCL-22 and K562 cells were treated with the BCR-ABL kinase inhibitor imatinib. SIRT1 protein levels decreased in a drug concentration-dependent manner. In contrast, the treatment did not change SIRT1 expression in KCL-22M cells that express the imatinib-resistant T315I kinase domain mutant BCR-ABL or in a prostate cancer cell line (FIG. 26D). To determine specificity of imatinib effect on SIRT1, BCR-ABL was knocked down using lentiviral shRNA. As a result, it was found that SIRT1 protein levels decreased upon BCR-ABL knockdown in KCL-22, KCL- 22M and K562 cells (FIG. 26E). These data further support that BCR-ABL regulates SIRT1 expression in CML cells.

Since SIRT1 expression is subjected to multiple levels of regulation including protein phosphorylation (Ford et al., 2008), mRNA stability (Abdelmohsen et al., 2007) and transcription (Nemoto et al., 2004; Chen et al., 2005), it was determined how BCR-ABL activates SIRT1 expression. It was found that BCR-ABL knockdown only affected endogenous SIRT1 protein expression but not the exogenously introduced SIRT1 (FIG. 36B), indicating that BCR-ABL does not affect SIRT1 protein stability per se. After blocking transcription by actinomycin D, imatinib treatment did not alter the half life of SIRT1 mRNA and thus its stability (FIG. 36C). To examine if BCR-ABL expression activates SIRT1 promoter, reporter constructs of the SIRT1 promoter were transfected into KCL-22 and K562 cells followed by imatinib treatment. Imatinib treatment significantly inhibited SIRT1 promoter activity (FIG. 26F). Together, this data indicates that BCR-ABL transformation of human hematopoietic progenitors selectively activates SIRT1 promoter and transcription.

Figure 27:
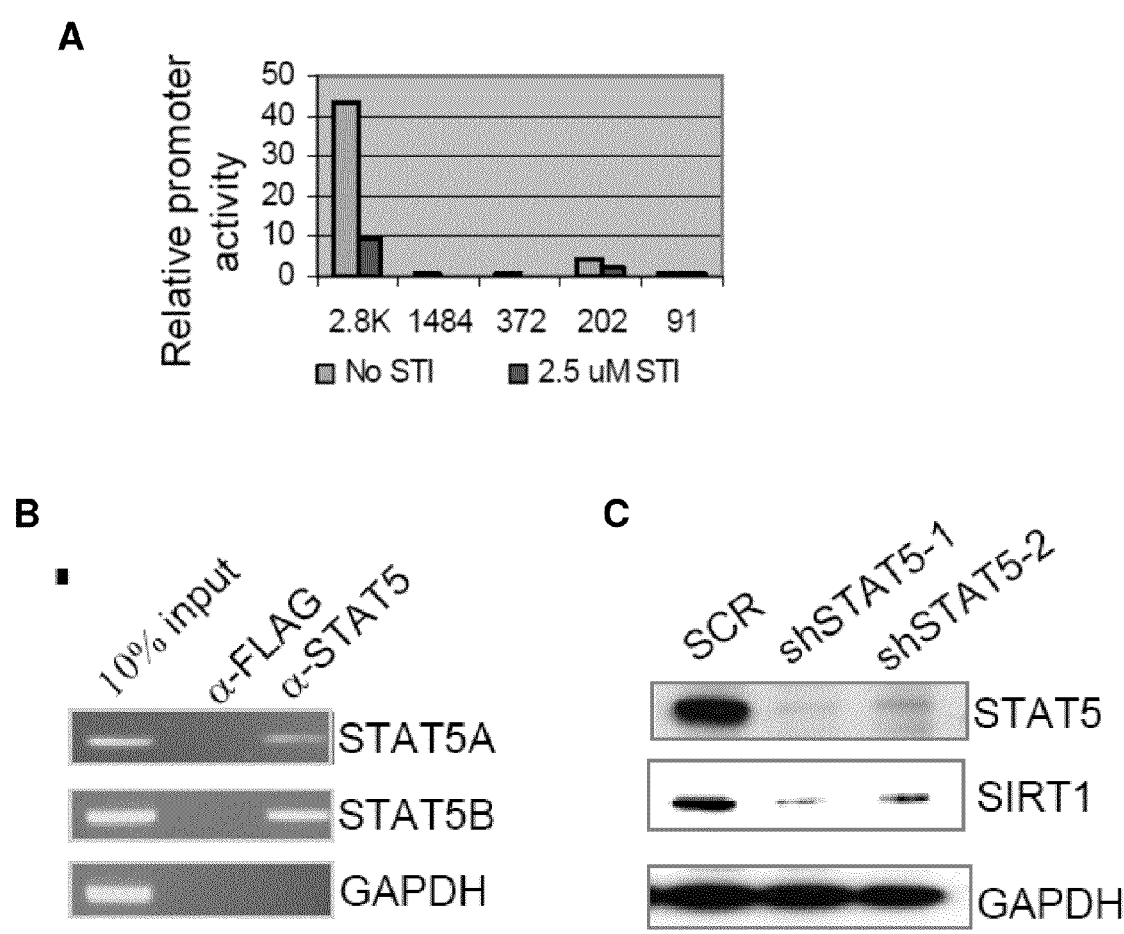
FIG. 27 further illustrates that SIRT1 is activated by BCR-ABL transformation in human hematopoietic progenitors. (A) Luciferase reporter assay of SIRT1 promoters. BCR-ABL activated 2.85 kb but not shorter SIRT1 promoter in CML cells, and imatinib treatment suppressed SIRT1 promoter. (B) STAT5 A/B bound on the endogenous SIRT1 promoter analyzed by ChIP. FLAG antibody as a control. (C) STAT5 knockdown inhibited SIRT1 expression.

As shown in FIG. 26A, SIRT1 expression was found to be tightly correlated with BCR-ABL levels in CD34$^+$ hematopoietic progenitors from human CML patients (FIG. 26A). SIRT1 expression was hard to detect in normal CD34$^+$ progenitors, but expression of BCR-ABL dramatically increased SIRT1 protein and RNA levels (FIGS. 26B and 26C). BCR-ABL expression in normal fibroblast W138 cells and several solid tumor cell lines did not increase SIRT1 expression, indicating a relatively specific activation mechanism in hematopoietic progenitor cells. Conversely, inhibition of BCR-ABL by shRNA knockdown or imatinib in blast crisis CML cells reduced SIRT1 expression (FIG. 26E). As shown in FIG. 26F, BCR-ABL expression activated SIRT1 promoter, with a major responsive element located between −1.48 kb and −2.8 kb (FIG. 27A). The binding of STAT5 (signal transducer and activator of transcription 5) in this region was identified as a novel mechanism for SIRT1 activation in hematopoietic cells (FIGS. 27B and 27C). The rVista program (Loots & Ocharenko 2004) was used to search for potential transcriptional factors binding at this region that are related to BCR-ABL functions. Two putative binding sites for signal transducer and activator of transcription 5(STAT5A and 5B) located at −1838 and −2235(FIG. 51) were identified. No other STAT members were found in this region.

STAT5 is a key signal transducer of BCR-ABL in CML (Maria et al., 1996), and is also activated in AML and acute lymphoid leukemia (ALL) (Van Etten, 2007). STAT5 knockout suppresses BCR-ABL transformation and development of CML-like disease in mice (Ye et al., 2006; Hoelbl et al., 2006). Therefore, it may serve as a common activator of SIRT1 in leukemia. To validate the role of STAT5, a STAT5 knockdown was performed using shRNA in CML cells. It was found that SIRT1 expression was decreased accordingly (FIG. 27C). Using chromatin immunoprecipitation (ChIP) assay, it was found that both STAT5A and 5B were associated with the SIRT1 promoter (FIG. 27B). Together, these results indicate that BCR-ABL activates SIRT1 transcription in human CD34$_+$ progenitor cells for which STAT5 is a key mediator.

SIRT1 is Required for Efficient BCR-ABL Transformation of Stem Cells.

Figure 30:
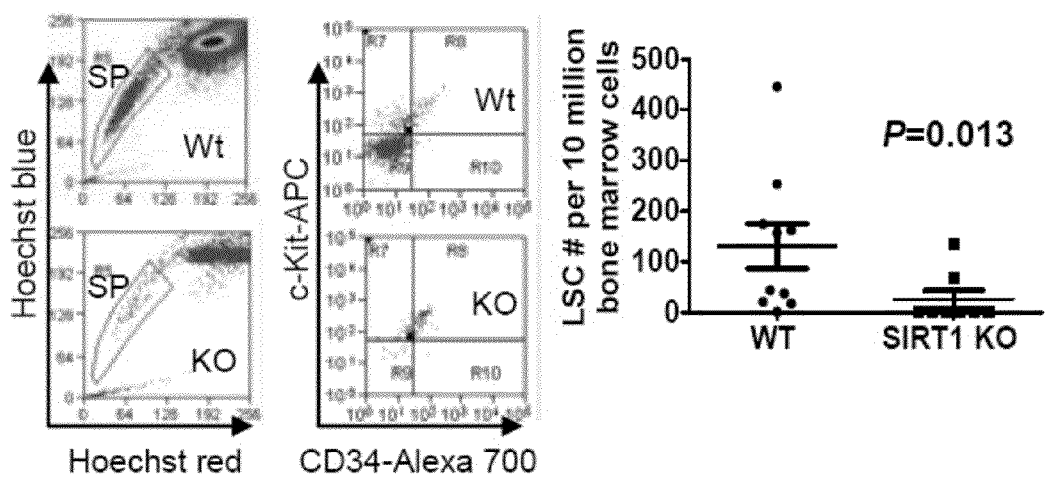
FIG. 30 illustrates that SIRT1 is required for CML stem cell survival. Analysis of CML stem cells in BCR-ABL transduced mice. GFP$^+$Lin-cells were gated for side population (SP) followed by c-Kit and CD34 labeling. Leukemic stem cells were GFP$^+$Lin$^-$cKit$^+$C34$^-$SP.
Figure 32:
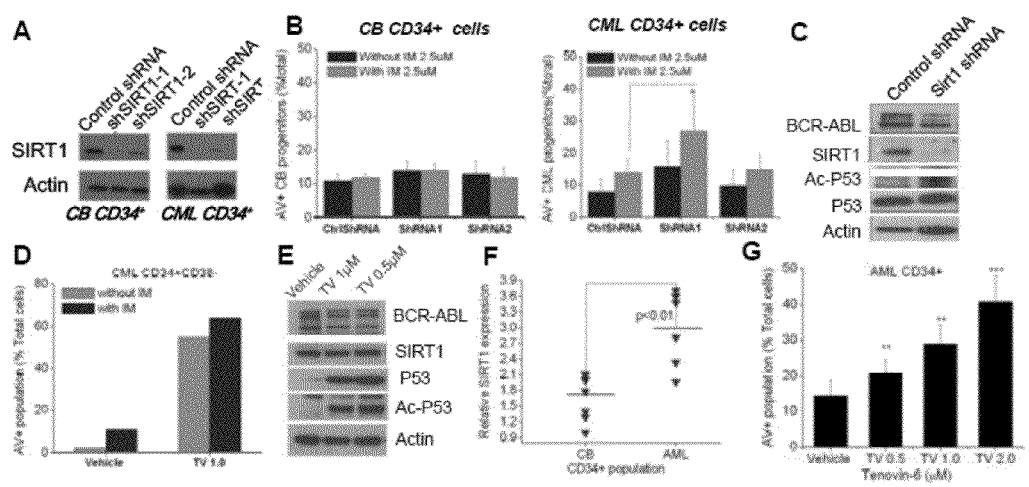
FIG. 32 illustrates that SIRT1 inhibition enhances apoptosis of human CML progenitor cells. (A) Inhibition of SIRT1 protein expression in CML and cord blood (CB) CD34+ cells by lentivirus-mediated expression of SIRT1 shRNA. (B) Increased apoptosis in CML (right) but not cord blood (left) CD34+ cells with or without imatinib (IM) treatment. (C) SIRT1 inhibition in CML CD34+ cells results in increased P53 acetylation. (D) Treatment with the SIRT1 inhibitor Tenovin-6(TV) results in increased apoptosis of primitive CML CD34+CD38-progenitors including the quiescent (CFSE bright) fraction that is resistant to IM. (E) Tenovin-6 treatment is associated with enhanced P53 acetylation in CML CD34+ cells. (F) SIRT1 expression in CB and AML CD34+ cells. (G) Tenovin-6 induced apoptosis on AML CD34+ cells.

As shown in FIGS. 8A and 28C (top), SIRT1 inhibition by small molecule inhibitors or shRNA knockdown sensitized CML cells to imatinib for growth suppression and induction of apoptosis. SIRT1 knockdown inhibited soft agar colony formation and growth of xenografted CML cells in immunodeficient mice (FIG. 28E). To further examine SIRT1 functions in CML, a mouse model employing retroviral BCR-ABL transduction of mouse bone marrow cells was used, followed by transplantation of these cells to syngeneic recipients (Pear et al., 1998). Many hallmarks of human CML are reproduced in this model and recipient mice develop a CML-myeloproliferative disease and die in 3-4 weeks. SIRT1 knockout mice were backcrossed to BALB/c background. The SIRT1 knockout did not affect normal hematopoiesis, stem cell frequency or engraftment, but the knockout inhibited BCR-ABL transformation and development of the myeloproliferative disease (FIG. 29A). As in human progenitor cells, SIRT1 expression was activated by BCR-ABL in mouse HSC. SIRT1 knockout significantly reduced the number of mouse CML stem cells (FIG. 30), identified as cKit$^+$ CD34$^-$ side population in BABL/c strain (Hu et al., 2006). It has shown that SIRT1 knockdown or inhibition resulted in increased p53 acetylation (FIGS. 32C and 32E) and enhanced imatinib-mediated apoptosis in human CML CD34$^+$ cells but not in normal (cord blood) CD34$_+$ cells (FIGS. 32B and 32D). Similarly, AML CD34$^+$ cells showed increased SIRT1 expression and increased apoptosis on SIRT1 inhibitor treatment (FIGS. 32F and 32G). The results of the studies described herein indicate that SIRT1 activation is required for efficient BCR-ABL transformation. SIRT1 inhibition suppresses disease development and induces apoptosis in leukemic but not normal stem cells.

SIRT1 Promotes BCR-ABL Mutations and Cancer Genome Instability.

Figure 10:
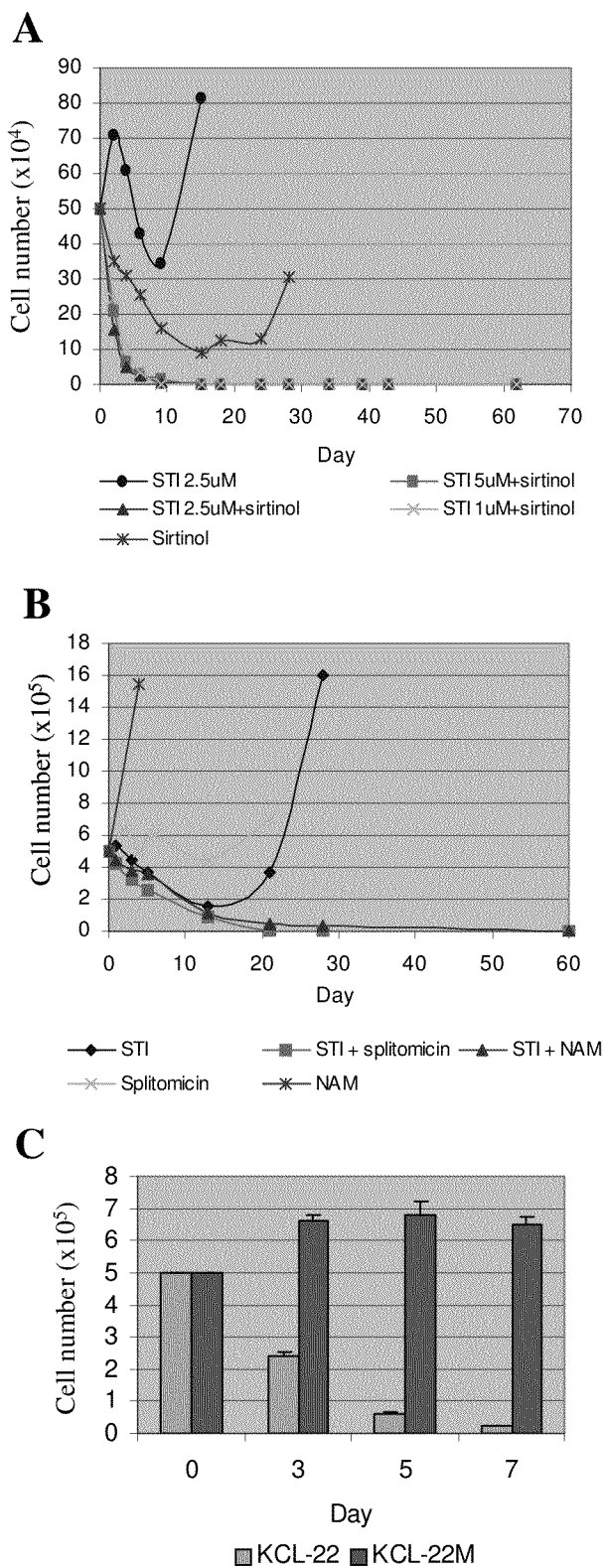
FIG. 10 shows SIRT1 inhibitors block relapse of CML on imatinib treatment. (A) One half million KCL-22 cells were treated with 50 µM sirtinol or STI-571 alone at the concentration indicated or in combination of the two drugs. Cells for STI-571 treatment alone all relapsed. Sirtinol blocked relapse at all dosages of STI-571. A small volume of drug-free medium was supplied after three to five weeks of treatment to restore the original volume during the prolonged culture for two to three months. (B) KCL-22 cells were treated with 300 µM splitomicin or 15 mM nicotinamide alone or their combination with 5 µM STI-571. Both splitomicin and nicotinamide blocked relapse. (C) Comparison of KCL-22M and KCL-22 cells in response to the treatment with 2.5 µM STI-571 combined with 50 µM sirtinol.
Figure 11:
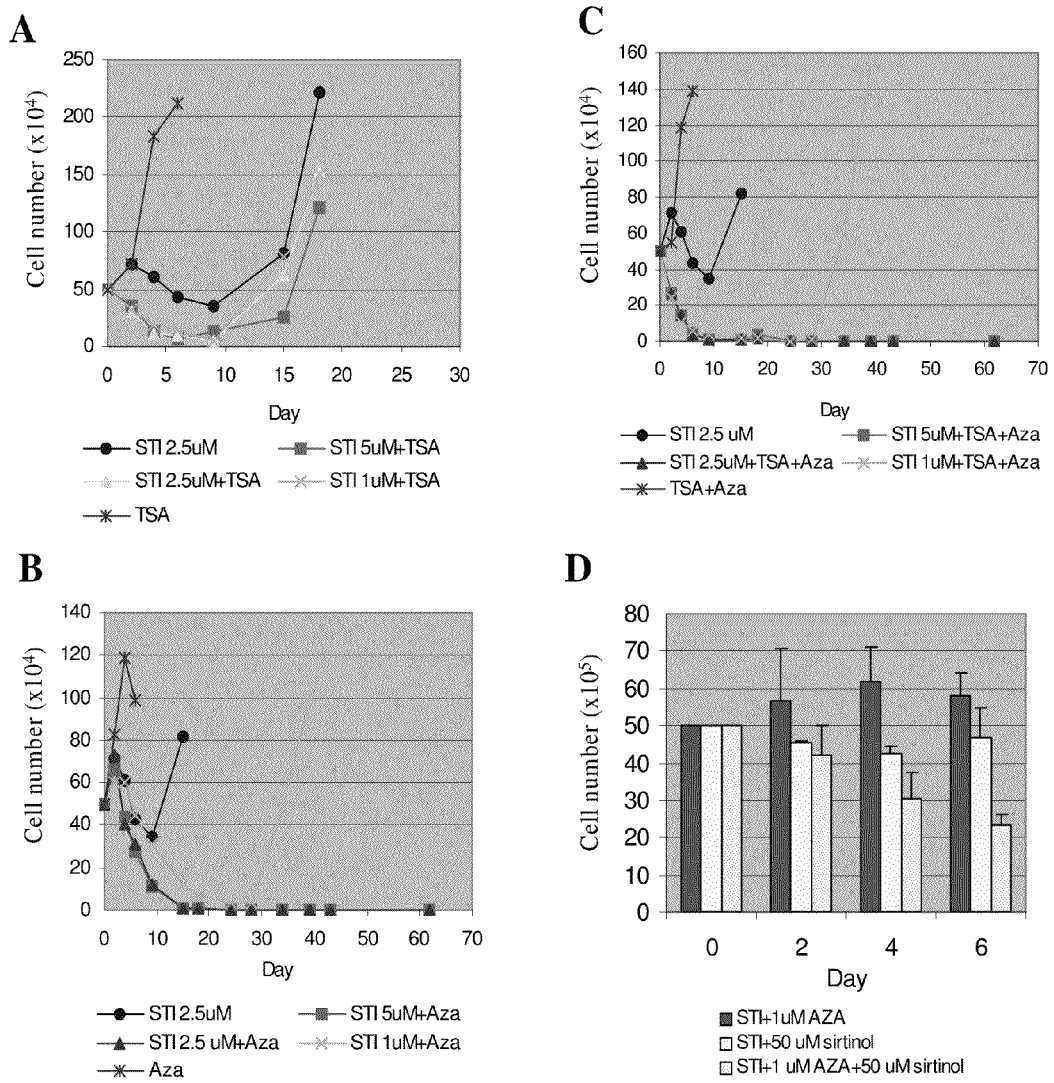
FIG. 11 shows effects of inhibitors for HDACs and DNMTs on CML chemoresistance. (A-C) KCL-22 cells were treated with 1 µM TSA (A), 1 µM AZA (azacytidine) (B), or 1 µM TSA (trichostatin A) plus 1 µM AZA (C) without and with STI-571 at the concentration indicated. AZA but not TSA blocked relapse at 2.5 and 5 µM of STI-571. (D) Responses of KCL-22M cells to the treatment with 2.5 µM STI-571 in combination with 1 µM AZA, 50 µM sirtinol, or 1 µM AZA plus 50 µM sirtinol.

Imatinib is the frontline treatment for CML; however, acquired resistance develops frequently due to secondary BCR-ABL mutations. A novel cell culture model in which a blast crisis human CML cell line KCL-22, following initial response to imatinib (or nilotinib and dasatinib), relapses in two weeks with acquisition of T315I mutation (Yuan et al., 2010) has been developed as described above. Acquisition of BCR-ABL mutations is dependent on expression of functionally intact BCR-ABL (Yuan et al., 2010). Inhibition of SIRT1 by small molecules, nicotinamide, tenovin-6, sirtinol or splitomicin, blocks relapse of CML cells upon imatinib (or nilotinib and dasatinib) treatment regardless if they can enhance apoptosis (FIGS. 10A-B and FIG. 47A). Tenovin-6 and nicotinamide blocked the relapse with a dose as low as 1 μM, below the concentrations to increase imatinib-mediated cell killing (FIGS. 10B, 47C and 55A). In contrast, HDAC inhibitor trichostatin A (TSA) fails to block relapse (FIG. 11A and FIG. 12B).

It was found that treatment with the potent second generation BCR-ABL inhibitors nilotinib and dasatinib also resulted in relapse and acquisition of T315I mutation in KCL-22 cells, but the combination with tenovin-6 or sirtinol effectively blocked the recurrence (FIGS. 47B-C). Four KCL-22 cell clones were generated, three of which can acquire different BCR-ABL mutations upon imatinib treatment, i.e. E255K (clone L1), Y253H (clone L7) and T315I (clone Ag11), whereas clone Ag3 develops resistance without BCR-ABL mutations. The combination of sirtinol with imatinib blocked relapse of all clonal KCL-22 cells on imatinib. In contrast, TSA failed to block relapse of these clonal cells (FIG. 47D). These results indicate that combination of SIRT1 inhibition with BCR-ABL inhibition is a powerful approach to overcome acquired resistance through BCR-ABL mutations.

By gene knockdown, it was found that the ability for KCL-22 cells to form BCR-ABL mutations or to relapse was proportional to the residual level of SIRT1 protein left after SIRT1 knockdown (FIGS. 33A-B). Further, the shSIRT1-2 vector moderately reduced SIRT1 level and was insufficient to increase significant apoptosis (FIG. 55B) also reduced BCR-ABL mutations (FIG. 33A). This is in line with the effect of tenovin-6 described herein and indicates that BCR-ABL mutation is more sensitive to SIRT1 function than apoptosis induction. To further validate that SIRT1 deacetylase activity is required for BCR-ABL mutagenesis, wild type or H363Y deacytylase-deficient SIRT1 was overexpressed in KCL-22 cells. The expression of either wild type or H363Y SIRT did not affect cell growth (FIG. 55C), but H363Y SIRT1 expression significantly reduced BCR-ABL mutations (FIG. 33C). Together, these results show that high levels of SIRT1 in CML cells promote BCR-ABL mutations for acquired resistance, a process that is dependent on SIRT1 deacetylase function.

Figure 39:
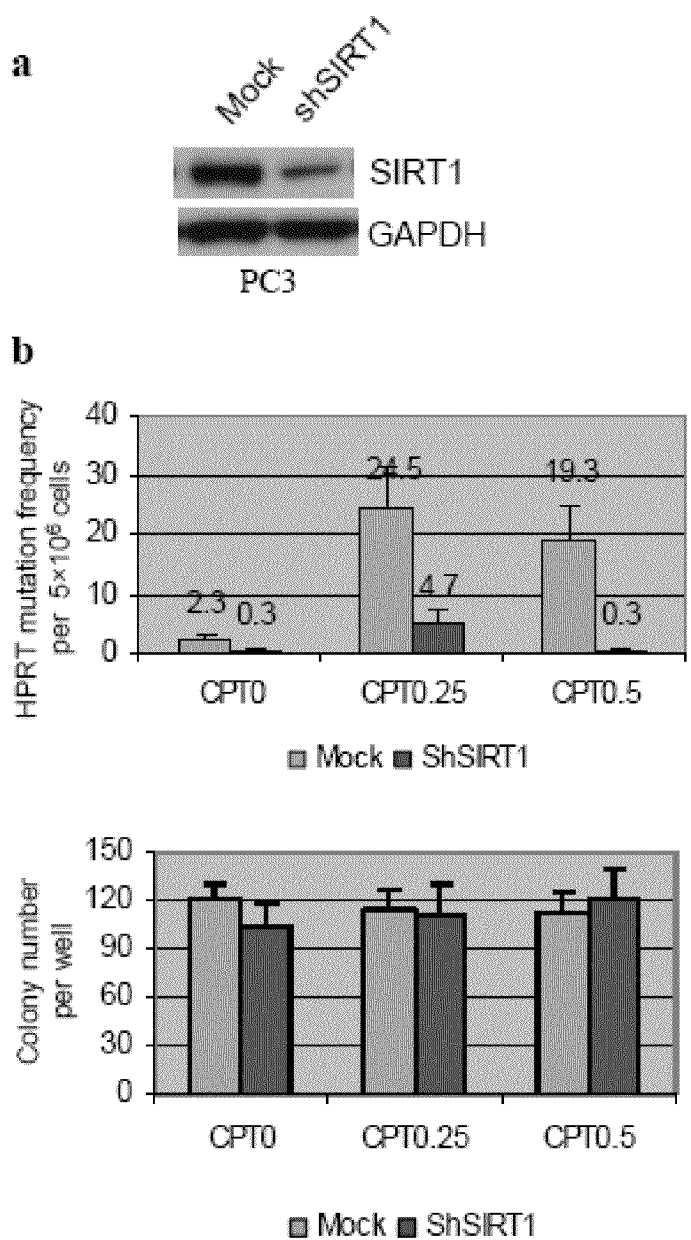
FIG. 39 illustrates that SIRT1 knockdown inhibits spontaneous or CPT-induced de novo HPRT mutation in prostate cancer cells. (A) SIRT1 level in shSIRT1 stable knockdown PC3 cells. (B) De novo HPRT mutations were analyzed similar to that in KCL-22 cells described for FIG. 6D. Top panel, five million HAT-selected and CPT treated cells per plate from mock or SIRT1 knockdown PC3 cells were analyzed for 6-thioguanine resistance. Bottom panel, plating efficiency of HAT-selected and CPT treated cells. Two hundred HAT-selected and CPT treated cells per well were seeded in 6-well plate without 6-TG selection. The number of colonies was counted 10 days after plating.

The ability of SIRT1 to promote mutations is not restricted to BCR-ABL in CML cells, as SIRT1 knockdown in prostate cancer cells also dramatically suppressed mutations on the HPRT induced by DNA damaging agent camptothecin (FIG. 39). It was further shown that an important mechanism for SIRT1 in BCR-ABL mutagenesis and CML cell survival was through deacetylation and activation of Ku70(FIG. 34A), an essential factor for error-prone non-homologous end joining DNA repair (Khanna et al., 2001) and a regulator of BAX-mediated apoptosis (Cohen et al., 2004). Knockdown of Ku70 completely blocked BCR-ABL mutations and CML cell relapse on imatinib treatment (FIG. 34D, right). Together, these studies indicate that SIRT1 plays an important role in molecular pathogenesis of CML and development of acquired resistance by promoting genetic mutations and cancer genome instability. SIRT1 may play a similar role in other leukemia and solid tumors where it is aberrantly activated.

EXAMPLE 5

SIRT1 Inhibitors

SIRT1 Inhibitor Sirtinol Synergizes with STI-571 for Apoptosis Induction in CML Cells.

Figure 7:
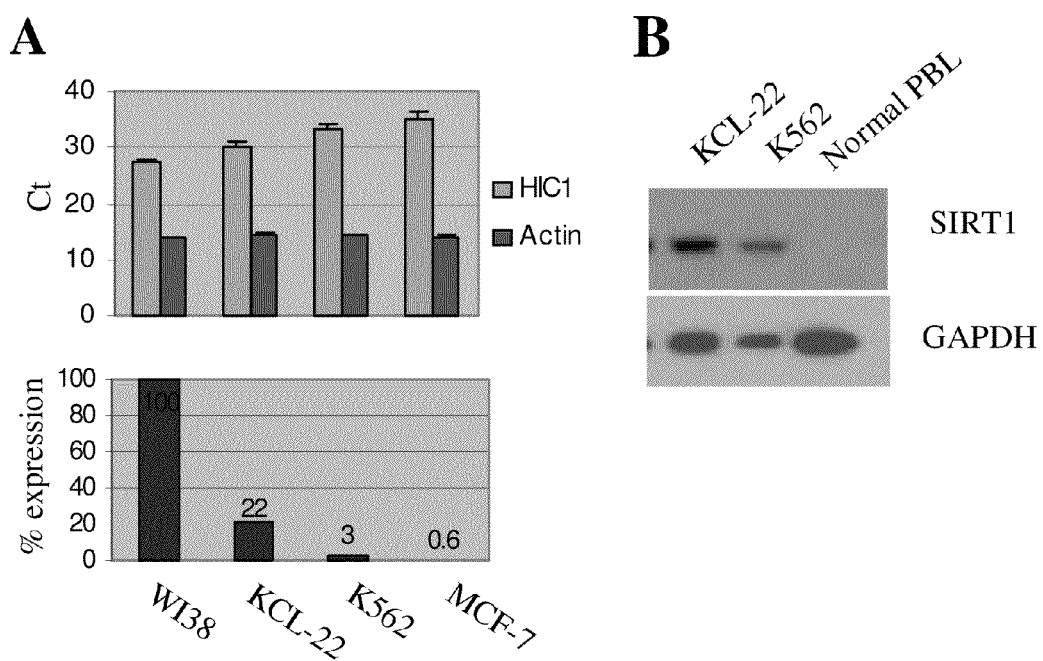
FIG. 7 shows HIC1 and SIRT1 expression in CML cells. (A) HIC1 expression by qRT-PCR. Ct of HIC1 or control actin for PCR amplification was first determined (top) and relative abundance of HIC1 level was calculated with WI-38 cells as positive control (100% expression) and MCF-7 as silencing control. (B) SIRT1 expression by Western blot. Normal peripheral blood mononuclear cells (PBL) as control.

Expression of HIC1 in CML cell lines KCL-22 and K562 was examined by quantitative real-time RT-PCR for the major HIC1 transcript from its promoter 1a. The gene was silenced or down regulated in both cell lines compared to full HIC1 expression in WI-38 cells and silencing in MCF-7 cells (FIG. 7A). This is a consequence of promoter hypermethylation (Chen et al., 2003; Issa et al., 1997). Western blot analysis showed that SIRT1 was overexpressed in both cell lines after HIC1 gene silencing (FIG. 7B).

Total cellular RNA was extracted with Trizol (Invitrogen) using a standard protocol. The first strand DNA was synthesized and HIC1 expression was analyzed by quantitative real-time RT-PCR using a kit with SYBR Green label (Invitrogen) as per the manufacture's instruction on BioRad machine OPTICON. HIC1 primers were used spanning introns, 5'-GGACGGACCAGCAGGACA-3' (exon 1a) (SEQ ID NO:14) and 5'-GCGCTGGTTGTTGAGCTG-3' (exon 2) (SEQ ID NO:15). SIRT1 expression was analyzed by Western blot using 1:5000 diluted rabbit monoclonal SIRT1 antibody (Epitomics). GAPDH was analyzed as a loading control with a rabbit antibody (Trevigen) at 1:5000 dilution.

Figure 8:
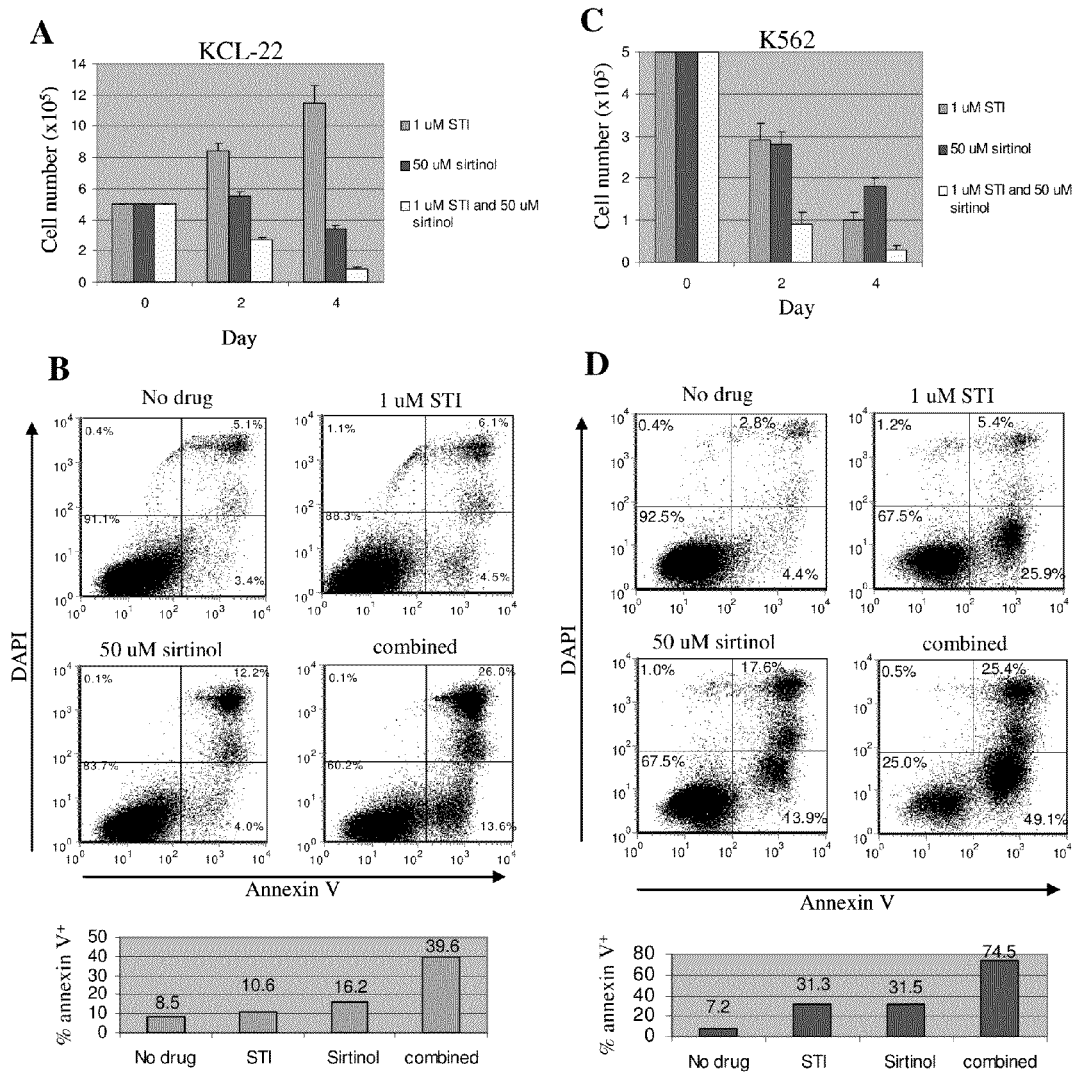
FIG. 8 shows Sirt1 inhibitor promotes apoptosis of CML cells. KCL-22 cells (A, B) or K-562 cells (C, D) were treated with 1 µM STI-571(STI) with or without 50 µM sirtinol. One half million cells per well were seeded in a 24-well plate and at 2 and 4 days after initiation of drug treatment, surviving cells were counted (A, B). Apoptosis in both cell lines was analyzed at two days (KCL-22) or one day (K-562) after drug treatment (C, D). The percentage of annexin V positive cells including early and late apoptotic cells was plotted underneath FACS charts.

Sirtinol inhibits SIRT1 and other sirtuin deacetylases with an $IC_{50}$ about 50 to 130 µM (Grozinger et al., 2001; Mai et al., 2005; Ota et al., 2005). STI-571 treatment alone induced rapid apoptosis in K562 cells with $IC_{50}$ of about 0.5 µM while it had a mild effect on KCL-22 cells (FIG. 8) (Mahon et al., 2000). Treatment with 50 µM sirtinol alone inhibited the growth of both cell lines, and the combination of two drugs synergized their inhibitory effects (FIGS. 8A and 8C). Sirtinol alone significantly induced annexin V positive apoptotic cells in both lines and when combined with STI-571, it induced more dramatic apoptosis than each individual drug (FIGS. 8B and 8D). Sirtinol and STI-571 both affected cell cycle of CML cells by reducing S/G2 and increasing sub-G1 population in KCL-22 cells (FIG. 9A) while they rapidly increased sub-G1 and apoptotic fraction in K562 cells (FIG. 9B). Cell cycle was analyzed by fixing cells with 70% ethanol and then stained with propidine iodine (50 µg/ml) for 30 min at room temperature. Cell apoptosis was analyzed with annexin V kit (BD Pharminggen) as per the manufacturer's instruction.

Pharmacological Inhibition of SIRT1 Prevents CML Relapse on STI-571.

Using the CML acquired resistance model as described herein, prevention of CML relapse on STI-571 was examined. Inhibition of SIRT1 with small molecule inhibitors prevented CML relapse on STI-571. KCL-22 cells were treated with STI-571 at 1, 2.5 and 5 µM in combination with various concentrations of sirtinol. At 50 µM and above, sirtinol effectively eliminated KCL-22 cells in two to three weeks and blocked relapse of KCL-22 cells on all three concentration of STI-571 in culture for two to three months and no viable cells were visible under microscope (FIG. 10A). As with STI-571, treatment with sirtinol alone resulted in relapse after two weeks (FIG. 10A). The combination of sirtinol and STI-571 is a powerful therapeutic approach for inhibiting acquired resistance of CML.

Testing of Additional SIRT1 Inhibitors.

Another sirtuin specific inhibitor, splitomicin (Bedalov et al., 2001; Hirao et al., 2003), was also tested for its ability to block relapse. Splitomicin is also a naphthol compound and structurally similar to sirtinol. Nicotinamide is a natural inhibitor of SIRT1 (Avalos et al., 2005; Bitterman et al., 2002). At 300 µM splitomicin and 15 mM nicotinamide, relapse of KCL-22 cells on 5 µM STI-571 was effectively blocked during prolonged culture as shown in FIG. 10B. In contrast to sirtinol, splitomicin and nicotinamide did not, by themselves, induce significant cell death and did not dramatically enhance cell killing by STI-571 during the first two weeks (FIG. 10B). These results indicate that prevention of relapse does not require enhanced cell killing.

The T315I mutation is resistant to treatment with nilotinib (Weisberg et al., 2005) as well as dasatinib (Shah et al., 2004). In murine cells transduced with wild type BCR-ABL, the T315I mutation is also commonly induced by these drugs (von Bubnoff et al., 2006; von Bubnoff et al., 2005). Using the KCL-22M cell line, combined treatment with sirtinol and STI-571 was able to inhibit cell growth (FIG. 10C).

Effects of inhibitors of deacetylases and DNA methyltransferases (DNMT) on chemoresistance of BCR-ABL positive leukemia. In vitro, enhanced killing of CML cells occurs when imatinib is combined with DNMT inhibitor 5-aza-2-deoxycytidine (AZA) (La Rosee et al., 2004) or with HDAC inhibitors (Kawano et al., 2004; Yu et al., 2003). Whether these inhibitors prevent CML relapse on STI-571 was examined. TSA (an HADC inhibitor) at 1 µM alone had little toxicity on KCL-22 cells, but when combined with STI-571, massive apoptosis and dramatic cell killing was observed on all dosages of STI-571(FIG. 11A). After ten days, cells on all dosages of STI-571 relapsed (FIG. 11A). These results indicate that an initial rapid and massive cell killing does not necessarily prevent relapse of CML on imatinib treatment. However, the combination of AZA with STI-571 while killing cells more slowly than TSA, did successfully block relapse on 2.5 and 5 µM (FIG. 11B). When AZA, TSA, and STI-571 were all combined, initial rapid cell death occurred due to the presence of TSA and relapse was blocked on 2.5 and 5 µM of imatinib due to the presence of AZA (FIG. 11C). TSA and AZA alone or in combination could not reactivate HIC1 expression or reduce SIRT1 level despite their effects on KCL-22 cells. This is in contrast to HIC1 reactivation by these drugs in carcinoma cells (Narayan et al., 2003; Rathi et al., 2003), indicating that hypermethylated HIC1 promoter is more difficult to reactivate in CML cells. For KCL-22M cells, TSA had no effect on cell growth, whereas 1 µM AZA inhibited its growth but did not promote significant cell death. The combination of 1 µM AZA with 50 µM sirtinol induced partial cell death (FIG. 11D).

Figure 31:
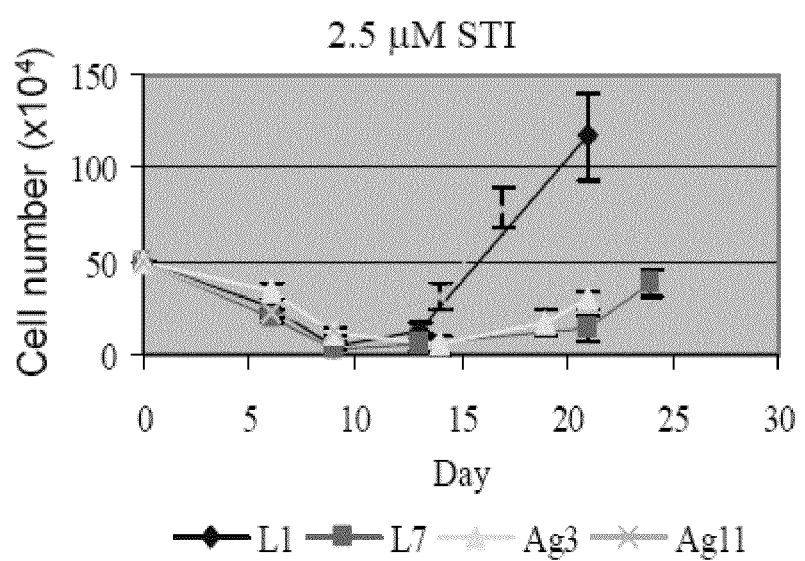
FIG. 31 is a line graph illustrates relapse, based on cell count, of clonal KCL-22 cells (L1, L7, Ag3 and Ag11) on STI treatment alone.

Using the acquired resistance model described herein, the effects of sirtinol and TSA was further investigated using clonal cells. These clones of KCL-22 cells develop acquired resistance to imatinib through different mutations in three clones (E255K for clone L1, Y253H for clone L7 and T315I for clone Ag11) and non-mutation mechanism in clone Ag3 (FIG. 31) (Yuan et al., 2008). As shown in FIGS. 12A and 12B, the combination of sirtinol with 2.5 µM imatinib blocked relapse in all four clones; in contrast, all clones relapsed on the combination of TSA with imatinib. Clone Ag3, developed resistance through non-BCR-ABL mutation mechanism by 2.5 µM imatinib alone, but developed resistance through T315I mutation upon the combined imatinib and TSA treatment. These data indicate that HDAC inhibitors transiently provide enhancement of cell killing, but promote genetic mutations of BCR-ABL and acquired resistance.

Sirtinol Overcomes Growth Factor-Induced Transient Resistance in CML Cells.

Figure 13:
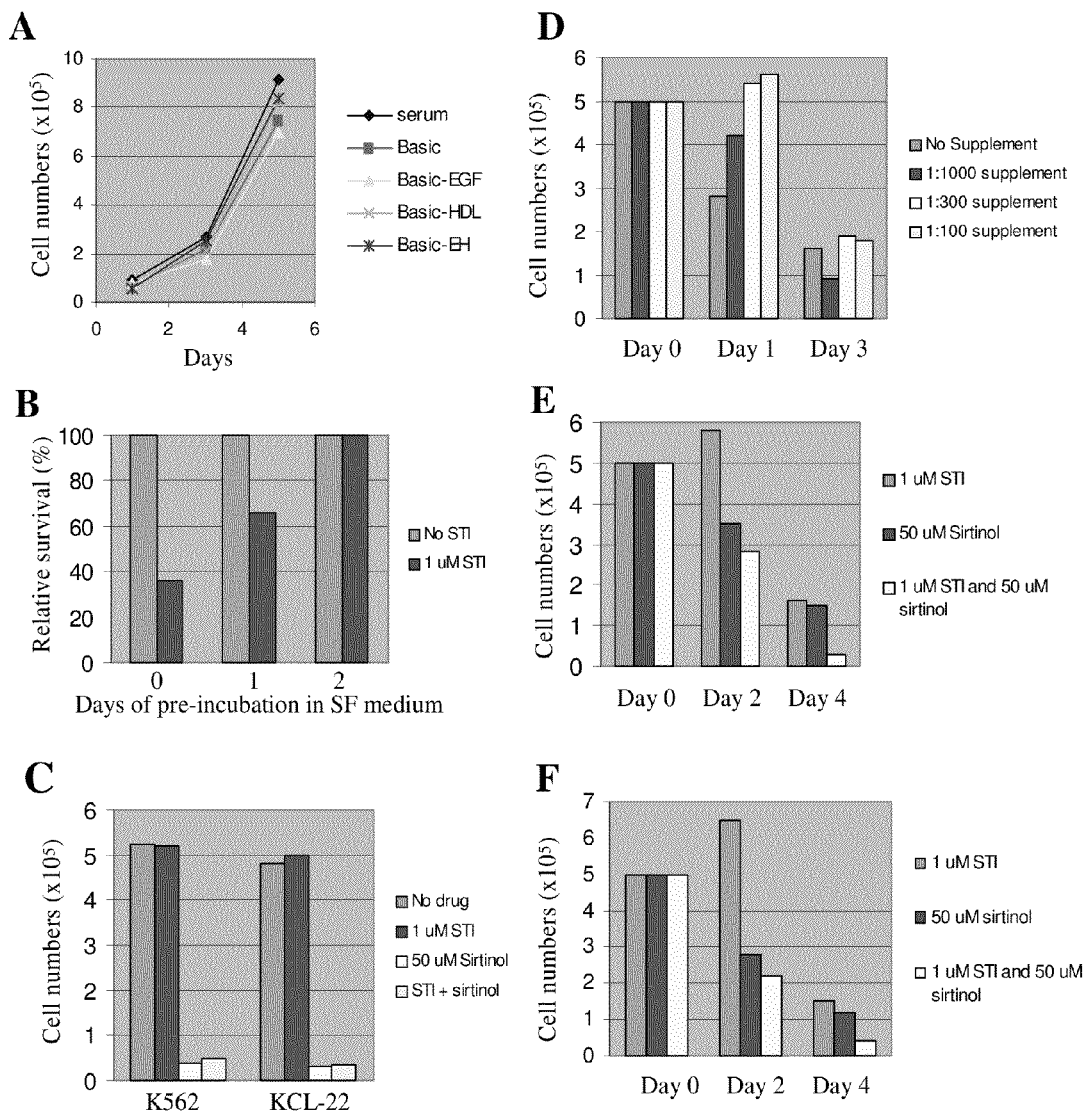
FIG. 13 shows sirtinol inhibits growth factor-induced transient resistance of CML cells. (A) Growth curves of K562 cells in serum medium, and serum-free medium supplied with basic supplements containing 5 µg/ml insulin and 5 µg/ml transferrin (basic) with or without 75 ng/ml EGF, 25 µg/ml HDL or both (EH). (B) Responses of K562 cells to STI-571 treatment in SF medium with basic supplements. Cells were immediately switched from serum to SF medium (Day 0) or pre-incubated in SF medium for 1 or 2 days before treatment with 1 µM STI-571. Relative survival of imatinib treated cells was calculated by comparison to no drug treatment. Pre-incubation for two days renders resistance. (C) K562 cells were pre-incubated in SF medium for two days as in B, and then treated with 1 µM STI-571, 50 µM sirtinol or both. Since sirtinol is insoluble in SF medium, HDL 25 µg/ml was added to help dissolve the drug. (D) Effects of basic supplements in serum medium. K562 cells were placed in serum medium and treated with 1 µM STI-571 with or without the supply of basic supplements to final dilution as 1:100, which gives 5 µg/ml insulin and 5 µg/ml transferrin, or lower as indicated. Viable cells were counted one and three days after the treatment. (E) K562 cells were placed in serum medium with the supply of basic supplements at 1:100 dilution and treated with 1 µM STI-571, 50 µM sirtinol or both. (F) Effects of insulin in resistance. K562 cells were cultured in serum medium with addition of 500 ng/ml insulin and treated with 1 µM STI-571, 50 µM sirtinol or both.

With the exception of KCL-22 cells, no other CML cell lines are known to survive 1 µM STI-571 treatment in serum containing culture. Whether serum-free medium supplied with select growth factors provides a better culture environment for developing CML chemoresistance was determined. Serum-free (SF) medium with insulin, transferring, epidermal growth factor (EGF) and high density lipoprotein (HDL) was used. SF medium with the basic supplements (5 µg/ml insulin and 5 µg/ml transferring) was sufficient to support growth of both K562 cells (FIG. 13A) and KCL-22 cells. Pre-incubation of K562 cells in SF medium with basic supplements for two days made K562 cells as refractory as KCL-22 cells for treatment with 1 µM STI-571 (FIG. 13B, C). Sirtinol alone or in combination with STI-571 resulted in rapid killing of both K562 and KCL-22 cells (FIG. 13C) and no relapse over prolonged culture. Sirtinol is able to overcome CML resistance in SF culture. Addition of basic supplements to routine serum media also provided K562 cells transient resistance to treatment with 1 µM STI-571 (FIG. 13D), which lasted up to two days. Again, treatment with 50 µM sirtinol abolished this transient resistance (FIG. 13E).

Transient resistance conferred by insulin and transferrin supplement is of interest as insulin receptor is overexpressed in about 90% primary CML cells. The key insulin downstream target phosphatidylinositol-3 kinase (PI3K) is required for BCR-ABL mediated transformation and inhibition of PI3K-Akt-mTor pathway has been explored to overcome CML chemoresistance. SIRT1 is a key gene for regulating insulin secretion and directly regulates Akt downstream target FOXO proteins through deacetylation. Therefore, the effect of insulin itself for transient resistance to imatinib and the response of sirtinol treatment were examined. The addition of a broad range of concentrations of insulin, from 1 ng/ml to 5 µg/ml, provided about equal transient resistance of K562 to the treatment with 1 µM STI-571; and again, sirtinol alone or in combination with STI-571 abolished this transient resistance (FIG. 13F). Together, these data show that activation of insulin pathway is sufficient to render CML cells transient resistance in vitro, and it can be inhibited by SIRT1 inhibition.

Molecular Basis of Differential Effects of Sirtinol and TSA on CML Chemoresistance.

Sirtinol inhibits NAD-dependent class III histone deacetylases (sirtuin family) while TSA inhibits class I and II histone deacetylases (HDACs). The sirtuin family deacetylases are structurally unrelated to HDACs. Both SIRT1 and HDACs are involved in regulating gene transcription and post-translational deacetylation of numerous proteins. However, two inhibitors exhibit sharply different outcomes on blocking KCL-22 relapse on STI-571. Gene expression microarray approach was used to search for differential transcriptional regulation and to use a proteomic approach to search for differential protein acetylation profiles.

The effects of these inhibitors on global gene transcription and global protein acetylation are analyzed. Total RNA is extracted from four groups of KCL-22 cells: untreated, treated with STI-571 alone, treated with STI-571 and sirtinol, and treated with STI-571 and TSA at three time points (2, 4 and 8 days) before relapse occurs. Each sample is collected in triplicate. Samples are then analyzed using Affymetrix expression arrays followed by statistical analyses of gene expression changes among different groups. Relevant genes are identified and RT-PCR or Western blot is used to confirm their expression. The functional significance of new genes/targets in CML chemoresistance is further studied by knockdown in KCL-22 cells similar to that described for SIRT1.

Total cell lysate is extracted from the four groups of KCL-22 cells at three time points as described for the expression array. Lysates are immunoprecipitated with anti-acetylated lysine antibody and bound proteins are eluted for gel electrophoresis. The gel is stained with Coomassie and differential bands are sliced for mass-spectrum analysis. Once key acetylation targets are identified, they are verified individually by immunoprecipitation and Western blot. The following antibodies for protein analysis by Western blot are used: rabbit monoclonal anti-SIRT1(1:5000, Epitomics), rabbit polyclonal anti-PGC-1a (1:1000, Chemicon) and anti-GAPDH (1:5000, Trevigen).

Inhibition of Acquired Resistance in Other Human Cancers.

Acquired resistance through secondary mutations on the targeted oncogenes are also predominant in other cancers, such as c-Kit receptor and the platelet-derived growth factor receptor (PDGFR) in gastrointestinal stromal tumors, and epidermal growth factor receptor (EGFR) in non-small cell lung cancer (NSCLC). SIRT1 in NSCLC resistance with and without secondary mutations would be assessed in cell lines H3255 and H1650. The H3255 line carries activating mutation L858R and the H1650 cells carry activating deletion (E746-A750) on the EGFR kinase domain, which render these cells sensitive to treatment with EGFR inhibitors gefitinib and erlotinib. Both cell lines can relapse upon gefitinib treatment, and H3255 cells develop resistance with the secondary T790M mutation (Engelman et al., 2006. Allelic dilution obscures detection of a biologically significant resistance mutation in EGFR-amplified lung cancer. *J Clin Invest* 116: 2695-2706) whereas H1650 cells develop resistance through mechanisms other than secondary mutations (Kwak et al., 2005. Irreversible inhibitors of the EGF receptor may circumvent acquired resistance to gefitinib. *Proc Natl Acad Sci USA* 102:7665-7670.) A previous H1650 resistance model was derived by exposing cells directly to 20 µM gefitinib and a H3255 model was derived by exposing cells to gradually increasing concentrations of gefitinib (starting with 40 nM)

for a few months. For patients receiving gefitinib 250 mg/d, the mean steady-state plasma concentration of the drug ranges from 0.4 to 1.4 µM, and higher concentrations of gefitinib result in off-target effects and toxicity (Cohen et al., 2004. United States Food and Drug Administration Drug Approval summary: Gefitinib (ZD1839; Iressa) tablets. *Clin Cancer Res* 10:1212-1218; Baselga et al., 2002. Phase I safety, pharmacokinetic, and pharmacodynamic trial of ZD1839, a selective oral epidermal growth factor receptor tyrosine kinase inhibitor, in patients with five selected solid tumor types. *J Clin Oncol* 20:4292-4302.). These previous methods did not use therapeutically effective concentrations of gefitinib. The NSCLC model provided herein employs approaches as those used in the described CML model studies.

NSCLC Resistant Models.

$2.5 \times 10^5$ cells of H3255 or H1650 per well are seeded in 6-well plates. Multiple wells of each cell line are plated to allow sampling of cells at different time points. After overnight seeding, cells are treated with 1 µM gefitinib, or a therapeutically effective dose. The drug is maintained in the culture until cells relapse and re-grow as described for the CML studies. Fresh medium is supplied to restore the original volume during the prolonged culture as needed. Relative cell numbers are measured at various time points by staining cells with crystal violet and quantifying cell mass with Infrared Imaging System.

The relapsed cells are expanded and tested for their resistance to gefitinib as compared to parental cells. Total RNA is extracted for synthesis of cDNA and sequencing of EGFR kinase domain (exons 18-24), and genomic DNA is extracted for direct sequencing to verify mutations detected by cDNA sequencing using primers described previously (Pao et al., PNAS 101:13306-13311, 2004). Because H3255 harbors more than 40 copies of EGFR that results in allelic dilution of the T790M mutation, a mutant-enriched PCR sequencing assay is used to detect the mutation. (Inukai et al., Cancer Res 66:7854-7858, 2006). Briefly, after round one of amplification of both wild type and mutant alleles, the wild type PCR products are selectively cleaved by restriction enzyme BstUI, which allows second round preferential amplification of the mutant allele for sequencing. The mutant-enriched PCR sequencing assay can detect one mutant allele among 1000 copies of wild type alleles, and thus is sensitive enough for analysis of T790M mutation in H3255 cells. Using the above described method, genetic mutants in the NSCLC acquired resistant cells are identified.

Effects of SIRT1 Inhibition on NSCLC Resistance.

SIRT1 expression levels in lung cancer cells are assessed. SIRT1 protein level was previously found increased in lung cancer cell lines H460 and H209 that bear wild type EGFR. SIRT1 expression in H3255 and H1650 cells before and after relapse, as compared to normal human lung lysates, is analyzed by Western blot. Combination treatment of sirtinol at various concentrations with 1 µM gefitinib may enhance apoptosis and inhibit growth of H3255 and H1650 cells. The apoptosis is analyzed by TUNEL staining and growth inhibition analyzed by crystal violet staining described above. The combination of the two drugs to block relapse of these two cell lines are examined for the prolonged culture up to two months. Third, mock and SIRT1 knockdown are generated in H3255 and H1650 NSCLC cells using lentiviral shRNA vectors developed for CML resistance studies as described above. The knockdown of SIRT1 is confirmed by Western blotting. Whether SIRT1 knockdown delays or blocks relapse of NSCLC cells upon gefitinib treatment is examined.

EXAMPLE 6

Development of Anti-Cancer SIRT1 Inhibitors

Development of Novel SIRT1 Inhibitors.

To develop a potent SIRT1 inhibitor, a pharmacophore model of SIRT1 inhibitors for the substrate binding pocket of SIRT1(FIG. 40A) was developed based on a sirtuin ligand database having 233 compounds specific to all sirtuin pockets. These highly conserved sirtuin pockets are based on small sirtuin protein crystal structures that show three pockets in each sirtuin protein for Zinc (Zn), Nicotinamide adenine dinucleotide (NAD) and a substrate. SIRT1 is about twice larger than other sirtuins and there is no crystal structure currently available.

The pharmacophore model was validated by selective identification of effective inhibitors for the SIRT1 substrate binding pockets after query of the ligand database. Using this pharmacophore model a search of a NCI library that included 250,253 compounds via Unity (SYBYL) 3D Flexible Database was performed. This search, coupled with active compound references, leadlikeness and diverse structure representation, led to the identification of a top hit list of 23 inhibitor compounds. Using the culture model for CML acquired resistance described above, these inhibitor compounds were tested to determine their ability to block CML cell relapse. Four of the identified compounds tested (NCl compounds #163580, 261408, 628445, and 687305), were more effective in preventing CML cell relapse upon imatinib treatment than an effective dose of sirtinol. The effective dose of sirtinol that was used in this study was 50 µM.

Figure 40:
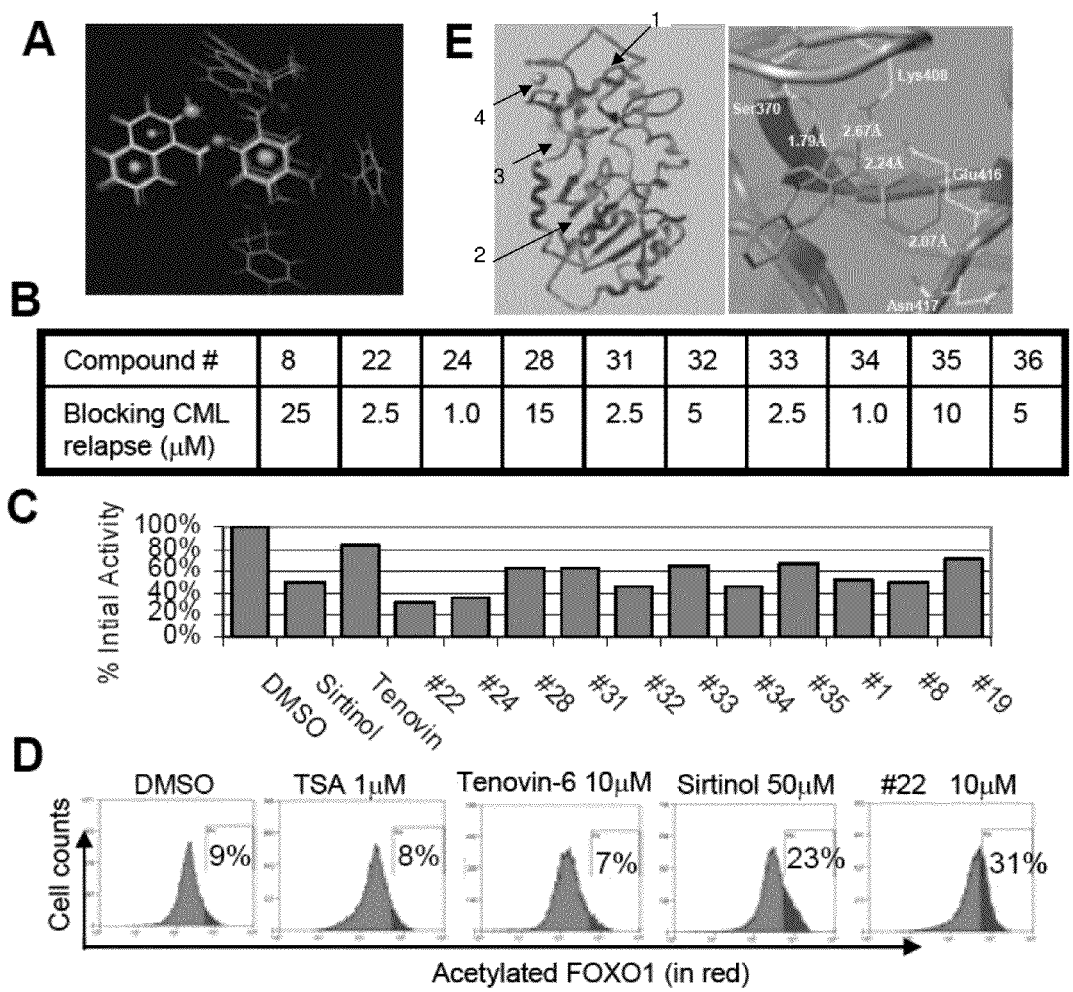
FIG. 40 illustrates the development of novel SIRT1 inhibitors. (A) A pharmacophore model of SIRT1 inhibitors for the ligand binding pocket. (B) Concentrations of new SIRT1 inhibitors to block KCL-22 cell relapse. (C) FRET-based SIRT1 inhibition assay. All compounds in 50 µM. Tenovin had limited activity in this assay. (D) Flow cytometry assay of acetylation of FOXO1 in KCL-22 cells after compound treatment for 24 h. (E) Docking of SIRT1 inhibitor #22 to the SIRT1 catalytic core model. Left panel: the Zinc binding domain is labeled as (1), the Rossmann domain is labeled as (2), compound 22 is labeled as (3) and the Zinc atom is labeled as (4). Right panel: Hydrogen bonds between the compound and protein are also shown. The distance of hydrogen bonds is between 1.8 to 2.7 Å (1.79 Å, 2.67 Å, 2.07 Å).
Figure 57:
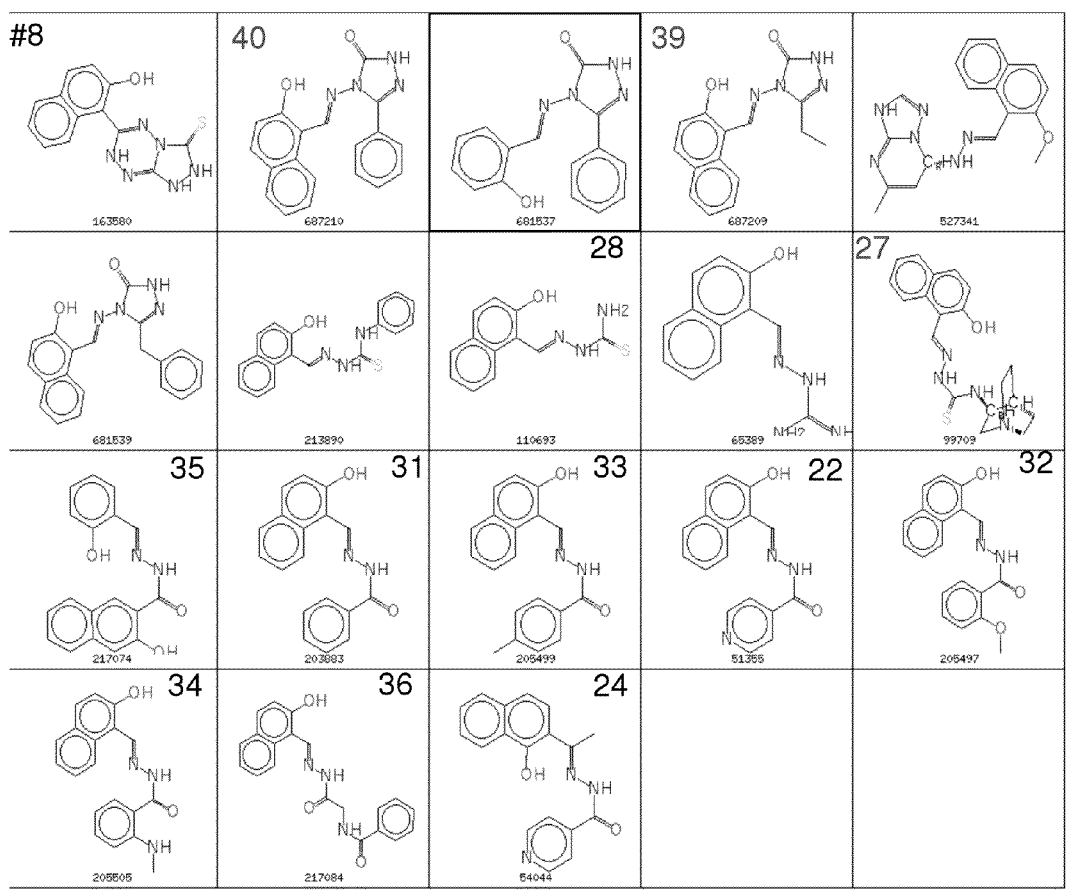
FIG. 57 illustrates the structures of compounds derived from a similarity search of compound 163580. Compounds that were available for testing are numbered. Compound numbers 8, 28, 35, 31, 33, 22, 32, 34, 36 and 24 showed better inhibitory activity than 163580 and compounds 40, 39 and 27 showed no improvement.

Compounds 628445 and 163580 were chosen as models to search for similar compounds against the NCl database because the structure of compound 687305 could not be confirmed by mass spectrum analysis and the compound 261408 was found too toxic to cells. Compounds derived from the 628445 search did not exhibit improvement of inhibitory activity. A similarity search for compound 163580 resulted in 17 potential NCl compounds, 12 of which were available for testing (FIG. 57). Nine of these 12 compounds derived from the similarity search of compound 163580 showed a significantly improved ability to block CML relapse with working concentrations as low as 1 µM (FIG. 40B). Most of them were water soluble and had a structural feature distinct from other known SIRT1 inhibitors, as described further below. As shown in FIG. 57, eight of these nine improved compounds exhibited two structural moieties in common: naphthol (#22) at one end and isonicotinamide (#24) or a similar structure at the other end. These two moieties were connected through a hydrophilic linker containing two-nitrogen bond. Consistently, the other four compounds lacking the isonicotinamide-like moiety did not exhibit an improved inhibitory activity (#27, 39, 40) or exhibited only moderate improvement (#28).

The compounds also showed SIRT1 inhibitory effects. For example, compounds #22 [N'-((2-hydroxyl-1-naphthyl)methylene)isonicotinohydrazide] and #24 [N'-(1-(1-hydroxy-2-naphthyl)ethylidene)isonicotinohydrazide] outperformed sirtinol and tenovin-6 as analyzed by a FRET (fluorescent energy transfer)-based biochemical assay (FIG. 40C) and cell-based analysis of acetylation of FOXO1, a cellular substrate of SIRT1(FIG. 40D). In sum, the addition of isonicotinamide or a similar structure to the naphthol structural base would likely increase the inhibitory activity. Further, isonicotinamide was shown to antagonize the effect of nicotinamide by blocking base-exchange step of sirtuin deacetylation reaction in mM concentration (Sauve et al. 2005). However, it is noted that isonicotinamide is not a per se requirement as it only exists in compounds #22 and #24. Therefore, it is likely the isonicotinamide-like structure feature that is important for the compounds.

Figure 58:
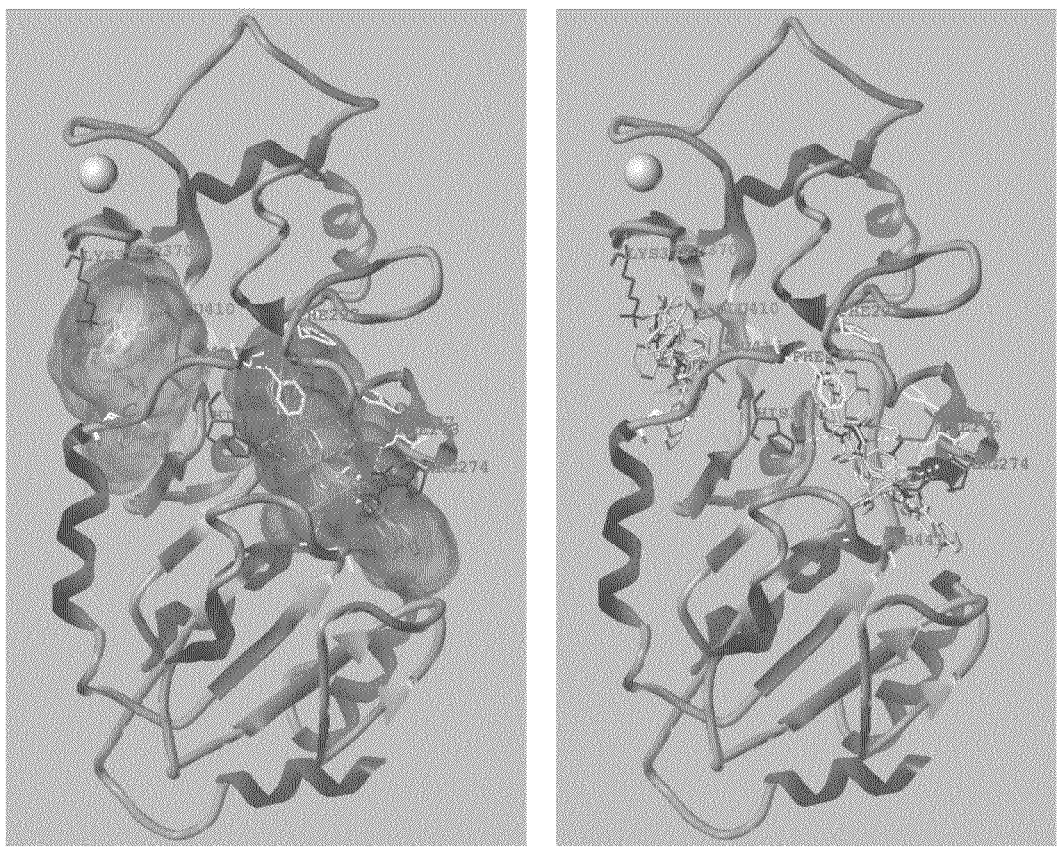
FIG. 58 shows the docking of six compounds to SIRT1 homology model. Six effective compounds from similarity search of 163580 were docked into the substrate binding pocket and NAD binding pocket of SIRT1 homology model.

In addition, a SIRT1 catalytic core structure was constructed by homology modeling based on human SIRT2 structure (PDB ID 1J8F), and docking the compounds to the SIRT1 homology model indicated that these inhibitors bound at the substrate binding pocket (FIG. 40E). Surprisingly, these compounds could also be docked into the $NAD^+$ binding pocket (FIG. 58). However, docking into the NAD binding is consistent with the presence of the moiety of isonicotinamide-like structure in these compounds, showing that this moiety may block $NAD^+$ binding, $NAD^+$ usage, or interfere with base-exchange and deacetylation steps through the $NAD^+$ binding pocket. Given that inhibitors from individual binding pockets are generally weak, simultaneous blocking substrate and $NAD^+$ binding may have a synergistic effect on SIRT1 inhibition.

Optimization of Lead Compounds into a Potent SIRT1 Inhibitor as a Candidate Anticancer Drug.

Optimization of lead compounds is carried out by two complimentary approaches: Improvement of the pharmacophore and isothermal titration calorimetry.

Optimization by improving pharmacophore. Structure-activity relationship (SAR) analysis is carried out on the lead NCI compounds identified through preliminary screens, as well as on compounds collected from literature. The pharmacophore model is optimized. A focused compound library consisting of 30 to 40 compounds is designed based on the SAR study and the improved pharmacophore model. All compounds are synthesized by the City of Hope Synthetic Chemistry Core.

Synthesized compounds are first screened for their effective concentrations to block development of the BCR-ABL T315I mutation using the CML KCL-22 cell culture model described above (Yuan et al., 2010). KCL-22 cells in liquid culture are treated with 2.5 µM imatinib and various concentrations of SIRT1 inhibitors alone and in combination. Cells are monitored for cell death and relapse, and the lowest concentrations of compounds that block relapse on imatinib in two to three weeks are identified, and confirmed with prolonged culture. The ability of the compounds to block other BCR-ABL mutations is similarly performed using three KCL-22 clonal cell lines previously developed (Yuan et al., 2010).

Inhibition of recombinant SIRT1 deacetylase activity is performed using a FRET-based SIRT1 activity assay (Cayman Chemicals and Cisbio) that does not produce altered substrate-SIRT1 interaction, and $IC_{50}$ of each compound is determined. To further validate non-isotopic biochemical assay, $^3H$ labeled acetylated histone peptide (Millipore) is used as a substrate for SIRT1 deacetylation assay. The released $^3H$ labeled acetate after the reaction is exacted and quantified by scintillation.

SIRT1 inhibitor-induced acetylation of cellular SIRT1 substrates, Ku70 and FOXO proteins, are determined by immunoprecipitation of these proteins followed by Western blot analysis for acetyl lysine. Acetylation of FOXO1 is also directly examined by flow cytometry-based analysis as done in FIG. 40D.

Next, cross reactivity of an inhibitor to HDACs and other sirtuins is examined using commercially available deacetylase assay kits (Biomol and Millipore). A second round of optimization is optionally performed. A further refined pharmacophore model may be deduced on the basis of the above studies of the designed compounds. The 3D pharmacophore search may be used to query an 80,000-diverse compound library purchased by City of Hope and the UCSF ZINC 13 million purchasable compound library to identify similar compounds for lead optimization. About 30-50 compounds with predicted favorable ADMET properties are synthesized and biological tests are carried out as described above. Three-dimensional Quantitative Structure Activity Relationship (3D QSAR) models are built for compounds whose $IC_{50}$ for SIRT1 is determined. The predictive power of the QSAR correlation is used to estimate the bioactivity for new compounds and to guide the modification and refinement of existing structures to obtain optimal activity.

Optimization by isothermal titration calorimetry (ITC). ITC is an emerging technique for drug discovery. ITC determines the enthalpy change associated with binding and provides a complete thermodynamic profile of the interaction, including binding affinity, number of binding sites, entropy change, and Gibbs energy of binding (Ladbury et al.). This approach offers an advantage for lead compound optimization in the absence of SIRT1 crystal structure. ITC study of the compounds is carried out at the City of Hope X-ray Crystallography Core using TA Instruments Nano ITC Low Volume. For these measurements, the SIRT1(200 µL) is titrated (25 injections; 2.5 µL each) with each inhibitor. The concentrations of the ligand and receptor are optimized to ensure accurate fitting (e.g., a clear sigmoidal curve). In addition, the ligand is titrated into the buffer to account for heat of dilution and subtracted from the ligand-receptor titration. The data is processed using the TA software package. The thermodynamic profiles obtained from these compounds guide modification to obtain a high affinity and specific SIRT1 inhibitor, i.e. compounds optimized for a more favorable (negative) enthalpy change or a more favorable (positive) entropy change to improve affinity and selectivity for SIRT1. New compounds are then synthesized for further ITC measurements, followed by cell-based analyses as described in the above section.

Alternative methods. An all-around docking algorithm has been designed to perform docking of the designed compound library cross-validated by QSAR and ITC analysis results into the predicted binding sites on the SIRT1 structure model. The protein-ligand binding free energies may be generated from CHARMM molecular dynamic (MD) simulation by implementing enhanced-sampling algorithms (Li et al., 2007; Li et al., 2006). The best predicted ligand binding mode then leads the optimization of improving binding affinity and the specificity.

Determination of the Specificity and Inhibition Mechanism of the Lead Candidate Inhibitors.

Drug specificity and inhibition mechanisms may be studied structurally and biologically as follows:

Ligand binding mode. Ligand binding mode shows how the inhibitor interacts with the protein. A homology model of SIRT1 has been built based on the structure of SIRT2 that shares more than 70% sequence homology for the substrate binding pocket. The lead compounds are examined by docking analysis with the SIRT1 homology model using Sybyl (Tripos) and Glide (Schrodinger) software, followed by molecular dynamic simulation. The docking and free energy component analysis will reveal amino acids of SIRT1 that interact with the compounds. As shown above in FIG. 40E, docking of compound #22 results in hydrogen bonding with residues Ser370, Lys408, Glu416, and Asn417 of SIRT1 were identified, and energetically favorable hydrophilic interactions were predicted between the compound and the substrate binding pocket. The conserved amino acids of SIRT1 that interact with most compounds docking into the substrate binding pocket are identified. The predicted ligand binding pocket and binding mode are validated by mutant SIRT1 proteins generated by site-directed mutagenesis, the ITC studies described above, and Biacore analyses. Biacore is another quantitative assay for specific interaction between a ligand and a protein immobilized on a sensor surface. Biacore analysis is performed at the City of Hope High Throughput Screen Core. The ligand binding pocket and the binding mode are further validated once the structure for SIRT1 catalytic core domain or a larger fragment is obtained. The ligand binding mode also guides the lead optimization to improve binding affinity and selectivity as described above.

Crystallography study of SIRT1 inhibition. The structures of several SIRT1 homologous proteins are available; however, the crystal structure of SIRT1, either catalytic core or full length, has not been solved. SIRT1 is the largest sirtuin protein with very long N- and C-termini that are flexible and difficult to be crystallized. Accordingly, additional structural information for SIRT1 enhances understanding of precise drug inhibition mechanism and efforts to determine specificity of SIRT1 inhibitors.

First, different constructs are expressed by creating a his-tagged SMT3-SIRT1 fusion. The N-terminal SMT3 typically improves expression and permits highly specific cleavage of the tag by the SMT3 specific protease, Ulp1, as previously described (Mossessova et al., 2000; Sun et al., 2009; Ahmed et al., 2010). Initially, a fragment that spans the catalytic core (residues 220-494 based on BLAST searches of SIRT1 and the PDB) and full-length protein are generated. Recombinant SIRT1 is expressed in bacteria and purified using standard chromatographic methods. Briefly, the clarified lysate is passed over a Ni-NTA column, washed extensively, and eluted with imidazole, and the SMT3 tag is cleaved with histag-Ulp1 and dialyzed. A second Ni-NTA column removes the SMT3 and Ulp1. The cleaved SIRT1 protein is concentrated and passed over a size exclusion column (Superdex G75). Progress is monitored by SDS-PAGE. An ion-exchange column is used if additional steps are required. Approximately 5 to 100 mgs of protein are typically generated using this system.

In addition, limited proteolysis techniques are used on the full length protein to experimentally define the molecular boundaries of a stable construct. Briefly, the purified full length SIRT1 is exposed to papain and subtilisin at different concentrations for a defined period. SDS-PAGE is used identify stable fragments. These fragments are excised from the gel and subjected to N-terminal protein sequencing and mass spectrometry. New constructs are generated, expressed and purified based on this information. Deacetylase activity of truncated SIRT1 is validated by biochemical assays as described above.

Next, a generate crystal structure of the stable SIRT1 fragments are generated in the presence and absence of an inhibitor or an acetylated p53 peptide. Crystallization and structure determination are performed at the City of Hope X-ray Crystallography Core. Specifically, a Mosquito Crystallization robot is used to generate 200 mL drops for each condition. Each screen (4 are initially tested) consists of 96 different crystallization conditions. Crystallization trials are monitored robotically using the Formulatrix Rock Imager at 4° C. and 22° C. (in total, 768 conditions are initially tested per sample). Promising leads are optimized and the diffraction properties of each lead are tested. The data is collected and analyzed. The apo structure, acetylated peptide bound and inhibitor bound structures are analyzed, and compared to known SIRT2, SIRT3 and SIRT5 structures. Common and unique features of SIRT1 crystal structures for substrate and inhibitor binding are identified.

Successful determination of the structure will point to residues that are important for ligand and inhibitor binding. This structural information is used to improve the SIRT1 homology. Residues that are important for inhibitor binding are confirmed by site-directed mutagenesis. Deacetylase activity of mutant proteins is measured as described above, and interaction of mutant proteins with compounds is characterized by ITC as described above.

Mechanisms of target inhibition in LSC. Next, the effects of in vitro inhibitor treatment on acetylation of SIRT1 targets in human $CD34^+$CML cells are examined. Human $CD34^+$ CML cells are isolated and cultured in vitro using a protocol previously described (Bhatia et al., 2003; Holtz et al., 2002). Acetylation of p53 and FOXO proteins upon inhibitor treatment is analyzed by Western blotting, or by flow cytometry based assay as described above. The ability of inhibitors to selectively alter gene expression associated with SIRT1 signaling is evaluated by microarray analysis. Affymetrix Gene-Chip Human Genome U133 Plus 2.0 Arrays were used to analyze gene expression changes in LSC upon imatinib and HDAC inhibitor treatment (Zhang et al., 2010). SIRT1 related gene expression patterns are determined by analysis of expression changes in $CD34^+$CML cells following SIRT1 shRNA knockdown. Gene Set Enrichment Analysis (GSEA) is used to determine pathways significantly altered by SIRT1 expression. Connectivity Map (CMAP) (Lamb et al., 2006) is used for the gene signatures derived above to explore the functional connection of genetic perturbation and drug activities. Signaling pathways affected by specific SIRT1 inhibitors should significantly overlap with those by SIRT1 shRNA knockdown, but should be distinct from those affected by HDAC inhibitors (Zhang et al., 2010). In vivo target inhibition specificity is examined as described below.

Alternative methods. Another approach that may be used is to mutate surface residues with high entropy (e.g. predicts residues 235-238 within the catalytic core should be mutated to alanines—http://nihserver.mbi.ucla.edu/SER/). In addition, the SIRT2 and other sirtuin homologues may be used to identify productive crystal contacts (n.b., the human SIRT2 homologue diffracted to 1.7 Å). In both cases, site directed mutagenesis is used to modify these residues and the assays described above are used to ensure that these mutations do not affect the activity. Functional constructs are subjected to similar crystallization trials.

Determination of the Efficacy for Eradicating Leukemia Stem Cells (LSC) in a Mouse Model of CML.

In vivo drug treatment. The protocol for bone marrow transduction and transplantation is performed as previously described (Pear et al., 1998). Briefly, donor mice were primed by 5-fluorouracil 3 days before harvest. Bone marrow cells were transduced with retroviral vectors by co-sedimentation. Typically, $2.5 \times 10^6$ transduced mononuclear cells are transplanted to each recipient. A typical study consists of four groups of mice: vehicle, imatinib, SIRT1 inhibitor, and imatinib plus SIRT1 inhibitor, with 12 mice per group. Drugs are given for 10 consecutive days, beginning on day 10 after transplantation as described (Wolff et al., 2001). Imatinib is administered orally 50 mg/kg in the morning and 100 mg/kg in the afternoon with 8 hours apart. Two of the lead compounds discussed above are used to set up assays initially. Pharmacokinetics is performed as described below to determine the optimal drug doses and delivery routes before they are used for treatment. Two doses (or routes) each inhibitor are examined. After 10 day treatment, peripheral blood is collected and analyzed by differential blood cell counts using HemaVet (Drew Scientific) to determine the effects of the drug treatment. Mice are monitored for up to six months, and Kaplan-Meier survival analysis is performed with log-rank test used for calculating statistical significance.

Eradication of leukemia stem cells. CML stem cells are identified as a fraction of side population (GFP$^+$cKit$^+$CD34$^-$Hoe$^-$) in BABL/c background (Hu et al., 2006). To determine if SIRT1 inhibitor treatment eradicates LSC, bone marrow of the above described CML mice in different treatment groups is harvested. Lineage positive cells are depleted using immunomagnetic beads (EasySep, Stem cell Technology). The enriched cells will then be labeled with Hoechst 33342, CD34 and c-Kit for LSC analysis as shown in the Preliminary Studies. To further examine the eradication of CML stem cells, serial bone marrow transplantation is performed by transplanting $5 \times 10^6$ bone marrow cells from mock and drug treated groups into lethally irradiated secondary recipients. The disease development and LSC is examined similarly as in primary recipients. The same regimen of drug treatment is tested in normal mice to determine impact of drugs on normal HSC.

Mechanisms of in vivo drug treatment. The effect of drug treatment on cell cycle and apoptosis of LSC is examined. LSC is labeled with Pyronin Y and Hoechst 33342 to identify G0 and 01 population. Apoptosis of LSC is monitored by annexin V staining. To determine the in vivo target specificity of a SIRT1 inhibitor in mouse LSC, microarray-based gene expression analysis is carried out by the City of Hope Functional Genomics Core and Division of Biostatistics. Mock and BCR-ABL transformed HSC is isolated from SIRT1$^{+/+}$ and SIRT1$^{-/-}$ mice to identify the altered signaling pathways by SIRT1 knockout using Affymetrix mouse 430 2.0 arrays coupled with a molecular amplification technique developed in the Core for analyzing small number of cells. Since LSC in SIRT1$^{-/-}$ mice are few, LSC may be harvested from bone marrow and spleen, and pool LSC from 5 to 10 mice for the assay if necessary. Gene expression profiling will then be performed on LSC derived from wild type CML mice immediately after 10-day treatment with SIRT1 inhibitors or vehicle, 8 mice each. SIRT1 inhibitor-induced signaling pathway alteration is compared with SIRT1 knockout to determine if the inhibitor selectively inhibits SIRT1 signaling in vivo.

Determination of the Efficacy for Killing Human Leukemia Stem Cells In Vitro and In Vivo.

In vitro assays. CD34$^+$ cells are isolated from samples from CML patients who have not received Imatinib and normal healthy controls using immunomagnetic columns (Miltenyi). CD34$^+$CD38$^-$ and CD34$^+$CD38$^+$ cells are selected using flow cytometry sorting. Cells are cultured in medium supplemented with low concentrations of growth factors, with the following treatments: (i) No treatment, (ii) SIRT1 inhibitor alone, (iii) Imatinib alone, and (iv) SIRT1 inhibitor combined with Imatinib. Cell proliferation is examined by 5-(and 6-) CFSE labeling and apoptosis by annexin-V labeling. A proliferation index (PI) is calculated based on the CFSE fluorescence profile as described previously (Bhatia et al., 2003; Holtz et al., 2002). The percentage of annexin V$^+$ cells for total as well as dividing and non-dividing cells (CFSE low and high respectively) is calculated. Colony forming cells (CFC) assays are performed by plating cells in methylcellulose progenitor culture for 14-18 days. A similar approach is used to study the efficacy of the drug on AML stem cells using samples from newly diagnosed untreated AML patients.

In vivo studies. To analyze the effect of drug treatment on CML and normal human HSC capable of initiating multilineage engraftment in NOD/SCID mice [SCID-repopulating cell (SRC)], the NOD/SCID-IL2Rγ chain KO (NSG) model that supports improved engraftment of human hematopoietic cells is used. Although larger numbers of CML cells are required to establish engraftment in NSG mice compared to normal cells, it has been found that engraftment with BCR-ABL$^+$ cells is consistently observed and can be reproducibly measured. This assay has been used to demonstrate targeting of CML SRC by HDAC inhibitor and Imatinib combination (Zhang et al., 2010). CML and normal human CD34$_+$ cells (CML $1 \times 10^6$ per mouse, normal $2 \times 10^5$ cells/mouse) are exposed in vitro to a SIRT1 inhibitor, Imatinib or the combination of the two agents are followed by injection into sublethally irradiated (300 cGy) 8 week NSG mice via tail vein injection. Blood samples are obtained to monitor human cell engraftment 4 weeks after injection (by flow cytometry for human CD45$_+$ cells). At 8-12 weeks animals are euthanized and marrow content of femurs and tibiae, spleen cells and blood obtained. Human cell engraftment is analyzed by flow cytometry after labeling with anti-human CD45 antibody. Specific human cell subsets are detected with antibodies to human CD34, CD38, CD14, CD11b, CD33, Glycophorin A, CD19 and CD3. The proportion of BCR-ABL$^+$ human cells is evaluated by Q-PCR analysis of cells engrafted in mouse tissue for BCR-ABL and BCR (human) levels. A similar approach is used to analyze the effects of drug treatment on AML stem cells.

Determination of Pharmacokinetics (PK), Safety and Toxicity.

Four lead compounds from each round of optimization discussed above are tested for PK and toxicity.

Determination of the Maximum Tolerated Dose (MTD) and Toxicity. The initial dose will start with the equivalent to IC$_{50}$ dose of SIRT1 inhibitors in vitro via intravenous (IV) injection. All animals are monitored for 4 hr immediately following administration of the inhibitor and will continue to be monitored for 1 week to observe for signs of delayed toxicity, which includes loss of appetite, changes in waste elimination, hunched posture, coat ruffling, eye crustiness, and changes in activity level. The mice will also be weighed 24 hr post-treatment, and animals that lose 20% or more of its body weight are euthanized. Dose escalation (by 1.5 fold increase) or reduction (by ⅓) is carried out until the MTD is reached or until solubility limits the procedure. Once single dose MTD is identified, multi-dose studies are carried out accordingly.

PK determination. A three-phase single-dose PK study is performed in mice at the MTD following intravenous (IV) or oral administration to determine the half-life (T$_{1/2}$) of the SIRT1 inhibitors. Blood samples are collected at different time points (0.25-48 hours) for LC-MS analysis of drug concentrations. Once the T$_{1/2}$ is determined, phase 2 PK studies are conducted to characterize the dose-dependent PKs, volume of distribution (Vd), clearance (CL), maximal drug concentration (C$_{max}$), and the systemic bioavailability following both IV and oral single-dose administrations. Phase 3 PK studies will collect normal tissues for an assessment of drug distribution.

Alternative methods. A SIRT1 inhibitor for in vivo use must also consider factors such as stability, clearance, toxicity and solubility, so metrics such as formulation, PK, toxicity, and efficacy data are used to guide further chemical modifications to optimize inhibitors and to choose additional backup inhibitors.

REFERENCES

The references listed below, and all references cited in the specification above, are hereby incorporated by reference in their entirety, as if fully set forth herein.

American Cancer Society, Cancer Facts. (2010).
Abdelmohsen, K., et al. Phosphorylation of HuR by Chk2 regulates SIRT1 expression. Mol Cell 25, 543-557(2007).
Ahmed, S. Sun, A. E. Siglin et al., Biochemistry (2010).
Anand, S., S. Penrhhyn-Lowe, and A. R. Venkitaraman. 2003. AURORA-A amplification overrides the mitotic spindle assembly checkpoint, inducing resistance to Taxol. Cancer Cell 3:51-62.
Andrews, P. D. 2005. Aurora kinases: shining lights on the therapeutic horizon? Oncogene 24:5005-5015.
Avalos, I. Celic, S. Muhammad et al., Mol Cell 10(3), 523 (2002).
Avalos, J. L., Bever, K. M., and Wolberger, C. (2005). Mechanism of sirtuin inhibition by nicotinamide: altering the NAD(+) cosubstrate specificity of a Sir2 enzyme. Mol Cell 17, 855-868.
Azam, M., Latek, R. R., and Daley, G. Q. (2003) Cell 112, 831-843
Balaban, R. S., S, Nemoto, and T. Finkel. 2005. Mitochondria, oxidants, and aging. Cell 120:483-495.
Baselga, J. 2006. Targeting tyrosine kinases in cancer: the second wave. Science 312:1175-1178.
Baselga, J., D. Rischin, M. Ranson, H. Calvert, E. Raymond, D. G. Kieback, S. B. Kaye, L. Gianni, A. Harris, T. Bjork, S. D. Averbuch, A. Feyereislova, H. Swaisland, F. Rojo, and J. Albanell. 2002. Phase I safety, pharmacokinetic, and pharmacodynamic trial of ZD1839, a selective oral epidermal growth factor receptor tyrosine kinase inhibitor, in patients with five selected solid tumor types. J Clin Oncol 20:4292-4302.
Bassan, R., Gatta, G., Tondini, C., and Willemze, R. (2004). Adult acute lymphoblastic leukaemia. Crit. Rev Oncol Hematol 50, 223-261.
Baur, J. A., K. J. Pearson, N. L. Price, H. A. Jamieson, C. Lerin, A. Kalra, V. V. Prabhu, J. S. Allard, G. Lopez-Lluch, K. Lewis, P. J. Pistell, S. Poosala, K. G. Becker, O. Boss, D. Gwinn, M. Wang, S. Ramaswamy, K. W. Fishbein, R. G. Spencer, E. G. Lakatta, D. Le Couteur, R. J. Shaw, P. Navas, P. Puigserver, D. K. Ingram, R. de Cabo, and D. A. Sinclair. 2006. Resveratrol improves health and survival of mice on a high-calorie diet. Nature 444:337-342.
Bedalov, A., T. Gatbonton, W. P. Irvine, D. E. Gottschling, and J. A. Simon. 2001. Identification of a small molecule inhibitor of Sir2p. Proc Natl Acad Sci USA 98:15113-15118.
Bennardo, N., Cheng, A., Huang, N. & Stark, J. M. Alternative-NHEJ is a mechanistically distinct pathway of mammalian chromosome break repair. *PLoS genetics* 4, e1000110 (2008).
Berrigan, D., Perkins, S. N., Haines, D. C. & Hursting, S. D. Adult-onset calorie restriction and fasting delay spontaneous tumorigenesis in p53-deficient mice. Carcinogenesis 23, 817-822(2002).
Bhatia, R., et al. Persistence of malignant hematopoietic progenitors in chronic myelogenous leukemia patients in complete cytogenetic remission following imatinib mesylate treatment. Blood 101, 4701-4707(2003).
Bi, S., T. Hughes, J. Bungey, A. Chase, P. de Fabritiis, and J. M. Goldman. 1992. p53 in chronic myeloid leukemia cell lines. Leukemia 6:839-842.
Bitterman, K. J., R. M. Anderson, H. Y. Cohen, M. Latorre-Esteves, and D. A. Sinclair. 2002. Inhibition of silencing and accelerated aging by nicotinamide, a putative negative regulator of yeast sir2 and human SIRT1. J Biol Chem 277:45099-45107.
Blume-Jensen, P., and T. Hunter. 2001. Oncogenic kinase signalling. Nature 411:355-365.
Boily, G., He, X. H., Pearce, B., Jardine, K. & McBurney, M. W. SirT1-null mice develop tumors at normal rates but are poorly protected by resveratrol. Oncogene (2009).
Boily, G., et al. SirT1 regulates energy metabolism and response to caloric restriction in mice. PLoS ONE 3, e1759 (2008).
Bordone, L., Motta, M. C., Picard, F., Robinson, A., Jhala, U.S., Apfeld, J., McDonagh, T., Lemieux, M., McBurney, M., Szilvasi, A., et al. (2006). Sirt1 regulates insulin secretion by repressing UCP2 in pancreatic beta cells. PLoS Biol 4, e31.
Borra, B. C. Smith, and J. M. Denu, J Biol Chem 280(17), 17187(2005)
Bradbury, C. A., et al. Histone deacetylases in acute myeloid leukaemia show a distinctive pattern of expression that changes selectively in response to deacetylase inhibitors. Leukemia 19, 1751-1759(2005).
Bradeen, H. A., Eide, C. A., O'Hare, T., Johnson, K. J., Willis, S. G., Lee, F. Y., Druker, B. J., and Deininger, M. W. (2006) Blood 108, 2332-2338.
Branford, S., Z. Rudzki, S. Walsh, A. Grigg, C. Arthur, K. Taylor, R. Herrmann, K. P. Lynch, and T. P. Hughes. 2002. High frequency of point mutations clustered within the adenosine triphosphate-binding region of BCR/ABL in patients with chronic myeloid leukemia or Ph-positive acute lymphoblastic leukemia who develop imatinib (STI571) resistance. Blood 99:3472-3475.
Brunet, A., Sweeney, L. B., Sturgill, J. F., Chua, K. F., Greer, P. L., Lin, Y., Tran, H., Ross, S. E., Mostoslaysky, R., Cohen, H. Y., et al. (2004). Stress-dependent regulation of FOX()transcription factors by the SIRT1 deacetylase. Science 303, 2011-2015.
Burchert, A., Wang, Y., Cai, D., von Bubnoff, N., Paschka, P., Muller-Brusselbach, S., Ottmann, O. G., Duyster, J., Hochhaus, A., and Neubauer, A. (2005). Compensatory P13-kinase/Akt/mTor activation regulates imatinib resistance development. Leukemia 19, 1774-1782.
Burgess, M. R., Skaggs, B. J., Shah, N. P., Lee, F. Y., and Sawyers, C. L. (2005) Proc. Natl. Acad. Sci. U.S.A. 102, 3395-3400.
Burkhart-Schultz, K. J., Thompson, C. L., and Jones, I. M. (1996). Spectrum of somatic mutation at the hypoxanthine phosphoribosyltransferase (hprt) gene of healthy people. Carcinogenesis 17, 1871-1883.
Canitrot, Y., Lautier, D., Laurent, G., Frechet, M., Ahmed, A., Turhan, A. G., Salles, B., Cazaux, C., and Hoffmann, J. S. (1999). Mutator phenotype of BCR-ABL transfected Ba/F3 cell lines and its association with enhanced expression of DNA polymerase beta. Oncogene 18, 2676-2680.
Carter, M. G., M. A. Johns, X. Zeng, L. Zhou, M. C. Zink, J. L. Mankowski, D. M. Donovan, and S. B. Baylin. 2000. Mice deficient in the candidate tumor suppressor gene Hic1 exhibit developmental defects of structures affected in the Miller-Dieker syndrome. Hum Mol Genet. 9:413-419.
Carter, T. A., L. M. Wodicka, N. P. Shah, A. M. Velasco, M. A. Fabian, D. K. Treiber, Z. V. Milanov, C. E. Atteridge, W. H. Biggs, 3rd, P. T. Edeen, M. Floyd, J. M. Ford, R. M. Grotzfeld, S. Herrgard, D. E. Insko, S. A. Mehta, H. K. Patel, W. Pao, C. L. Sawyers, H. Varmus, P. P. Zarrinkar, and D. J. Lockhart. 2005. Inhibition of drug-resistant mutants of ABL, KIT, and EGF receptor kinases. Proc Natl Acad Sci USA 102:11011-11016.
Chen, P. M., Kwan, S. H., Hwang, T. S., Chiang, B. N., and Chou, C. K. (1983). Insulin receptors on leukemia and lymphoma cells. Blood 62, 251-255.

Chen, W. Y., and Baylin, S. B. (2005). Inactivation of Tumor Suppressor Genes: Choice Between Genetic and Epigenetic Routes. Cell Cycle 4.

Chen, W. Y., Cooper, T. K., Zahnow, C. A., Overholtzer, M., Zhao, Z., Ladanyi, M., Karp, J. E., Gokgoz, N., Wunder, J. S., Andrulis, I. L., et al. (2004). Epigenetic and genetic loss of Hic1 function accentuates the role of p53 in tumorigenesis. Cancer Cell 6, 387-398.

Chen, W. Y., D. H. Wang, R. C. Yen, J. Luo, W. Gu, and S. B. Baylin. 2005. Tumor suppressor HIC1 directly regulates SIRT1 to modulate p53-dependent DNA-damage responses. Cell 123:437-448.

Chen, W. Y., Zeng, X., Carter, M. G., Morrell, C. N., Chiu Yen, R. W., Esteller, M., Watkins, D. N., Herman, J. G., Mankowski, J. L., and Baylin, S. B. (2003). Heterozygous disruption of Hic1 predisposes mice to a gender-dependent spectrum of malignant tumors. Nat Genet. 33, 197-202.

Cheng, H. L., et al. Developmental defects and p53 hyperacetylation in Sir2 homolog (SIRT1)-deficient mice. Proc Natl Acad Sci USA 100, 10794-10799(2003).

Chu, F., P. M. Chou, X. Zheng, B. L. Mirkin, and A. Rebbaa. 2005. Control of multidrug resistance gene mdr1 and cancer resistance to chemotherapy by the longevity gene sirt1. Cancer Res 65:10183-10187.

Cohen, H. Y., Miller, C., Bitterman, K. J., Wall, N. R., Hekking, B., Kessler, B., Howitz, K. T., Gorospe, M., de Cabo, R., and Sinclair, D. A. (2004). Calorie restriction promotes mammalian cell survival by inducing the SIRT1 deacetylase. Science 305, 390-392.

Cohen, M. H., G. A. Williams, R. Sridhara, G. Chen, W. D. McGuinn, Jr., D. Morse, S. Abraham, A. Rahman, C. Liang, R. Lostritto, A. Baird, and R. Pazdur. 2004. United States Food and Drug Administration Drug Approval summary: Gefitinib (ZD1839; Iressa) tablets. Clin Cancer Res 10:1212-1218.

Cohen, S. Lavu, K. J. Bitterman et al., Mol Cell 13(5), 627 (2004).

Cragg, M. S., J. Kuroda, H. Puthalakath, D.C. Huang, and A. Strasser. 2007. Gefitinib-induced killing of NSCLC cell lines expressing mutant EGFR requires BIM and can be enhanced by BH3 mimetics. PLoS Med 4:1681-1689; discussion 1690.

Crane, R., A. Kloepfer, and J. V. Ruderman. 2004. Requirements for the destruction of human Aurora-A. J Cell Sci 117:5975-5983.

Czechowska, A., Poplawski, T., Drzewoski, J., and Blasiak, J. (2005). Imatinib (STI571) induces DNA damage in BCR/ABL-expressing leukemic cells but not in normal lymphocytes. Chem Biol Interact 152, 139-150.

Daitoku, H., M. Hatta, H. Matsuzaki, S. Aratani, T. Ohshima, M. Miyagishi, T. Nakajima, and A. Fukamizu. 2004. Silent information regulator 2 potentiates Foxo1-mediated transcription through its deacetylase activity. Proc Natl Acad Sci USA 101:10042-10047.

de Ruijter, A. J., van Gennip, A. H., Caron, H. N., Kemp, S., and van Kuilenburg, A. B. (2003). Histone deacetylases (HDACs): characterization of the classical HDAC family. Biochem J 370, 737-749.

Deininger, M. W., and Druker, B. J. (2003). Specific targeted therapy of chronic myelogenous leukemia with imatinib. Pharmacol Rev 55, 401-423.

Deininger, M. W., Goldman, J. M., Lydon, N., and Melo, J. V. (1997). The tyrosine kinase inhibitor CGP57148B selectively inhibits the growth of BCR-ABL-positive cells. Blood 90, 3691-3698.

Dinkelmann, M., et al. Multiple functions of MRN in end-joining pathways during isotype class switching. Nature structural & molecular biology 16, 808-813(2009).

Engelman, J. A., K. Zejnullahu, T. Mitsudomi, Y. Song, C. Hyland, J. O. Park, N. Lindeman, C. M. Gale, X. Zhao, J. Christensen, T. Kosaka, A. J. Holmes, A. M. Rogers, F. Cappuzzo, T. Mok, C. Lee, B. E. Johnson, L. C. Cantley, and P. A. Janne. 2007. MET amplification leads to gefitinib resistance in lung cancer by activating ERBB3 signaling. Science 316:1039-1043.

Engelman, J. A., T. Mukohara, K. Zejnullahu, E. Lifshits, A. M. Borras, C. M. Gale, G. N. Naumov, B. Y. Yeap, E. Jarrell, J. Sun, S. Tracy, X. Zhao, J. V. Heymach, B. E. Johnson, L. C. Cantley, and P. A. Janne. 2006. Allelic dilution obscures detection of a biologically significant resistance mutation in EGFR-amplified lung cancer. J Clin Invest 116:2695-2706.

Finnin, J. R. Donigian, and N. P. Pavletich, Nat Struct Biol 8(7), 621(2001)

Firestein, G. Blander, S. Michan et al., PLoS ONE 3(4), e2020(2008)

Ford, J., M. Jiang, and J. Milner. 2005. Cancer-specific functions of SIRT1 enable human epithelial cancer cell growth and survival. Cancer Res 65:10457-10463.

Ford, J., Ahmed, S., Allison, S., Jiang, M. & Milner, J. JNK2-dependent regulation of SIRT1 protein stability. Cell Cycle 7, 3091-3097(2008).

Frommer, M., McDonald, L. E., Millar, D. S., Collis, C. M., Watt, F., Grigg, G. W., Molloy, P. L., and Paul, C. L. (1992). A genomic sequencing protocol that yields a positive display of 5-methylcytosine residues in individual DNA strands. Proc Natl Acad Sci USA 89, 1827-1831.

Frye, R. A. 1999. Characterization of five human cDNAs with homology to the yeast SIR2 gene: Sir2-like proteins (sirtuins) metabolize NAD and may have protein ADP-ribosyltransferase activity. Biochem Biophys Res Commun 260:273-279.

Frye, R. A. 2000. Phylogenetic classification of prokaryotic and eukaryotic Sir2-like proteins. Biochem Biophys Res Commun 273:793-798.

Gambacorti-Passerini, C. B., Gunby, R. H., Piazza, R., Galietta, A., Rostagno, R., and Scapozza, L. (2003). Molecular mechanisms of resistance to imatinib in Philadelphia-chromosome-positive leukaemias. Lancet Oncol 4, 75-85.

Gaymes, T. J., Mufti, G. J. & Rassool, F. V. Myeloid leukemias have increased activity of the nonhomologous end-joining pathway and concomitant DNA misrepair that is dependent on the Ku70/86 heterodimer. Cancer Res 62, 2791-2797(2002).

Giles, F. J., J. Cortes, D. Jones, D. Bergstrom, H. Kantarjian, and S. J. Freedman. 2007. MK-0457, a novel kinase inhibitor, is active in patients with chronic myeloid leukemia or acute lymphocytic leukemia with the T315I BCR-ABL mutation. Blood 109:500-502.

Gorre, M. E., Mohammed, M., Ellwood, K., Hsu, N., Paquette, R., Rao, P. N., and Sawyers, C. L. (2001). Clinical resistance to STI-571 cancer therapy caused by BCR-ABL gene mutation or amplification. Science 293, 876-880.

Grozinger, C. M., E. D. Chao, H. E. Blackwell, D. Moazed, and S. L. Schreiber. 2001. Identification of a class of small molecule inhibitors of the sirtuin family of NAD-dependent deacetylases by phenotypic screening. J Biol Chem 276:38837-38843.

Guarente, L. 2000. Sir2 links chromatin silencing, metabolism, and aging. Genes Dev 14:1021-1026.

Guerardel, C., Deltour, S., Pinte, S., Monte, D., Begue, A., Godwin, A. K., and Leprince, D. (2001). Identification in the human candidate tumor suppressor gene HIC-1 of a new major alternative TATA-less promoter positively regulated by p53. J Biol Chem 276, 3078-3089.

Haber, D. A., D. W. Bell, R. Sordella, E. L. Kwak, N. Godin-Heymann, S. V. Sharma, T. J. Lynch, and J. Settleman. 2005. Molecular targeted therapy of lung cancer: EGFR mutations and response to EGFR inhibitors. Cold Spring Harb Symp Quant Biol 70:419-426.

Harrington, E. A., D. Bebbington, J. Moore, R. K. Rasmussen, A. O. Ajose-Adeogun, T. Nakayama, J. A. Graham, C. Demur, T. Hercend, A. Diu-Hercend, M. Su, J. M. Golec, and K. M. Miller. 2-4. VX-680, a potent and selective small-molecule inhibitor of the Aurora kinases, suppresses tumor growth in vivo. Nat Med 10:262-267.

Harvey, M., et al. Spontaneous and carcinogen-induced tumorigenesis in p53-deficient mice. Nat Genet. 5, 225-229 (1993).

Heltweg, T. Gatbonton, A. D. Schuler et al., Cancer Res 66(8), 4368(2006). Hennighausen, L. & Robinson, G. W. Interpretation of cytokine signaling through the transcription factors STAT5A and STAT5B. Genes Dev 22, 711-721 (2008).

Herman, J. G., Graff, J. R., Myohanen, S., Nelkin, B. D., and Baylin, S. B. (1996). Methylation-specific PCR: a novel PCR assay for methylation status of CpG islands. Proc Natl Acad Sci USA 93, 9821-9826.

Hirao, M., Posakony, J., Nelson, M., Hruby, H., Jung, M., Simon, J. A., and Bedalov, A. (2003). Identification of selective inhibitors of $NAD_+$-dependent deacetylases using phenotypic screens in yeast. J Biol Chem 278, 52773-52782.

Hoelbl, B. Kovacic, M. A. Kerenyi et al., Blood 107(12), 4898(2006).

Holtz, M. L. Slovak, F. Zhang et al., Blood 99(10), 3792 (2002).

Howitz, K. T., K. J. Bitterman, H. Y. Cohen, D. W. Lamming, S. Lavu, J. G. Wood, R. E.

Zipkin, P. Chung, A. Kisielewski, L. L. Zhang, B. Scherer, and D. A. Sinclair. 2003. Small molecule activators of sirtuins extend *Saccharomyces cerevisiae* lifespan. Nature 425:191-196.

Hu, Y., et al. Targeting multiple kinase pathways in leukemic progenitors and stem cells is essential for improved treatment of $Ph_+$ leukemia in mice. Proc Natl Acad Sci USA 103, 16870-16875(2006).

Huffman, D. M., W. E. Grizzle, M. M. Bamman, J. S. Kim, I. A. Eltoum, A. Elgavish, and T. R. Nagy. 2007. SIRT1 Is Significantly Elevated in Mouse and Human Prostate Cancer. Cancer Res 67:6612-6618.

Huntly, B. J., Bench, A., and Green, A. R. (2003) Blood 102, 1160-1168.

Ilaria, Jr. and R. A. Van Etten, J Biol Chem 271(49), 31704 (1996).

Imai, S., C. M. Armstrong, M. Kaeberlein, and L. Guarente. 2000. Transcriptional silencing and longevity protein Sir2 is an NAD-dependent histone deacetylase. Nature 403: 795-800.

Inukai, M., S. Toyooka, S. Ito, H. Asano, S. Ichihara, J. Soh, H. Suchisa, M. Ouchida, K. Aoe, M. Aoe, K. Kiura, N. Shimizu, and H. Date. 2006. Presence of epidermal growth factor receptor gene T790M mutation as a minor clone in non-small cell lung cancer. Cancer Res 66:7854-7858.

Issa, J. P., Zehnbauer, B. A., Kaufmann, S. H., Biel, M. A., and Baylin, S. B. (1997). HIC1 hypermethylation is a late event in hematopoietic neoplasms. Cancer Res 57, 1678-1681.

Jamieson, C. H., et al. Granulocyte-macrophage progenitors as candidate leukemic stem cells in blast-crisis CML. N Engl J Med 351, 657-667(2004).

Jang, K. Y., et al. SIRT1 expression is associated with poor prognosis of diffuse large B-cell lymphoma. The American journal of surgical pathology 32, 1523-1531(2008).

Jang, K. Y., et al. Expression and prognostic significance of SIRT1 in ovarian epithelial tumours. Pathology 41, 366-371(2009).

Jiang, X., Saw, K. M., Eaves, A., and Eaves, C. (2007) J. Natl. Cancer Inst. 99, 680-693.

Jin, W. Wei, Y. Jiang et al., J Biol Chem 284(36), 24394 (2009).

Jones, P. A., and Baylin, S. B. (2002). The fundamental role of epigenetic events in cancer. Nat Rev Genet. 3, 415-428.

Jordan, M. L. Guzman, and M. Noble, N Engl J Med 355(12), 1253(2006).

Jung-Hynes, B., Nihal, M., Zhong, W. & Ahmad, N. Role of sirtuin histone deacetylase SIRT1 in prostate cancer. A target for prostate cancer management via its inhibition? J Biol Chem 284, 3823-3832(2009).

Kabra, N., Z. Li, L. Chen et al., J Biol Chem (2009)

Kaeberlein, M., McVey, M., and Guarente, L. (1999). The SIR2/3/4 complex and SIR2 alone promote longevity in *Saccharomyces cerevisiae* by two different mechanisms. Genes Dev 13, 2570-2580.

Kaeberlein, T. McDonagh, B. Heltweg et al., J Biol Chem 280(17), 17038(2005)

Kantarjian, H., Giles, F., Wunderle, L., Bhalla, K., O'Brien, S., Wassmann, B., Tanaka, C., Manley, P., Rae, P., Mietlowski, W., et al. (2006). Nilotinib in imatinib-resistant CML and Philadelphia chromosome-positive ALL. N Engl J Med 354, 2542-2551.

Karpinets, T., Greenwood, Dj., Pogribny, I., and Samatova, N. (2006) Curr. Genomics 7, 481-496.

Kawano, T., Horiguchi-Yamada, J., (wase, S., Akiyama, M., Furukawa, Y., Kan, Y., and Yamada, H. (2004). Depsipeptide enhances imatinib mesylate-induced apoptosis of Bcr-Abl-positive cells and ectopic expression of cyclin D1, c-Myc or active MEK abrogates this effect. Anticancer Res 24, 2705-2712.

Keen, N., and S. Taylor. 2004. Aurora-kinase inhibitors as anticancer agents. Nat Rev Cancer 4:927-936.

Kelly, D. P., and R. C. Scarpulla. 2004. Transcriptional regulatory circuits controlling mitochondrial biogenesis and function. Genes Dev 18:357-368.

Khanna, K. K. & Jackson, S. P. DNA double-strand breaks: signaling, repair and the cancer connection. Nat Genet. 27, 247-254(2001).

Kharbanda, S., P. Pandey, S. Jin, S. Inoue, A. Bharti, Z. M. Yuan, R. Weichselbaum, D. Weaver, and D. Kufe. 1997. Functional interaction between DNA-PK and c-Abl in response to DNA damage. Nature 386:732-735.

Kiel, M. J., et al. SLAM family receptors distinguish hematopoietic stem and progenitor cells and reveal endothelial niches for stem cells. Cell 121, 1109-1121(2005).

Klejman, A., Rushen, L., Morrione, A., Slupianek, A., and Skorski, T. (2002). Phosphatidylinositol-3 kinase inhibitors enhance the anti-leukemia effect of ST1571. Oncogene 21, 5868-5876.

Kobayashi, S., T. J. Boggon, T. Dayaram, P. A. Janne, O. Kocher, M. Meyerson, B. E.

Johnson, M. J. Eck, D. G. Tenen, and B. Halmos. 2005. EGFR mutation and resistance of non-small-cell lung cancer to gefitinib. N Engl J Med 352:786-792.

Kojima, R. Ohhashi, Y. Fujita et al., Biochem Biophys Res Commun 373(3), 423 (2008).

Koptyra, M., R. Falinski, M. O, Nowicki, T. Stoklosa, I. Majsterek, M. Nieborowska-Skorska, J. Blasiak, and T. Skorski. 2006. BCR/ABL kinase induces self-mutagenesis via reactive oxygen species to encode imatinib resistance. Blood 108:319-327.

Kosaka, T., Y. Yatabe, H. Endoh, K. Yoshida, T. Hida, M. Tsuboi, H. Tada, H. Kuwano, and T. Mitsudomi. 2006. Analysis of epidermal growth factor receptor gene mutation in patients with non-small cell lung cancer and acquired resistance to gefitinib. Clin Cancer Res 12:5764-5769.

Kowolik, C. M., Yam, P., Yu, Y., and Yee, J. K. (2003). HIV vector production mediated by Rev protein transduction. Mol Ther 8, 324-331.

Kubonishi, I., and Miyoshi, I. (1983) Int. J. Cell Cloning 1, 105-117.

Kuzmichev, A., R. Margueron, A. Vaquero, T. S. Preissner, M. Scher, A. Kirmizis, X. Ouyang, N. Brockdorff, C. Abate-Shen, P. Farnham, and D. Reinberg. 2005. Composition and histone substrates of polycomb repressive group complexes change during cellular differentiation. Proc Natl Acad Sci USA 102:1859-1864.

Kwak, E. L., R. Sordella, D. W. Bell, N. Godin-Heymann, R. A. Okimoto, B. W. Brannigan, P. L. Harris, D. R. Driscoll, P. Fidias, T. J. Lynch, S. K. Rabindran, J. P. McGinnis, A. Wissner, S. V. Sharma, K. J. Isselbacher, J. Settleman, and D. A. Haber. 2005. Irreversible inhibitors of the EGF receptor may circumvent acquired resistance to gefitinib. Proc Natl Acad Sci USA 102:7665-7670.

Ladbury, G. Klebe, and E. Freire, Nat Rev Drug Discov 9(1), 23.

Lagouge, M., C. Argmann, Z. Gerhart-Hines, H. Meziane, C. Lerin, F. Daussin, N. Messadeq, J. Milne, P. Lambert, P. Elliott, B. Geny, M. Laakso, P. Puigserver, and J. Auwerx. 2006. Resveratrol improves mitochondrial function and protects against metabolic disease by activating SIRT1 and PGC-1alpha. Cell 127:1109-1122.

Lain, J. J. Hollick, J. Campbell et al., Cancer Cell 13(5), 454(2008). Lamb, E. D. Crawford, D. Peck et al., Science (New York, N.Y. 313(5795), 1929(2006).

La Rosee, P., Corbin, A. S., Stoffregen, E. P., Deininger, M. W., and Druker, B. J. (2002). Activity of the Bcr-Abl kinase inhibitor PD180970 against clinically relevant Bcr-Abl isoforms that cause resistance to imatinib mesylate (Gleevec, STI571). Cancer Res 62, 7149-7153.

La Rosee, P., Johnson, K., Corbin, A. S., Stoffregen, E. P., Moseson, E. M., Willis, S., Mauro, M. M., Melo, J. V., Deininger, M. W., and Druker, B. J. (2004). In vitro efficacy of combined treatment depends on the underlying mechanism of resistance in imatinib-resistant Bcr-Abl-positive cell lines. Blood 103, 208-215.

La Rosee, P., Corbin, A. S., Stoffregen, E. P., Deininger, M. W., and Druker, B. J. (2002). Activity of the Bcr-Abl kinase inhibitor PD180970 against clinically relevant Bcr-Abl isoforms that cause resistance to imatinib mesylate (Gleevec, STI571). Cancer Res 62, 7149-7153.

Landry, J., A. Sutton, S. T. Tafrov, R. C. Heller, J. Stebbins, L. Pillus, and R. Sternglanz. 2000. The silencing protein SIR2 and its homologs are NAD-dependent protein deacetylases. Proc Natl Acad Sci USA 97:5807-5811.

Le Coutre, P., L. Mologni, L. Cleros, E. Marchesi, E. Buchdunger, R. Giardini, F. Formelli, and C. Gambacorti-Passerini. 1999. In vivo eradication of human BCR/ABL-positive leukemia cells with an ABL kinase inhibitor. J Natl Cancer Inst 91:163-168.

Li, G. Li, B. A. Berg et al., J Chem Phys 125(14), 144902 (2006).

Li, M. Fajer, and W. Yang, J Chem Phys 126(2), 024106 (2007)

Li, M. J., G. Bauer, A. Michienzi, J. K. Yee, N. S. Lee, J. Kim, S. Li, D. Castanotto, J. Zaia, and J. J. Rossi. 2003. Inhibition of HIV-1 infection by lentiviral vectors expressing Pol III-promoted anti-HIV RNAs. Mol Ther 8:196-206.

Li, M. J., McMahon, R., Snyder, D. S., Yee, J. K., and Rossi, J. J. (2003) Oligonucleotides 13, 401-409.

Li, Y., Xu, W., McBurney, M. W. & Longo, V. D. SirT1 inhibition reduces IGF-I/IRS-2/Ras/ERK1/2 signaling and protects neurons. Cell Metab 8, 38-48(2008).

Lin, S. J., P. A. Defossez, and L. Guarente. 2000. Requirement of NAD and SIR2 for life-span extension by calorie restriction in *Saccharomyces cerevisiae*. Science 289:2126-2128.

Littlepage, L. E., and J. V. Ruderman. 2002. Identification of a new APC/C recognition domain, the A box, which is required for the Cdh1-dependent destruction of the kinase Aurora-A during mitotic exit. Genes Dev 16:2274-2285.

Littlepage, L. E., H. Wu, T. Andresson, J. K. Deanehan, L. T. Amundadottir, and J. V. Ruderman. 2002. Identification of phosphorylated residues that affect the activity of the mitotic kinase Aurora-A. Proc Natl Acad Sci USA 99:15440-15445.

Loots G. G. & Ovcharenko, I. rVISTA 2.0: evolutionary analysis of transcription factor binding sites. Nucleic Acids Res 32, W217-221(2004).

Lucas, C. M., Harris, R. J., Giannoudis, A., Davies, A., Knight, K., Watmough, S. J., Wang, L., and Clark, R. E. (2009) Haematologica 94, 1362-1367.

Luo, J., Nikolaev, A. Y., Imai, S., Chen, D., Su, F., Shiloh, A., Guarente, L., and Gu, W. (2001). Negative control of p53 by Sir2alpha promotes cell survival under stress. Cell 107, 137-148.

Ly, C., Arechiga, A. F., Melo, J. V., Walsh, C. M., and Ong, S. T. (2003). Bcr-Abl kinase modulates the translation regulators ribosomal protein S6 and 4E-BP1 in chronic myelogenous leukemia cells via the mammalian target of rapamycin. Cancer Res 63, 5716-5722.

Lynch, T. J., D. W. Bell, R. Sordella, S. Gurubhagavatula, R. A. Okimoto, B. W. Brannigan, P. L. Harris, S. M. Haserlat, J. G. Supko, F. G. Haluska, D. N. Louis, D.C. Christiani, J. Settleman, and D. A. Haber. 2004. Activating mutations in the epidermal growth factor receptor underlying responsiveness of non-small-cell lung cancer to gefitinib. N Engl J Med 350:2129-2139.

Maguer-Satta, V., Burl, S., Liu, L., Damen, J., Chahine, H., Krystal, G., Eaves, A., and Eaves, C. (1998). BCR-ABL accelerates C2-ceramide-induced apoptosis. Oncogene 16, 237-248.

Mahon, F. X., Deininger, M. W., Schultheis, B., Chabrol, J., Reiffers, J., Goldman, J. M., and Melo, J. V. (2000). Selection and characterization of BCR-ABL positive cell lines with differential sensitivity to the tyrosine kinase inhibitor STI571: diverse mechanisms of resistance. Blood 96, 1070-1079.

Mai, A., S. Massa, S. Lavu, R. Pezzi, S. Simeoni, R. Ragno, F. R. Mariotti, F. Chiani, G. Camilloni, and D. A. Sinclair. 2005. Design, synthesis, and biological evaluation of sirtinol analogues as class III histone/protein deacetylase (Sirtuin) inhibitors. J Med Chem 48:7789-7795.

Marumoto, T., D. Zhang, and H. Saya. 2005. Aurora-A—a guardian of poles. Nat Rev Cancer 5:42-50.

McWhirter, J. R., Galasso, D. L., and Wang, J. Y. (1993) Mol. Cell. Biol. 13, 7587-7595.

Michan, S, and D. Sinclair, Biochem J 404(1), 1(2007).

Michor, F., Hughes, T. P., Iwasa, Y., Branford, S., Shah, N. P., Sawyers, C. L., and Nowak, M. A. (2005). Dynamics of chronic myeloid leukaemia. Nature 435, 1267-1270.

Melo, J. V. & Barnes, D. J. Chronic myeloid leukaemia as a model of disease evolution in human cancer. Nat Rev Cancer 7, 441-453(2007).

Min, J. Landry, R. Sternglanz et al., Cell 105(2), 269(2001)

Mossessova and C. D. Lima, Mol Cell 5(5), 865(2000)

Motta, M. C., N. Divecha, M. Lemieux, C. Kamel, D. Chen, W. Gu, Y. Bultsma, M. McBurney, and L. Guarente. 2004. Mammalian SIRT1 represses forkhead transcription factors. Cell 116:551-563.

Moynihan, K. A., Grimm, A. A., Plueger, M. M., Bernal-Mizrachi, E., Ford, E., Cras-Meneur, C., Permutt, M. A., and Imai, S. (2005). Increased dosage of mammalian Sir2 in pancreatic beta cells enhances glucose-stimulated insulin secretion in mice. Cell Metab 2, 105-117.

Napper, J. Nixon, T. McDonagh et al., J Med Chem 48(25), 8045(2005).

Narala, S. R., et al. SIRT1 acts as a nutrient-sensitive growth suppressor and its loss is associated with increased AMPK and telomerase activity. Molecular biology of the cell 19, 1210-1219(2008).

Narayan, G., Arias-Pulido, H., Koul, S., Vargas, H., Zhang, F. F., Villella, J., Schneider, A., Terry, M. B., Mansukhani, M., and Murty, V. V. (2003). Frequent Promoter Methylation of CDH1, DAPK, RARB, and HIC1 Genes in Carcinoma of Cervix Uteri: Its Relationship to Clinical Outcome. Mol Cancer 2, 24.

Neering, S. J., et al. Leukemia stem cells in a genetically defined murine model of blast-crisis CML. Blood 110, 2578-2585(2007).

Nemoto, S., M. M. Fergusson, and T. Finkel. 2004. Nutrient availability regulates SIRT1 through a forkhead-dependent pathway. Science 306:2105-2108.

Neubauer, A., M. He, C. A. Schmidt, D. Huhn, and E. T. Liu. 1993. Genetic alterations in the p53 gene in the blast crisis of chronic myelogenous leukemia: analysis by polymerase chain reaction based techniques. Leukemia 7:593-600.

North, B. J., and Verdin, E. (2004). Sirtuins: Sir2-related NAD-dependent protein deacetylases. Genome Biol 5, 224.

Nosho, K., et al. SIRT1 histone deacetylase expression is associated with microsatellite instability and CpG island methylator phenotype in colorectal cancer. Mod Pathol (2009).

Nowell, P. and D Hungerford, Science (New York, N.Y. 132, 1497(1960)

Nowicki, M. O., et al. BCR/ABL oncogenic kinase promotes unfaithful repair of the reactive oxygen species-dependent DNA double-strand breaks. Blood 104, 3746-3753 (2004).

O'Hare, T. and M. W. Deininger, Clin Cancer Res 14(24), 7971(2008).

Oberdoerffer, P., et al. SIRT1 redistribution on chromatin promotes genomic stability but alters gene expression during aging. Cell 135, 907-918(2008).

Ogino, A., H. Kitao, S. Hirano, A. Uchida, M. Ishiai, T. Kozuki, N. Takigawa, M. Takata, K. Kiura, and M. Tanimoto. 2007. Emergence of epidermal growth factor receptor T790M mutation during chronic exposure to gefitinib in a non small cell lung cancer cell line. Cancer Res 67:7807-7814.

Osterholm, A. M., Falt, S., Lambert, B., and Hou, S. M. (1995). Classification of mutations at the human hprt-locus in T-lymphocytes of bus maintenance workers by multiplex-PCR and reverse transcriptase-PCR analysis. Carcinogenesis 16, 1909-1912.

Ota, H., Tokunaga, E., Chang, K., Hikasa, M., Iijima, K., Eto, M., Kozaki, K., Akishita, M., Ouchi, Y., and Kaneki, M. (2005). Sirt1 inhibitor, Sirtinol, induces senescence-like growth arrest with attenuated Ras-MAPK signaling in human cancer cells. Oncogene Oncogene 25(2), 176(2006)

Pacholec, J. E. Bleasdale, B. Chrunyk et al., J Biol Chem 285(11), 8340(2010).

Paez, J. G., P. A. Janne, J. C. Lee, S. Tracy, H. Greulich, S. Gabriel, P. Herman, F. J. Kaye, N. Lindeman, T. J. Boggon, K. Naoki, H. Sasaki, Y. Fujii, M. J. Eck, W. R. Sellers, B. E. Johnson, and M. Meyerson. 2004. EGFR mutations in lung cancer: correlation with clinical response to gefitinib therapy. Science 304:1497-1500.

Pan, J., Q. Wang, and W. J. Snell. 2004. An aurora kinase is essential for flagellar disassembly in *Chlamydomonas*. Dev Cell 6:445-451.

Pao, W., V. A. Miller, K. A. Politi, G. J. Riely, R. Somwar, M. F. Zakowski, M. G. Kris, and H. Varmus. 2005. Acquired resistance of lung adenocarcinomas to gefitinib or erlotinib is associated with a second mutation in the EGFR kinase domain. PLoS Med 2:e73.

Pao, W., V. Miller, M. Zakowski, J. Doherty, K. Politi, I. Sarkaria, B. Singh, R. Heelan, V.

Rusch, L. Fulton, E. Mardis, D. Kupfer, R. Wilson, M. Kris, and H. Varmus. 2004. EGF receptor gene mutations are common in lung cancers from "never smokers" and are associated with sensitivity of tumors to gefitinib and erlotinib. Proc Natl Acad Sci USA 101:13306-13311.

Pear, W. S., J. P. Miller, L. Xu, J. C. Pui, B. Soffer, R. C. Quackenbush, A. M. Pendergast, R. Bronson, J. C. Aster, M. L. Scott, and D. Baltimore. 1998. Efficient and rapid induction of a chronic myelogenous leukemia-like myeloproliferative disease in mice receiving P210 bcr/abl-transduced bone marrow. Blood 92:3780-3792.

Peng, B., P. Lloyd, and H. Schran. 2005. Clinical pharmacokinetics of imatinib. Clin Pharmacokinet 44:879-894.

Podlutsky, A., Osterholm, A. M., Hou, S. M., Hofmaier, A., and Lambert, B. (1998). Spectrum of point mutations in the coding region of the hypoxanthine-guanine phosphoribosyltransferase (hprt) gene in human T-lymphocytes in vivo. Carcinogenesis 19, 557-566.

Posakony, M. Hirao, S. Stevens et al., J Med Chem 47(10), 2635(2004)

Ramaraj, P., Singh, H., Niu, N., Chu, S., Holtz, M., Yee, J. K., and Bhatia, R. (2004) Cancer Res. 64, 5322-5331.

Rapozzi, V., and L. E. Xodo. 2004. Efficient silencing of bcr/abl oncogene by single- and double-stranded siRNAs targeted against b2a2 transcripts. Biochemistrry 43:16134-16141.

Rass, E., et al. Role of Mre11 in chromosomal nonhomologous end joining in mammalian cells. Nature structural & molecular biology 16, 819-824(2009).

Rathi, A., Virmani, A. K., Harada, K., Timmons, C. F., Miyajima, K., Hay, R. J., Mastrangelo, D., Maitra, A., Tomlinson, G. E., and Gazdar, A. F. (2003). Aberrant methylation of the HIC1 promoter is a frequent event in specific pediatric neoplasms. Clin Cancer Res 9, 3674-3678.

Ray, A., Cowan-Jacob, S. W., Manley, P. W., Mestan, J., and Griffin, J. D. (2007) Blood 109, 5011-5015

Reynolds, A., Leake, D., Boese, Q., Scaringe, S., Marshall, W. S., and Khvorova, A. (2004). Rational siRNA design for RNA interference. Nat Biotechnol 22, 326-330.

Ricci, C., Scappini, B., Divoky, V., Gatto, S., Onida, F., Verstovsek, S., Kantarjian, H. M., and Beran, M. (2002) Cancer Res. 62, 5995-5998.

Roche-Lestienne, C., Soenen-Cornu, V., Grardel-Duflos, N., Lai, J. L., Philippe, N., Facon, T., Fenaux, P., and Preudhomme, C. (2002) Blood 100, 1014-1018.

Rodgers, J. T., C. Lerin, W. Haas, S. P. Gygi, B. M. Spiegelman, and P. Puigserver. 2005. Nutrient control of glucose homeostasis through a complex of PGC-1 alpha and SIRT1. Nature 434:113-118.

Rosenberg, S. M. (2001) Nat. Rev. Genet. 2, 504-515.

Rosenhahn, J., Weise, A., Michel, S., Hennig, K., Hartmann, I., Schiefner, J., Schubert, K., Liehr, T., von Eggeling, F., and Loncarevic, I. F. (2007) Int. J. Oncol. 31, 121-128.

Rowley, J. D., N Engl J Med 289(4), 220(1973).

Santini, V., Kantarjian, H. M., and Issa, J. P. (2001). Changes in DNA methylation in neoplasia: pathophysiology and therapeutic implications. Ann Intern Med 134, 573-586.

Sattler, M., S. Verma, G. Shrikhande, C. H. Byrne, Y. B. Pride, T. Winkler, E. A. Greenfield, R. Salgia, and J. D. Griffin. 2000. The BCR/ABL tyrosine kinase induces production of reactive oxygen species in hematopoietic cells. J Biol Chem 275:24273-24278.

Saunders, L. R., and Verdin, E. (2007). Sirtuins: critical regulators at the crossroads between cancer and aging. Oncogene 26, 5489-5504.

Sauve A A, Moir R D, Schramm V L, Willis I M. Chemical activation of Sir2-dependent silencing by relief of nicotinamide inhibition Mol. Cell. 2005, 17(4):595-601

Schindler, T., Bornmann, W., Pellicena, P., Miller, W. T., Clarkson, B., and Kuriyan, J. (2000). Structural mechanism for STI-571 inhibition of abelson tyrosine kinase. Science 289, 1938-1942.

Schuetz, J. Min, T. Antoshenko et al., Structure 15(3), 377 (2007)

Shafman, T., K.K. Khanna, P. Kedar, K. Spring, S. Kozlov, T. Yen, K. Hobson, M. Gatei, N. Zhang, D. Watters, M. Egerton, Y. Shiloh, S. Kharbanda, D. Kufe, and M. F. Lavin. 1997. Interaction between ATM protein and c-Abl in response to DNA damage. Nature 387:520-523.

Shah, N. P., and Sawyers, C. L. (2003). Mechanisms of resistance to ST1571 in Philadelphia chromosome-associated leukemias. Oncogene 22, 7389-7395.

Shah, N. P., C. Tran, F. Y. Lee, P. Chen, D. Norris, and C. L. Sawyers. 2004. Overriding imatinib resistance with a novel ABL kinase inhibitor. Science 305:399-401.

Shah, N. P., Nicoll, J. M., Nagar, B., Gorre, M. E., Paquette, R. L., Kuriyan, J., and Sawyers, C. L. (2002). Multiple BCR-ABL kinase domain mutations confer polyclonal resistance to the tyrosine kinase inhibitor imatinib (ST1571) in chronic phase and blast crisis chronic myeloid leukemia. Cancer Cell 2, 117-125.

Shi, J., Liu, Q., and Sommer, S. S. (2007) Hum. Mutat. 28, 131-136.

Skorski, T., Kanakaraj, P., Nieborowska-Skorska, M., Ratajczak, M. Z., Wen, S.C., Zon, G., Gewirtz, A. M., Perussia, B., and Calabretta, B. (1995). Phosphatidylinositol-3 kinase activity is regulated by BCR/ABL and is required for the growth of Philadelphia chromosome-positive cells. Blood 86, 726-736.

Slupianek, A., Nowicki, M. 0., Koptyra, M., and Skorski, T. (2006). BCR/ABL modifies the kinetics and fidelity of DNA double-strand breaks repair in hematopoietic cells. DNA Repair (Amst) 5, 243-250.

Smith, K. M., Yacobi, R., and Van Etten, R. A. (2003) Mol. Cell. 12, 27-37. Solomon, R. Pasupuleti, L. Xu et al., Mol Cell Biol 26(1), 28(2006).

Soverini, S., Colarossi, S., Gnani, A., Rosti, G., Castagnetti, F., Poerio, A., Iacobucci, I., Amabile, M., Abruzzese, E., Orlandi, E., et al. (2006). Contribution of ABL kinase domain mutations to imatinib resistance in different subsets of Philadelphia-positive patients: by the GIMEMA Working Party on Chronic Myeloid Leukemia. Clin Cancer Res 12, 7374-7379.

Stamos, J., M. X. Sliwkowski, and C. Eigenbrot. 2002. Structure of the epidermal growth factor receptor kinase domain alone and in complex with a 4-anilinoquinazoline inhibitor. Biol Chem 277:46265-46272.

Sun, A. Siglin, J. C. Williams et al., J Am Chem Soc 131(29), 10113(2009)

Szabo, Tang, Reed, Silva, Tsark, Mann. 2002. The chicken beta-globin insulator element conveys chromatin boundary activity but not imprinting at the mouse Igf2/H19 9domain. Development 129:897-904.

Talpaz, M., N. P. Shah, H. Kantarjian, N. Donato, J. Nicoll, R. Paquette, J. Cortes, S. O'Brien, C. Nicaise, E. Bleickardt, M. A. Blackwood-Chirchir, V. Iyer, T. T. Chen, F. Huang, A. P. Decillis, and C. L. Sawyers. 2006. Dasatinib in imatinib-resistant Philadelphia chromosome-positive leukemias. N Engl J Med 354:2531-2541.

Tang, S. H., F. J. Silva, W. M. Tsark, and J. R. Mann. 2002. A Cre/loxP-deleter transgenic line in mouse strain 12951/SvImJ. Genesis 32:199-202.

Tanner, K. G., J. Landry, R. Sternglanz, and J. M. Denu. 2000. Silent information regulator 2 family of NAD-dependent histone/protein deacetylases generates a unique product, 1-O-acetyl-ADP-ribose. Proc Natl Acad Sci USA 97:14178-14182.

Tanny, J. C., and D. Moazed. 2001. Coupling of histone deacetylation to NAD breakdown by the yeast silencing protein Sir2: Evidence for acetyl transfer from substrate to an NAD breakdown product. Proc Natl Acad Sci USA 98:415-420.

Tipping, A. J., Deininger, M. W., Goldman, J. M., and Melo, J. V. (2003) Exp. Hematol. 31, 1073-1080.

Tissenbaum, H. A., and Guarente, L. (2001). Increased dosage of a sir-2 gene extends lifespan in *Caenorhabditis elegans*. Nature 410, 227-230.

van der Horst, A., L. G. Tertoolen, L. M. de Vries-Smits, R. A. Frye, R. H. Medema, and B. M. Burgering. 2004. FOXO4 is acetylated upon peroxide stress and deacetylated by the longevity protein hSir2(SIRT1). J Biol Chem 279:28873-28879.

Van Etten, Oncogene 26(47), 6738(2007).

Vaziri, H., Dessain, S. K., Ng Eaton, E., Imai, S. I., Frye, R. A., Pandita, T. K., Guarente, L., and Weinberg, R. A. (2001). hSIR2(SIRT1) functions as an NAD-dependent p53 deacetylase. Cell 107, 149-159.

Venkatachalam, S., et al. Retention of wild-type p53 in tumors from p53 heterozygous mice: reduction of p53 dosage can promote cancer formation. Embo J 17, 4657-4667 (1998).

Ventura, A., Meissner, A., Dillon, C. P., McManus, M., Sharp, P. A., Van Parijs, L., Jaenisch, R., and Jacks, T. (2004). Cre-lox-regulated conditional RNA interference from transgenes. Proc Natl Acad Sci USA 101, 10380-10385.

von Bubnoff, N., C. Peschel, and J. Duyster. 2003. Resistance of Philadelphia-chromosome positive leukemia towards the kinase inhibitor imatinib (STI571, Glivec): a targeted oncoprotein strikes back. Leukemia 17:829-838.

von Bubnoff, N., D. R. Veach, H. van der Kuip, W. E. Aulitzky, J. Sanger, P. Seipel, W. G. Bornmann, C. Peschel, B. Clarkson, and J. Duyster. 2005. A cell-based screen for resistance of Bcr-Abl-positive leukemia identifies the mutation pattern for PD166326, an alternative Abl kinase inhibitor. Blood 105:1652-1659.

von Bubnoff, N., Manley, P. W., Mestan, J., Sanger, J., Peschel, C., and Duyster, J. (2006). Bcr-Abl resistance screening predicts a limited spectrum of point mutations to be associated with clinical resistance to the Abl kinase inhibitor nilotinib (AMN107). Blood 108, 1328-1333.

Wales, M. M., M. A. Biel, W. el Deiry, B. D. Nelkin, J. P. Issa, W. K. Cavenee, S. J. Kuerbitz, and S. B. Baylin. 1995. p53 activates expression of HIC-1, a new candidate tumour suppressor gene on 17p13.3. Nat Med 1:570-577.

Wang, R. H., et al. Impaired DNA damage response, genome instability, and tumorigenesis in SIRT1 mutant mice. Cancer Cell 14, 312-323(2008).

Wang, C., L. Chen, X. Hou et al., Nat Cell Biol 8(9), 1025 (2006).

Weinstock, D. M., Nakanishi, K., Helgadottir, H. R. & Jasin, M. Assaying double-strand break repair pathway choice in mammalian cells using a targeted endonuclease or the RAG recombinase. Methods in enzymology 409, 524-540 (2006).

Weisberg, E., Manley, P. W., Breitenstein, W., Bruggen, J., Cowan-Jacob, S. W., Ray, A., Huntly, B., Fabbro, D., Fendrich, G., Hall-Meyers, E., et al. (2005). Characterization of AMN107, a selective inhibitor of native and mutant Bcr-Abl. Cancer Cell 7, 129-141.

Wertheim, J. A., Forsythe, K., Druker, B. J., Hammer, D., Boettiger, D., and Pear, W. S. (2002) Blood 99, 4122-4130.

Westerheide, S. D., J. Anckar, S. M. Stevens, Jr. et al., Science 323(5917), 1063 (2009).

Willis, S. G., Lange, T., Demehri, S., Otto, S., Crossman, L., Niederwieser, D., Stoffregen, E. P., McWeeney, S., Kovacs, I., Park, B., Druker, B. J., and Deininger, M. W. (2005) Blood 106, 2128-2137.

Wolff and R. L. Ilaria, Jr., Blood 98(9), 2808(2001).

Woo, R. A., and Poon, R. Y. (2004). Activated oncogenes promote and cooperate with chromosomal instability for neoplastic transformation. Genes Dev 18, 1317-1330.

Wood, J. G., B. Rogina, S. Lavu, K. Howitz, S. L. Helfand, M. Tatar, and D. Sinclair. 2004. Sirtuin activators mimic caloric restriction and delay ageing in metazoans. Nature 430:686-689.

Xiao, H., Li, T. K., Yang, J. M., and Liu, L. F. (2003). Acidic pH induces topoisomerase II-mediated DNA damage. Proc Natl Acad Sci USA 100, 5205-5210.

Xie, A., Kwok, A. & Scully, R. Role of mammalian Mre11 in classical and alternative nonhomologous end joining. Nature structural & molecular biology 16, 814-818(2009).

Ye, N. Wolff, L. Li et al., Blood 107(12), 4917(2006)

Yu, C., Rahmani, M., Almenara, J., Subler, M., Krystal, G., Conrad, D., Varticovski, L., Dent, P., and Grant, S. (2003). Histone deacetylase inhibitors promote STI571-mediated apoptosis in STI571-sensitive and -resistant Bcr/Abl+ human myeloid leukemia cells. Cancer Res 63, 2118-2126.

Yuan, Z. Wang, C. Gao et al., J Biol Chem 285(7), 5085 (2010).

Yuan, H. F., Bhatia, R., and Chen, W. Y. (2008). Induction of BCR-ABL mutations for acquired resistance of chronic myelogenous leukemia by imatinib To be submitted.

Yuan, Z., Zhang, X., Sengupta, N., Lane, W. S., and Seto, E. (2007). SIRT1 regulates the function of the Nijmegen breakage syndrome protein. Mol Cell 27, 149-162.

Zhang, A. C. Strauss, S. Chu et al., Cancer Cell 17(5), 427 (2010).

Zhao, X., Ghaffari, S., Lodish, H., Malashkevich, V. N., and Kim, P. S. (2002) Nat. Struct. Biol. 9, 117-120.

Zhao, X. Chai, A. Clements et al., Nat Struct Biol 10(10), 864(2003).

Zhelev, Z., Bakalova, R., Ohba, H., Ewis, A., Ishikawa, M., Shinohara, Y., and Baba, Y. (2004) FEBS Lett. 570, 195-204.

---

What is claimed is:

1. A method for developing a SIRT1 inhibitor for treating cancer, the method comprising:
   identifying one or more SIRT1 inhibitor test compounds from a model in which compounds are selected based on at least one siruitin binding pocket;
   administering the one or more SIRT1 inhibitor test compounds to a CML acquired resistant culture model;
   determining an effective test dosage for the one or more SIRT1 inhibitor test compounds that blocks CML cell relapse;
   comparing the effective test dosage to an effective sirtinol dosage; and
   selecting one or more of the SIRT1 inhibitor test compounds as a SIRT1 inhibitor lead compound when the effective test dosage is lower than the effective sirtinol dosage.

2. The method of claim 1, further comprising optimizing the one or more lead compounds.

3. The method of claim 2, wherein optimizing the one or more lead compounds is accomplished by using the one or more lead compound to refine the binding profile of the SIRT1 inhibitor test model.

4. The method of claim 2, wherein optimizing the one or more lead compounds is accomplished by isothermal titration calorimetry.

5. The method of claim 1, further comprising determining the efficacy of the one or more lead compounds.

6. The method of claim 1, further comprising determining the cytotoxicity of the one or more lead compounds.

* * * * *

UNITED STATES PATENT AND TRADEMARK OFFICE
CERTIFICATE OF CORRECTION

PATENT NO. : 8,580,488 B2
APPLICATION NO. : 12/901139
DATED : November 12, 2013
INVENTOR(S) : WenYong Chen et al.

It is certified that error appears in the above-identified patent and that said Letters Patent is hereby corrected as shown below:

In the Specification

In the Government Interest section, Column 1, Lines 17-19: please delete "The present invention was supported by the Department of Defense (Grant No. W81XWH-06-1-0268). The government may have certain rights in the present invention." and replace with --This invention was made with government support under W81XWH-06-1-0268 awarded by the Medical Research and Development Command. The government has certain rights in the invention.--

Signed and Sealed this
Twenty-third Day of April, 2024

*Katherine Kelly Vidal*

Katherine Kelly Vidal
*Director of the United States Patent and Trademark Office*

SEQUENCE LISTING

```
<160> NUMBER OF SEQ ID NOS: 45

<210> SEQ ID NO 1
<211> LENGTH: 24
<212> TYPE: DNA
<213> ORGANISM: Artificial Sequence
<220> FEATURE:
<223> OTHER INFORMATION: ABL kinase domain (ABL-k) forward primer

<400> SEQUENCE: 1
gcgcaacaag cccactgtct atgg                                          24

<210> SEQ ID NO 2
<211> LENGTH: 22
<212> TYPE: DNA
<213> ORGANISM: Artificial Sequence
<220> FEATURE:
<223> OTHER INFORMATION: ABL kinase domain (ABL-k) reverse primer

<400> SEQUENCE: 2
gccaggctct cgggtgcagt cc                                            22

<210> SEQ ID NO 3
<211> LENGTH: 20
<212> TYPE: DNA
<213> ORGANISM: Artificial Sequence
<220> FEATURE:
<223> OTHER INFORMATION: ABL kinase domain (ABL-k), T315I mutation
      forward primer
```

```
<400> SEQUENCE: 3
gcagagtcag aatccttcag                                              20

<210> SEQ ID NO 4
<211> LENGTH: 20
<212> TYPE: DNA
<213> ORGANISM: Artificial Sequence
<220> FEATURE:
<223> OTHER INFORMATION: ABL kinase domain (ABL-k), T315I mutation
      forward primer

<400> SEQUENCE: 4
gagccacgtg ttgaagtcct                                              20

<210> SEQ ID NO 5
<211> LENGTH: 20
<212> TYPE: DNA
<213> ORGANISM: Artificial Sequence
<220> FEATURE:
<223> OTHER INFORMATION: ABL kinase domain (ABL-k), T315I mutation
      reverse primer

<400> SEQUENCE: 5
tttgtaaaag gctgcccggc                                              20

<210> SEQ ID NO 6
<211> LENGTH: 21
<212> TYPE: DNA
<213> ORGANISM: Artificial Sequence
<220> FEATURE:
<223> OTHER INFORMATION: ABL kinase domain (ABL-k), E255K/Y253H
      mutations forward primer

<400> SEQUENCE: 6
gcctgtctct gtgggctgaa g                                            21

<210> SEQ ID NO 7
<211> LENGTH: 20
<212> TYPE: DNA
<213> ORGANISM: Artificial Sequence
<220> FEATURE:
<223> OTHER INFORMATION: ABL kinase domain (ABL-k), E255K/Y253H
      mutations reverse primer

<400> SEQUENCE: 7
taatgccagc agacgccttg                                              20

<210> SEQ ID NO 8
<211> LENGTH: 19
<212> TYPE: DNA
<213> ORGANISM: Artificial Sequence
<220> FEATURE:
<223> OTHER INFORMATION: BCR-ABL oligomerization domain, forward primer

<400> SEQUENCE: 8
gagtgggcgg gcattgttc                                               19

<210> SEQ ID NO 9
<211> LENGTH: 21
<212> TYPE: DNA
<213> ORGANISM: Artificial Sequence
<220> FEATURE:
<223> OTHER INFORMATION: BCR-ABL oligomerization domain, reverse primer

<400> SEQUENCE: 9 gggactttttt gcgctccatc t                                           21
```

<210> SEQ ID NO 10
<211> LENGTH: 20
<212> TYPE: DNA
<213> ORGANISM: Artificial Sequence
<220> FEATURE:
<223> OTHER INFORMATION: hypoxanthine phosphoribosyl transferase (HPRT)
      forward primer

<400> SEQUENCE: 10
accggcttcc tcctcctgag                                                   20

<210> SEQ ID NO 11
<211> LENGTH: 20
<212> TYPE: DNA
<213> ORGANISM: Artificial Sequence
<220> FEATURE:
<223> OTHER INFORMATION: hypoxanthine phosphoribosyl transferase (HPRT)
      reverse primer

<400> SEQUENCE: 11 gataattta ctggcgatgt                                                    20

<210> SEQ ID NO 12
<211> LENGTH: 22
<212> TYPE: DNA
<213> ORGANISM: Artificial Sequence
<220> FEATURE:
<223> OTHER INFORMATION: BCR-ABL junction, forward primer

<400> SEQUENCE: 12
gaagcttctc cctgacatcc gt                                                22

<210> SEQ ID NO 13
<211> LENGTH: 20
<212> TYPE: DNA
<213> ORGANISM: Artificial Sequence
<220> FEATURE:
<223> OTHER INFORMATION: BCR-ABL kinase domain (ABL-k) reverse primer

<400> SEQUENCE: 13
caaggcgtct gctggcatta                                                   20

<210> SEQ ID NO 14
<211> LENGTH: 18
<212> TYPE: DNA
<213> ORGANISM: Artificial Sequence
<220> FEATURE:
<223> OTHER INFORMATION: HIC1 exon 1a primer

<400> SEQUENCE: 14
ggacggacca gcaggaca                                                     18

<210> SEQ ID NO 15
<211> LENGTH: 18
<212> TYPE: DNA
<213> ORGANISM: Artificial Sequence
<220> FEATURE:
<223> OTHER INFORMATION: HIC1 exon 2 primer

<400> SEQUENCE: 15
gcgctggttg ttgagctg                                                     18

<210> SEQ ID NO 16
<211> LENGTH: 20
<212> TYPE: DNA
<213> ORGANISM: Artificial Sequence

```
<220> FEATURE:
<223> OTHER INFORMATION: GAPDH forward primer

<400> SEQUENCE: 16
ggaaggtgaa ggtcggagtc                                              20

<210> SEQ ID NO 17
<211> LENGTH: 20
<212> TYPE: DNA
<213> ORGANISM: Artificial Sequence
<220> FEATURE:
<223> OTHER INFORMATION: GAPDH reverse primer

<400> SEQUENCE: 17
ttcccgttct cagccttgac                                              20

<210> SEQ ID NO 18
<211> LENGTH: 24
<212> TYPE: DNA
<213> ORGANISM: Artificial Sequence
<220> FEATURE:
<223> OTHER INFORMATION: SIRT1 forward primer

<400> SEQUENCE: 18
tggctctatg aaactgttct tggt                                         24

<210> SEQ ID NO 19
<211> LENGTH: 22
<212> TYPE: DNA
<213> ORGANISM: Artificial Sequence
<220> FEATURE:
<223> OTHER INFORMATION: SIRT1 reverse primer

<400> SEQUENCE: 19
cagcatcttg cctgatttgt aa                                           22

<210> SEQ ID NO 20
<211> LENGTH: 20
<212> TYPE: DNA
<213> ORGANISM: Artificial Sequence
<220> FEATURE:
<223> OTHER INFORMATION: GAPDH forward primer

<400> SEQUENCE: 20
ggaaggtgaa ggtcggagtc                                              20

<210> SEQ ID NO 21
<211> LENGTH: 21
<212> TYPE: DNA
<213> ORGANISM: Artificial Sequence
<220> FEATURE:
<223> OTHER INFORMATION: BCR-ABL cDNA reverse primer

<400> SEQUENCE: 21
tagtccagga ggttcccgta g                                            21

<210> SEQ ID NO 22
<211> LENGTH: 54
<212> TYPE: DNA
<213> ORGANISM: Artificial Sequence
<220> FEATURE:
<223> OTHER INFORMATION: SIRT1 shRNA sequence, Sh1 sense

<400> SEQUENCE: 22
tgttgacctc ctcattgtta ttcaagagat aacaatgagg aggtcaactt tttt        54
```

<210> SEQ ID NO 23
<211> LENGTH: 59
<212> TYPE: DNA
<213> ORGANISM: Artificial Sequence
<220> FEATURE:
<223> OTHER INFORMATION: SIRT1 shRNA sequence, Sh1 antisense

<400> SEQUENCE: 23
tcgagaaaaa agttgacctc ctcattgtta tctcttgaat aacaatgagg aggtcaaca    59

<210> SEQ ID NO 24
<211> LENGTH: 54
<212> TYPE: DNA
<213> ORGANISM: Artificial Sequence
<220> FEATURE:
<223> OTHER INFORMATION: SIRT1 shRNA sequence, Sh2 sense

<400> SEQUENCE: 24
tgttggatga tatgacactg ttcaagagac agtgtcatat catccaactt tttt    54

<210> SEQ ID NO 25
<211> LENGTH: 59
<212> TYPE: DNA
<213> ORGANISM: Artificial Sequence
<220> FEATURE:
<223> OTHER INFORMATION: SIRT1 shRNA sequence, Sh2 antisense

<400> SEQUENCE: 25
tcgagaaaaa agttggatga tatgacactg tctcttgaac agtgtcatat catccaaca    59

<210> SEQ ID NO 26
<211> LENGTH: 1430
<212> TYPE: DNA
<213> ORGANISM: Homo sapiens

<400> SEQUENCE: 26
cattcaacgg tggccgacgg gctcatcacc acgctccatt atccagcccc aaagcgcaac    60
aagcccactg tctatggtgt gtcccccaac tacgacaagt gggagatgga acgcacggac   120
atcaccatga agcacaagct gggcgggggc cagtacgggg aggtgtacga gggcgtgtgg   180
aagaaataca gcctgacggt ggccgtgaag accttgaagg taggaggaca ccatggaggt   240
ggaagagttc ttgaaagaag ctgcagtcat gaaagagatc aaacacccta acctggtgca   300
gctccttggt gagtaagccc ggggctctga agagagggtc tcgcgccgca cccccagggt   360
gacacaggcg ctggggaaga cgcacgggcg gctcactgca caaaacctcg ttggaatatt   420
tgtgctctgc cgacgttcag ccgcgggtaa aatgaggcct gtatgggatg ggtgtgtgcg   480
tgtgtgcaca tatgcacatg tatgtatgag agggagaatg tgattatttt aagtggatac   540
ctaaaagcag tcaaatgcaa atctgaaatt agtttctgaa acttgggcat tttccagagt   600
tttctcactg aagtgattct gtaagtagac acataaccat cagacctaac cattcagggg   660
taaactgacg gtggtgaagg tcatttgagg tggggccagg tctgcgtctg aattctgtgg   720
cagcctctcc ctgcgtaaat tcaagttcac tggcttgaga agaagaaaag agcctggcca   780
tgtccctccc acacgagcac agtctcagga tgcaggtgct tgggaccatg ttggaagttg   840
ggcccaggac tgaggagcag agtcagaatc cttcagaagg cttttctctt agacagttgt   900
ttgttcagtt gggagcggag ccacgtgttg aagtcctcgt tgtcttgttg cagggggtct   960
gcacccggga gccccgttc tatatcatca ctgagttcat gacctacggg aacctcctgg   1020
actacctgag ggagtgcaac cggcaggagg tgaacgccgt ggtgctgctg tacatggcca   1080
ctcagatctc gtcagccatg gagtacctgg agaagaaaaa cttcatccac aggtaggggc   1140

| | |
|---|---|
| ctggccaggc agcctgcgcc atggagtcac agggcgtgga gccgggcagc cttttacaaa | 1200 |
| aagcccctct tagagatctt gctgcccgaa actgcctggt aggggagaac cacttggtga | 1260 |
| aggtagctga ttttggcctg agcaggttga tgacagggga cacctacaca gcccatgctg | 1320 |
| gagccaagtt ccccatcaaa tggactgcac ccgagagcct ggcctacaac aagttctcca | 1380 |
| tcaagtccga cgtctggggt aagggctgct gctgcactga agtggtcctt | 1430 |

<210> SEQ ID NO 27
<211> LENGTH: 821
<212> TYPE: DNA
<213> ORGANISM: Artificial Sequence
<220> FEATURE:
<223> OTHER INFORMATION: Primer for BCR-ABL kinase domain

<400> SEQUENCE: 27

| | |
|---|---|
| gcagcaggta cagaggccct gaggccttt attgtgtctt tttgcttgag cgagtaactt | 60 |
| agagcacacg tagagaaaga cagcagaagt gatcttctaa acactctgtc ctgtgtggag | 120 |
| agctccttat gtgagatttt gctgtgtagt gaattaaggc tcagccaaac tggctcacgt | 180 |
| gagctctttg agcttgcctg tctctgtggg ctgaaggctg ttccctgttt ccttcagctc | 240 |
| tacgtctcct ccgagagccg cttcaacacc ctggccgagt tggttcatca tcattcaacg | 300 |
| gtggccgacg ggctcatcac cacgctccat tatccagccc caaagcgcaa caagcccact | 360 |
| gtctatggtg tgtcccccaa ctacgacaag tgggagatgg aacgcacgga catcaccatg | 420 |
| aagcacaagc tgggcggggg ccagtacggg gaggtgtacg agggcgtgtg gaagaaatac | 480 |
| agcctgacgg tggccgtgaa gaccttgaag gtaggctggg actgccgggg gtgcccaggg | 540 |
| tacgtggggc aaggcgtctg ctggcattag gcgatgcatc tgcctggaag tctacctcct | 600 |
| gcctgctgtc cgagggcttc attggcgcca cggaattgac ttttccgtct tatatcattc | 660 |
| ctgtgtcttt gtaggagtgg aatcattctc atagtccgag tgtgtttcca catatggtga | 720 |
| gagctgacaa gcatggaggg gttttggtgt aaaaagatta gtcatttgga gaggttttct | 780 |
| cattttatgg caaggttctt ttaaagccgt ggatttccat g | 821 |

<210> SEQ ID NO 28
<211> LENGTH: 1331
<212> TYPE: DNA
<213> ORGANISM: Homo sapiens

<400> SEQUENCE: 28

| | |
|---|---|
| tcttgctgcg cctccgcctc ctcctctgct ccgccaccgg cttcctcctc ctgagcagtc | 60 |
| agcccgcgcg ccggccggct ccgttatggc gacccgcagc cctggcgtcg tgattagtga | 120 |
| tgatgaacca ggttatgacc ttgatttatt ttgcatacct aatcattatg ctgaggattt | 180 |
| ggaaagggtg tttattcctc atggactaat tatggacagg actgaacgtc ttgctcgaga | 240 |
| tgtgatgaag gagatgggag ccatcacat tgtagccctc tgtgtgctca agggggggcta | 300 |
| taaattcttt gctgacctgc tggattacat caaagcactg aatagaaata gtgatagatc | 360 |
| cattcctatg actgtagatt ttatcagact gaagagctat tgtaatgacc agtcaacagg | 420 |
| ggacataaaa gtaattggtg gagatgatct ctcaacttta actggaaaga atgtcttgat | 480 |
| tgtggaagat ataattgaca ctggcaaaac aatgcagact ttgctttcct tggtcaggca | 540 |
| gtataatcca aagatggtca aggtcgcaag cttgctggtg aaaaggaccc cacgaagtgt | 600 |
| tggatataag ccagacttg ttggatttga aattccagac aagtttgttg taggatatgc | 660 |
| ccttgactat aatgaatact tcagggattt gaatcatgtt tgtgtcatta gtgaaactgg | 720 |

-continued

```
aaaagcaaaa tacaaagcct aagatgagag ttcaagttga gtttggaaac atctggagtc    780
ctattgacat cgccagtaaa attatcaatg ttctagttct gtggccatct gcttagtaga    840 gcttttgca tgtatcttct aagaattta tctgttttgt actttagaaa tgtcagttgc     900
tgcattccta aactgtttat ttgcactatg agcctataga ctatcagttc cctttgggcg    960
gattgttgtt taacttgtaa atgaaaaaat tctcttaaac cacagcacta ttgagtgaaa   1020
cattgaactc atatctgtaa gaaataaaga gaagatatat tagttttta attggtattt   1080 taatttttat atatgcagga agaataagaa gtgattgaat attgttaatt ataccaccgt   1140
gtgttagaaa agtaagaagc agtcaatttt cacatcaaag acagcatcta agaagttttg   1200
ttctgtcctg gaattatttt agtagtgttt cagtaatgtt gactgtattt tccaacttgt   1260
tcaaattatt accagtgaat ctttgtcagc agttcccttt aaatgcaaa tcaataaatt    1320 cccaaaaatt t                                                      1331
```

<210> SEQ ID NO 29
<211> LENGTH: 19
<212> TYPE: DNA
<213> ORGANISM: Artificial Sequence
<220> FEATURE:
<223> OTHER INFORMATION: ABL shRNA sequence

<400> SEQUENCE: 29
gttggttcat catcattca                                                 19

<210> SEQ ID NO 30
<211> LENGTH: 21
<212> TYPE: DNA
<213> ORGANISM: Artificial Sequence
<220> FEATURE:
<223> OTHER INFORMATION: BCR-ABL primer for RNA

<400> SEQUENCE: 30
cgtgcagagt ggagggagaa c                                              21

<210> SEQ ID NO 31
<211> LENGTH: 22
<212> TYPE: DNA
<213> ORGANISM: Artificial Sequence
<220> FEATURE:
<223> OTHER INFORMATION: BCR-ABL primer for RNA

<400> SEQUENCE: 31
gcatctgact ttgagcctca gg                                             22

<210> SEQ ID NO 32
<211> LENGTH: 28
<212> TYPE: DNA
<213> ORGANISM: Artificial Sequence
<220> FEATURE:
<223> OTHER INFORMATION: BCR-ABL forward outer primer for ASO-PCR

<400> SEQUENCE: 32
cgtgaagacc ttgaaggagg acaccatg                                       28

<210> SEQ ID NO 33
<211> LENGTH: 28
<212> TYPE: DNA
<213> ORGANISM: Artificial Sequence
<220> FEATURE:
<223> OTHER INFORMATION: BCR-ABL reverse outer primer for ASO-PCR

<400> SEQUENCE: 33
ttctccaggt actccatggc tgacgaga                28

<210> SEQ ID NO 34
<211> LENGTH: 31
<212> TYPE: DNA
<213> ORGANISM: Artificial Sequence
<220> FEATURE:
<223> OTHER INFORMATION: BCR-ABL reverse T315I mutation primer for
      ASO-PCR

<400> SEQUENCE: 34
tccaggaggt tcccgtaggt catgaactaa a             31

<210> SEQ ID NO 35
<211> LENGTH: 28
<212> TYPE: DNA
<213> ORGANISM: Artificial Sequence
<220> FEATURE:
<223> OTHER INFORMATION: BCR-ABL forward T315I mutation primer for
      ASO-PCR

<400> SEQUENCE: 35
cccgggagcc cccgttctat atcataac                 28

<210> SEQ ID NO 36
<211> LENGTH: 26
<212> TYPE: DNA
<213> ORGANISM: Artificial Sequence
<220> FEATURE:
<223> OTHER INFORMATION: BCR-ABL forward T315I mutation primer for
      Bi-PAP

<400> SEQUENCE: 36
ggagcccccg ttctatatca tcaddt                   26

<210> SEQ ID NO 37
<211> LENGTH: 27
<212> TYPE: DNA
<213> ORGANISM: Artificial Sequence
<220> FEATURE:
<223> OTHER INFORMATION: BCR-ABL reverse T315I mutation primer for
      Bi-PAP

<400> SEQUENCE: 37
aggttcccgt aggtcatgaa ctcadda                  27

<210> SEQ ID NO 38
<211> LENGTH: 20
<212> TYPE: DNA
<213> ORGANISM: Artificial Sequence
<220> FEATURE:
<223> OTHER INFORMATION: STAT5A binding site primer (sense) for ChIP PCR

<400> SEQUENCE: 38
gcatctctga cctctcagca                          20

<210> SEQ ID NO 39
<211> LENGTH: 22
<212> TYPE: DNA
<213> ORGANISM: Artificial Sequence
<220> FEATURE:
<223> OTHER INFORMATION: STAT5A binding site primer (antisense) for
      ChIP PCR

<400> SEQUENCE: 39
cagaaacaaa attcccagct tt                       22

-continued

```
<210> SEQ ID NO 40
<211> LENGTH: 20
<212> TYPE: DNA
<213> ORGANISM: Artificial Sequence
<220> FEATURE:
<223> OTHER INFORMATION: STAT5B binding site primer (sense) for ChIP
      PCR

<400> SEQUENCE: 40
gggattggta tgaaggaacg                                                 20

<210> SEQ ID NO 41
<211> LENGTH: 20
<212> TYPE: DNA
<213> ORGANISM: Artificial Sequence
<220> FEATURE:
<223> OTHER INFORMATION: STAT5B binding site primer (antisense) for ChIP
      PCR

<400> SEQUENCE: 41
agcgaaactc cgtctcaaaa                                                 20

<210> SEQ ID NO 42
<211> LENGTH: 20
<212> TYPE: DNA
<213> ORGANISM: Artificial Sequence
<220> FEATURE:
<223> OTHER INFORMATION: GAPDH primer (sense) for ChIP PCR

<400> SEQUENCE: 42
tctggggact aggggaagga                                                 20

<210> SEQ ID NO 43
<211> LENGTH: 20
<212> TYPE: DNA
<213> ORGANISM: Artificial Sequence
<220> FEATURE:
<223> OTHER INFORMATION: GAPDH primer (antisense) for ChIP PCR

<400> SEQUENCE: 43
ccgcaaggag agctcaaggt                                                 20

<210> SEQ ID NO 44
<211> LENGTH: 540
<212> TYPE: DNA
<213> ORGANISM: Artificial Sequence
<220> FEATURE:
<223> OTHER INFORMATION: STAT5 binding site on SIRT1 promoter

<400> SEQUENCE: 44
catctctgac ctctcagcat actaacaata atattgatca catagcattt cttgtagttc     60
ataaacttca cgtgtcaata atatactata aatataaatg aattaatgaa caacaggatg   120
ctcataagct tacagacatc ttttttctcaa aaaagctggg aatttttgttt ctgtttttatt  180 gggatactga ctctcaacat ttcatatatt gcattccacc aacgtagctg agagtcaatt   240
tatgaaatat tttgtagtgt aagacagaaa gtggggagga ccaagtatgt caaccactag   300
gagtgtggtg cctagtcagg aattgggagg agtgtagcaa gaaaggaagg acaacaggat   360
ttggtcattg attggtcaga tggatttcag agggattggt atgaaggaac gcttcaaaga   420
tttttttttt aatttaagtt ccaggataca ggtgcagaat gtgtaggttt gttacatact   480
tataggtgag ccatggtggt ttgctgcacc aatcaacccc tcatctaggt tttatttata   540

<210> SEQ ID NO 45
```

-continued

```
<211> LENGTH: 540
<212> TYPE: DNA
<213> ORGANISM: Artificial Sequence
<220> FEATURE:
<223> OTHER INFORMATION: STAT5 binding site on SIRT1 promoter

<400> SEQUENCE: 45
catctctgac ctctcagcat actaacaata atattgatca catagcatttt cttgtagttc     60 ataaacttca cgtgtcaata atatactata aatataaatg aattaatgaa caacaggatg    120
ctcataagct tacagacatc tttttctcaa aaaagctggg aattttgttt ctgttttatt    180
gggatactga ctctcaacat ttcatatatt gcattccacc aacgtagctg agagtcaatt    240
tatgaaatat tttgtagtgt aagacagaaa gtggggagga ccaagtatgt caaccactag    300
gagtgtggtg cctagtcagg aattgggagg agtgtagcaa gaaaggaagg acaacaggat    360
ttggtcattg attggtcaga tggatttcag agggattggt atgaaggaac gcttcaaaga    420
tttttttttt aatttaagtt ccaggataca ggtgcagaat gtgtaggttt gttacatact    480
tataggtgag ccatggtggt ttgctgcacc aatcaacccc tcatctaggt tttatttata    540
```